(12) United States Patent
Igoe et al.

(10) Patent No.: US 8,930,204 B1
(45) Date of Patent: Jan. 6, 2015

(54) DETERMINING LIFESTYLE RECOMMENDATIONS USING AGGREGATED PERSONAL INFORMATION

(75) Inventors: Patrick T. Igoe, Philadelphia, PA (US); Charles A. Eldering, Furlong, PA (US)

(73) Assignee: Resource Consortium Limited (VG)

( * ) Notice: Subject to any disclaimer, the term of this patent is extended or adjusted under 35 U.S.C. 154(b) by 1440 days.

(21) Appl. No.: 11/668,751

(22) Filed: Jan. 30, 2007

Related U.S. Application Data

(63) Continuation of application No. 11/566,947, filed on Dec. 5, 2006.

(60) Provisional application No. 60/837,959, filed on Aug. 16, 2006, provisional application No. 60/839,898, filed on Aug. 23, 2006, provisional application No. 60/839,987, filed on Aug. 23, 2006, provisional application No. 60/827,140, filed on Sep. 27, 2006, provisional application No. 60/827,143, filed on Sep. 27, 2006.

(51) Int. Cl.
*G06F 9/00* (2006.01)

(52) U.S. Cl.
USPC ........................................ 705/2; 705/3; 705/4

(58) Field of Classification Search
USPC .................. 600/300; 705/39, 2–4; 709/204
See application file for complete search history.

(56) References Cited

U.S. PATENT DOCUMENTS

| | | | |
|---|---|---|---|
| 5,673,691 A * | 10/1997 | Abrams et al. | 600/300 |
| 5,722,418 A * | 3/1998 | Bro | 600/545 |
| 5,794,210 A | 8/1998 | Goldhaber et al. | |
| 5,868,669 A * | 2/1999 | Iliff | 600/300 |
| 5,918,014 A | 6/1999 | Robinson | |
| 5,956,400 A | 9/1999 | Chaum et al. | |
| 6,039,688 A * | 3/2000 | Douglas et al. | 600/300 |
| 6,044,349 A | 3/2000 | Tolopka et al. | |
| 6,095,949 A | 8/2000 | Arai | |
| 6,139,494 A * | 10/2000 | Cairnes | 600/300 |
| 6,175,831 B1 | 1/2001 | Weinreich | |
| 6,205,478 B1 | 3/2001 | Sugano et al. | |
| 6,697,824 B1 | 2/2004 | Bowman-Amuah | |
| 6,741,993 B1 | 5/2004 | Zitaner et al. | |
| 6,820,062 B1 | 11/2004 | Gupta et al. | |
| 6,954,753 B1 | 10/2005 | Jeran | |
| 6,983,282 B2 | 1/2006 | Stern et al. | |
| 7,016,877 B1 | 3/2006 | Steele et al. | |
| 7,054,886 B2 | 5/2006 | Stern | |

(Continued)

FOREIGN PATENT DOCUMENTS

WO    WO 00/33228    6/2000

OTHER PUBLICATIONS

Golbeck, Jennifer, Combining Provenance with Trust in Social Networks for Semantic Web Content Filter, www.mindswap.org/papers/PAW_Trust.pdf, May 22, 2006, 8 pgs. University of Maryland, College Park, MD.

(Continued)

*Primary Examiner* — Hiep V Nguyen
*Assistant Examiner* — Teresa Woods
(74) *Attorney, Agent, or Firm* — The Belles Group, P.C.

(57) ABSTRACT

A computer-implemented method for determining lifestyle recommendations includes receiving lifestyle information and healthcare information corresponding to an individual from a personal information aggregator. Lifestyle recommendations are determined based on the lifestyle information and the healthcare information and are provided to the individual.

29 Claims, 103 Drawing Sheets

(56) References Cited

U.S. PATENT DOCUMENTS

| | | |
|---|---|---|
| 7,069,308 B2 | 6/2006 | Abrams |
| 7,076,558 B1 | 7/2006 | Dunn |
| 7,103,592 B2 | 9/2006 | Huret |
| 7,120,928 B2 | 10/2006 | Sheth |
| 7,155,401 B1 | 12/2006 | Cragun et al. |
| 7,158,943 B2 | 1/2007 | Van der Riet |
| 7,256,816 B2 | 8/2007 | Profanchik et al. |
| 7,285,090 B2 * | 10/2007 | Stivoric et al. ............... 600/300 |
| 7,475,020 B2 | 1/2009 | Hasan et al. |
| 7,539,697 B1 | 5/2009 | Akella et al. |
| 7,584,223 B1 | 9/2009 | Pinkas et al. |
| 7,595,725 B1 | 9/2009 | Joseph et al. |
| 7,660,572 B2 | 2/2010 | Bucher et al. |
| 7,672,974 B2 | 3/2010 | Doctorow et al. |
| 7,730,092 B2 | 6/2010 | Lawson et al. |
| 8,190,681 B2 * | 5/2012 | Markus et al. ............... 709/204 |
| 8,453,044 B2 * | 5/2013 | Markus et al. ............... 715/205 |
| 2001/0002469 A1 | 5/2001 | Bates et al. |
| 2001/0049610 A1 | 12/2001 | Hazumi |
| 2001/0054019 A1 | 12/2001 | de Fabrega |
| 2001/0056359 A1 | 12/2001 | Abreu |
| 2002/0010597 A1 * | 1/2002 | Mayer et al. ............... 705/2 |
| 2002/0029254 A1 | 3/2002 | Davis et al. |
| 2002/0035605 A1 | 3/2002 | McDowell et al. |
| 2002/0046163 A1 | 4/2002 | Shahidi |
| 2002/0049743 A1 | 4/2002 | Hall |
| 2002/0062249 A1 | 5/2002 | Iannacci |
| 2002/0069253 A1 | 6/2002 | Kazui et al. |
| 2002/0090954 A1 | 7/2002 | Tanaka |
| 2002/0111816 A1 | 8/2002 | Lortscher et al. |
| 2002/0128864 A1 | 9/2002 | Maus et al. |
| 2002/0128865 A1 | 9/2002 | von Alten |
| 2002/0174010 A1 | 11/2002 | Rice |
| 2002/0184088 A1 | 12/2002 | Rosenberg |
| 2003/0006911 A1 | 1/2003 | Smith et al. |
| 2003/0009465 A1 | 1/2003 | Brown et al. |
| 2003/0033199 A1 | 2/2003 | Coleman |
| 2003/0059747 A1 | 3/2003 | Yoshida |
| 2003/0078097 A1 | 4/2003 | Okamoto |
| 2003/0105682 A1 | 6/2003 | Dicker et al. |
| 2003/0135391 A1 | 7/2003 | Edmundson et al. |
| 2003/0149781 A1 | 8/2003 | Yared et al. |
| 2003/0154125 A1 | 8/2003 | Mittal et al. |
| 2003/0182290 A1 | 9/2003 | Parker |
| 2003/0191703 A1 | 10/2003 | Chen et al. |
| 2003/0208382 A1 | 11/2003 | Westfall |
| 2003/0220817 A1 | 11/2003 | Larsen et al. |
| 2004/0030741 A1 | 2/2004 | Wolton et al. |
| 2004/0039601 A1 | 2/2004 | Anderson |
| 2004/0054610 A1 | 3/2004 | Amstutz et al. |
| 2004/0098366 A1 | 5/2004 | Sinclair et al. |
| 2004/0117310 A1 | 6/2004 | Mendez et al. |
| 2004/0122855 A1 | 6/2004 | Ruvolo |
| 2004/0166832 A1 | 8/2004 | Portman et al. |
| 2004/0210458 A1 | 10/2004 | Evans et al. |
| 2004/0236602 A1 * | 11/2004 | Greene ............... 705/2 |
| 2004/0243435 A1 | 12/2004 | Williams |
| 2004/0255004 A1 | 12/2004 | Weseloh |
| 2004/0267613 A1 | 12/2004 | Chan et al. |
| 2005/0009193 A1 | 1/2005 | Roberts |
| 2005/0027606 A1 * | 2/2005 | Pearson ............... 705/26 |
| 2005/0027995 A1 | 2/2005 | Menschik et al. |
| 2005/0040230 A1 | 2/2005 | Swartz et al. |
| 2005/0075794 A1 | 4/2005 | Hoffman et al. |
| 2005/0113649 A1 | 5/2005 | Bergantino |
| 2005/0124320 A1 | 6/2005 | Ernst et al. |
| 2005/0131757 A1 | 6/2005 | Chan et al. |
| 2005/0131761 A1 | 6/2005 | Trika et al. |
| 2005/0144114 A1 | 6/2005 | Ruggieri et al. |
| 2005/0149357 A1 * | 7/2005 | Doyel et al. ............... 705/2 |
| 2005/0159970 A1 | 7/2005 | Buyukkokten et al. |
| 2005/0192870 A1 * | 9/2005 | Geddes ............... 705/26 |
| 2005/0197859 A1 | 9/2005 | Wilson et al. |
| 2005/0198121 A1 | 9/2005 | Daniels et al. |
| 2005/0203800 A1 | 9/2005 | Sweeney et al. |
| 2005/0204300 A1 | 9/2005 | Mindrum |
| 2005/0216347 A1 | 9/2005 | Williams et al. |
| 2005/0233743 A1 | 10/2005 | Karaoguz et al. |
| 2005/0234885 A1 | 10/2005 | Szeto et al. |
| 2005/0235062 A1 | 10/2005 | Lunt |
| 2005/0256756 A1 | 11/2005 | Lam et al. |
| 2005/0261987 A1 | 11/2005 | Bezos et al. |
| 2005/0278443 A1 | 12/2005 | Winner et al. |
| 2006/0004588 A1 | 1/2006 | Ananda |
| 2006/0015843 A1 | 1/2006 | Sabbouh |
| 2006/0026036 A1 | 2/2006 | Mahmood |
| 2006/0041478 A1 | 2/2006 | Zheng |
| 2006/0059141 A1 | 3/2006 | Yonezawa |
| 2006/0111941 A1 | 5/2006 | Blom |
| 2006/0129821 A1 | 6/2006 | Zugenmaier et al. |
| 2006/0136419 A1 | 6/2006 | Brydon et al. |
| 2006/0143068 A1 | 6/2006 | Calabria |
| 2006/0143464 A1 | 6/2006 | Ananthanarayanan et al. |
| 2006/0161455 A1 * | 7/2006 | Anastasia ............... 705/2 |
| 2006/0173985 A1 | 8/2006 | Moore |
| 2006/0178907 A1 | 8/2006 | Humble |
| 2006/0178915 A1 | 8/2006 | Chao |
| 2006/0190616 A1 | 8/2006 | Mayerhofer et al. |
| 2006/0195341 A1 | 8/2006 | Haaksma et al. |
| 2006/0218111 A1 | 9/2006 | Cohen |
| 2006/0218225 A1 | 9/2006 | Hee Voon et al. |
| 2006/0219776 A1 | 10/2006 | Finn |
| 2006/0224416 A1 | 10/2006 | Lloyd et al. |
| 2006/0271281 A1 | 11/2006 | Ahn et al. |
| 2007/0015974 A1 * | 1/2007 | Higgins et al. ............... 600/300 |
| 2007/0043582 A1 | 2/2007 | Peveto et al. |
| 2007/0121843 A1 | 5/2007 | Atazky et al. |
| 2007/0138253 A1 | 6/2007 | Libin et al. |
| 2007/0143148 A1 | 6/2007 | Kol et al. |
| 2007/0143151 A1 * | 6/2007 | Fey et al. ............... 705/3 |
| 2007/0149179 A1 | 6/2007 | Kashiwabara |
| 2007/0168233 A1 | 7/2007 | Hymel |
| 2007/0288330 A1 | 12/2007 | Vaid |
| 2008/0033871 A1 * | 2/2008 | Birbara et al. ............... 709/204 |
| 2008/0052127 A1 | 2/2008 | Rosenfeld et al. |
| 2008/0103900 A1 | 5/2008 | Flake et al. |
| 2008/0201206 A1 | 8/2008 | Pokorney et al. |
| 2008/0221920 A1 | 9/2008 | Courtney |
| 2008/0228819 A1 | 9/2008 | Minnis et al. |

OTHER PUBLICATIONS

Sigel, Mark, Envisioning RSS as a Web 2.0 Platform, www.oreilynet.com/digital media/blog, Aug. 9, 2005, 4 pgs.
The Appleseed Project, Project Overview, http://appleseed.sourceforge.net, Feb. 12, 2007, 1 pg.
Vantage Solutions: Expert Clinical Information at the Point of Care, www.multum.com/mdoc/Multum_Vantage.pdf, Cerner Multum 2005, 1 pg.
Open Financial Exchange Specification 1.0; Overview, www.microsoft.com/finserv/ofxfin1.zip, Apr. 25, 1997, 3 pgs.
Millard, Elizabeth, Online Social Networks and the Profit Motive, www.ecommercetimes.com, Jun. 12, 2004, 3 pgs.
Web page, ProTrack2005, ProTrack's Features, www.dakotafit.com/features.htm, Dec. 13, 2006, 1 pg.
Web page, OFX Migration Support, http://web.intuit.com/support/ofx, Nov. 14, 2006, 1 pg.
Web pages, Quicken Premier 2007, http://quicken.intuit.com/premier, Oct. 6, 2006, 2 pgs.
Web pages, LiVEJOURNAL, What is LiveJournal, www.livejournal.com, Sep. 19, 2006, 2 pgs.
Searching ZoomInfo; Frequently Asked Questions (for users), www.zoominfo.com/Search, Oct. 9, 2006, 3 pgs.
Miller, Libby and Brickley, Dan, The Friend of a Friend (FOAF) project, www.foaf-project.org, Feb. 8, 2007, 2 pgs.
Wood, Molly, Five reasons social networking doesn't work, www.cnet.com, Jun. 2, 2005, 5 pgs.
Web pages, Microsoft's Zune Delivers Connected Music and Entertainment Experience, www.microsoft.com/presspass, Sep. 14, 2006, 2 pgs.
Web pages, Microsoft Money Essentials, www.microsofe.com/money/ProductDetails, Oct. 6, 2006, 2 pgs.

(56) References Cited

OTHER PUBLICATIONS

Kirkpatrick, Marshall, The New Multiply 3.0 vs. Vox, www.techcrunch.com, Nov. 13, 2006, 3 pgs.
Hof, Rob, The Next Social Networks won't Like MySpace, www.businessweek.com/the-thread, Apr. 24, 2006, 2 pgs.
Web pages, Company Pages:Our mission is to make college more affordable for American Familes, https://lty.s.upromise.com, Oct. 27, 2006, 3 pgs.
Golbeck, Jennifer and Mannes, Aaron, Using Trust and Provenance for Content Filtering on the Semantic Web, http://trust.minswap.org/papers/WWWTrust_Trust.pdf, May 22, 2006, 9 pgs. University of Maryland, College Park MD.
Pincus, Marcus, What's next for social networking?, http://markpincus.typepad.com/markpincus, Apr. 23, 2006, 5 pgs.
Web pages, 43things, www.43things.com, Sep. 19, 2006, 2 pgs.
Web pages, How do I schedule when Quicken updates my account information?, https://.quicken.custhelp.com, Oct. 27, 2006, 2 pgs.
Web page, SmartStik-MD keeps your medical records on a biometric flash drive, 222.engadget.com/2006, Dec. 5, 2006, 1 pg.
Bazeley, Michael, Search engine use is spiking, study reveals, www.mercurynews.com, Nov. 21, 2005, 1 pg.
Web page, Social network, http://en.wikipedia.org/wiki/Social_network, Feb. 8, 2006, 6 pgs.
Roush, Wade, Social Networking 3.0, www.technologyreview.com, Nov. 18, 2005, 1 pg.
Allen, Christopher, My Advice to Social Networking Services, www.lifewithalacrity.com/2004, Feb. 3, 2004, 16 pgs.
Churchill, Elizabeth F. and Halverson, Christine A. Social Networks and Social Networking, www.dsonline.computer.org, 11 pgs.
Linder, Brad, PVR on the go—record your life 8 hours at a time, www.pvrwire.com, Nov. 13, 2006, 5 pgs.
Sohn, Dongyoung and Leckenby, John D., Social Dimensions of Interactive Advertising, www.ciadvertising.org/studies, Mar. 2002, 18 pgs.
Schonfeld, Erick and Borzo, Jeanette, Social Networking for Dollars, http://money.cnn.com/2006, Sep. 20, 2006, 2 pgs.
Shipley, Chris, Social networks and my big a-ha, http://wistechnology.com, Jun. 24, 2004, 3 pgs.
Del Conte, Natali, Spokeo Aggregates Social Networks and Blogs, www.techcrunch.com/2006, Nov. 29, 2006, 2 pgs.
Web pages, Newsweek Media Research Index, www.vmr.com/research, Nov. 15, 2006, 8 pgs.
Richardson, Matthew and Domingos, Pedro, Mining Knowledge-Sharing Sites for Viral Marketing, http://research.microsoft.com, 2002, 10 pgs.
Yang, Wan-Shiou, et al, Mining Social Networks for Targeted Advertising, Proceedings of the 39th Hawaii International Conference on System Sciences—2006, 10 pgs.
Kirkpatrick, Marshall, Mpire to Unveil Power-Shopping Plug-In, www.techcrunch.com/2006, Nov. 21, 2006, 2 pgs.
Deluxe Quicken 2000 Making the Most of Your Money Manual, www.Quicken.com, Jun. 1999, 96 pgs.
Meskill, Judith, Home of the Social Networking Services Meta List, http://socialsoftware.weblogsinc.com, Feb. 14, 2005, 70 pgs.
Freeman, Linton C. Spheres, Cubes and Boxes: Graph Dimensionality and Network Structure, 1983, 18 pgs., Elsevier Scince Publishers B.V.
Johnson, Carolyn Y., Locating pals at MIT, privately, www.boston.com/buisness/personaltech, Dec. 13, 2006, 2 pgs.
Info rings save us from hassle of human interaction, http://blog.scifi.com, Sep. 25, 2006, 2 pgs.
iScribe ePrescribing, www.iscribe.com/ePrescribing, Nov. 20, 2006, 1 pg.
Murphy, Darren, EMI puts your medical history on digital business card, www.engadget.com, Nov. 23, 2006, 1 pg.
Markoff, John, Entrepreneurs See a Web Guided by Common Sense, www.nytimes.com, Nov. 12, 2006, 4 pgs.
Kirkpatricks, Marshall, Facebook to put viral ads in your feeds? www.techcrunch.com, Sep. 28, 2006, 9 pgs.

\* cited by examiner

PERSONAL INFORMATION AGGREGATOR: MAIN MENU

WELCOME "SMITH FAMILY"

SELECT PROFILE:

208 ☐ Robert  [VIEW]  UPDATES / REQUESTS

☐ Sue  [VIEW]  UPDATES / REQUESTS

☐ Robbie Jr.  [VIEW]  UPDATES / REQUESTS

☐ VIEW/EDIT  FAMILY NETWORK & SOCIAL CONNECTIONS

700 ☐ VIEW/EDIT  FAMILY PURCHASE HISTORY

☐ VIEW/EDIT  FAMILY PROFILE

FAMILY MESSAGES / ALERTS / REQUESTS  800  1218

☐ BEST BUY MUSIC SURVEY WITH CASH-BACK COUPON

☐ ACME SUPERMARKET APRIL 2006 STATEMENT

☐ !ALERT! – Dr. Wilson needs Robert's files

☐ RUBY TUESDAY'S NEW MENU AVAILABLE

☐ SUBSCRIBE TO THE NY POST TODAY/ RECEIVE A FREE GIFT

☐ TOYS R US SALE THIS WEEKEND

☐ SUE SMITH – COMMERCE BANK  APRIL 2006 STATEMENT

☐ !ALERT! – RITE-AID Pharmacy needs access to Robbie Jr. files

☐ REQUEST TO JOIN PTA DISCUSSION GROUP

☐ DELETE SELECTED    ☐ SAVE SELECTED

*Fig. 12*

USER PROFILE: Robert Smith

USER BASIC INFORMATION:      SOCIAL NETWORK INFORMATION:

[ADD] [EDIT] [VIEW] PERSONAL INFO / BIO ~ 1201    [ADD] [EDIT] [VIEW] CONTACTS & CONNECTIONS ~ 1203

[ADD] [EDIT] [VIEW] PURCHASE HISTORY    [ADD] [EDIT] [VIEW] CONTACT TYPES & FEEDS ~ 1204

[VIEW] FULL MEDICAL RECORDS    [ADD] [EDIT] [VIEW] GROUPS & CLUBS ~ 1205

☐ !ALERT! – Dr. Wilson is requesting access to your medical records

☐ NEW MESSAGE FROM "MODERN DRUMMER MAGAZINE"

☐ ROLLING STONE 2006 MUSIC AWARDS BALLOT

☐ JUNE 2006 COMMERCE BANK STATEMENT FOR "ROBERT SMITH"

☐ EXPRESS FOR MEN – STORE SURVEY WITH BONUS COUPON

☐ FRANK JOHNSON WANTS TO BE ADDED TO YOUR "FRIENDS"

☐ !ALERT! – ACME SUPERMARKET is requesting access to your "FOOD PURCHASES"

☐ DELETE SELECTED   ☐ SAVE SELECTED   ☐ KEEP AS NEW   ☐ VIEW RECENTLY DELETED

*Fig. 13*

PERSONAL INFORMATION AGGREGATOR (PIA) — 602

¡ATTENTION! "Doylestown & Warrington Family Practice"

Is requesting access to
medical files for his/her appointment on ___/___/___

* Request Received @ _____
  AM / PM on ___/___/___

[ALLOW ACCESS]  [DENY ACCESS] — 701

[DETAILS]

[NEXT ALERT →] — 1207

FULL LIST OF MESSAGES & ALERTS:

- ☐ Doylestown & Warrington Family Practice for "_____"
- ☒ ACME SUPERMARKETS shopping report for May 2006
- ☒ Philadelphia Motorcycle Club wants to join your network

DETAILS OF TRANSMISSION:

☐ Request from: Doylestown & Warrington Family Practice ∼1208
Information requested at: 8:30 AM on 6/29/06

PATIENT: "Patient Name"

DOCTOR: "Doctor Name" PhD ∼1209

FILES REQUESTED: "Patient Name"'s full medical history file for appointment on 6/30/06

SECURITY LEVEL: HIGH (patient sensitive materials)

FILES EXPIRE WITHIN: "48" hours after appointment

[ ALLOW ACCESS ] ∼701    [ DENY ACCESS ]

6. HEALTHCARE   PROFILE: Bob Smith

[EDIT PERSONAL INFO]   [CHECK RECENT UPDATES]   [VIEW FULL MEDICAL FILE]

[VIEW RECENT UPDATES] — 1214

MY DOCTORS: — 803
- ☐ DR. JANE WILSON @ DOYLESTOWN & WARRINGTON FAMILY PRACTICE   [ADD] [ERASE] [SEARCH]
- ☐ DR. BRUCE DICKENSON @ ALLIED HEALTH SERVICES

MY INSURANCE:
- ☐ BLUE CROSS / BLUE SHIELD – PPO   CHALFONT, PA OFFICE   215-345-0100   [ADD] [ERASE] [SEARCH]
  CONTACT: FRED THOMAS

MY PHARMACIES:
- ☐ ACME SUPERMARKET PHARMACY   DOYLESTOWN, PA   267-880-1001   [ADD] [ERASE] [SEARCH]
- ☐ RITE AID PHARMACY   PHILADELPHIA, PA   610-745-5000

MY HOSPITALS:
- ☐ DOYLESTOWN HOSPITAL   DOYLESTOWN, PA   215-348-0101   [ADD] [ERASE] [SEARCH]

CONTACT TYPES & FEEDS

SELECT LINK TO EDIT

| | | | |
|---|---|---|---|
| ☐ | FRIENDS | ☐ | SCHOOLS |
| ☐ | CO-WORKERS | ☐ | FEDERAL GOVERNMENT |
| ☐ | FAMILY | ☐ | STATE GOVERNMENT |
| ☐ | BUSINESS ASSOCIATES | ☐ | LOCAL GOVERNMENT |
| ☐ | GROUPS & CLUBS | | |
| ☐ | HEALTHCARE | | |
| ☐ | COMPANIES / SERVICES | ☐ | CALENDAR / OUTLOOK |

608

CONTACT TYPE: Companies / Services → "XYZ Corporation"

Output Feeds to Share: "Purchase Data" (requested)

| | | | | | |
|---|---|---|---|---|---|
| ☐ | ALL PURCHASES | ☐ | ALL ENTERTAINMENT | ☐ | CALENDAR / OUTLOOK |
| ☐ | FOOD | ☐ | ELECTRONICS | | |
| ☐ | MUSIC | ☐ | SPORTS & OUTDOORS | | |
| ☐ | MOVIES | ☐ | TOYS & BABY | | |
| ☐ | CLOTHING | ☐ | VIDEO GAMES | | |
| ☐ | AUTOMOTIVE | ☐ | SMALL BUSINESS | | |
| ☐ | BOOKS / MAGAZINES | ☐ | FLOWERS / GIFTS | | |
| ☐ | HOME & GARDEN | ☐ | PERSONAL ACCESSORIES | | |
| ☐ | PERSONAL CARE | ☐ | OTHER | | |

*Fig. 19*

"CONTACT TYPES & OUTPUT FEED BREAKDOWN" – "FRIENDS"

PROFILE: Bob Smith

☐ FRIENDS (ALL)

OUTPUT FEEDS SENT:   ☐ ALL PURCHASE DATA

☐ MUSIC PURCHASE DATA
☐ DVD PURCHASE DATA
☐ BLOOD PRESSURE DATA
☐ EVENT TICKET PURCHASE DATA
☐ CALENDAR / OUTLOOK "FRIEND" SHARED APPOINTMENT DATA

804 ↗

☐ FRIENDS (PREFERRED LIST)

☐ KURT THOMAS – ALL PURCHASE DATA
☐ BETTY DAVIS – DVD PURCHASE DATA
☐ SALLY SMITH – EVENT TICKET PURCHASE DATA
☐ BRYAN GISONE – HEALTHCARE DATA
☐ DENISE HARE – MUSIC & DVD PURCHASE DATA

805 ↗

OTHER CONTACT TYPES

☐ FAMILY
☐ CO-WORKERS
☐ BUSINESS ASSOCIATES
☐ GROUPS & CLUBS
☐ HEALTHCARE
☐ SEE MORE CONTACTS

☐ FRIEND HIERARCHY

☐ 1ST DEGREE FRIENDS
☐ 2ND DEGREE FRIENDS
☐ 3RD DEGREE FRIENDS
☐ ENTIRE NETWORK

PURCHASE HISTORY DATA: *"ENTERTAINMENT"*

PROFILE: Bob Smith

VIEW DATA BY:
- ☐ DAY
- ☒ MONTH
- ☐ YEAR

JULY 2005

1. 7/29/05 – 8:35 PM – BEST BUY – MONTGOMERYVILLE, PA
   - ☐ AMERICAN PIE – DVD – $15.99
   - ☐ MUSE – "SHOWBIZ" – CD – $9.99

2. 7/14/05 – 12:35 PM – BEST BUY – WILLOW GROVE, PA
   - ☐ THE KILLERS – "HOT FUSS" – CD – $11.99

3. 7/12/05 – 4:57 PM – CIRCUIT CITY – WARRINGTON, PA
   - ☐ YAMAHA AM/FM RECEIVER DX-1000 – ELECTRONICS – $299.99
   - ☐ LED ZEPPELIN – "CODA" – CD – $7.99
   - ☐ ANIMAL HOUSE – DVD – $9.99

4. 7/4/05 – 8:50 AM – TARGET – WARRINGTON, PA
   - ☐ BLOC PARTY – CD – $9.99
   - ☐ SHARP UNIVERSAL TV REMOTE – ELECTRONICS – $19.99

SORT DATA BY:
- ☐ ELECTRONICS
- ☐ CDs
- ☐ DVDs
- ☐ OTHERS

*Fig. 21*

PURCHASE HISTORY DATA: *"ENTERTAINMENT → CD PURCHASES"* ⎯ 611

PROFILE: Bob Smith

VIEW DATA BY:  ☐ STORE   ☒ DATE OF PURCHASE   ☐ GENRE / STYLE ⎯ 705

1. 7/29/05 – 8:35 PM – BEST BUY – MONTGOMERYVILLE, PA
   ☐ MUSE – "SHOWBIZ" – CD – $9.99

2. 7/14/05 – 12:35 PM – BEST BUY – WILLOW GROVE, PA
   ☐ THE KILLERS – "HOT FUSS" – CD – $11.99

3. 7/12/05 – 4:57 PM – CIRCUIT CITY – WARRINGTON, PA
   ☐ LED ZEPPELIN – "CODA" – CD – $7.99     ⎯ 1216

4. 7/4/05 – 8:50 AM – TARGET – WARRINGTON, PA
   ☐ BLOC PARTY – CD – $9.99

5. 6/29/05 – 5:43 PM – TRAK RECORDS – DOYLESTOWN, PA
   ☐ REEL BIG FISH – "TURN THE RADIO OFF" – CD – $10.99
   ☐ METHOD MAN – "TICAL" – CD – $12.99

6. 6/15/05 – 6:48 PM – AMAZON.COM – ONLINE PURCHASE
   ☐ KELLER WILLIAMS – "LAUGH" – CD – $8.99

[ VIEW OLDER PURCHASES ]

*Fig. 22*

CONTACT TYPE: HEALTHCARE → BLUE CROSS / BLUE SHIELD

SELECT INFO TO PASS THROUGH FILTER

☐ HEIGHT
☐ WEIGHT
☐ DIAGNOSED ILLNESSES
☐ PRESCRIPTIONS
☐ RESTING HEARTRATE
☐ BLOOD PRESSURE
☐ CHOLESTEROL LEVEL
☐ SMOKING STATUS

[ SAVE FILTER ]   [ CANCEL ]

NODE $a_{01}$ CHARACTERISTICS # of 1st ORDER CONTACTS .......................... 37
# of 2nd ORDER CONTACTS ......................... 379
 .
 .
 .
# of $n^{th}$ ORDER CONTACTS ......................... 5,752
1st ORDER MEAN AGE ............................. 27
2nd ORDER MEAN AGE ............................ 31
 .
 .
 .
$n^{th}$ ORDER MEAN AGE ............................. 32
NODE MEAN AGE ................................ 283
NODE MEAN INCOME ............................ $73,000
NODE MEAN EDUCATION ......................... 17 years
% MALE ....................................... 37%
% FEMALE ..................................... 63%
NODE RECOMMENDED GROUP MEAN AGE ........... 26
NODE RECOMMENDED GROUP MEAN INCOME ........ $62,000
NODE RECOMMENDED GROUP MEAN EDUCATION ..... 15 years

*Fig. 72*

RECOMMENDATION STATISTICS

```
# INTRODUCTION NODES (i) . . . . . . . . . . . . . . . . . . . . . . . . 12
R₀ PEAK RECOMMENDATION RATE . . . . . . . . . . . . . . . . . 37
R₀ PEAK RECOMMENDATION TIME . . . . . . . . . . . . . . . . . . 11 hours
R₁ PEAK RECOMMENDATION RATE . . . . . . . . . . . . . . . . . 63
R₁ PEAK RECOMMENDATION TIME . . . . . . . . . . . . . . . . . . 18 hours
    .
    .
    .
Rₙ PEAK RECOMMENDATION RATE . . . . . . . . . . . . . . . . . 270
Rₙ PEAK RECOMMENDATION TIME . . . . . . . . . . . . . . . . . . 90 hours
CUMULATIVE RECOMMENDATIONS . . . . . . . . . . . . . . . . . 3,725
ADOPTION TIME . . . . . . . . . . . . . . . . . . . . . . . . . . . . . . . . 80 hours
# CONNECTED NODE RECOMMENDATIONS . . . . . . . . . . . 120
# VIEWINGS/LISTENINGS . . . . . . . . . . . . . . . . . . . . . . . . . . 2,305
# VIEWINGS/LISTENINGS COMPLETED . . . . . . . . . . . . . . . 1,712
RECOMMENDATIONS IN ADOPTION TIME . . . . . . . . . . . . . 2,720
RECOMMENDATION IN ADOPTION TIME / i . . . . . . . . . . . . 870
```

*Fig. 73*

NODE $a_{01}$ DESCRIPTOR

1st LEVEL CONTACTS .............. $a_{11}, a_{12}, a_{13}, a_{14}, ...$
2nd LEVEL CONTACTS .............. $a_{22}(a_{12}), a_{23}(a_{13}), ...$
3rd LEVEL CONTACTS .............. $a_{31}(a_{22}), a_{33}(a_{22}), ...$

NODE $a_{01}$ RECOMMENDATION DESCRIPTOR $R_0 (a_{01} \rightarrow a_{12}), R_0 (a_{01} \rightarrow a_{13}), ...$
$R_1 (a_{12} \rightarrow a_{21})$
$R_2 (a_{22} \rightarrow a_{31})$

*Fig. 74*

RECOMMENDED VIDEOS:

SELECT TO VIEW

- ☐ Chappelle Show – Episode 43 – July 29, 2006    recommended by: Kurt    27 minutes
- ☐ Talladega Nights "The Ballad of Ricky Bobby" Trailor – July 28, 2006    recommended by Kate    2:15 minutes
- ☐ World Series of Poker – Semifinals '05 – July 23, 2006    recommended by Bryan    58 minutes
- ☐ Last Comic Standing 7-12-06 Show – July 13, 2006    recommended by The Comedy Club    57 minutes
- ☐ Pink "Dear Mr. President" Music Video – July 13, 2006    recommended by Patti    4:30 minutes
- ☐ Crocodile Hunter Diaries – Episode 35 – July 12, 2006    recommended by Wendy    29 minutes
- ☐ Cold Case Files "Blood Money; Precious Doe" – July 9, 2006    recommended by Bob & Frank    60 minutes
- ☐ Crossing Jordan "Death Toll" – July 7, 2006    recommended by Dana    60 minutes

PAGE ① OF 4    PREVIOUS / NEXT

- ☐ VIEW PREVIOUS RECOMMENDATIONS (UNVIEWED)
- ☐ SHARE RECOMMENDATIONS WITH CONTACTS
- ☐ VIEW SAVED PROGRAMS
- ☐ VIEW AUDIO RECOMMENDATIONS

DETERMINING LIFESTYLE RECOMMENDATIONS USING AGGREGATED PERSONAL INFORMATION

CROSS REFERENCE TO RELATED APPLICATIONS

This application is a continuation of co-pending U.S. patent application Ser. No. 11/566,947, filed Dec. 5, 2006, entitled Aggregating Personal Information in a Personal Information Aggregator, and claims the benefit of U.S. Provisional Patent Application No. 60/837,959, filed Aug. 16, 2006, and entitled Personal Information Aggregator; U.S. Provisional Patent Application No. 60/839,898, filed Aug. 23, 2006, entitled, N-Dimensional Social Network; U.S. Provisional Patent Application No. 60/839,987, filed Aug. 23, 2006, entitled, Personalized Recommendation System; U.S. Provisional Patent Application No. 60/827,140, filed Sep. 27, 2006, entitled, Using Aggregated Personal Information to Determine the Effectiveness of Advertisements; and U.S. Provisional Patent Application No. 60/827,143, filed Sep. 27, 2006, entitled, Using Aggregated Personal Information and Multidimensional Networks to Target Advertisements, the entire disclosures of which are incorporated herein by reference.

This application is related to co-pending U.S. patent application Ser. No. 11/567,168, filed Dec. 5, 2006, entitled Aggregating Personal Information in a Personal Information Aggregator; U.S. patent application Ser. No. 11/567,169, filed Dec. 5, 2006, entitled Aggregating Purchase Information using a Personal Information Aggregator; U.S. patent application Ser. No. 11/567,170, filed Dec. 5, 2006, entitled Providing Aggregated Personal Information from a Personal Information Aggregator; U.S. patent application Ser. No. 11/567,172, filed Dec. 5, 2006, entitled Providing Incentives Based on Aggregated Purchases; U.S. patent application Ser. No. 11/567,174, filed Dec. 5, 2006, entitled Aggregating Personal Information in a Personal Information Aggregator; U.S. patent application Ser. No. 11/567,175, filed Dec. 5, 2006, entitled Receiving Incentives for Aggregated Purchase Information; U.S. patent application Ser. No. 11/567,179, filed Dec. 5, 2006, entitled Obtaining Personal Information from a Personal Information Aggregator; U.S. patent application Ser. No. 11/567,200, filed Dec. 5, 2006, entitled Targeting Advertisements to Groups Using Aggregated Personal Information; U.S. patent application Ser. No. 11/567,183, filed Dec. 5, 2006, entitled Determining the Effectiveness of Advertisements; U.S. patent application Ser. No. 11/567,184, filed Dec. 5, 2006, entitled Determining Insurance Needs Using a Personal Information Aggregator; U.S. patent application Ser. No. 11/567,185, filed Dec. 5, 2006, entitled Generating Financial Plans using a Personal Information Aggregator; U.S. patent application Ser. No. 11/567,187, filed Dec. 5, 2006, entitled Aggregating Personal Healthcare Information; U.S. patent application Ser. No. 11/567,188, filed Dec. 5, 2006, entitled Targeting Advertisements using Aggregated Personal Information; U.S. patent application Ser. No. 11/567,190, filed Dec. 5, 2006, entitled Targeting Advertisements in a Multi-Dimensional Personal Information Network; U.S. patent application Ser. No. 11/567,192, filed Dec. 5, 2006, entitled Targeting Advertisements in a Multi-Dimensional Personal Information Network; U.S. patent application Ser. No. 11/567,194, filed Dec. 5, 2006, entitled Creating a Projection of a Multi-Dimensional Network; U.S. patent application Ser. No. 11/567,195, filed Dec. 5, 2006, entitled Accessing Information in a Multi-Dimensional Network; U.S. patent application Ser. No. 11/567,197, filed Dec. 5, 2006, entitled Creating a Projection of a Multi-Dimensional Personal Information Network; U.S. patent application Ser. No. 11/567,198, filed Dec. 5, 2006, entitled Obtaining Lists of Nodes of a Multi-Dimensional Network; U.S. patent application Ser. No. 11/567,201, filed Dec. 5, 2006, entitled Providing Notifications to an Individual in a Multi-Dimensional Personal Information Network; U.S. patent application Ser. No. 11/567,202, filed Dec. 5, 2006, entitled Sending Personal Information to a Personal Information Aggregator; U.S. patent application Ser. No. 11/668,737, filed Jan. 30, 2007, entitled Targeting Advertisements Using Aggregated Personal Information; U.S. patent application Ser. No. 11/668,739, filed Jan. 30, 2007, entitled Targeting Advertisements Using Aggregated Personal Information; U.S. patent application Ser. No. 11/668,744, filed Jan. 30, 2007, entitled Determining Contraindications Using Aggregated Personal Information; U.S. patent application Ser. No. 11/668,757, filed Jan. 30, 2007, entitled Generating Recommendations in a Multi-Dimensional Personal Information Network; U.S. patent application Ser. No. 11/668,776, filed Jan. 30, 2007, entitled Generating Recommendations in a Multi-Dimensional Personal Information Network; and U.S. patent application Ser. No. 11/668,801, filed Jan. 30, 2007, entitled Generating Recommendations in a Multi-Dimensional Personal Information Network, the entire disclosures of which are incorporated herein by reference.

BRIEF DESCRIPTION OF THE DRAWINGS

The following detailed description will be better understood when read in conjunction with the appended drawings, in which there is shown one or more of the multiple embodiments of the present invention. It should be understood, however, that the various embodiments of the present invention are not limited to the precise arrangements and instrumentalities shown in the drawings.

In the Drawings:

FIGS. 12-24 are examples of user interface displays for the PIA in accordance with multiple embodiments of the present invention;

FIG. 31 is a diagram showing an example of personal information stored in a PIA in accordance with one embodiment of the present invention;

FIG. 72 illustrates node characteristics within a social network in accordance with one embodiment of the present invention;

FIG. 73 illustrates node recommendation statistics in accordance with one embodiment of the present invention;

FIG. 74 illustrates an example of node and recommendation descriptors in accordance with one embodiment of the present invention;

FIG. 85 is an example of a presentation screen utilized in accordance with one embodiment of the present invention;

DETAILED DESCRIPTION

Figure 1:
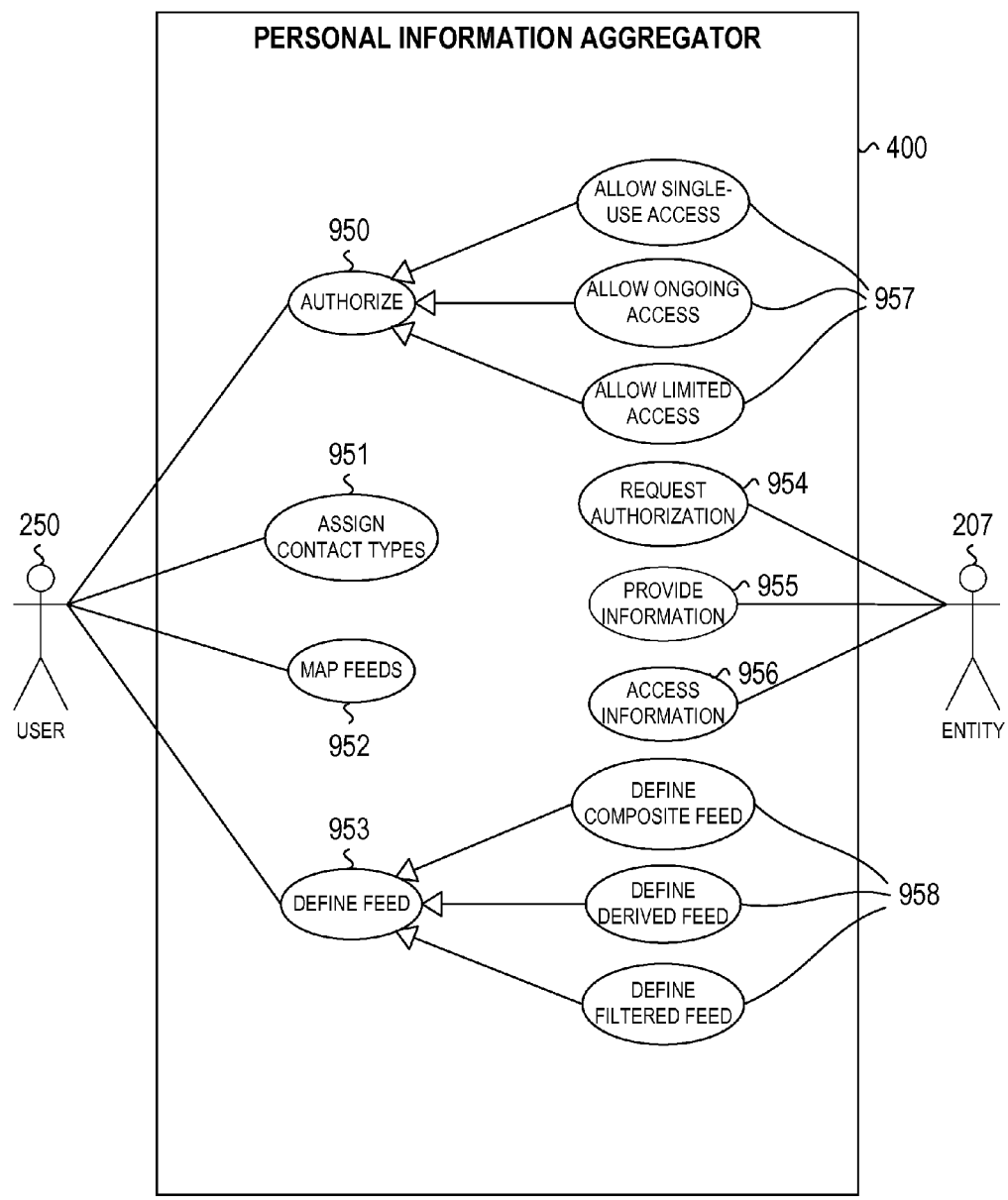
FIG. 1 is a use case diagram for a personal information aggregator (PIA) in accordance with one embodiment of the present invention.

Certain terminology is used herein for convenience only and is not to be taken as a limitation on the embodiments of the present invention. In the drawings, the same reference letters are employed for designating the same elements throughout the several figures.

Unified Modeling Language ("UML") can be used to model and/or describe methods and systems and provide the basis for better understanding their functionality and internal operation as well as describing interfaces with external components, systems and people using standardized notation. When used herein, UML diagrams including, but not limited to, use case diagrams, class diagrams, activity diagrams and sequence diagrams, are meant to serve as an aid in describing the embodiments of the present invention, but do not constrain implementation thereof to any particular hardware or software embodiments. Unless otherwise noted, the notation used with respect to the UML diagrams contained herein is consistent with the UML 2.0 specification or variants thereof and is understood by those skilled in the art.

Personal Information Aggregator

A Personal Information Aggregator (PIA) provides a user with the ability to store, organize and control personal information. The PIA obtains personal information that may be controlled by separate entities (e.g., credit reporting agencies, financial institutions and merchants), aggregates the information and organizes the information in manners that have been selected by the user. The user controls access to the personal information stored in the PIA by authorizing access by other entities to subsets of the personal information stored in the PIA. In many cases, the use of the authorized information is bound and restricted by legal contract, and therefore, the user has legal remedies available to enforce proper use of the information.

The user of a PIA can be any person, group or entity that wishes to manage and control his (or its) personal information. For example, a family can use a PIA to aggregate personal information that the family members have in common (place of residence, family vacations, etc.).

An entity that accesses the information stored in a PIA can be an individual person, a group, entity or equipment (e.g., digital video recorder) or software (e.g., web browser) that has been configured to access the PIA. The nature and composition of a group that accesses a PIA can encompass a broad range of organizations, e.g., a health clinic, an auto dealership, a coin collectors club, etc.

The personal information obtained by and/or stored in a PIA encompasses a broad array of types of information about a person's life, social interactions, health and healthcare, consumer behavior including consumer purchases, entertainment consumption and habits, fitness activity, travel, financial, employment, education, hobbies and personal computing and/or other aspects of a person's world that can be reduced in any way to data. The personal information stored in the PIA is obtained from a variety of sources, including input data feeds that are generated by providers of goods and services, healthcare providers, organizations, clubs, social contacts and other persons and entities. In addition, personal information stored in the PIA may be entered directly by the user.

The personal information stored in the PIA can span a wide range of disparate types of data. For example, financial data (which might include information regarding bank accounts and investments) and consumer purchases are disparate in type, and as noted above, both types of data can be stored in the PIA.

In some cases, there may be data regarding the user that is contained on the Internet, private networks, or in personal data storage. In one embodiment, the PIA "crawls" such networks or storage areas, searching for information to add to its store of personal information associated with the user. For instance, in one embodiment, the PIA imports personal data from a spreadsheet or personal finance program to provide initial data sets in certain areas.

A community information aggregator (CIA) performs functions that are similar to those of a PIA for a community of users (e.g., an association of architects or a chess club) A CIA provides a community with the ability to store, organize and control information associated with the community and personal information associated with members of the community. The CIA obtains, aggregates and organizes such information, and makes the information available to other authorized entities in a manner similar to that described herein with respect to PIAs.

A CIA may obtain data by searching other sources of information, e.g., web sites on the Internet. In one embodiment, a CIA gathers information about a user that is not published by that user's PIA by crawling public and/or private information sources. In one embodiment, a marketer's CIA uses a known piece of information about a user to search for and store additional information about the user. For example, a user's known e-mail address can be used to locate Internet postings of product reviews, blog postings and comments, listings in membership directories or other information associated with the user. This additional information could be used as input for recommendations targeted to the user.

Figure 31:
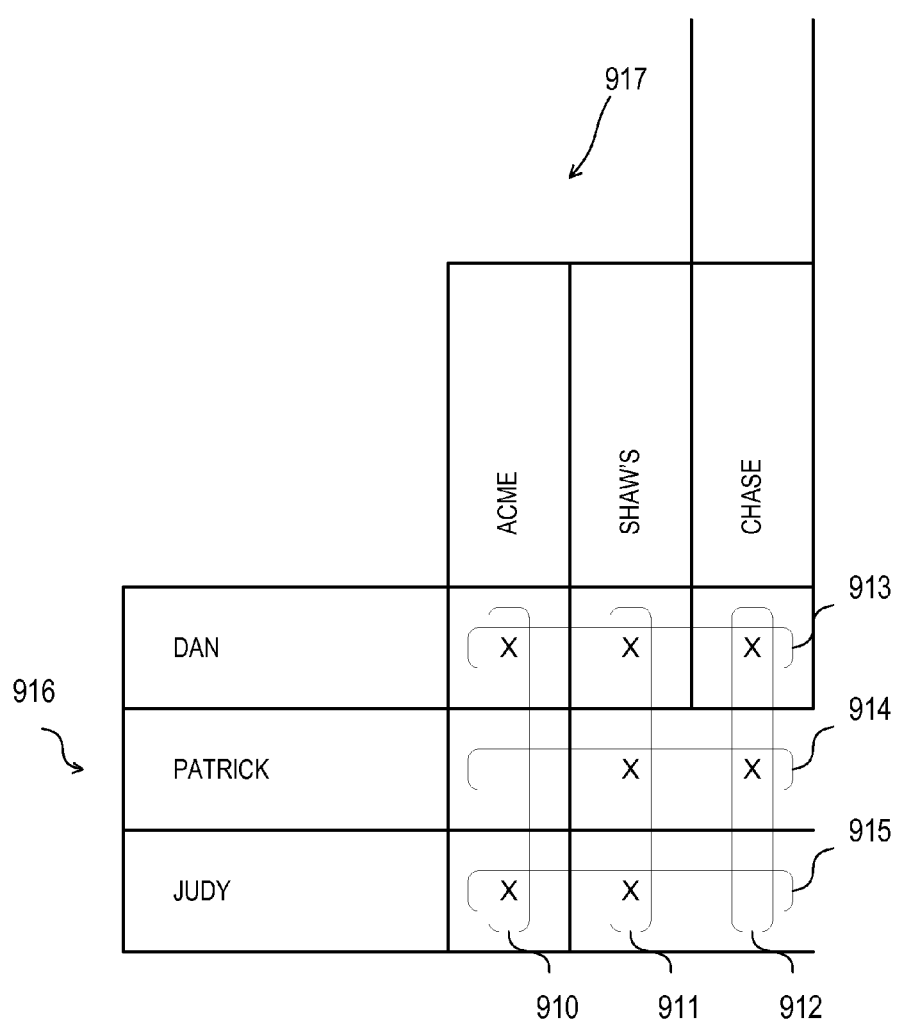

Referring to FIG. 31, the PIA provides a "user-centric" view of a user's personal information, and aggregates information regarding a particular user from a variety of sources. In FIG. 31, an example of the organization of personal information held by three entities 917 (Acme, Shaw's and Chase) regarding three users 916 (Dan, Patrick and Judy) is shown. An 'X' in a cell of the matrix indicates that personal information regarding the associated user is held by the corresponding entity. Each of the entities 917 has an "entity-centric" view of the information, i.e., each entity has knowledge of information associated with itself and generally not of the other entities. Of course, each entity may hold information about multiple users. Specifically, Acme holds information 910 about purchases from Acme made by each of the three users 916, Shaw's holds information 911 about purchases from Shaw's made by each of the three users 916, and Chase holds Chase-related financial data 912 for each of the three users 916. On the other hand, the information stored in a PIA is "user-centric", since the PIA holds information associated with a single user, where the information may be related to one or multiple entities. Specifically, Dan's PIA holds information 913 about his purchases at Acme and Shaw's and his financial data at Chase, Patrick's PIA holds information 914 about his purchases at Acme and his financial data at Chase, and Judy's PIA holds information 915 about her purchases at Acme and Shaw's.

A user controls the information coming in to the PIA by granting authorization to desired sources and denying authorization to unwanted sources. The source of the information may request authorization to provide information to the PIA. Alternatively, the user or the PIA may initiate the operation of receiving data from a source. The authorized information received by the PIA is organized and stored in the PIA. The PIA generates composite and derived output data feeds from the stored personal information. These data feeds may be accessed by providers of goods and services, healthcare providers, communities (e.g., organizations and clubs), social contacts, CIAs, other PIAs and other persons and entities if authorized by the user In some embodiments, the PIA can be configured to notify the user or automatically reject requests from entities known to be invalid, such as spammers.

Referring to FIG. 1, an entity 207 requests authorization for access to a user's PIA 400 by using the Request Authorization use case 954. The user 250 can authorize the request using one of the access type use cases 957 (e.g., Allow Single-use Access, Allow Ongoing Access, Allow Limited Access) of the Authorize use case 950. If authorized, the entity 207 may access the requested output data feed of personal information if the request was for access by using the Access Information use case 956. Similarly, the entity 207 may provide information to the requested input data feed of the PIA if the request was to provide data by using the Provide information use case 955. It should be noted that an entity 207 is not limited to authorization for a single feed, nor is an entity 207 limited to an exclusively input or output role. Rather, an entity 207 may have authorization to concurrently access one or more input data feeds and provide data to one or more input data feeds.

A PIA data feed may be either listed or unlisted, according to the configuration of the PIA. An entity can connect to a PIA and request a list of its "listed" data feeds, and in reply to the request the PIA will provide the names of its listed data feeds to the entity. The name of an "unlisted" data feed can not be discovered through such a request, and therefore, the entity must have prior knowledge of the existence of an unlisted data feed in order to request and gain access to the data feed. For example, a user may be willing to publish the existence of his music preferences data feed with any entity, and in that case, will configure the PIA to list his music preferences data feed. The user may not, however, want any entity to discover that his PIA has a data feed containing Citibank financial records, and therefore, would configure the Citibank data feed as an unlisted feed.

The personal information stored in the PIA may include raw data received from input feeds, e.g., data that is in the native format and protocol of its source. For example, the raw input data feed from a laboratory information system (LIS) might be in the HL-7 (Health Level 7) format commonly used for data exchange between medical systems. In some embodiments, a PIA might provide a raw data feed as output, essentially performing a "pass-through" of a raw data feed received as input.

The stored personal information may also contain composite data aggregated from multiple input feeds. For example, a PIA might generate a Grocery Purchases composite output data feed from the raw input data feeds of several supermarkets that are frequented by the user. Similarly, a social network might provide a composite data feed as input to a PIA.

Another type of data that the stored personal information may also contain is derived data, i.e., data that is the result of processing the data contained in one or more data feeds. For example, a PIA might generate a derived Average Purchase Total output data feed from several supermarket raw data feeds.

Yet another type of data that the stored personal information may also contain is filtered data, i.e., data that generated by "filtering out" specific data elements without alteration from one or more input data feeds. For example, a PIA might generate a White Blood Cell Count (WBC) filtered data feed by selecting only the WBC data elements contained in the raw data feed from an LIS.

In one embodiment, the user uses the PIA's graphical user interface (GUI) in order to configure the types of data feeds of the PIA, discussed in greater detail below.

In another embodiment, a configuration file contains information regarding the data feed configuration of the PIA. This file may, for example, be uploaded to a portable PIA from a personal computer, or it may reside on a computer in a network (local or Internet) and be accessed over the network by a PIA.

Figure 3:
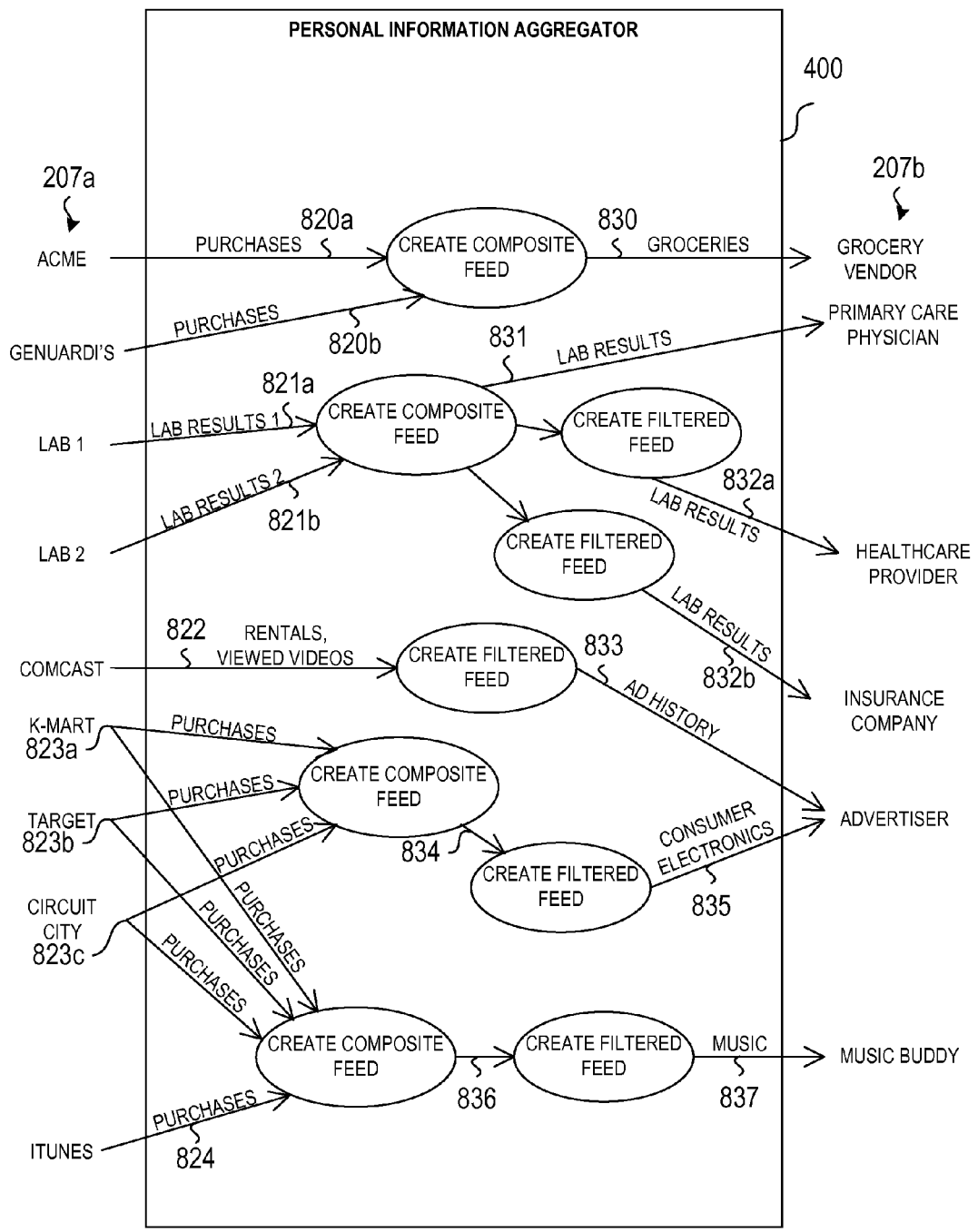
FIG. 3 is a data flow diagram for the PIA of FIG. 1.

FIG. 3 shows an example of the types of data that may be provided to the PIA 400 from entities 207a and the types of entities 207b that receive data feeds. In FIG. 3, nine entities 207a that provide personal information to the PIA 400 are shown: two supermarkets (ACME and Genuardi's), two clinical laboratories (Lab1 and Lab2), a video content provider (Comcast), two general merchandise retailers (K-Mart and Target), a consumer electronics retailer (Circuit City), and a music content provider (iTunes). In the example of FIG. 3, there are six entity types 207b (Grocery Vendor, Primary Care Physician, Healthcare Provider, Insurance Company, Advertiser and Music Buddy) to which output data feeds of the PIA 400 are mapped.

The purchase input data feeds 820a, 820b received from ACME and Genuardi's are combined into a composite output data feed 830 that contains grocery records, which is mapped to Grocery Vendor contacts. For example, a supermarket (perhaps one of those providing input data feeds) might be classified as a Grocery Vendor entity type, and thus would obtain information about the user's grocery purchases at competing supermarkets.

The laboratory results input data feeds 821a, 821b from Lab1 and Lab2, respectively, are combined into a composite laboratory feed. Thus, a lab results output data feed 831 is mapped to Primary Care Physicians. This, for example, would allow the user's primary care physician (who might change over time) to access all of the laboratory results for the user, including the results from tests ordered by other physicians. The composite laboratory results may also be used to generate two other filtered output data feeds 832a, 832b which are mapped to Healthcare Providers and Insurance Companies. These filtered output data feeds 832a, 832b are generated by filtering the composite laboratory results feed. For example, the filtered output data feed 832b mapped to Insurance Companies might contain only those laboratory results that are used by an insurance company in determining life insurance premiums.

The input data feed 822 from Comcast, which contains, for example, information regarding videos that the user has rented or viewed, is filtered to generate an output data feed 833 of the advertisements that have been viewed by the user, and mapped to Advertisers.

The purchase input data feeds 823a, 823b, 823c from K-Mart, Target and Circuit City are combined into a composite purchase feed 834 and then filtered to generate an output data feed 835 that contains consumer electronics purchases that is mapped to Advertisers. An advertiser might, for example, correlate the consumer electronics data received in the data feed 835 with the viewed advertisements data feed 833 described above, in order to determine the effectiveness of specific advertisements.

The purchase input data feeds 823a, 823b, 823c and 824 from K-Mart, Target, Circuit City and iTunes are also combined into a composite purchase feed 836 that is filtered to generate an output data feed 837 that contains music purchases. This output data feed 837 is mapped to the user's "Music Buddies", i.e., friends of the user who might be interested in learning about the music that the user has purchased.

Those skilled in the art will recognize that there are many possible configurations of output data feeds for the PIA. Raw feeds, composite feeds, derived feeds and filtered feeds can be combined in a multitude of ways by the user to suit his needs. In addition, the configuration of a PIA's output data feeds can be modified by the user, so that the user can adjust the configuration according to changes in his personal situation or other changing needs. For example, the lab results output data feed 831 in FIG. 3 might include data from more than two laboratories, or the filtered purchase output feed 835 sent to the advertiser might contain information on the user's purchases of home appliances, rather than consumer electronics.

Figure 4:
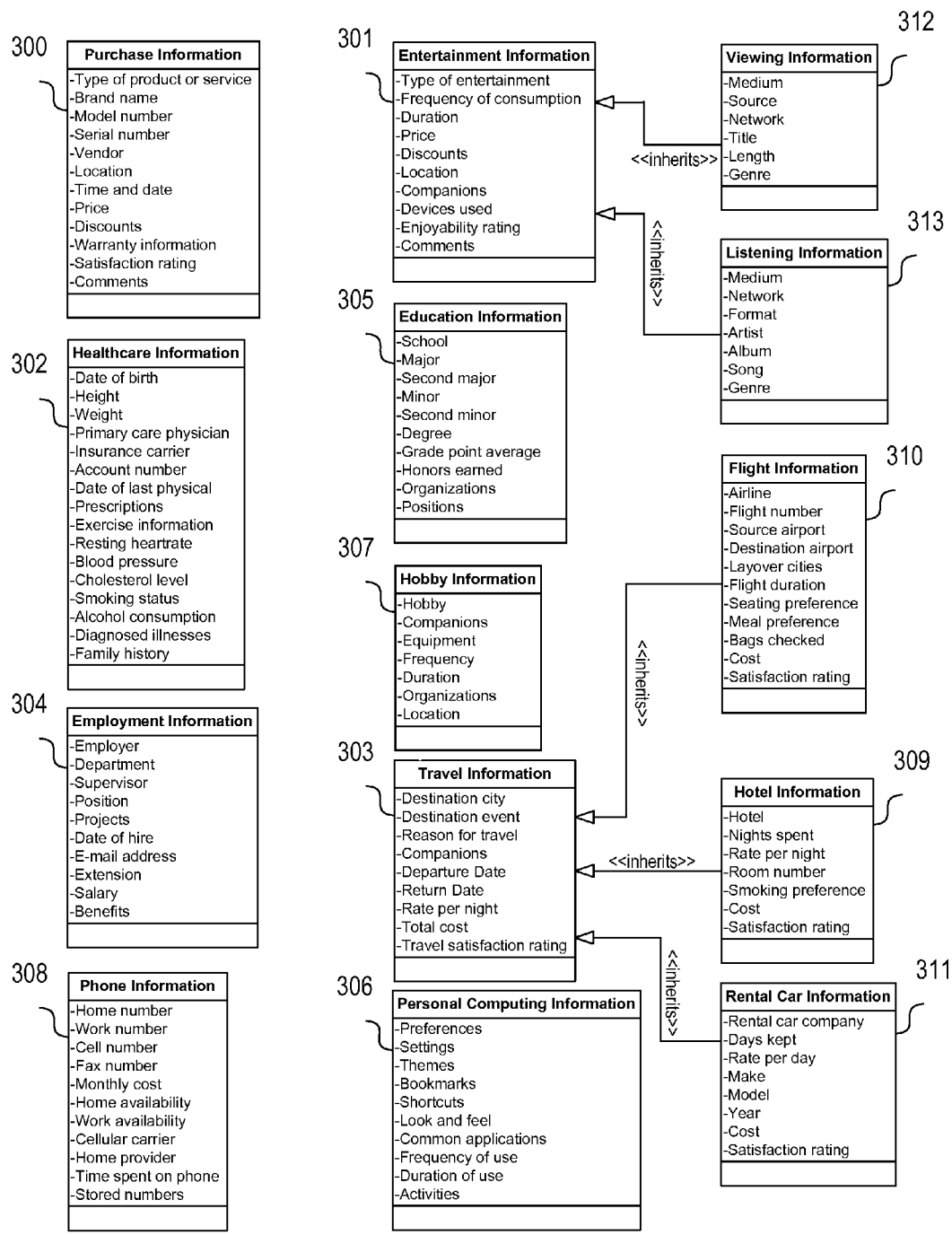
FIG. 4 is a class diagram for the structure of the personal information stored in the PIA in accordance with one embodiment of the present invention.

The personal information stored by the PIA may reside in data structures that are implemented as tables in a relational database management system (DBMS) and that can be accessed by the PIA's application program. FIG. 4 illustrates an example of data structures used to store the personal information in a PIA. In FIG. 4, each data structure used to store information in the PIA is represented by a programming class in an object-oriented language (e.g., Java or C++), and the type of information stored in the PIA for each class of data is represented by the attributes of the class.

Purchase Information 300 includes information related to a purchase: type of product or service, quantity (not shown), name of product or service (not shown), brand name of product or service, model number of product or service, serial number of product or service, store or merchant name, retail location (e.g., zip code), time and date, price, discounts applied (if any), and warranty information.

Entertainment Information 301 includes information such as the type of entertainment, the frequency of consumption by the user, date and time that the entertainment was consumed (not shown), duration of the entertainment, price and discounts, location, companions that viewed or listened along with the user, devices used in the consumption of the entertainment (e.g., a digital video recorder (DVR)), an enjoyment rating by the user and additional comments by the user.

Additional entertainment-related information (e.g., for video entertainment) may be included in a child class, Viewing Information 312, that inherits from Entertainment Information 301. Viewing Information 312 includes information such as the medium on which the video was delivered, the source of the video, the network (if any) that provided the video, and the title, length and genre of the video. Additional viewing information (not shown) might include favorite channels, channel history, program history and fast-forward history.

Similarly, additional entertainment-related information (e.g., for audio entertainment) may be included in a child class, Listening Information 313, that inherits from Entertainment Information 301. Listening Information 313 includes information such as the medium on which the audio piece was delivered, the network (if any) that provided the audio piece, the format (e.g., MP3) of the audio piece, and the artist, album, song and genre of the audio piece. Additional listening information (not shown) might include: favorite stations, station history, and station history. For video or audio delivered on the Internet, entertainment habits may also include (not shown) favorite websites and browsing history.

Healthcare Information 302 includes date of birth, height and weight, name of primary care physician, insurance account information (e.g., carrier and account number), date of last physical exam, physiological measurements (e.g., resting heart rate, blood pressure and cholesterol level), laboratory test results, prescriptions (e.g., for medications, tests or procedures), diagnosed illnesses and conditions, smoking status, level of alcohol consumption, family medical history and past medical history. Additional healthcare information (not shown) might include: demographic information, information on diet and exercise, nutrition information, medical examination findings, surgical history, obstetric history, medical allergies, social history, habits, immunization history, growth chart, referrals information, education materials provided to the user, future plans for care, instructions for self-care, and return visits information.

Travel Information 303 includes the user's travel history, e.g., destination city, event, reason for travel, names of travel companions, departure and return dates. In addition, travel information may include Hotel Information 309 (e.g., nights spent, rate per night, and floor level and smoking preferences), Flight Information 310 (e.g., airline, flight number, source and destination airports, flight duration, and seating and meal preferences) and Rental Car Information 311 (e.g., rental company, days kept, make, model and year of the car, daily cost and electronic toll transactions (not shown)).

Employment Information 304 includes the user's job history (e.g., employer, department, supervisor, position, projects, date of hire, e-mail address, phone extension, salary, benefit package) and information regarding the user's employment references (not shown), and other related information.

Education Information 305 includes the user's transcripts from educational institutions that he has attended: grades, grade point averages (GPA), majors, minors, degrees and honors.

Personal Computing Information 306 includes preferences (e.g., Windows or Mac), bookmarks, shortcuts and commonly-used applications. In addition, personal computing information might include a user's search history (not shown), e.g., the history of searches that the user has performed using Google™.

Hobby Information 307 includes the hobby name, companions that share the same hobby, equipment used in the hobby, frequency and duration of time spent on the hobby, organizations associated with the hobby of which the user is a member and the location where the user engages in the hobby.

Phone Information 308 includes the user's home, work, cell and fax numbers, monthly cost of phone service, the days and times that the user is available at the home and work phones, the names of the cellular carrier and home phone service providers, and phone numbers stored by the user.

Those skilled in the art will recognize that there are many types of personal information that can be stored in the PIA 400. Similarly, the design of the data structures used to store the information can vary greatly, depending on various factors such as the design requirements for the PIA (e.g., response time) and the selected platforms used to implement the PIA (e.g., DBMS, operating system, etc.). For example, the data structures of FIG. 4 might be, if dictated by design requirements, further normalized by moving the Medium attribute from Viewing Information 312 and Listening Information 313 to their parent class, Entertainment Information 301.

There are various mechanisms for the user 250 to map the PIA's output data feeds to contacts or contact types. In some embodiments, the user uses the PIA's GUI in order to provide the PIA with the mapping between output data feeds and those authorized to access the feeds. Depending on the embodiment, the PIA's GUI may be presented on the screen of a personal computer or handheld device or on some other suitable display.

Alternatively, information regarding the mappings for the data feeds of the PIA may be located in a configuration file. The configuration file may reside on a personal computer or server in a network (local or Internet). The PIA accesses the configuration file over the network and configures itself according to the mapping information contained with the configuration file.

An output data feed may be mapped to a single receiver or to more than one receiver. For example, a feed containing video viewing information might be simultaneously mapped to an advertiser and to a social contact group; the advertiser might use the information in his analysis of ad effectiveness, while the social contacts might use the information to guide them in their selection of video content.

In one embodiment, an output data feed may be mapped to a community, such as an organization, association or club. For example, an output feed might be mapped to a chess club. In this case, only the chess club entity, and not the user members of the chess club, may access the feed. In contrast, if an output data feed is mapped to a social contact type, e.g., "chess players", each social contact who is a "chess player" may access the feed.

Figure 2:
FIG. 2 is a use case diagram in accordance with the PIA of FIG. 1.

Referring to FIGS. 1-2, a user 250 configures the PIA 400 by using one of the feed definition use cases 958 (Define Composite Feed, Define Derived feed, Define Filtered Feed) of the Define Feed use case 953 to define the output feeds of the PIA. An Assign Contact Types use case 951 allows the user 250 to assign contact types to users and entities. The user 250 maps the input and output feeds to contacts by using the Map Feeds use case 952.

An Upload Data use case 960 (see FIG. 2) allows entities 207a to upload data to be stored in the PIA 400; the Review Data 961 use case allows the user 250 to review the uploaded data. The following entities 207a are shown uploading data to the PIA 400: a grocery store at which the user 250 shops, the user's doctor, an auto dealership/mechanic utilized by the user, a web browser used by the user, the user's television, the user's employer, the user's stereo, a department store at which the user shops, and a bank at which the user does business. The user 250 can use the PIA 400 to review the data uploaded by the various entities 207a.

Figure 28:
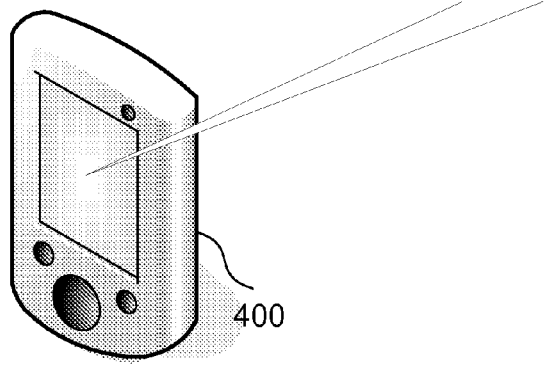

In one embodiment, the user 250 controls access to both the input and output data feeds of the PIA. Specific authorization must be granted to allow an input data feed to be accepted by the PIA 400. Similarly, specific authorization must be granted to allow access to an output data feed provided by the PIA. Authorization can be granted by various mechanisms, for example, in various embodiments as seen in FIGS. 25-28. In FIG. 28, a request for authorization 613 is sent to the user's PIA 400 which then displays a prompt to the user; in response to the prompt the user can either grant or deny the requested authorization. In alternative embodiments, the user may receive an authorization request as a text message sent to the user's mobile phone 401 (see FIG. 25), as an instant message or e-mail sent to the user's dedicated PIA appliance 402 (see FIG. 26) or as a GUI on a personal computer 403 (see FIG.

27). Those skilled in the art will recognize that an authorization request may be sent to the PIA using a wide variety of available hardware and technologies generally known in the art, other than those described with reference to FIGS. 25-28.

Authorization may be granted only for a "single use" of a data feed. For example, a user might grant authorization for an insurer to access a composite "Medical Record" output data feed for only a single use in order to process an insurance claim. Alternatively, the authorization might also be contingent upon the agreement that any data received from the output data feed is to be destroyed after the single use of the data.

The authorization request might also specify a "nature of use" for the requested data. For example, a healthcare provider might specify in an authorization request that the data will only be used by a specified doctor during a specified episode of care.

Authorization might be granted for only a portion of the requested data. This situation might be handled by creating one or more data feeds that contain only the authorized subset of the requested data.

Figure 5:
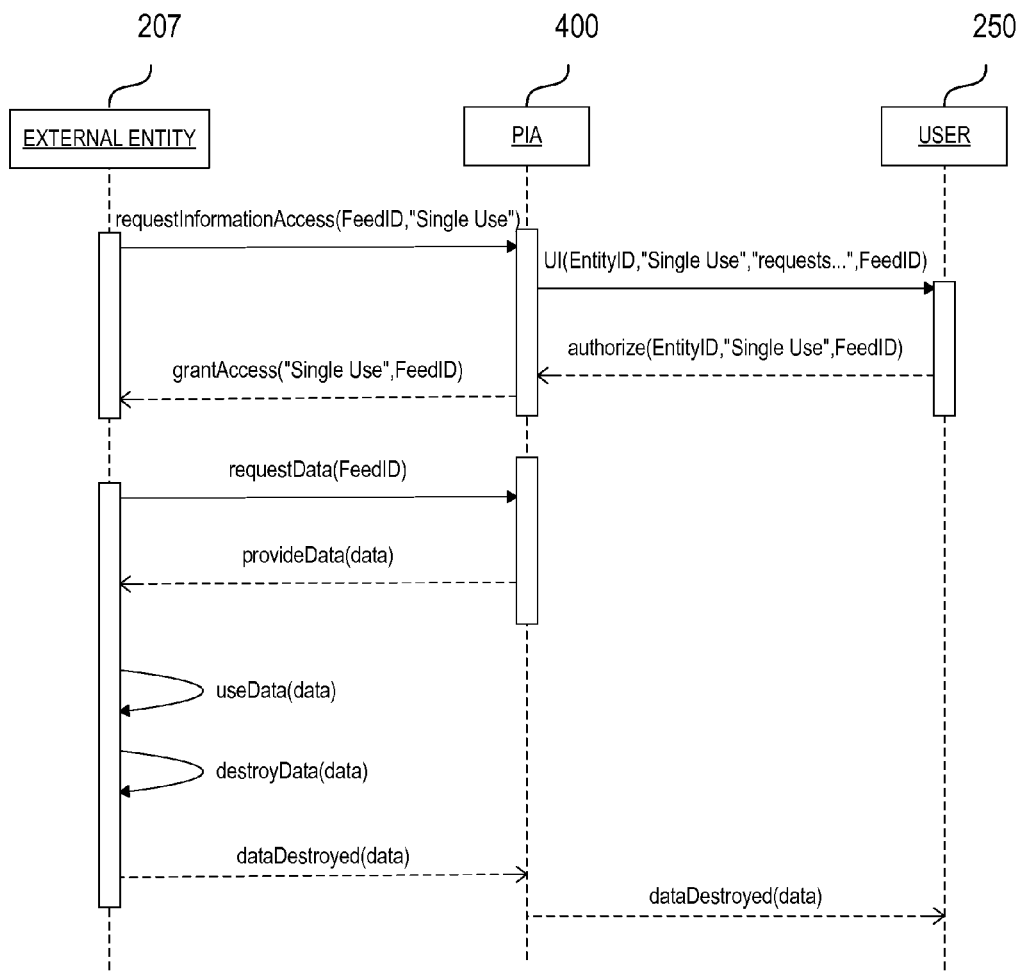
FIG. 5 is a sequence diagram for the interactions associated with a PIA single-use authorization request to receive data from the PIA in accordance with one embodiment of the present invention.

FIG. 5 depicts the interactions associated with a PIA single-use authorization request in one embodiment of the invention. The External Entity 207 sends a requestInformationAccess message to the PIA 400, with arguments indicating the requested data feed (FeedID) and the nature of the request ("Single Use"). Upon receiving the request from the External Entity 207, the PIA 400 sends a UI message to the user 250. The arguments of the UI request provide the ID of the entity (EntityID), the nature of the request, the ID of the of requested data, and the text to be displayed to the user ("requests . . . "). The User 250 responds by sending an authorize message to the PIA 400, passing back in the message's arguments the entity's ID, the nature of the authorization ("Single Use"), and the data feed (FeedID) for which authorization is granted. The PIA 400 notifies the External Entity 207 that the authorization has been granted by sending it a grantAccess message with arguments indicating the nature of the authorization and the data feed for which authorization is granted.

After receiving notification of the authorization, the External Entity 207 sends the PIA 400 a requestData message with an argument specifying the data feed that is being requested. If the feed ID matches that for which authorization has been granted, the PIA 400 responds by sending the requested data to the External Entity 207 in a provideData message. After receiving the requested data from the PIA 400, the External Entity 207 uses the data (useData). Since the authorization was for a single use, the External Entity 207 destroys the data (destroyData) after its use. To notify the PIA 400 of the data's destruction, the External Entity 207 sends a dataDestroyed message, which the PIA 400 passes on to the User 250. In one embodiment, the PIA 400 might utilize a timer to remind itself to check for notification that the data has been destroyed, and to send a message to the user 250 if not notified within a prescribed time period.

Figure 6:
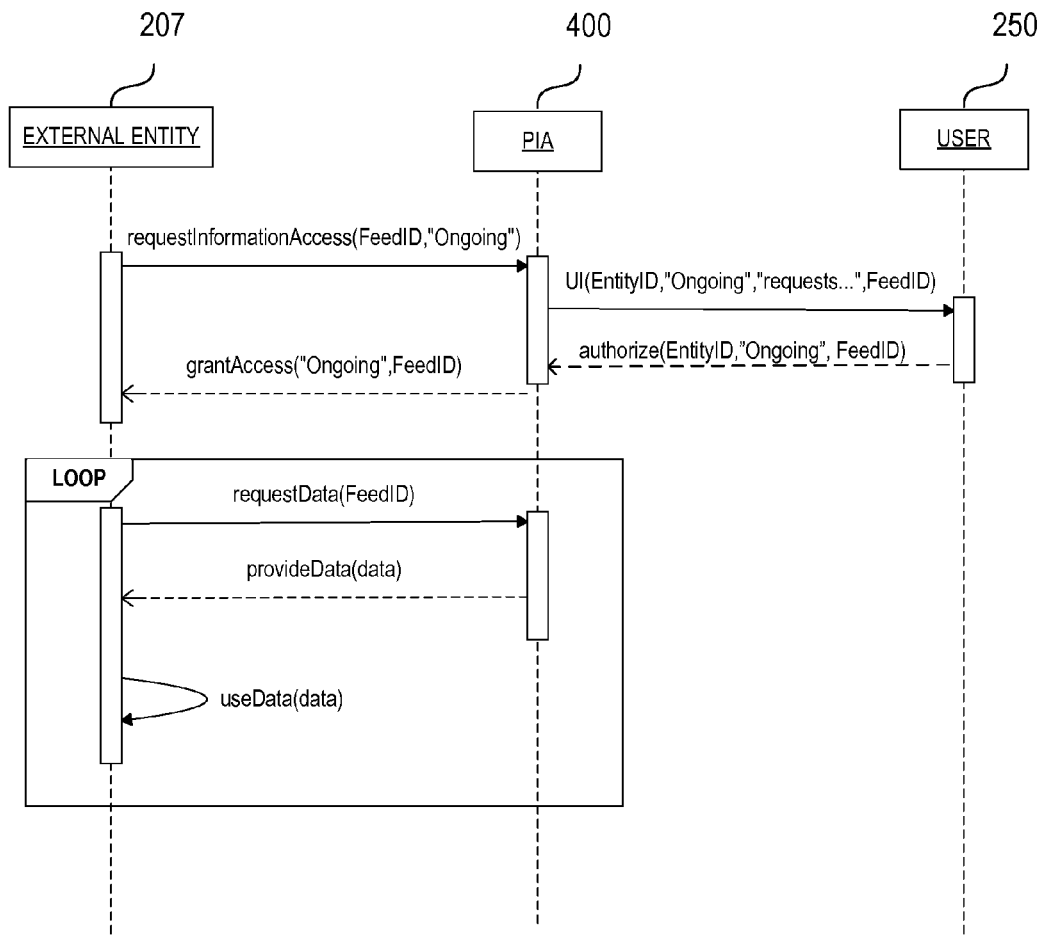
FIG. 6 is a sequence diagram for the interactions associated with a PIA ongoing-use authorization request to receive data from the PIA in accordance with one embodiment of the present invention.

FIG. 6 depicts the interactions associated with a ongoing-use authorization request in one embodiment of the invention. The External Entity 207 sends a requestInformationAccess message to the PIA 400, with arguments indicating requested data feed (FeedID) and the nature of the request ("Ongoing"). Upon receiving the request from the External Entity 207, the PIA 400 sends a UI message to the user 250. The arguments of the UI request provide the ID of the entity (EntityID), the nature of the request, the requested data feed, and the text to be displayed to the user ("requests . . . "). The User 250 responds by sending an authorize message to the PIA 400, passing back in the message's arguments the entity's ID, the nature of the authorization ("Ongoing"), and the data feed for which authorization is granted. The PIA 400 notifies the External Entity 207 that the authorization has been granted by sending it a grantAccess message with arguments indicating the nature of the authorization and the data feed for which authorization is granted.

After receiving notification of the authorization, the External Entity 207 sends the PIA 400 a requestData message with an argument specifying the data feed that is being requested. If the feed ID matches that for which authorization has been granted, the PIA 400 responds by sending the requested data to the External Entity 207 in a provideData message. After receiving the requested data from the PIA 400, the External Entity 207 uses the data (useData). Since the authorization is for ongoing access, this cycle of a requestData message followed by a provideData message continues indefinitely.

Figure 7:
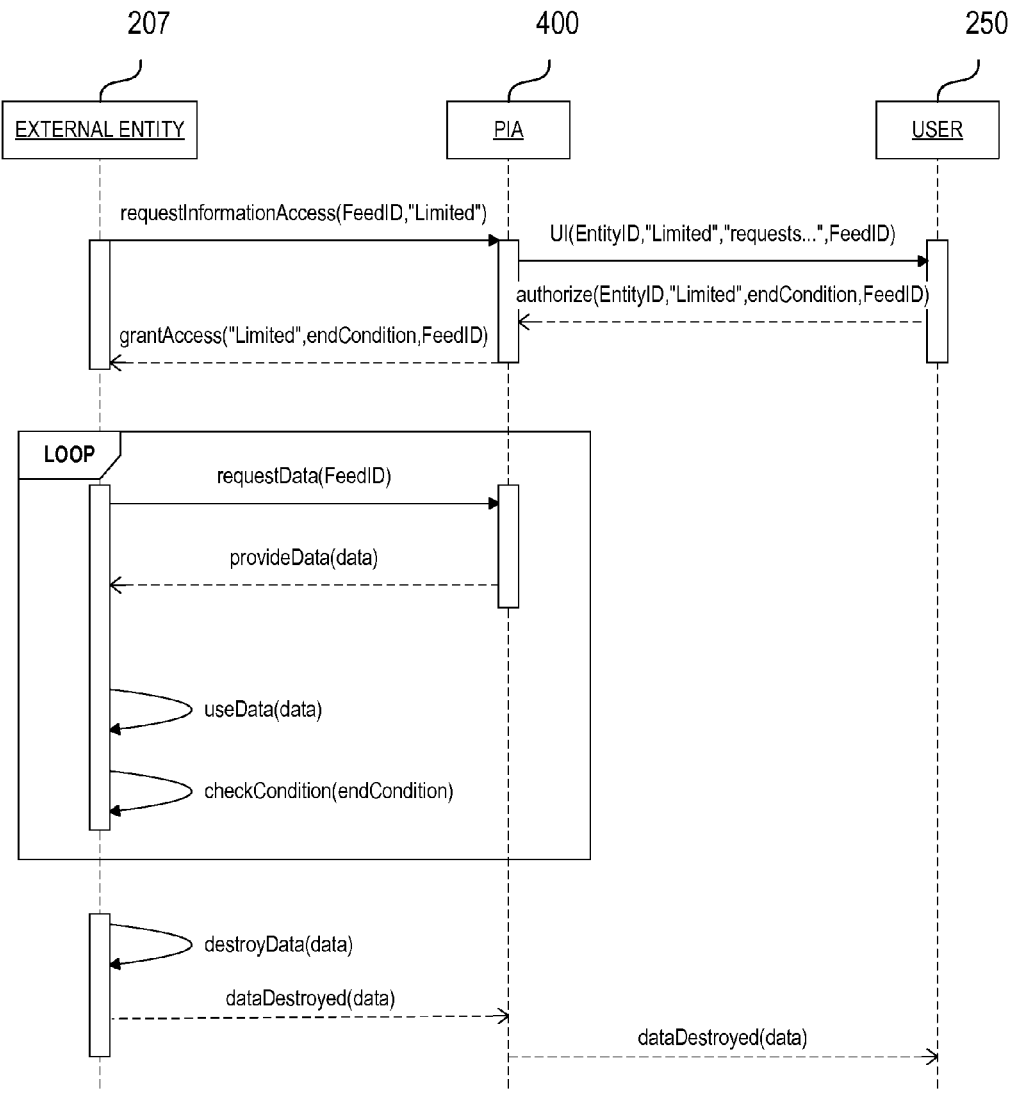
FIG. 7 is a sequence diagram for the interactions associated with a PIA limited-use authorization request to receive data from the PIA in accordance with one embodiment of the present invention.

FIG. 7 depicts the interactions associated with a limited-use authorization request. In this example, authorization is granted for limited use of a data feed, and the authorization is revoked on a specific termination date or due to some other set of termination conditions. For example, the travel department at the user's employer might be granted authorization to access a composite Travel Preferences input data feed so long as the user is still employed by the employer. The PIA 400 keeps a persistent record of the authorization, so that authorization needs only to be granted once, rather than repeatedly, and revokes the authorization if the employment is terminated.

The External Entity 207 sends a requestInformationAccess message to the PIA 400, with arguments indicating the requested data feed (FeedID) and the nature of the request ("Limited"). Upon receiving the request from the External Entity 207, the PIA 400 sends a UI message to the user 250. The arguments of the UI request provide the ID of the entity (EntityID), the nature of the request, the requested data feed, and the text to be displayed to the user ("requests . . . "). The User 250 responds by sending an authorize message to the PIA 400, with arguments that specify the entity's ID, the nature of the authorization ("Limited"), the termination criteria (endCondition) and the data feed for which authorization is granted. The PIA 400 notifies the External Entity 207 that the authorization has been granted by sending it a grantAccess message with arguments indicating the nature of the authorization, the termination conditions and the data feed for which authorization is granted.

After receiving notification of the authorization, the External Entity 207 sends the PIA 400 a requestData message with an argument specifying the data feed that is being requested. If the feed ID matches that for which authorization has been granted, the PIA 400 responds by sending the requested data to the External Entity 207 in a provideData message.

After receiving the requested data from the PIA 400, the External Entity 207 uses the data (useData) and then, since the authorization was for limited use, checks for the existence of the termination conditions (checkCondition). If the termination conditions are met, the External Entity 207 destroys all of the data (destroyData) which it has received under this authorization. To notify the PIA 400 of the data's destruction, the External Entity 207 sends a "dataDestroyed" message, which the PIA 400 passes on to the User 250. In another embodiment, the PIA 400, instead of the external entity, might check for the termination conditions, and notify the external entity 207 when the conditions are met.

Figure 8:
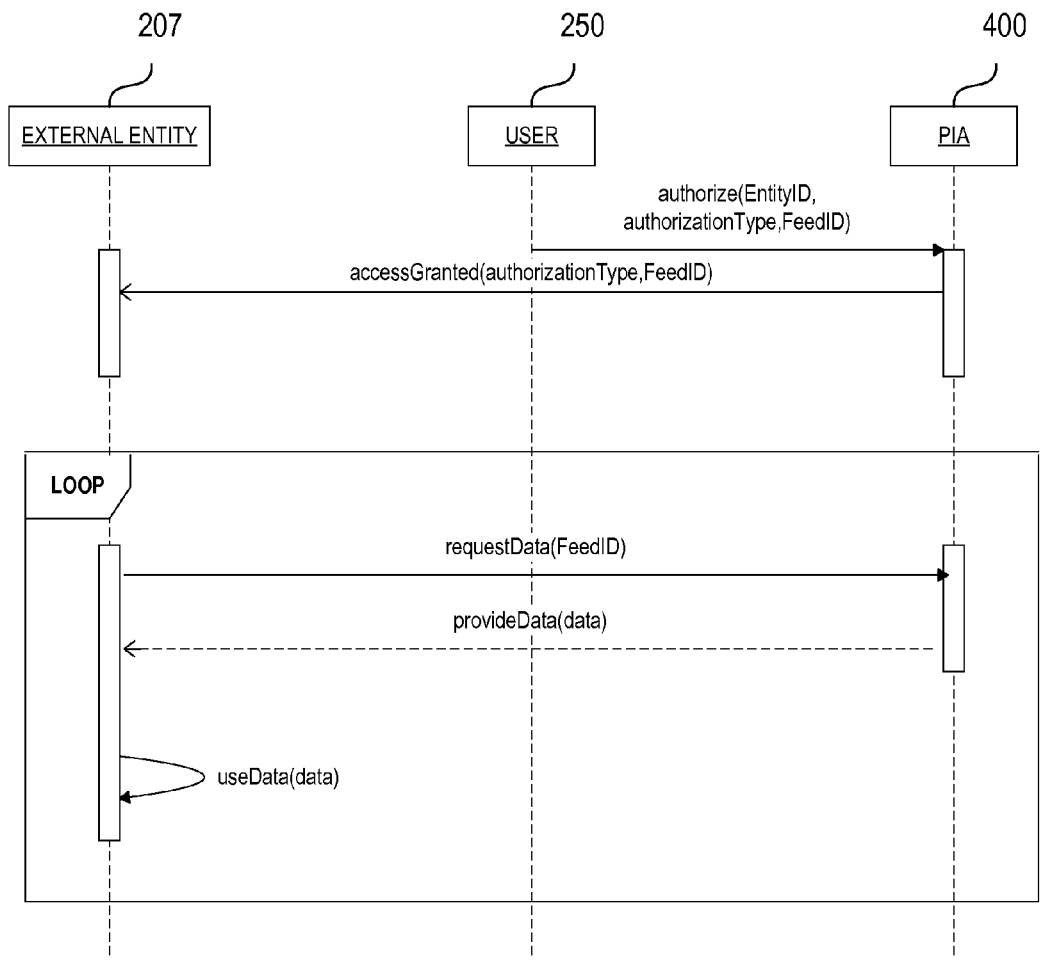
FIG. 8 is a sequence diagram for the interactions associated with a user-initiated PIA authorization to provide data from the PIA in accordance with one embodiment of the present invention.

In an alternate embodiment, the user 250, instead of the external entity, might initiate the authorization. FIG. 8 depicts the interactions associated with a PIA authorization request for such a situation. Although an ongoing authorization request is shown in the example of FIG. 8, it is understood that a user-initiated authorization request may also be for single or limited use. In FIG. 8, the User 250 initiates the authorization by sending an authorize message to the PIA 400, with arguments that specify the entity's ID (EntityID), the nature of the authorization (authorizationType), and the data feed (FeedID) for which authorization is granted. Upon receiving the authorization from the User 250, the PIA 400 notifies the External Entity 207 of the authorization by sending a accessGranted message with an argument specifying the nature of the authorization and identifying the authorized data feed.

After receiving notification of the authorization, the External Entity 207 sends the PIA 400 a requestData message with an argument specifying the data feed that is being requested. If the feed ID matches that for which authorization has been granted, the PIA 400 responds by sending the requested data to the External Entity 207 in a provideData message. After receiving the requested data from the PIA 400, the External Entity 207 uses the data (useData). Since the authorization is for ongoing access, this cycle of a requestData message followed by a provideData message continues indefinitely.

Figure 32:
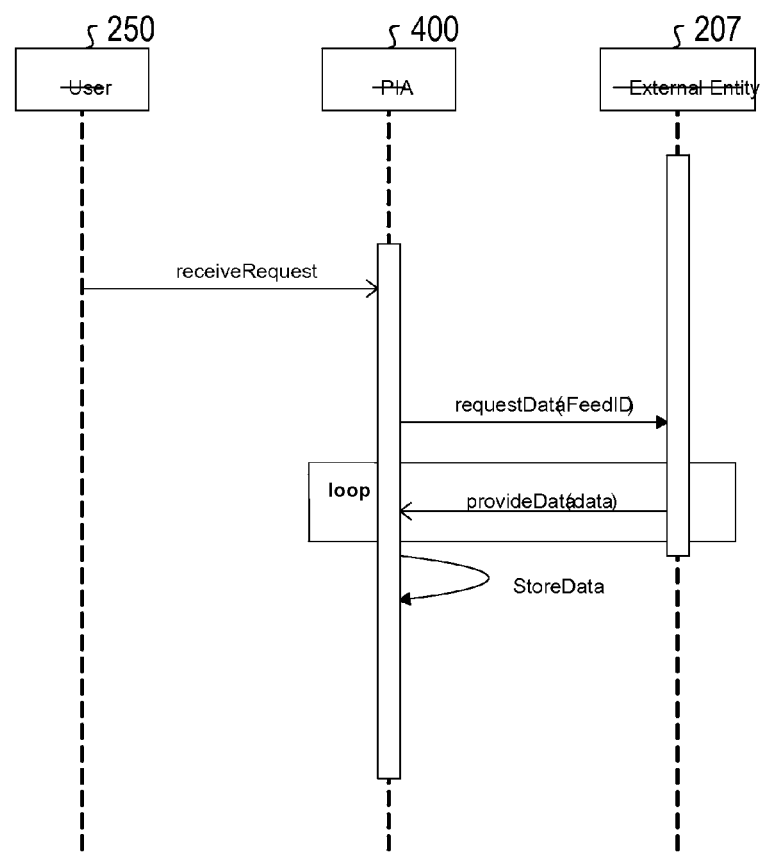
FIG. 32 is a sequence diagram for the interactions associated with user-initiated receiving of data by the PIA in accordance with one embodiment of the present invention.

With regard to the receipt of input data feeds by the PIA 400, the user 250, in one embodiment, might request the PIA 400 to receive data from the external entity. FIG. 32 depicts the interactions associated with such a situation. The User 250 requests the PIA 400 to receive a data feed from the External Entity 207 by sending a receiveRequest message to the PIA 400. The PIA 400 requests the data feed from the External Entity 207 by sending a requestData message to the External Entity 207. The External Entity 207 provides the requested data feed to the PIA 400 by sending the provideData message to the PIA 400. After receiving the requested data from the External Entity 207, the PIA 400 stores the data.

It should be noted that in another embodiment, the External Entity 207 may be configured to provide data to the PIA 400 once the PIA has configured itself to accept the data feed from the External Entity 207, and thus, the requestData message would be eliminated from the interaction.

Figure 33:
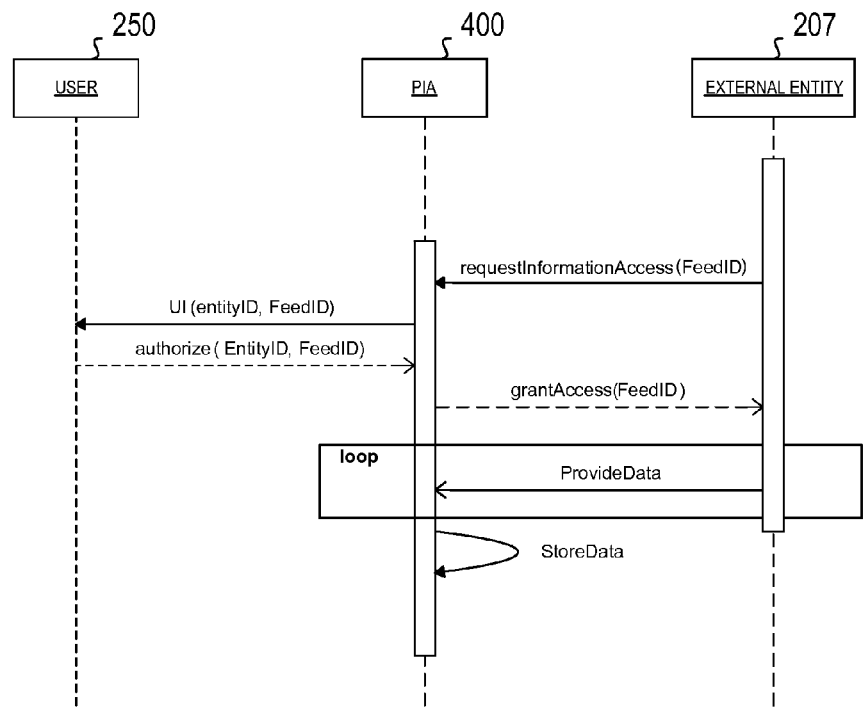
FIG. 33 is a sequence diagram for the interactions associated with an authorization request to provide data to the PIA in accordance with one embodiment of the present invention.

In an alternate embodiment, the External Entity 207 requests authorization to provide data feeds to the PIA 400. FIG. 33 depicts the interactions associated with such a situation. The External Entity 207 requests authorization to provide data to the PIA 400 by sending a requestInformationAccess message to the PIA 400. The PIA 400 notifies the User 250 of the authorization request by sending a UI message to the User 250. The User 250 approves the authorization request by sending an authorize message to the PIA 400. The PIA 400 notifies the External Entity 207 of the approval by sending a grantAccess message to the External Entity 207. The External Entity 207 provides the requested data feed to the PIA 400 by sending the provideData message to the PIA 400. After receiving the requested data from the External Entity 207, the PIA 400 stores the data.

In any interaction in which the PIA receives data from an external entity, an additional operation might be used to authenticate the source of the data, i.e., the external entity and the data feeds provided by that source. A person skilled in the art will recognize that there are various well-known technologies that might be used to provide this assurance; some examples are the use of public and private keys, digital signatures and hashcodes.

Figure 9:
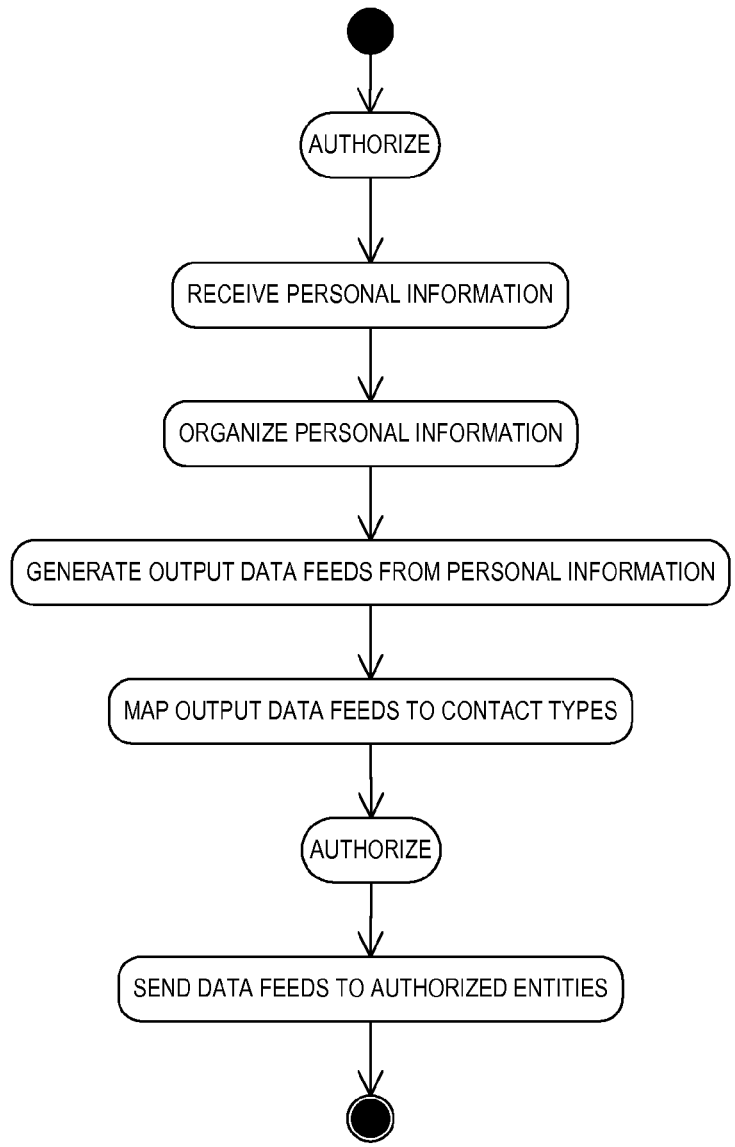
FIGS. 9 and 10 are activity diagrams for the steps performed by the PIA in accordance with one embodiment of the present invention.
Figure 10:
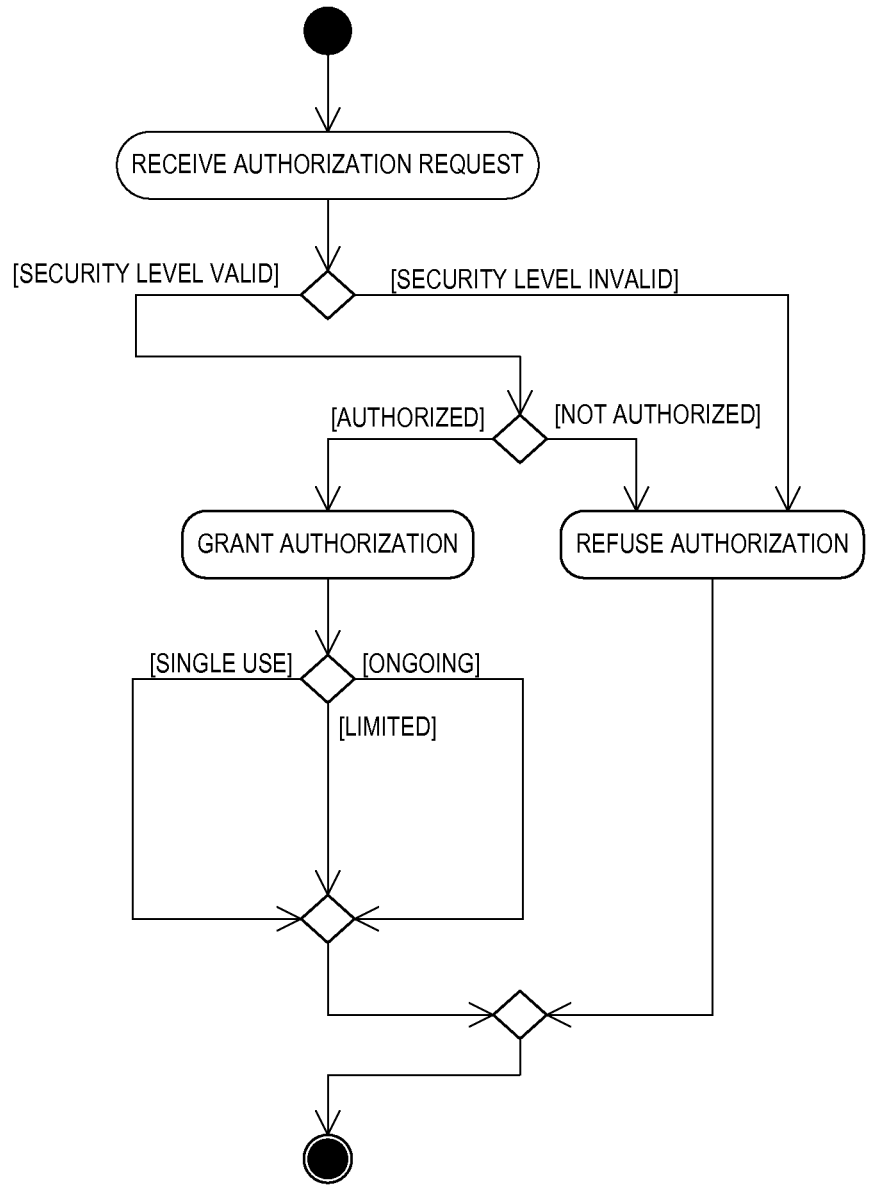

Referring to the activity diagram of FIG. 9, in one embodiment the PIA authorizes an entity to provide personal information to the PIA, described in greater detail with respect to FIG. 10. Once authorization has been granted to the entity, the PIA receives the personal information provided by the entity through an input data feed. The received personal information is then organized by the PIA. For example, if the data feed contains grocery purchase information from a particular supermarket, the PIA might add this information to its internal data store of grocery purchases from all supermarkets.

After organizing the personal information, the PIA generates output data feeds based on the organized personal information. The output data feeds are specified by the configuration of the PIA, which has been performed at some earlier point by the user or other means. An output feed might contain, for example, only the data for soft drink purchases that are contained within the PIA's internal grocery purchases data store. The generated output data feeds are mapped by the PIA to specific contact types. For example, the soft drink data feed described above might be mapped to beverage suppliers for the purpose of analyzing trends in beverage consumption. The PIA then authorizes specific requests for access to the output data feeds (see FIG. 10), and sends the output data feeds to authorized entities.

FIG. 10 is an activity diagram corresponding to the Authorize steps in FIG. 9. In the depicted embodiment, the requesting entity has an associated security level. This security level is used as an additional condition for obtaining access to the PIA's data feeds. The PIA receives an authorization request and checks the requesting entity's security level. If the security level is allowable for the requested data feed based on the entity's security level and the nature of the authorization request (single-use, limited use or ongoing), then the PIA next determines if it will authorize the request based on factors independent of the entity's security level. In one example, the user may only allow a certain entity access during normal work day hours, and not during the evening or on weekends. In another example, an entity may only be allowed single-use access, and therefore the entity will be refused authorization if ongoing or limited use is requested.

A PIA, depending upon the particular embodiment, may present user interface displays to the user for managing the user's personal information. In one embodiment, the user interface (UI), which may be a GUI or a text-based interface, may be presented on a computer display screen. Alternatively, the user interface may be presented on the display of a PIA appliance, or on a smaller screen contained within a handheld device associated with the PIA.

FIG. 12 is an example of a main menu user interface 1218 for a family PIA in one embodiment of the invention. In the example of FIG. 12, each member of the family 208 has configured his PIA to allow a family PIA to access certain data feeds from the PIAs of the individual family members. As depicted in FIG. 12, there are three members of the family 208: Robert, Sue and Robbie, Jr. Certain data feeds have been "family-aggregated." For example, the main menu 1218 provides buttons 700 for viewing or editing the family's connections (an aggregation of the users' connections), purchase history (an aggregation of the users' purchase histories), and profile (an aggregation of the users' profiles). In addition, family messages 800 are shown in a section of the display, and can be accessed, saved or deleted.

FIG. 13 is an example of a main menu user interface 601 for an individual user in one embodiment of the invention. The user, Robert Smith, is provided with buttons for managing his basic information 1201 and his messages 1202. In addition, the user is provided with buttons for managing his social network contacts 1203, contact types and data feeds 1204 and communities 1205 (groups and clubs).

FIG. 14 is an example of a user interface 602 that informs the user of a request for medical files. In this example, the healthcare provider, "Doylestown & Warrington Family Practice", is requesting the files in preparation for the user's upcoming appointment. The user can allow or deny access using the buttons 701 provided on the user interface 602. If the user wishes, he may select the button 1207 to view the details of the request. In addition, the user interface 602 displays a list 1206 of the user's current messages.

FIG. 15 is an example of a user interface 603 that includes the details of a request for medical files. In this example, the healthcare provider 1208 and doctor 1209 are identified, and the user, i.e., the patient, is informed that the medical files will be accessed for a single use, which will expire 48 hours after the appointment. The user can allow or deny access using the buttons 701 provided on the user interface 603.

Figure 16:
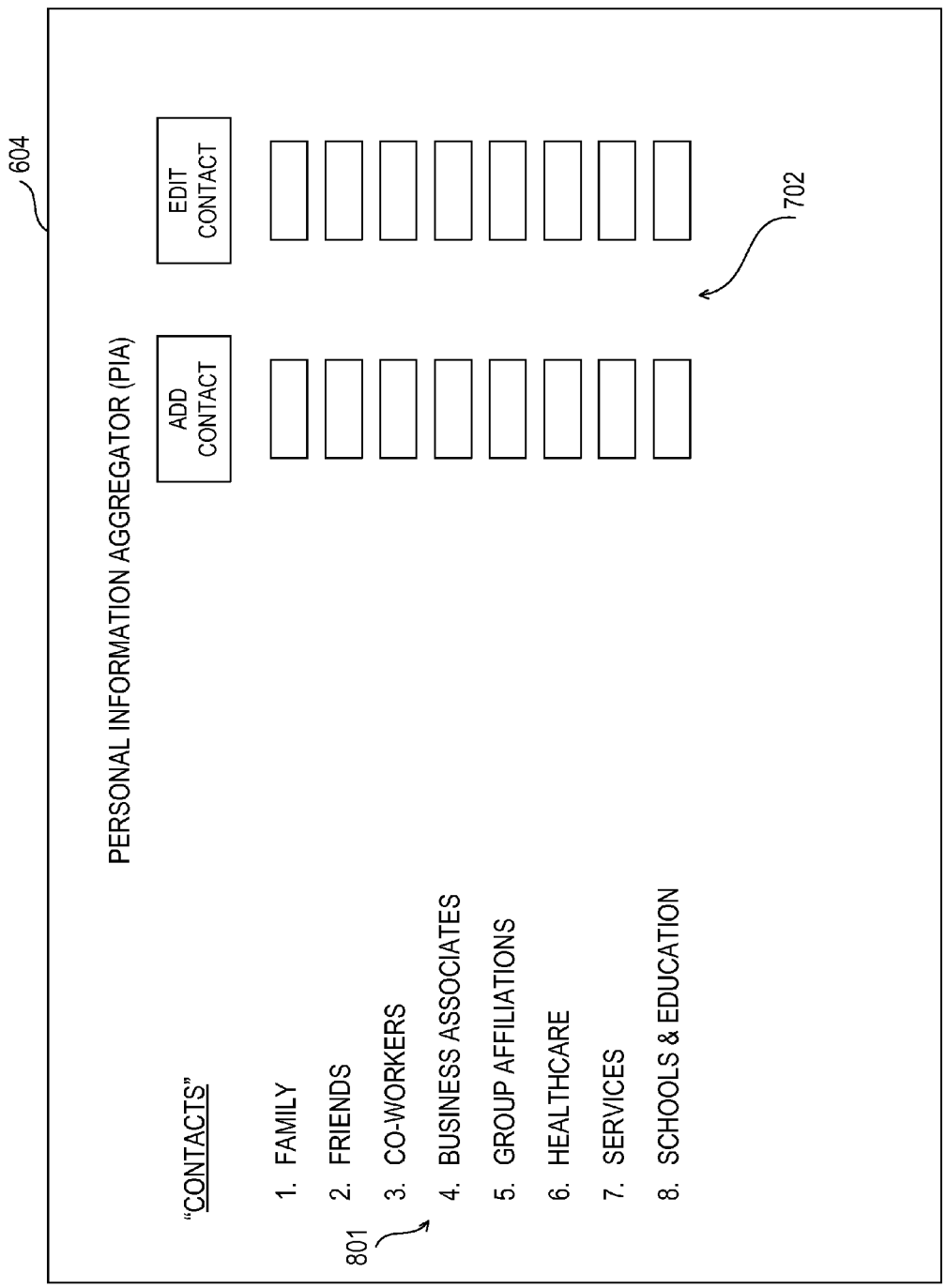

FIG. 16 is an example of a user interface 604 that allows a user to manage his contacts. The contacts 801 are listed by contact type: family, friends, co-workers, business associates, group affiliations, healthcare, services and schools and education. For each of the listed contact types, the user is provided with buttons 702 that enable him to add or edit the contact type.

Figure 17:
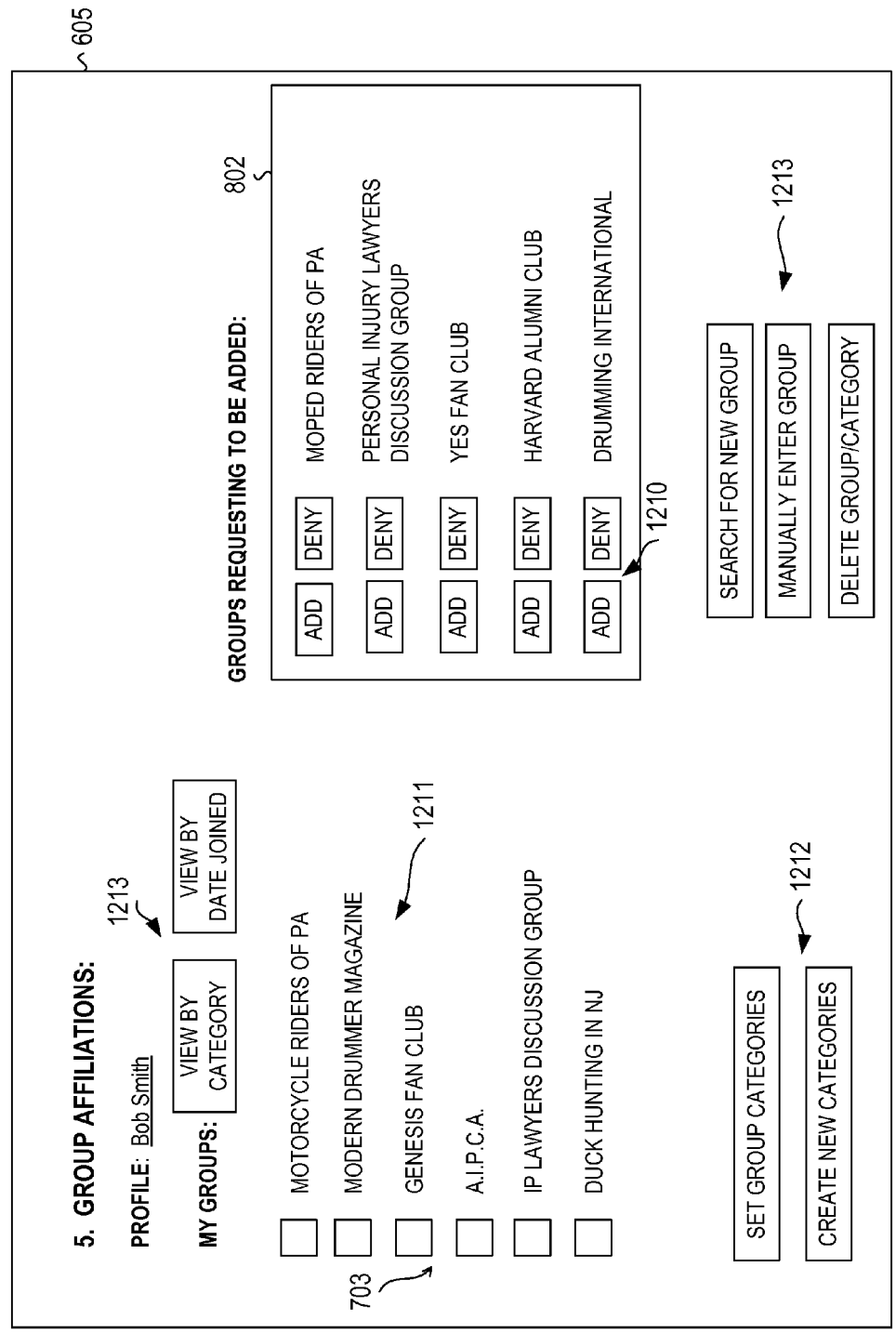

FIG. 17 is an example of a user interface 605 that allows a user to manage his group affiliations. The individual groups with which the user is affiliated appear in a list 1211, and buttons 703 are provided for management of the groups. The user is provided with buttons 1213 to select viewing the list 1211 sorted by category or by the date that the user joined a group. In addition, groups that are requesting to be added to the user's contacts are listed in a section 802 of the display. For each requesting group, the user is provided with buttons 1210 with which he can add or deny the request. The user interface 605 also provides buttons 1212 for the user to set or create group categories, and buttons 1213 for the user to search for a new group, manually enter a group name, or delete a group or category of groups.

FIG. 18 is an example of a user interface 606 that allows the user to manage his healthcare information. The user's doctors, health insurance information, pharmacies and hospitals are displayed in a list 803, and buttons 1214 are provided for the user to edit (add, erase or search) each category.

FIG. 24 is an example of a user interface 614 that allows the user to create a filtered output data feed of healthcare information, and to map the output data feed to a particular entity. In this example, the user has specified, prior to the display of the user interface 614, that he will be mapping a data feed to a particular healthcare insurance provider, Blue Cross Blue Shield; this is indicated in field 806 at the top of the user interface 614. The user interface 614 provides buttons 706 to the user for selecting the filtered healthcare information for the output data feed. For example, the user might select that only height, weight and cholesterol level are to be contained in the output data feed.

FIG. 19 is an example of a user interface 607 that allows the user to manage his contacts and feeds. In addition to contact types such as friends and co-workers, the user can select to manage his calendar (e.g., Microsoft Outlook™), which can be configured as an input data feed to the PIA. FIG. 19 also includes an example of a user interface 608 of a request to access certain output data feeds of a user's PIA. In this example, "XYZ Corporation" has requested access to the user's purchase data, and the user can select to allow access to all purchases, or just certain types of purchases, e.g., food and automotive.

FIG. 20 is an example of a user interface 609 that displays a summary of output data feeds provided by the user's PIA to contacts of type "friends." Data feeds 804 that are available to all friends are listed, as well as data feeds that are available to a preferred list of friends 805.

FIG. 21 is an example of a user interface 610 that displays a summary 1215 of a user's entertainment purchase history. The user is provided with buttons 704 to view the data by day, month or year, and buttons 705 to sort the data by various categories.

FIG. 22 is an example of a user interface 611 that displays a summary 1216 of a particular category (CD purchases) of a user's entertainment purchase history. The user is provided with buttons 705 to sort the data by store, data of purchase and genre.

Figure 23:
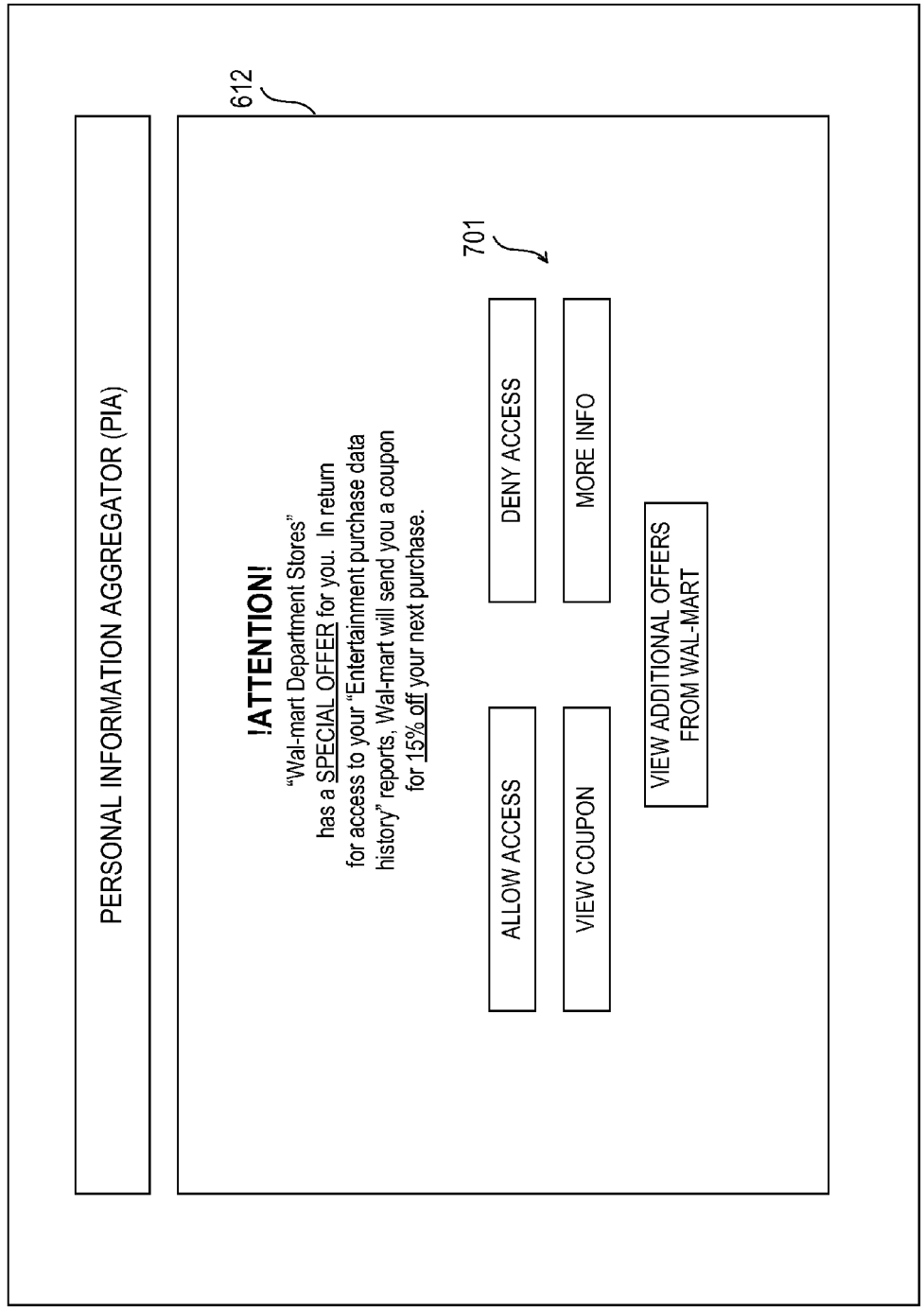
Figure 25:
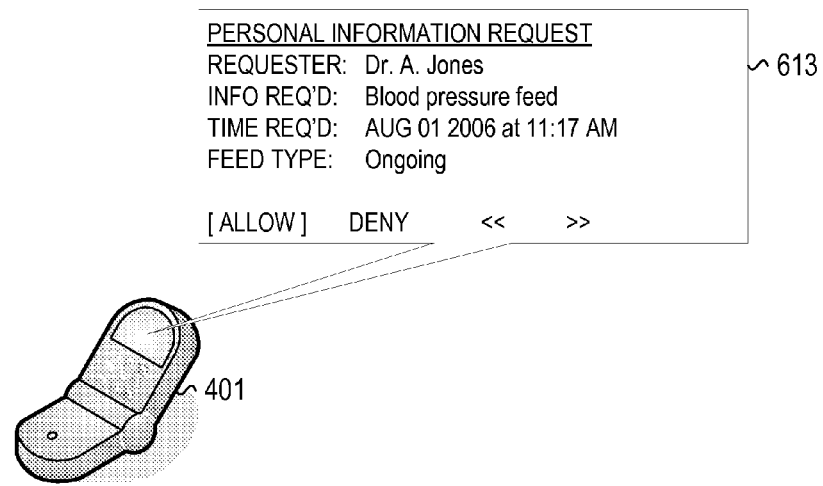
FIGS. 25-28 are examples of data access requests received by various physical embodiments of the PIA.

FIG. 23 is an example of a user interface 612 that displays a request for access to a particular output data feed. The entity making the request, "Wal-Mart", is requesting access to the user's entertainment purchase history in exchange for a coupon that can applied to the user's next purchase at Wal-Mart. The user can allow or deny the request, view the coupon, view more information or additional offers by selecting one of the buttons 701.

Figure 26:
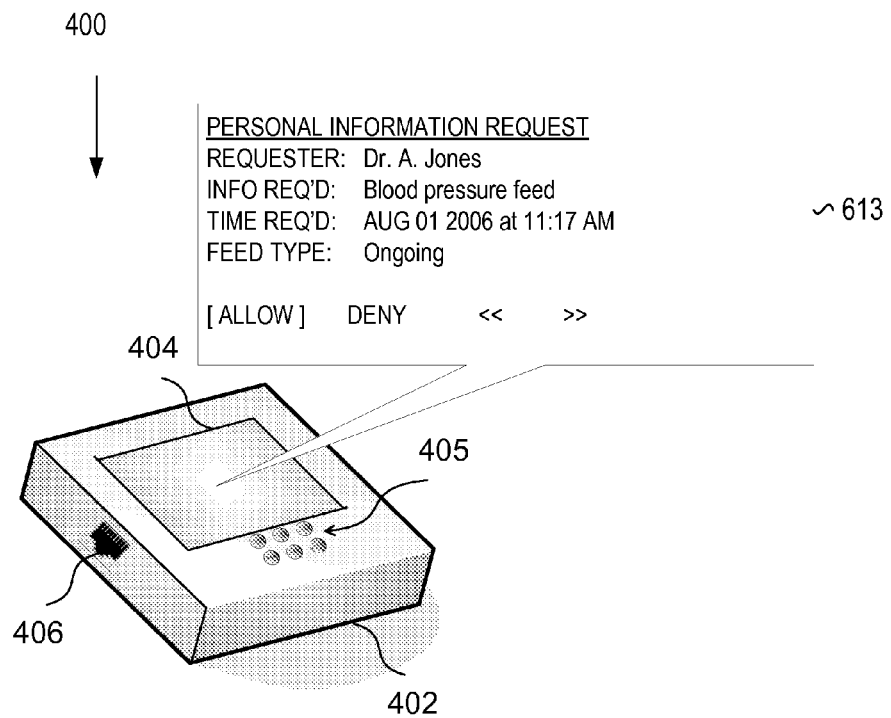
Figure 27:
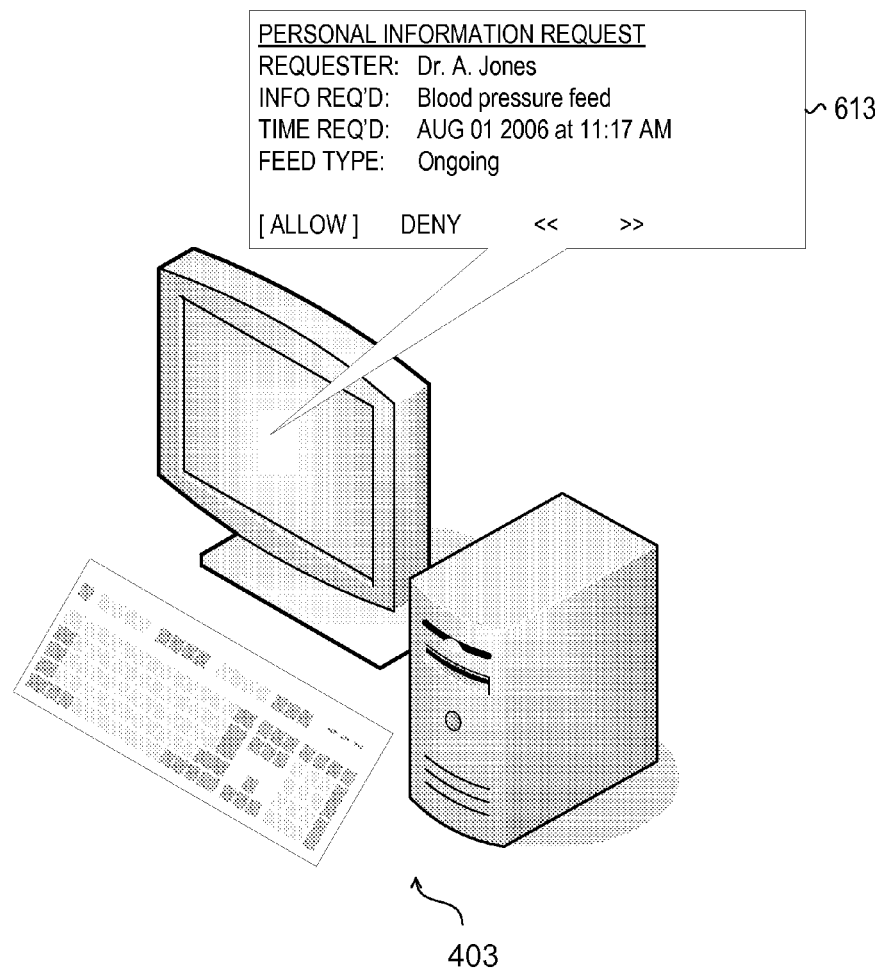

The PIA 400 or CIA may be implemented on a variety of hardware and software platforms, e.g., a handheld device, a personal computer or a dedicated appliance. The latter, an example of which is shown in FIG. 26, is a device that provides a user with the functions of a PIA 400. In this example, the PIA 400, which is implemented as the appliance 402 includes a display 404 and a set of buttons 405 which provide the user with a user interface. In addition, the PIA appliance 402 in this example has a port 406 which may be used for connecting the PIA appliance 402 to a network (e.g., Internet) for transmitting and receiving input and output data feeds as well as any configuration information or data used by the PIA 400. Those skilled in the art will recognize that the PIA 400 and the CIA may be implemented on a variety of hardware and software platforms, and that such implementation is not limited by the example of FIG. 26.

Similarly, the type of hardware that is used by the PIA to store personal information can vary considerably, depending in part on such factors as user preferences and available technologies. In one embodiment, the personal information is stored in a device that is under the physical possession and control of the user, e.g., a small handheld portable device. The device may be dedicated solely to providing the functions of a PIA; alternatively, the device may also have other functions. For example, a mobile phone may be configured to provide the additional functions of a PIA. In such an embodiment, a database management system (DBMS) such as Microsoft SQL Server CE™ might be used for storing and managing the personal information.

In other embodiments, the personal information is stored in other types of devices that are under the physical possession and control of the user, e.g., the user's personal computer or a dedicated PIA appliance. In these embodiments, a database package such as Microsoft Access™ or a DBMS such as Microsoft SQL Server™, mySQL or postgreSQL might be used for storing the personal information.

Figure 30:
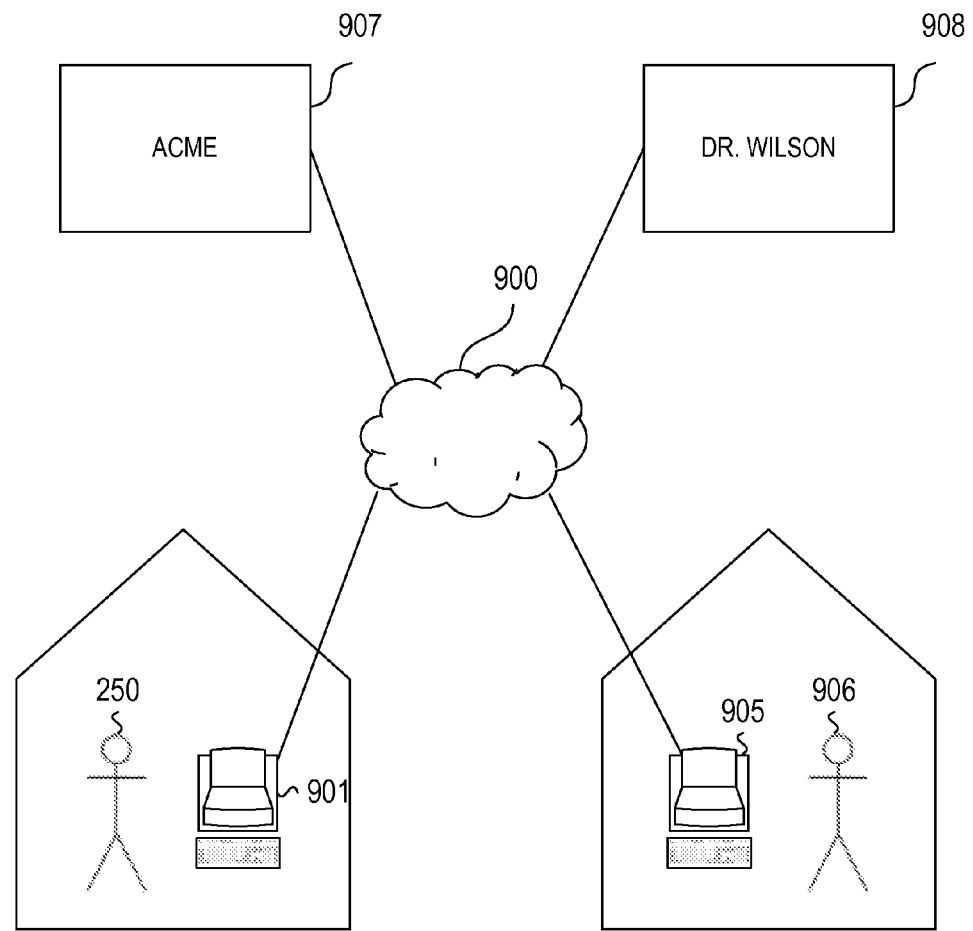
FIG. 30 is an example of a PIA implemented on a user's personal computer in accordance with one embodiment of the present invention.

FIG. 30 illustrates an example of two users 250 and 906 with PIAs (not shown) that are implemented on personal computers. The first user 250 uses his PIA, which is implemented on a personal computer 901, in his home. The first user's PIA is connected through a computer network 900 to two entities that have been granted authorization to access the first user's PIA, Acme Supermarket 907 and Dr. Wilson 908. Similarly, the second user 906 uses his PIA, also implemented on a personal computer 905, in his home. The second user's PIA is connected through the computer network 900 to Dr. Wilson 908, who has been granted authorization to access the second user's PIA.

The computer network 900 may be implemented with a variety of hardware platforms. For example, the computer network 900 may be implemented using the IEEE 802.3 (Ethernet) or IEEE 802.11 (wireless) networking technologies, either separately or in combination. In addition, the computer network 900 may be implemented with a variety of communication tools. For example, the computer network 900 may be implemented using the well-known TCP/IP suite of protocols. The Internet and some corporate intranets are examples of computer networks that use the technologies and standards described above.

Figure 29:
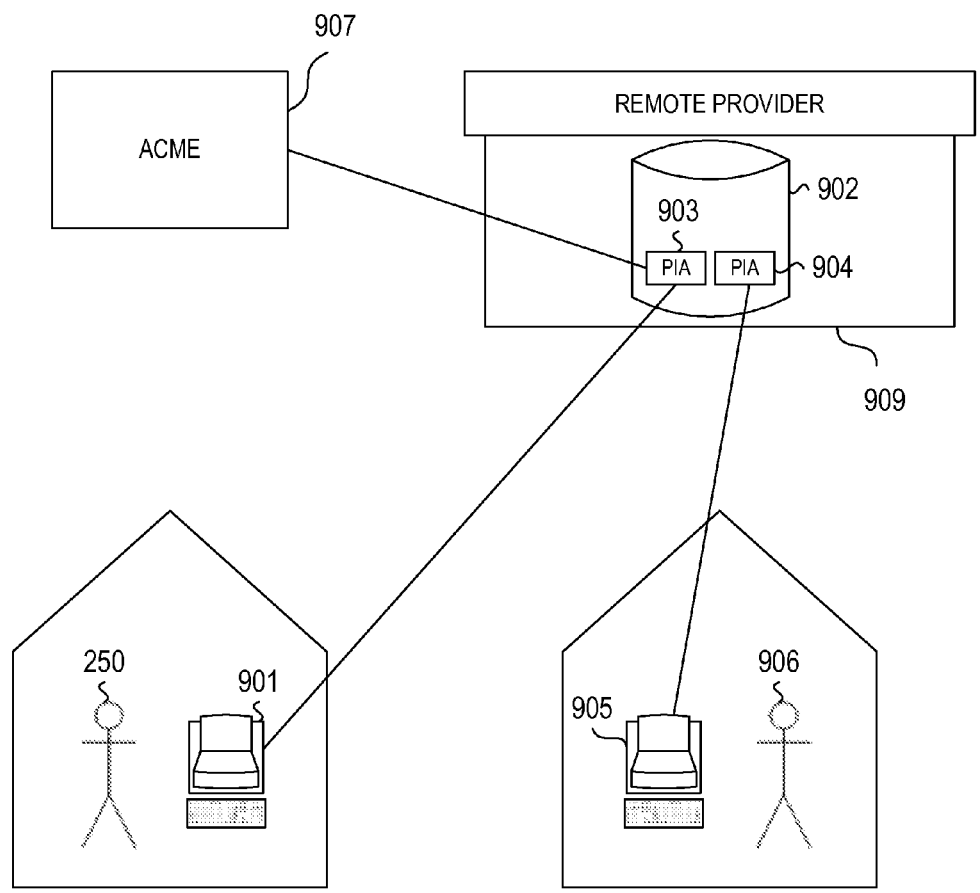
FIG. 29 is an example of a remote PIA provider in accordance with one embodiment of the present invention.

In yet another embodiment, the personal information is stored in a remote server that is operated by a separate PIA provider and provides "virtual" PIA functions to one or more users. The PIA provider operating the remote computer ensures that the user has exclusive control over his personal information by providing one or more mechanisms for validating the user's identity before allowing the user to exercise control over his personal information. In this embodiment, a DBMS such as IBM DB2™ or mySQL might be used for storing and managing the personal information FIG. 29 illustrates an example of two users 250 and 906 with virtual PIAs 903 and 904, respectively, that are implemented by a remote provider 909. The first user 250 uses his personal computer 901 to connect to his virtual PIA 903 which is stored on the remote server 902 operated by the remote provider 909; similarly, the second user 906 uses his personal computer 905 to connect to his virtual PIA 904 which is also stored on the remote server 902. Acme Supermarket 907, which has been granted authorization (not shown) by the first user 250, is connected to the first user's virtual PIA 903 on the remote server 902.

Those skilled in the art will recognize that there are a wide variety of choices other than the examples given above regarding the selection and arrangement of the equipment, technologies, platforms and systems used to store personal information in the PIA. For example, in another embodiment, the remote provider 909 in FIG. 29 might provide the functions of the PIA to the first user through the remote server 902, while the personal information might be stored locally on the first user's personal computer 901.

The technologies used by a PIA to send and receive its data feeds are varied and depend upon the specific embodiment. In an embodiment in which the PIA is implemented on a handheld device, the technologies might include Bluetooth for local feeds or wireless short message service (SMS) for remote feeds. Bluetooth might be used, e.g., to establish a data connection between the PIA and a blood pressure monitor in a physician's office, and this data connection would then be used feed the blood pressure measurements taken by the monitor as input to the PIA. SMS might be used, e.g., to send the latest healthcare information, which would include, e.g., the blood pressure measurements, to a remote Personal Information Profiler (PIP) for use by a health risk profile application.

In an embodiment in which the PIA is implemented on a personal computer or a remote computer, Internet access through an Internet Service Provider (ISP) might be used for sending and receiving data. In this embodiment, the ISP might provide access to the Internet as a dial-up service, or through a higher-speed technology such as broadband or DSL. Since the Internet can expose the data being sent and received to unauthorized persons and systems, the data feeds, in this embodiment, might be encrypted, e.g., by using the HTTPS protocol, or by implementing a virtual private network (VPN) between the PIA and the sources and receivers of the data feeds.

In some embodiments, it may be desirable (or required) for a recipient of a PIA's output data to validate the integrity of the data. For example, an entity receiving credit-related information from a user's PIA might want an assurance that the information was valid and had been unaltered by the user or anyone else. Those skilled in the art will recognize that there are various well-known technologies that might be used to provide this assurance; some examples include the use of public and private keys, digital signatures and hashcodes.

The control of personal information given to the user 250 by the PIA 400 allows the user 250 to arrange to obtain compensation (e.g., cash, cash rebates, micropayments, store credit, store discounts or gifts, coupons, or loyalty program points) for providing access to his personal information. In some embodiments, the PIA 400 manages the exchange of personal information for compensation by providing a user interface for configuring which personal information may be accessed, by whom, and the amount of compensation required for access to the personal information. In addition, the PIA 400 can store data associated with compensation, such as a history of transactions and the accumulated amounts of compensation.

The PIA 400 allows the user 250 to exercise control over the accuracy of his stored personal information. For example, the correction of an error in credit-related information received by the PIA 400 from sources such as credit card companies, banks and merchants, is under the user's control. The process of correcting such an error is conducted directly between the user 250 and the source of the information, without the involvement of a credit reporting agency such as Equifax, Experian and TransUnion.

The user 250 is more likely to include more complete and comprehensive personal information to be stored in the PIA 400 than he would provide to an external entity. For example, the user 250 might store certain details regarding a purchase (e.g., if the purchased item is a gift or is to be used at a family party) in the PIA 400, but might not be willing to provide such details to the merchant of the purchased item, because the user 250 can be assured that he has control over the information stored in the PIA 400.

The PIA 400 can also be used to organize and control the data regarding purchases by the user 250 from multiple supermarkets. This enables the PIA 400 or an external system to perform an analysis of purchase information using data that is generally more comprehensive than the data typically collected by a single supermarket through a user's "loyalty card." The results of such an analysis can be provided, with the authorization of the user 250, to interested merchants who desire the more complete purchasing profile that results from using comprehensive information. As discussed above, the user 250 can provide the comprehensive purchase information (or an analysis based on the purchase information) to merchants in exchange compensation. In addition, the user 250 may receive predictions of certain events, such as running out of a certain product, or may receive recommendations, such as for needed products, in exchange for providing the comprehensive purchase information (or analysis). The user 250 may also receive an incentive, such as a coupon, to purchase more of a certain product when he is running out of that product. Such an incentive may be provided to the user 250 via a mechanism such as e-mail or text message, where the PIA 400 receives an indication of the incentive, or alternatively, the incentive may be provided directly to the PIA 400.

In some embodiments, a healthcare provider can use the personal information received from the PIA 400 in the process of delivering healthcare. The aggregated healthcare information that is stored in the PIA 400 is from multiple healthcare providers, and thus can be more comprehensive than the information generally available to a single healthcare provider.

In one example of using a user's healthcare information, a physician is granted authorization for limited access to a user's healthcare information in order to treat the user's fractured wrist; the authorization only applies for the duration of the episode of care for the fracture. In other words, access is only authorized from the first office visit regarding the fracture through the last office visit regarding the fracture.

The user may not want the physician treating his fracture to have access to all of his healthcare information; instead the user may want to provide access only to information that will be relevant to the treatment of the fracture. At the first office visit, the user grants authorization for the physician to access several data feeds: a composite data feed that contains information on all prescription medicines and over-the-counter supplements that the user is taking or has taken in the last three months, a raw data feed of all of the user's x-rays of previous fractures, a raw data feed of the user's lab test results in the last ten years, and a filtered data feed of the user's diagnoses and treatments in the last five years that excludes information related to mental health and sexually-transmitted diseases.

In another example of using a user's healthcare information, a pharmacy is granted authorization for ongoing access to a user's healthcare information in order to detect and alert the user if a prescribed medication might result in an adverse reaction due to another prescribed medication or the user's medical condition. The user grants authorization for the pharmacy to access the following data feeds: a composite data feed of the user's prescription history at the pharmacy and the prescription history at other pharmacies, a raw data feed of the user's lab test results in the last ten years, and a filtered data feed of the user's diagnoses in the last ten years.

Figure 11:
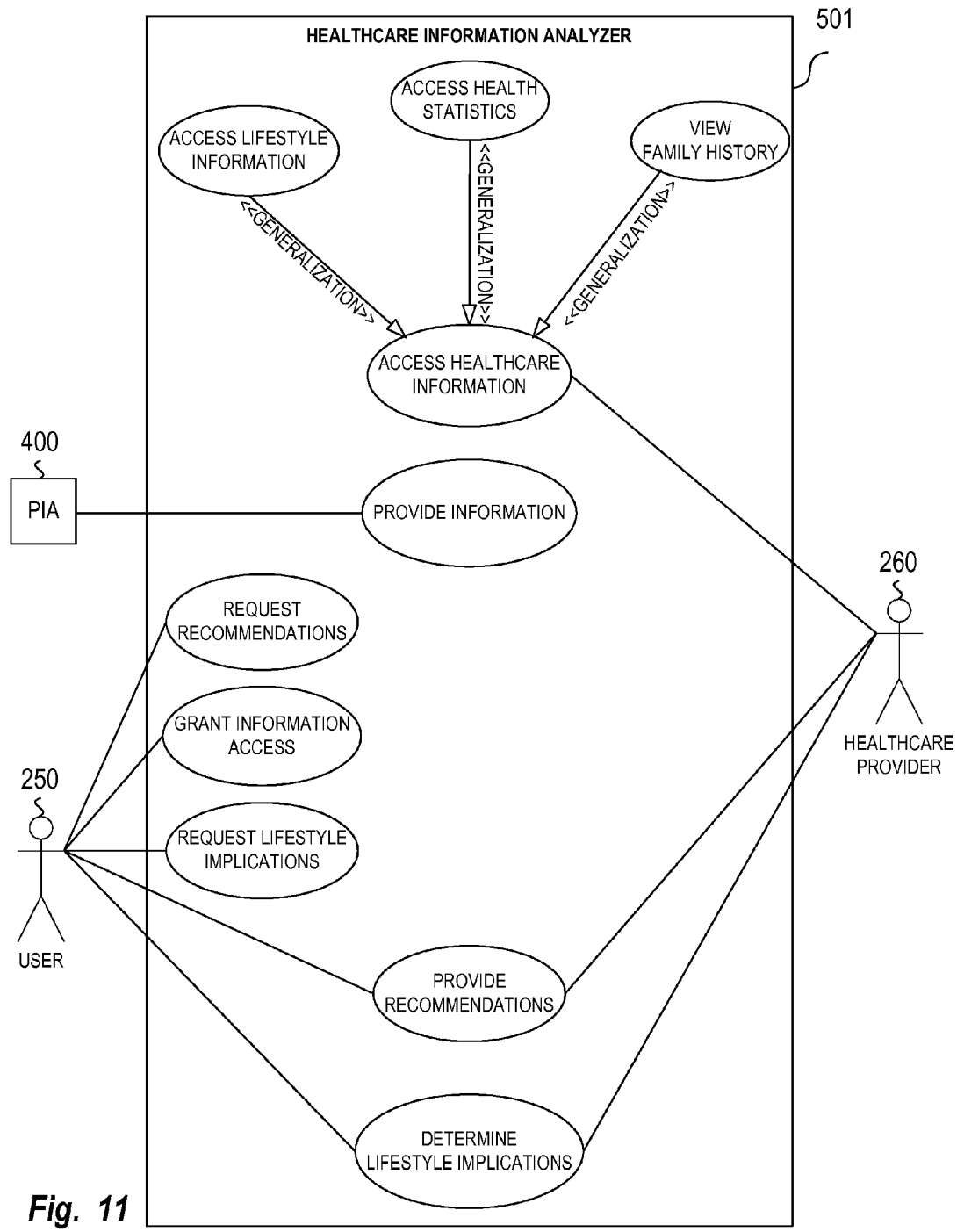
FIG. 11 is a use case diagram for a healthcare PIA application in accordance with one embodiment of the present invention.

Referring to FIG. 11, a healthcare information analyzer application 501 may use data from a user's PIA 400 in order to determine the implications of the user's lifestyle and to provide the user 250 with recommendations to improve his or her health. In FIG. 11, a healthcare provider 260 has access to the output data feeds of a user's PIA 400 that contain the user's healthcare and lifestyle information. The user 250 grants access by the healthcare provider 260 to the healthcare and lifestyle information feeds output by the user's PIA 400. Once access has been granted, the user 250 requests the healthcare provider 260 to inform him or her of lifestyle implications and recommendations based on the healthcare and lifestyle information. The healthcare information analyzer 501 processes the user's healthcare and lifestyle information to determine certain implications regarding the user's lifestyle. In addition, the healthcare information analyzer 501 determines and provides recommendations (e.g., dietary changes to lower cholesterol levels) to the user 250.

The healthcare information analyzer application 501 may also analyze the user's healthcare information to determine the existence of medical contraindications. Medical contraindications can include, but are not limited to, risks involved with using a particular drug or medical procedure, engaging in a particular activity, and possible drug interactions. Notifications of medical contraindications may be provided to the user or the user's healthcare providers by the healthcare information analyzer application 501.

As noted above, a PIA's data feeds may be provided to a personal information profiler (PIP). The PIP receives data feeds from a user's PIA and processes the data received from those feeds to generate various profiles associated with the user, e.g., a user's health risk, financial and work profiles. As with any source or receiver of PIA data, a PIP must be authorized and mapped to access particular data feeds of the PIA. There are numerous applications for the profiles generated by a PIP. Examples of such applications include an insurance analyzer, targeted advertising analyzer, lifestyle analyzer and financial analyzer, described in grater detail below.

In one embodiment, the PIP receives consumer purchase data, healthcare data and fitness activity data feeds from a user's PIA. The data from those feeds is processed by the PIP to determine the user's health risk profile. The health risk profile specifies adverse health outcomes for which the user is at risk. For example, the health risk profile might specify that a user is prone to a stroke or heart attack.

The consumer purchase data feed might contain grocery purchase records from several supermarkets, records of meal purchases from fast food chains, and records of alcohol purchases from liquor stores. The PIP would process the consumer purchase data to determine the eating habits of the user. For example, the eating habits might indicate that the user eats reasonably low amounts of animal fat but consumes an inordinate amount of red wine.

The healthcare data feed might contain medical records from several doctors, records of filled prescriptions, records from any hospital stays, and test results (e.g., cholesterol, liver function, etc.) from a number of clinical laboratories. The PIP would process the healthcare data to determine the user's health status. For example, the health status might contain current diseases or conditions, allergies, genetic information and current height and weight.

The fitness activity data might contain workout records and fitness test results from gyms and fitness centers used by the user. The PIP would process the fitness activity data to determine the user's activity profile. For example, the activity profile might indicate that the user is getting enough aerobic exercise, is lacking the appropriate amount of weight training, has an above average body mass index (BMI), and an acceptable value of body fat percentage.

After determining the user's eating habits, healthcare data, health status and activity profile, the PIP analyzes such data to determine the user's health risk profile. For example, the analysis might determine that the amount of sugar consumed by the user is contraindicated by the user's diabetes, and that the user is therefore at risk for complications, i.e., adverse health outcomes, such as heart disease, blindness, nerve damage, and kidney damage.

In another embodiment, a lifestyle analyzer application uses the health risk, financial and work profiles generated by a PIP to make recommendations of lifestyle changes to the user. For example, a user at risk for heart disease might not be exercising enough, but might not be able to afford to join a fitness center. In this case, the lifestyle analyzer might recommend exercises that can be performed in the user's home using inexpensive equipment. A customized exercise schedule, changes in diet, including a customized diet schedule, or changes in work habit are examples of other types of lifestyle recommendations that might be generated by the lifestyle analyzer application.

In one embodiment, an advertising analyzer application uses the health risk and financial profiles generated by a PIP to select advertisements targeted to the user. For example, a user at risk for diabetes might already be eating appropriately, but might not be exercising enough, in which case, advertisements for fitness centers might be selected.

In one embodiment, the PIP receives a financial data feed from a user's PIA. The data from that feed is processed by the PIP to determine the user's financial profile. The financial profile specifies various aspects of the user's financial situation. For example, the financial profile might contain the values of the user's net worth (liquid and other assets), retirement accounts (tax-exempt and tax-deferred), salary, stock options, consumer debt, home mortgage debt and monthly payment and student loans.

The PIP may receive an employment data feed from a user's PIA. The data from that feed is processed by the PIP to determine the user's work profile. The work profile contains information regarding the user's employment history, as well as work habits such as hours per week, and day or night shifts. For example, the work profile might indicate that the user works an excessive number of hours per week, and typically stays with the same employer for several years before changing jobs.

A financial analyzer application uses a combination of one or more of the PIP profiles to generate a financial plan for the user. For example, the financial analyzer might combine the health risk, financial and work profiles generated by a PIP to generate an appropriate financial plan for the user. In such a case, the financial analyzer would take into account, for example, not only a user's desired retirement age, but also the user's risk of dying prior to attaining that age, to generate a financial plan that is appropriate to the user. The financial plan may include an assessment of the user's tolerance for risk, and may also be based on previously generated financial plans. The financial analyzer application may also offer financial services or investment advice to the user based on the financial plan that it generates.

In one embodiment, an insurance analyzer application uses information generated by the PIP to determine a user's insurance profile. The insurance profile might contain, e.g., a breakdown of the user's health risks into insurance-related categories. For example, the insurance profile might specify the risk levels for becoming short-term disabled, permanently disabled and dying at various ages. The insurance analyzer application can also incorporate information from a financial data feed from the user's PIA in making its analysis of the user's insurance needs.

The insurance analyzer application thus uses the insurance profile to determine and recommend a particular insurance package that is suitable for the user's needs. For example, the user's health risk profile might warrant an insurance package that includes a long-term care policy. Other types of packages that might be recommended by the insurance analyzer application are life insurance, health insurance, dental insurance, and disability insurance.

In another embodiment, the insurance analyzer application determines one or more quotes of the user's insurance premiums based on his insurance profile. For example, the user might be entitled to lower than average premiums based on his good health and lifestyle.

In another embodiment, the insurance analyzer application uses the user's insurance profile as a factor in actuarial analyses. For example, the insurance analyzer might generate morbidity, disability or fertility tables as part of an actuarial analysis. In another example, the user's permanent disability risk, if specified by the insurance profile, could be factored in to the calculations which generate a disability table used by an insurance company for establishing insurance premiums.

The PIA may also be used to search for and aggregate additional information regarding the user. In one embodiment, an external aggregator (e.g., an advertiser) that is authorized to receive personal information from the user's PIA obtains a personal identifier from the PIA's data feeds. The external aggregator searches a computer network (e.g., the public Internet or a private intranet) for occurrences of the personal identifier. Examples of a personal identifier that might be obtained from the PIA and used in the search include the user's e-mail address, an identification number associated with the user, and the user's postal address. When locations in the computer network that contain occurrences of the personal identifier are found, the external aggregator retrieves additional information from those locations. For example, the additional information might include the URL or text of a web page on which the personal identifier was found.

The external aggregator analyzes the retrieved additional information and derives additional personal information regarding the user. For example, the URL of a web page found in the search might belong to a website for volleyball coaches, and therefore, the external aggregator might derive the additional personal information that the user may be a volleyball coach. The additional personal information obtained from multiple occurrences of the user's personal identifier is aggregated and stored by the external aggregator.

The aggregated additional personal information can be further analyzed to create an aggregated profile of the user. For example, if another web page found in the search belongs to a website for baseball coaches, then an aggregated user profile is created that includes the indication that the user has a preference for coaching sports teams. The aggregated user profile can also be a consumer profile, indicating the user's preferences for certain products and services, in which case the user's consumer profile may be used to select advertisements targeted to the user based on his aggregated consumer profile.

N-Dimensional Social Network

An N-dimensional social network (NDSN), also called a multi-dimensional personal information network, captures and manages multi-dimensional relationships between persons and other entities that are users of the network. A user (i.e., a member or participant) of the NDSN may be an individual (i.e., person), a group (e.g., healthcare clinic, law firm, supermarket chain, etc), or entity. The NDSN uses multiple dimensions of association to characterize the relationships between users or members. For example, while friendship is a dimension that might be used by the NDSN, the NDSN might also utilize other dimensions such as family, professional connection, consumer (e.g., consumer-to-merchant) relationship and healthcare-relation (e.g., providers, insurers, etc.) to characterize the relationship between two or more users. In addition, the NDSN might utilize dimensions that link participants by preferences and behaviors, e.g., a preference for a type of product or service.

The NDSN 100 permits the user to discover and utilize the indirect relationships to other users that are connected to him through first-degree users. The multiple dimensions of the NDSN 100 and the ability to discover and use indirect relationships are described in more detail below. The NDSN 100 also provides a decentralized architecture outside the control of a single entity.

Figure 99:
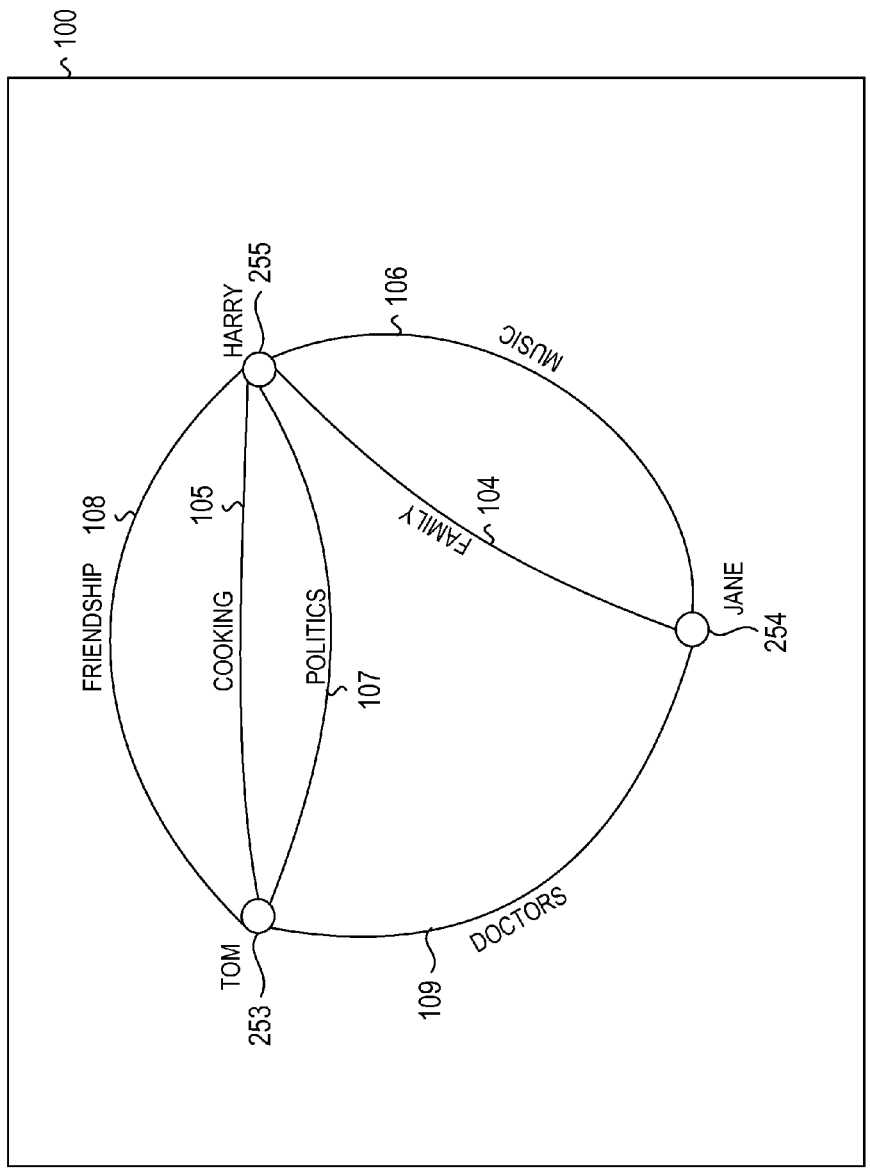
FIG. 99 is an example of an NDSN in accordance with one embodiment of the present invention.

FIG. 99 illustrates an example of multi-dimensional relationships between three participants in the NDSN 100: Tom 253, Jane 254 and Harry 255. Jane 254 and Harry 255 have relationships in two dimensions, Family 104 and Music 106. Harry 255 and Tom 253 have relationships in three dimensions, Friendship 108, Cooking 105 and Politics 107. Tom 253 and Jane 254 have a relationship in only one dimension, Doctors 109.

The NDSN 100 can also provide a "projected" view of a subset of the members of the NDSN to the user based on a subset of the NDSN's multiple dimensions. Such a "projected" view allows the user to use and manage smaller portions of the entire social network. The projected social network is described in more detail below.

In one embodiment, the NDSN 100 comprises interconnected nodes, where individual users, members, entities, communities, or other aggregations of entities within the NDSN 100 are associated with the nodes. Each node provides an associated entity with the ability to store and manage his profile and relationships with other users of the NDSN 100. Nodes may connect via different dimensions. Sets of nodes may exhibit high interconnectedness along some dimensions and little or no interconnection along other dimensions.

Each node is capable of communicating in a peer-to-peer fashion with other nodes in the NDSN 100, and thus is a user's point of connection to the NDSN 100, providing a user with access to information that can be obtained from other users of the NDSN 100 with whom the user has a relationship. Conversely, a node provides a user with the ability to selectively share (by providing access to) his personal information with other users of the NDSN 100.

A node may be, or may encompass, a user's PIA or CIA. The node may also encompass another type of device or software application, such as a user's Personal Recommendation System (PRS), described below in more detail.

Figure 34:
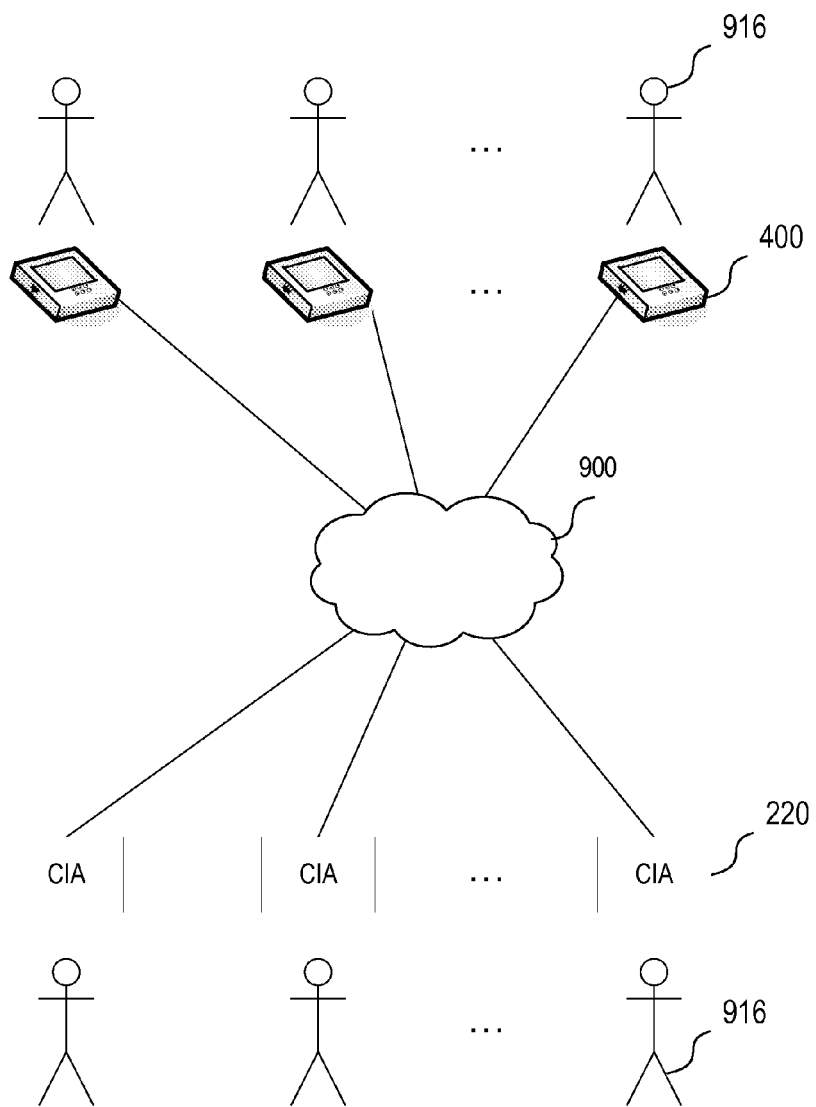
FIG. 34 is a network diagram of an N-Dimensional Social Network (NDSN) in accordance with one embodiment of the present invention.

Referring to FIG. 34, the NDSN 100 includes multiple users 916 and other entities associated therewith. Each of the users 916 or other entities of the NDSN 100 has an associated node which encompasses a PIA 400 or a CIA 220 or other device or software application (not shown). The PIAs 400 and CIAs 220 can be interconnected through the computer network 900.

Those skilled in the art will recognize that a node of the NDSN 100 may be implemented using a wide variety of available hardware and technologies generally known in the art, such as software on a personal computer or a handheld PDA. In addition, those skilled in the art will recognize that the nodes of the NDSN 100 may be interconnected and may communicate with each other using a wide variety of available hardware and technologies generally known in the art, such as TCP/IP over an Ethernet or a wireless network. In one embodiment, some users may have their nodes hosted in a common location, e.g., on a local or remote server.

Figure 35:
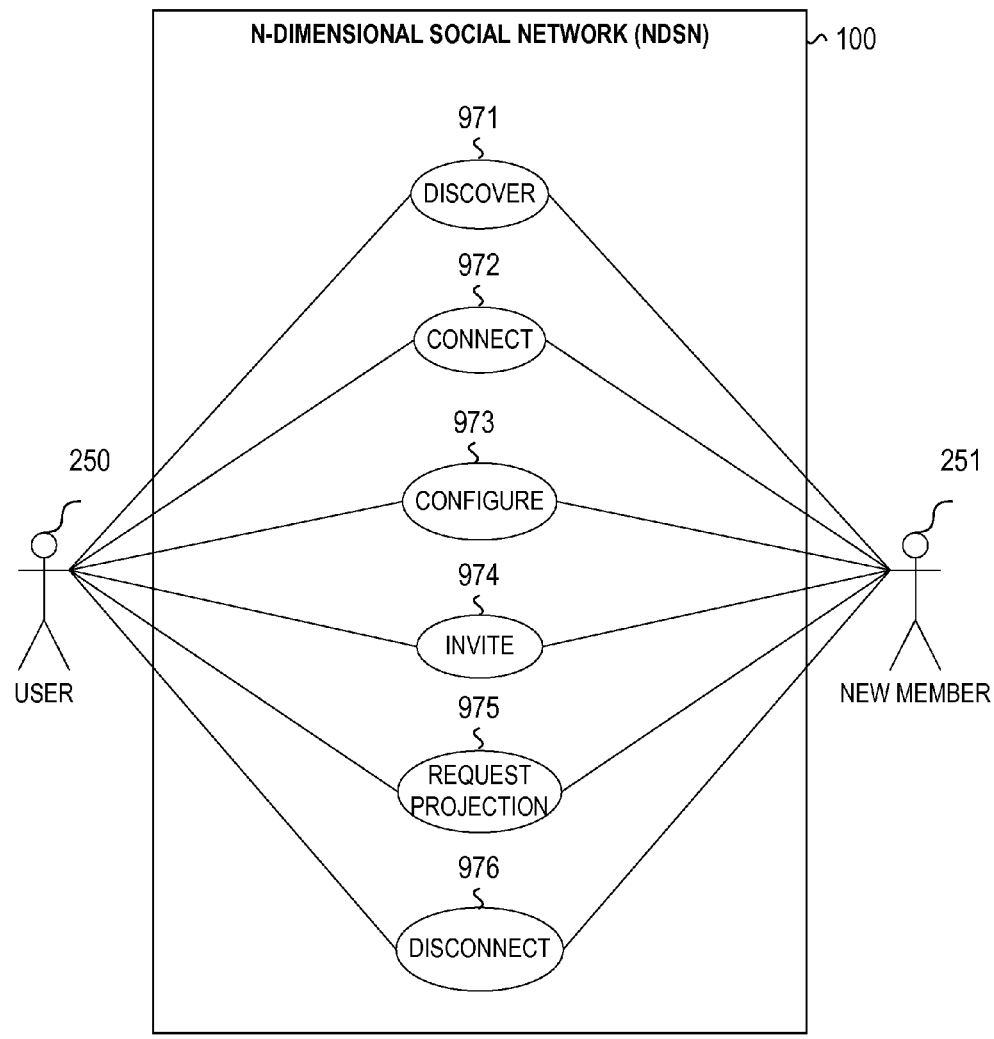
FIG. 35 is a use case diagram for the NDSN of FIG. 34.

A user's PIA 400 provides various functions that permit the user to connect to and interact with other members of the NDSN 100. Referring to FIG. 35, a user 250 employs the Discover use case 971 to discover the existence of other members of the NDSN 100. The user 250 may or may not have prior knowledge of the existence of members of the NDSN 100, and therefore, may not need to discover the existence of the members of the NDSN 100. The user 250 employs the Connect use case 972 to connect to other members of the NDSN 100 and configures his user profile by utilizing the Configure 973 use case. Once connection to other members of the NDSN 100 is established for the user 250, the user 250 can invite a new member 251 to connect to members of the NDSN 100 by utilizing the Invite use case 974. The user 250 employs the Request Projection 975 use case to obtain a projection of the NDSN. If the user 250 decides to disconnect himself from the other members of the NDSN 100, he employs the Disconnect use case 976. The new member 251 can similarly employ the use cases (Discover 971, Connect 972, Configure 973, Invite 974, Request Projection 975 and Disconnect 976) as described above.

Discovering, connecting to, configuring, and disconnecting from the NDSN 100, inviting a new user to connect to the NDSN, and requesting a projection of the NDSN are described in more detail below.

The NDSN 100 captures multiple various dimensions of the relationship between two users. The dimensions that are captured are wide-ranging and can cover many aspects of a user's life. Table 1 includes examples of dimensions that might be captured by the NDSN 100.

TABLE 1

| Dimension | Examples |
| --- | --- |
| Friend | Childhood, recent acquaintance |
| Family | Parent, child, sibling, grandparent, grandchild, cousin |
| Professional | Architect, roofer, accountant, lawyer |
| Consumer | Supermarket, toy store, auto dealer |
| Healthcare | Primary-care physician, specialist physician, nurse, acupuncturist, pharmacy |
| Community | Political party, coin collecting club |
| Interests | Music, food, cooking, health, hiking, environmental issues |
| Region | Geographic area, postal code, city, state/province, country |

Each relationship between two users in the NDSN 100 may have an attribute of affinity, i.e., trust or alignment. This permits the NDSN to characterize a relationship between users along a continuous range, rather than treating the relationships in a binary (i.e., true or false) fashion. For example, rather than characterizing another user as simply a friend (or not), the NDSN user can characterize the level of trust that he has in another user with whom he is related by friendship; in other words the NDSN can capture the level of friendship between two users. As another example, the level of alignment regarding political issues between two users related by their common membership in a political party can be captured by the NDSN.

Figure 36:
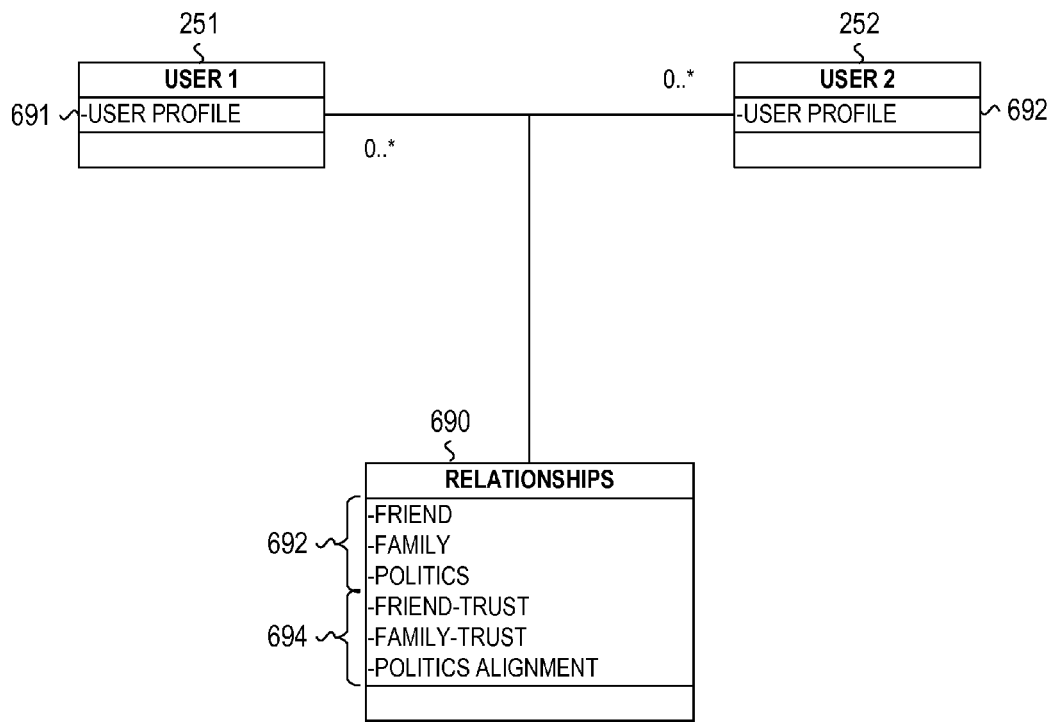
FIGS. 36-37 are class diagrams for the relationships between users of the NDSN of FIG. 34.

FIG. 36 shows an example of the relationship between two users in the NDSN 100. The Relationships association 690 between User1 251 and User2 252 has affinity attributes 694 for the multiple relationships (shown here as attributes 692) between User1 251 and User2 252. Each relationship attribute 692 (Friend, Family and Politics) between User1 251 and User2 252 has an affinity attribute 694 (Friend-trust, Family-trust and Politics-alignment) that specifies a level of trust or alignment for that relationship attribute. For example, the value of the Politics-alignment affinity attribute 694 indicates the level of political alignment between User1 251 and User2 252.

Figure 37:
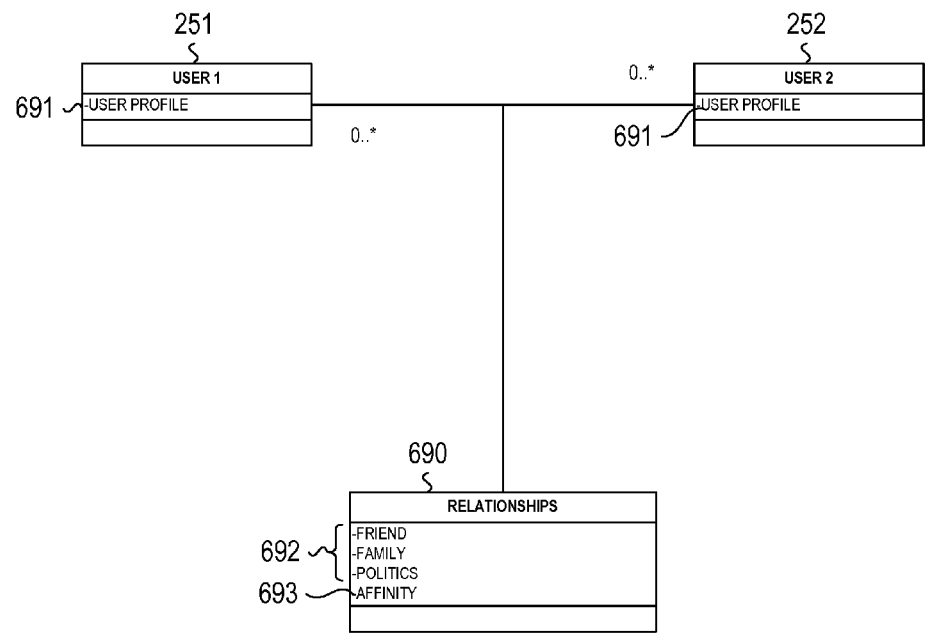

In other embodiments, the multiple relationships between two users may have a single affinity attribute, as opposed to one affinity attribute per relationship. For example, in FIG. 37, the Relationships association 690 between User1 251 and User2 252 includes the single affinity attribute 693, which applies to the multiple relationships 692 between User1 251 and User2 252. In the examples of FIG. 36 and FIG. 37, each user, User1 251 and User2 252, has a UserProfile attribute 691. The user profile is described in more detail below.

The value of the affinity attribute may be derived from the user attributes (which may be contained in the user profile) of one or both of the related nodes. For example, if both related users each have a user attribute that identifies them as basketball fans, then the derived affinity attribute along a Sports dimension would have a value of 0.9. However, if only one of the users has a user attribute that identifies him as a basketball fan, then the derived affinity attribute might have a lower value of 0.6.

Those skilled in the art will recognize that there are numerous well-known software and hardware technologies that may be utilized to implement the attributes of the users of the NDSN 100 and the attributes of the associations between the users.

Figure 43:
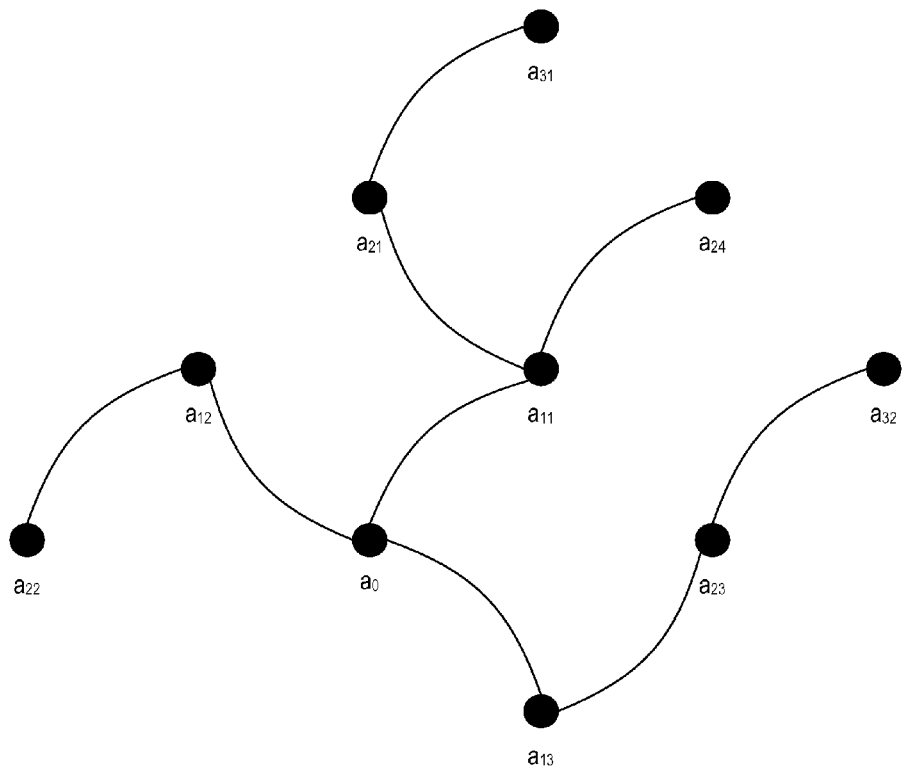
FIG. 43 is an example of nodes of the NDSN of FIG. 34.

A node of the NDSN 100 is connected to another node by one or more degrees or separation. A connection from one node directly to another node is considered to be of first-degree separation; a connection that goes indirectly through one other node is of second-degree separation; a connection that goes indirectly through two other nodes is of third-degree separation, and so on. In the example of FIG. 43, nodes $a_{11}$, $a_{12}$ and $a_{13}$ have first-degree separation from node $a_0$; nodes $a_{21}$, $a_{22}$ and $a_{23}$ have second-degree separation from $a_0$; and nodes $a_{31}$ and $a_{32}$ have third-degree separation from $a_0$.

Two nodes that are separated by two or more degrees of separation are indirectly connected. Either of such indirectly connected nodes may attempt to establish a direct connection with the other node, thus reducing the degree of separation to one.

Figure 44:
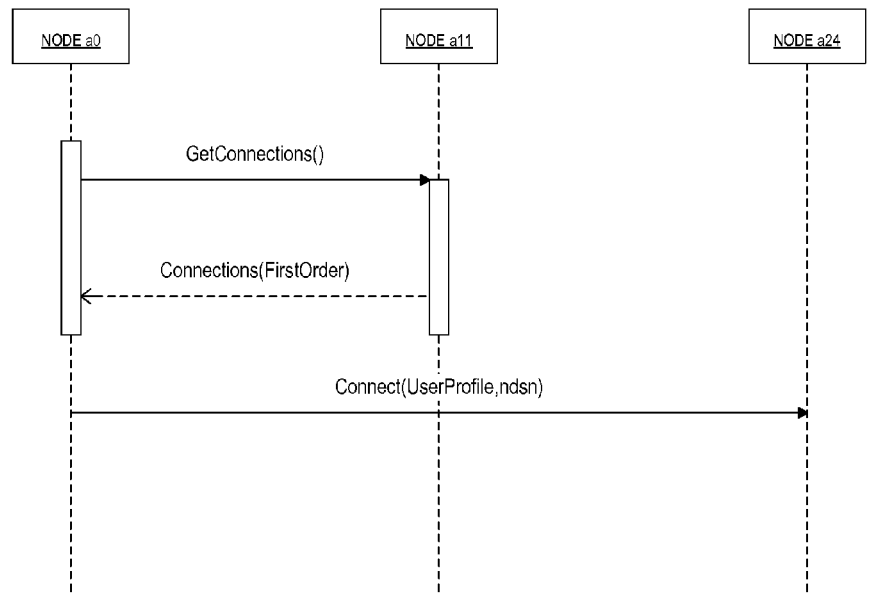
FIG. 44 is a sequence diagram for the interactions associated with the nodes of FIG. 43.

Referring to FIG. 44, node $a_0$ traverses the network of FIG. 43 to establish an indirect connection with node $a_{24}$. Node $a_0$ sends a GetConnections message to $a_{11}$ and other nodes (not shown) with which it has a first-degree separation. Node $a_{11}$ responds by sending a Connections message to $a_0$ with an argument FirstOrder that lists the addresses of the nodes with which it has first-degree connections (i.e., $a_{21}$ $_{and}$ $a_{24}$). Node $a_0$ sends a Connect message to node $a_{24}$ and to $a_{21}$ (not shown) with arguments that contain its user's profile (UserProfile) and identify the NDSN (ndsn), thus establishing a direct, first-degree separation connection with $a_{24}$.

Figure 45:
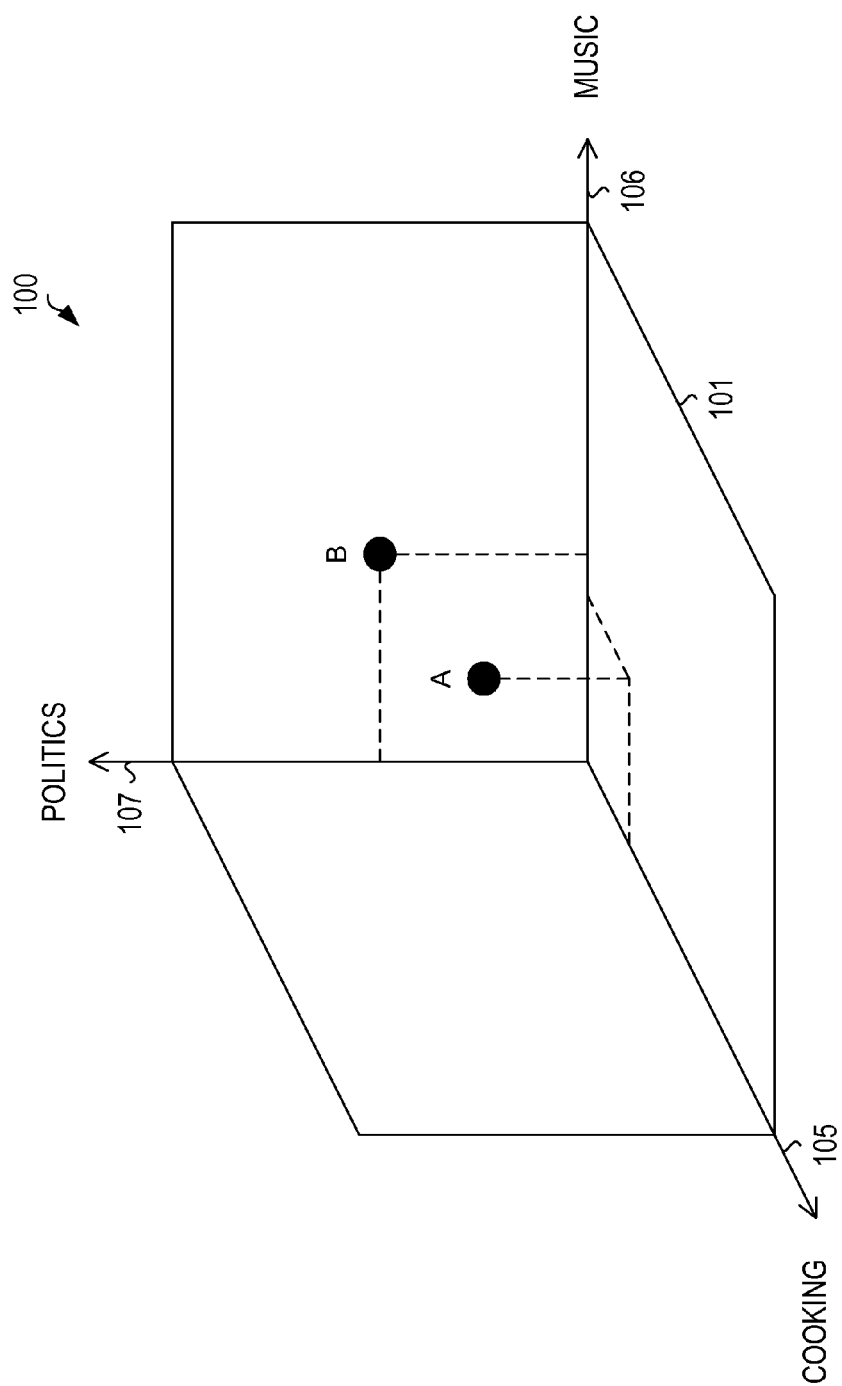
FIG. 45 is an example of a projected NDSN in accordance with one embodiment of the present invention.

A user might desire to work with a "projected" view, i.e., a subset of the nodes, of the NDSN 100. Such a desire might be based, for example, on a need to increase processing speed and reduce resource requirements such as CPU speed and memory size. A user can obtain a "projected" view of the NDSN 100, by employing the Request Projection use case 975 (see FIG. 35). Referring to FIG. 45, Node A and Node B are connected to the user 250. The relationship between the user 250 and Node A has components in three dimensions: Music 106, Politics 107 and Cooking 105, while the relationship between the user 250 and Node B has components in the Music 106 and Politics 107 dimensions, but not the Cooking dimension 105. In FIG. 45, the projected view 101 of the NDSN 100 includes those nodes (i.e., Node A) of the NDSN 100 that reside along a selected projection of the Cooking dimension 105 (and not the Music or Politics dimensions 106, 107). Nodes that reside in the two-dimensional plane formed by the Music dimension 106 and the Politics dimension 107 (i.e., Node B) are thus not included in the projected view 101 of the NDSN 100, since they do not include a Cooking component.

Figure 50:
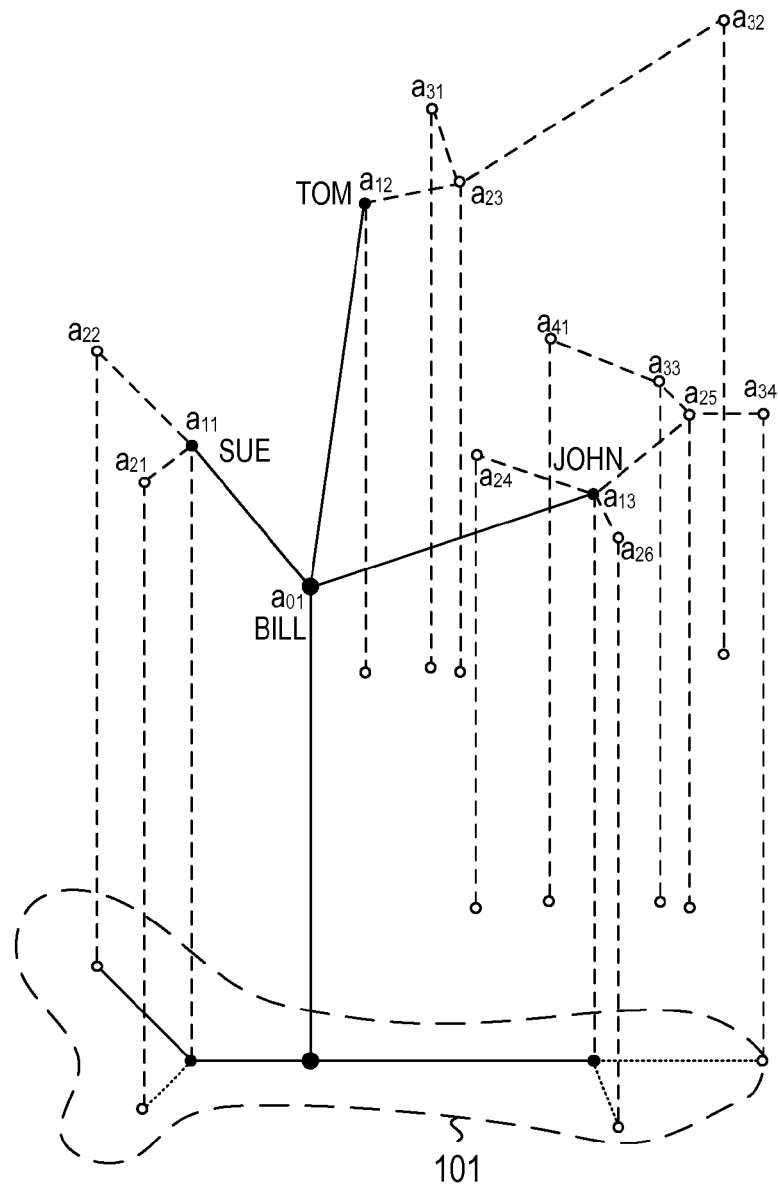
FIG. 50 is an example of a projected NDSN in accordance with one embodiment of the present invention.

A projection of the NDSN 100 may also be obtained along multiple dimensions, as shown by example in FIG. 50. The projected view denoted by the dashed outline 101 contains only those nodes that are connected, directly or indirectly, to Bill (node $a_{01}$) by relationships that have Cooking and Music dimensions (not shown). In this example, Sue ($a_{11}$) and John ($a_{13}$) are included in the projected view because each has a relationship with Bill along the Cooking dimension and the Music dimension. Similarly, the four nodes $a_{21}$, $a_{22}$, $a_{26}$, and $a_{34}$ are also included in the projected view because each is directly or indirectly connected to Sue or John (and thus indirectly to Bill) by relationships along the Cooking dimension and the Music dimension. Thus, the nodes $a_{01}$, $a_{11}$, $a_{21}$, $a_{22}$, $a_{13}$, $a_{26}$, and $a_{34}$ are within the dashed outline 101. The remaining eight nodes ($a_{12}$, $a_{23}$, $a_{24}$, $a_{25}$, $a_{31}$, $a_{32}$, $a_{33}$, and $a_{41}$) are not included in the projected view because none are connected to Sue or John along both the Cooking dimension and the Music dimension. Thus, these remaining eight nodes ($a_{12}$, $a_{23}$, $a_{24}$, $a_{25}$, $a_{31}$, $a_{32}$, $a_{33}$, and $a_{41}$) fall outside of the dashed outline 101 representing the projected view.

It should also be noted that the entire NDSN 100 can be considered to be a trivial projection along all of the dimensions of the NDSN 100. In other words, a projection along every dimension of the NDSN 100 is equivalent to the entire NDSN 100 (not a subset), since every node of the NDSN 100 is included in such a projection.

The affinity attributes between nodes of the NDSN 100 may also be used to determine the set of nodes that form a projection of the NDSN 100. For example, the set of nodes in a projection of the NDSN 100 might include those nodes that have a cooking dimension relationship with the user 250 and additionally have an affinity attribute along that dimension that exceeds a specified threshold.

Figure 51:
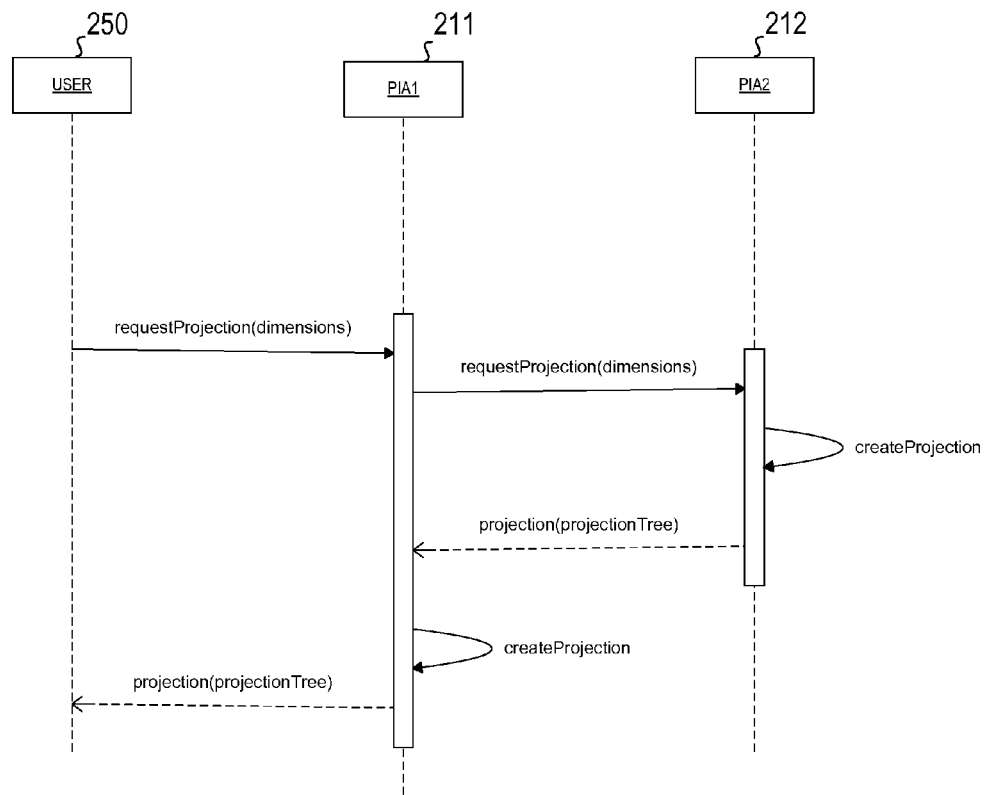
FIG. 51 is a sequence diagram for the interactions associated with creating a projection of the NDSN in accordance with one embodiment of the present invention.

FIG. 51 depicts an example of the interactions associated with creating a projection of the NDSN 100. In FIG. 51, the User 250 requests a projection by sending a requestProjection message to PIA1 211. PIA1 211 then requests a second projection by sending a requestProjection message to PIA2 212. PIA2 212 creates the second projection by sending itself a createProjection message, and provides the second projection by sending a projection message to PIA1 211 containing the argument projectionTree which holds the second projection. PIA1 creates the projection requested by the user by sending itself a createProjection message. The projection created by PIA1 211 is based on the second projection received from PIA2 212. In some embodiments, the projection created by PIA1 211 is further based on other projections requested and received from other PIAs (not shown).

In other embodiments, thresholds are employed to limit the extent of a requested projection. For example, a time limit may be imposed on the operation of creating a projection, i.e., the operation will terminate after a specified duration of time. As another example, a limit on the number of nodes contained in the projection may be used to place an upper bound on the size of the projection.

In some embodiments, a maximum measure of separation, which can be measured in various ways, may be used to limit the projection operation. In one embodiment, the User 250 specifies the maximum degree of separation, and the PIA1 211 requests a second projection from PIA2 212 with a maximum degree of separation that is one less than the degree specified by the User 250.

In another example of a measure of separation, the multiplicative product of the affinities between nodes as the NDSN 100 is traversed may be used to limit the extent of the projection. Alternatively, a combined affinity may first be formed by multiplying the affinities along several dimensions between two nodes, and then used in place of the single affinity between nodes in the previous example. In yet another example of a measure of separation, a measure of affinity deficit may be used to limit the extent of the projection. That is, if affinity may range from 0 to 1, and the affinity between two nodes is X, then the affinity deficit between the two nodes is 1-X. The accumulation of the affinity deficits between nodes as the NDSN 100 is traversed may be used to limit the extent of the projection.

In another embodiment, the projection is requested by an entity other than the User 250. For example, the projection may be requested by another PIA, or a PRS or an advertising system, each of which is described in more detail below.

Figure 52:
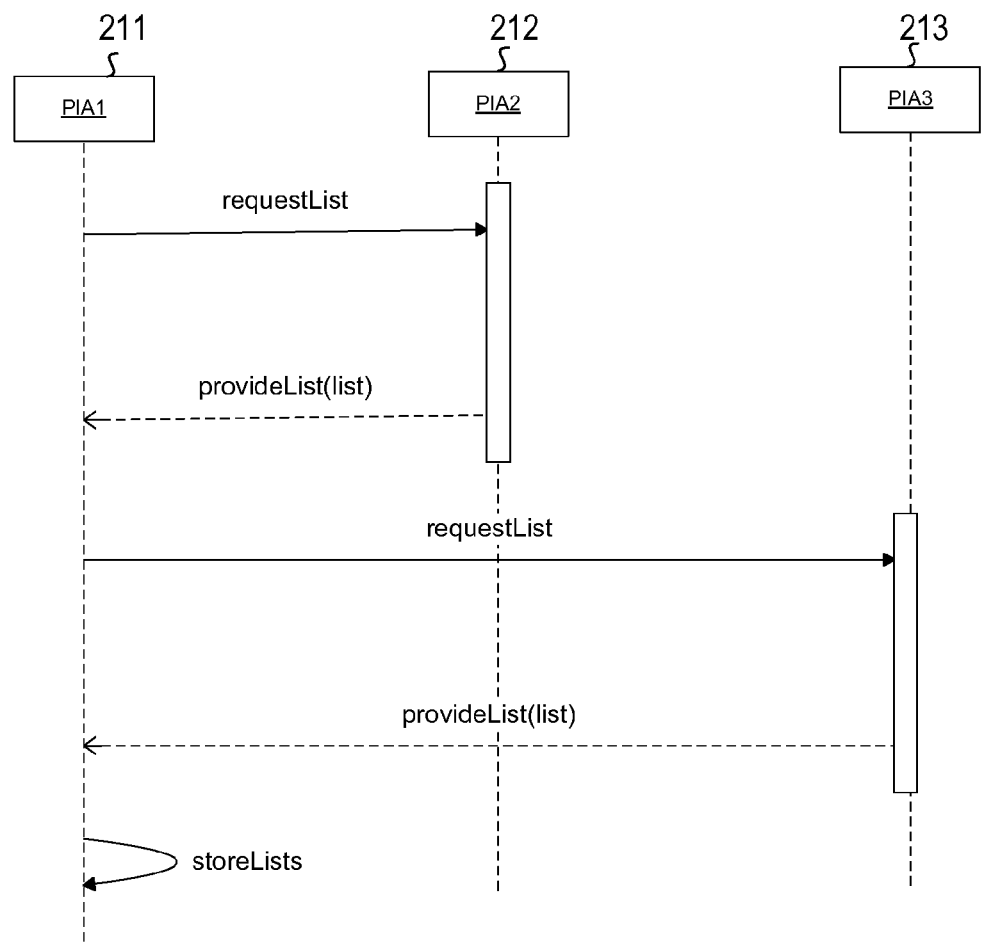
FIG. 52 is a sequence diagram for the interactions associated with obtaining lists of PIAs n accordance with one embodiment of the present invention.

The nodes of the NDSN 100 may also be traversed with methods that are more general than projection. For example, lists of nodes may be requested and obtained by a PIA as it traverses the nodes of the NDSN 100, and these lists may be used to request additional node lists from the PIAs contained in the first lists, and so on. Referring to FIG. 52, PIA1 211 requests lists that contain other PIAs by sending requestList messages to other PIAs of which it has knowledge, which, in this example, are PIA2 212 and PIA3 213. PIA2 212 and PIA3 213 provide the requested lists to PIA1 211 by sending provideList messages to PIA1 211. After receiving the requested lists, PIA1 211 stores the received lists.

In one embodiment, PIA2 212 and PIA3 213 are known to PIA1 111 because they each have one degree of separation from PIA1 211. In general, however, there are a variety of ways for a PIA to have knowledge of other PIAs; for example, a PIA may obtain this knowledge from a registry that stores the identities of PIAs.

A user node in the NDSN 100 may contain the user's profile, which may include information regarding the user's basic personal information (e.g., name, home address, work address, e-mail addresses and date of birth), demographics (e.g., age, age group, gender, years of education, income, net worth, occupation, marital status, geographic region, religion, ethnicity, etc.), user attributes, interests, affiliations and other information that can be used in the NDSN to characterize the user. The user node, which in some embodiments is a PIA, may collect some of this information without requiring direct entry by the user. Such information is extracted by monitoring, processing and analyzing data that enters the PIA through its input data feeds. The user also may have the option of directly entering, reviewing and modifying his user profile; these actions can be performed on a variety of types of devices or equipment that may provide the user with data connections to the other nodes of the NDSN, including, e.g., a PIA, a CIA, a personal computer, or a handheld device (e.g., a cell phone or personal digital assistant (PDA)).

As described above, a user 250 may have no prior knowledge of the existence of the members of the NDSN 100, and may choose to see if he can discover the existence of members of one or more NDSNs. Members of an NDSN may be discovered in various ways, including broadcasting a query, querying a CIA, querying neighboring nodes and querying other directories.

A node may be able to discover other nodes by broadcasting a message on the local network. Upon receipt of the broadcast message one or more of the other nodes may respond to the issuing node with, e.g., a list of available public feeds (if the node is a PIA), or other information.

A CIA may maintain a list of PIAs that can be accessed by another PIA such that direct connections to the member PIAs may be established. This would allow a member to easily find other members of a particular community. For example, a CIA associated with a chess club might have a list of its members, as well as lists of members of other chapters of the club, and thus would be able to provide a convenient way to find and connect with other chess players.

A node may also locate other nodes by querying known neighbor nodes and asking them for addresses of nodes of which they have knowledge that meet certain criteria. For instance, a node may ask its neighbors for addresses of their neighbors that are members of a certain demographic. The process could then be repeated with that new set of addresses obtained in the responses.

Other types of directories can be established that maintain addresses of certain collections of nodes of interest to simplify the establishment of new links in the NDSN. For example, a corporation might provide an internal directory organized by project descriptions, so that an employee could find other employees engaged in a particular activity, e.g., benchmarking the quality procedures of other divisions of the corporation.

A node may also learn of another peer node through receipt of an incoming discovery or connection request. For example, upon receipt of a broadcast message from another node, a node may store the address of the other node for later use.

Figure 38:
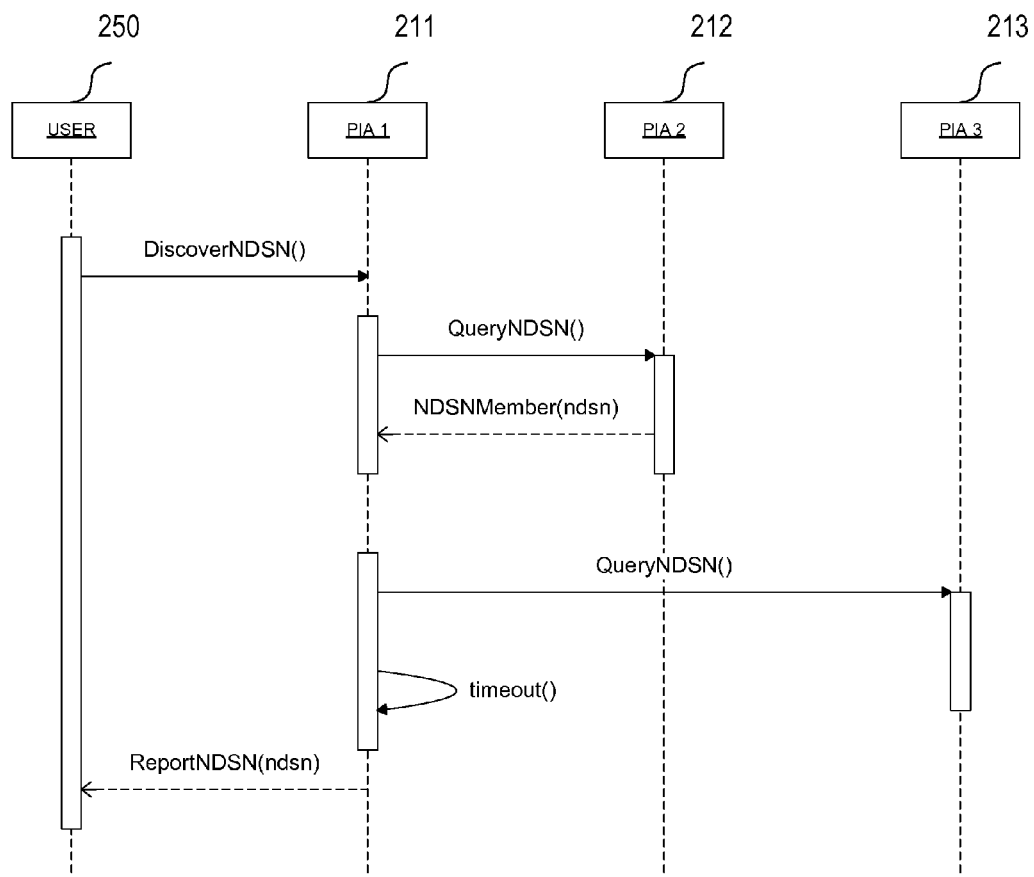
FIG. 38 is a sequence diagram for the interactions associated with a user discovering an NDSN in accordance with one embodiment of the present invention.

A user 250 may attempt to discover the existence of members of one or more NDSNs by employing the Discover use case 971 (see FIG. 35). Referring to FIG. 38, the User 250 requests PIA1 211 to attempt to discover the existence of members of an NDSN by sending a DiscoverNDSN message to PIA1 211. In order to satisfy this request, PIA1 211 utilizes a list (not shown) of candidate PIAs, i.e., those that may be members of an NDSN. This list may be generated by various techniques (not shown), e.g., by crawling the Internet or by contacting a registry that stores the identities of PIAs.

In the example of FIG. 38, the list of candidate PIAs used by PIA1 211 includes PIA2 212 and PIA3 213. PIA1 211 asks PIA2 212 if it is a member of an NDSN by sending a QueryNDSN message to PIA2 212. PIA2 212 responds that it is a member of an NDSN by sending an NDSNMember message to PIA1 211 containing the argument ndsn which identifies the particular NDSN of which PIA2 212 is a member. Similarly, PIA1 211 sends a QueryNDSN message to PIA3 213. PIA3 213 neither is a member of an NDSN nor understands the QueryNDSN message, and thus it does not respond to PIA1 211. After a timeout period has elapsed, PIA1 211 sends itself a timeout message to note that PIA3 213 has not responded. PIA1 211 satisfies the request from the User 250 to discover the existence of members of an NDSN by sending a ReportNDSN message to the User 250 with an argument ndsn that identifies the discovered NDSN.

Those skilled in the art will recognize that techniques of crawling the Internet and providing a registry are well-known in the art, and furthermore that a variety of other techniques may be utilized to generate the list of candidate PIAs.

In some embodiments, a user chooses to connect to the NDSN 100. In other embodiments, other mechanisms are used to connect to other users of the NDSN, e.g., all members of a club might be automatically connected to other users of the NDSN. Frequently, a new member is informed of the NDSN by another user, who recommends the NDSN to the new member. An entity, such as a club or professional organization, can connect to other users of the NDSN through a representative of the entity, e.g., an officer of a club. "Connection" in this context may refer to simple registration of the address of another PIA in the database of a PIA for later use. When information from the other PIA is needed, the PIA accesses the address, establishes a connection, accesses a feed of the other PIA, and then may not have further communication until more information is desired from the other PIA.

In one embodiment, PIAs and CIAs may only know the addresses of their own direct neighbors. In other embodiments, some redundancy may be established in the NDSN 100 by having PIAs and CIAs also know addresses of nodes separated from them by one or more degrees of separation. Thus, upon loss of a node, traversal through the network may still occur, skipping over the non-communicating node. A node may be a direct neighbor of a second node along one dimension, but may be separated by two or more degrees when another dimension is analyzed.

Figure 39:
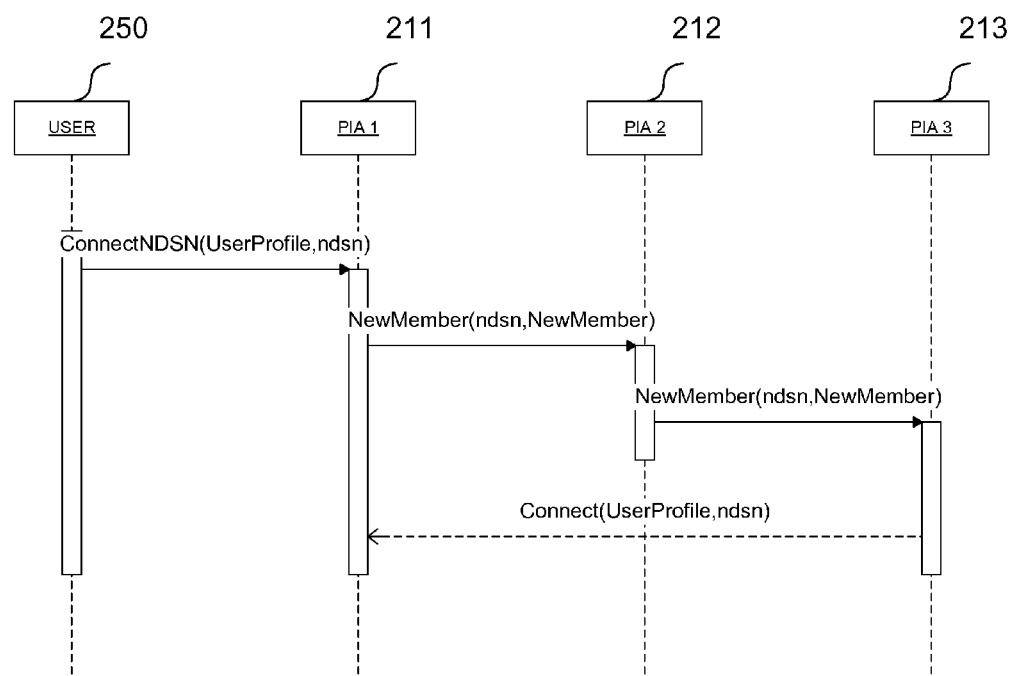
FIG. 39 is a sequence diagram for the interactions associated with a user connecting to other members of an NDSN in accordance with one embodiment of the present invention.

To connect to members of the NDSN, a user employs the Connect use case 972 (see FIG. 35). In the example of FIG. 39, the User 250 asks PIA1 211 to connect to an NDSN by sending a ConnectNDSN message to PIA1 211 with arguments that contain his user profile (UserProfile) and identify the NDSN (ndsn). PIA1 211 utilizes a list (not shown) of PIAs that belong to the NDSN. This list may be generated by various techniques (not shown), e.g., by crawling the Internet or by storing the identities of the PIA that have been discovered by employing the Discover use case 971 (see FIG. 35).

In the example of FIG. 39, the list of PIAs used by PIA1 211 includes PIA2 212. PIA1 211 informs PIA2 212 that the User 250 is becoming a new member of, i.e., connecting to the NDSN, by sending a NewMember message to PIA2 212 with an argument ndsn identifying the NDSN, and an argument NewMember identifying the PIA (PIA1 211) owned by the new user (User 250). PIA2 212, as a PIA of an existing member of the NDSN, has a list of PIAs owned by other members of the NDSN, which are unknown to the new member, User 250. In the example of FIG. 39, this list includes PIA3 213. PIA2 212 sends a NewMember message to PIA3 213 and the other PIAs (not shown) on the list with an argument ndsn identifying the NDSN, and an argument NewMember identifying the PIA (PIA1 211) owned by the new user (User 250). Each PIA on the list sends the NewMember message to other PIAs (not shown), thus propagating the news of the new member to other members of the NDSN.

PIAs that are thus informed of the existence of the new member, User 250, may decide to connect to PIA1 211. In the example of FIG. 39, PIA3 213 connects to PIA1 211 by sending a Connect message to PIA1 211 with arguments that contain a user profile corresponding to the owner of PIA3 213 (UserProfile) and identify the NDSN (ndsn).

Figure 53:
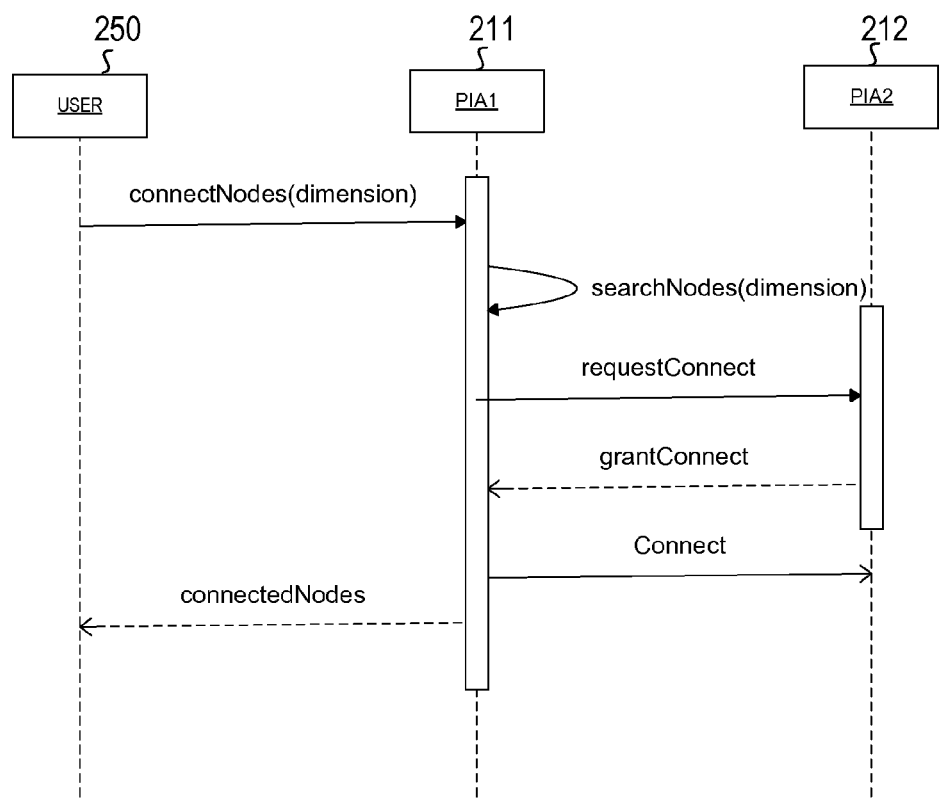
FIG. 53 is a sequence diagram for the interactions associated with a user connecting to other members of an NDSN in accordance with one embodiment of the present invention.

FIG. 53 provides another example of a PIA connecting to the NDSN 100. The User 250 instructs PIA1 211 to connect to other nodes of the NDSN 100 along a specific dimension by sending a connectNodes message with an argument dimension identifying the specified dimension to PIA1 211. PIA1 211 searches the NDSN 100 for nodes along the specified dimension by sending itself a searchNodes message. In this example, PIA2 212 is included in the nodes found by PIA1 211. PIA1 211 then requests to connect to PIA2 212 by sending a requestConnect message to PIA2 212. PIA2 212 grants the connection request by sending a grantConnect message to PIA1 211. PIA1 211 then connects to PIA2 212 by sending a Connect message to PIA2 212. PIA1 211 informs the User 250 that the requested connections have been made by sending a connectedNodes message to the User 250.

Figure 40:
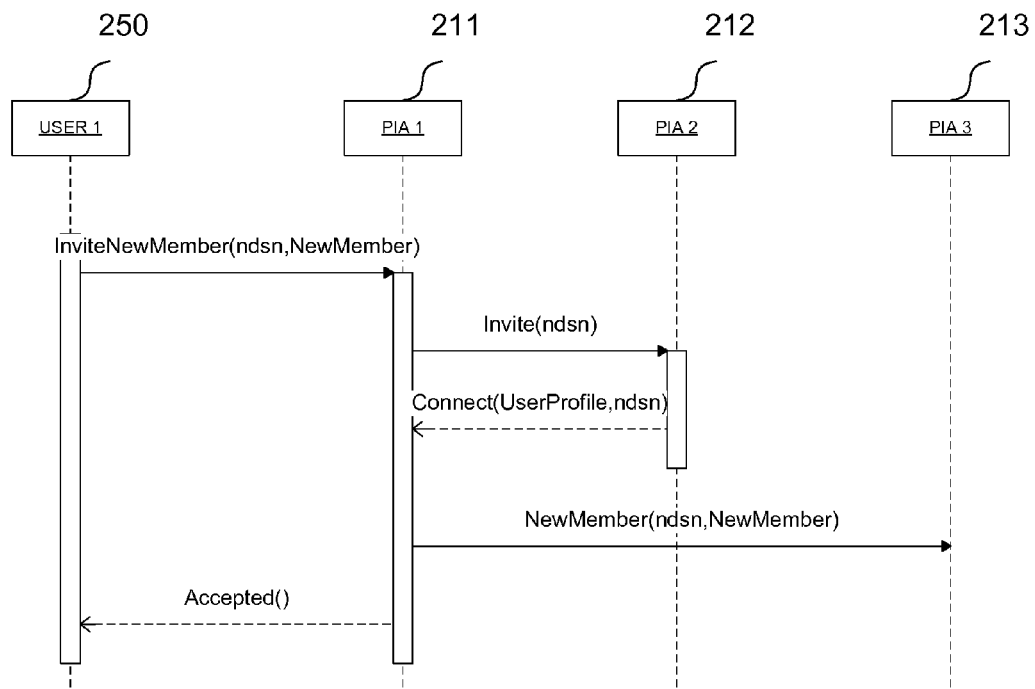
FIG. 40 is a sequence diagram for the interactions associated with a user inviting a new member to connect to the members of an NDSN in accordance with one embodiment of the present invention.

To invite a new member to connect to the members of the NDSN 100, a user employs the Invite use case 974 (see FIG. 35). In the example of FIG. 40, the User 250 asks PIA1 211 to invite User2 252 to connect to the members of the NDSN by sending an InviteNewMember message to PIA1 211 with an argument ndsn identifying the NDSN, and an argument NewMember identifying the potential new user (User2 252). PIA1 211 sends an Invite message to PIA2 212 with an argument ndsn identifying the NDSN. PIA2 212 might inform User2 252 by displaying a user interface prompt announcing the invitation (not shown). To accept the invitation, PIA2 212 responds by sending a Connect message to PIA1 211 with arguments that contain User2's user profile (UserProfile) and identify the NDSN (ndsn). If PIA2 212 were to decline the invitation, then PIA2 212 would respond by sending a Decline message (not shown) to PIA1 211.

PIA1 211 also sends a NewMember message to PIA3 213 and other members of the NDSN (not shown), with an argument ndsn identifying the NDSN, and an argument NewMember identifying the PIA (PIA2 212) owned by the new user (User2 252). As described in the example of FIG. 39, the news of the new member is thus propagated to other members of the NDSN. PIA1 211 sends an Accepted message to the User 250, informing the User 250 that User2 252 has accepted the invitation to connect to members of the NDSN.

Figure 41:
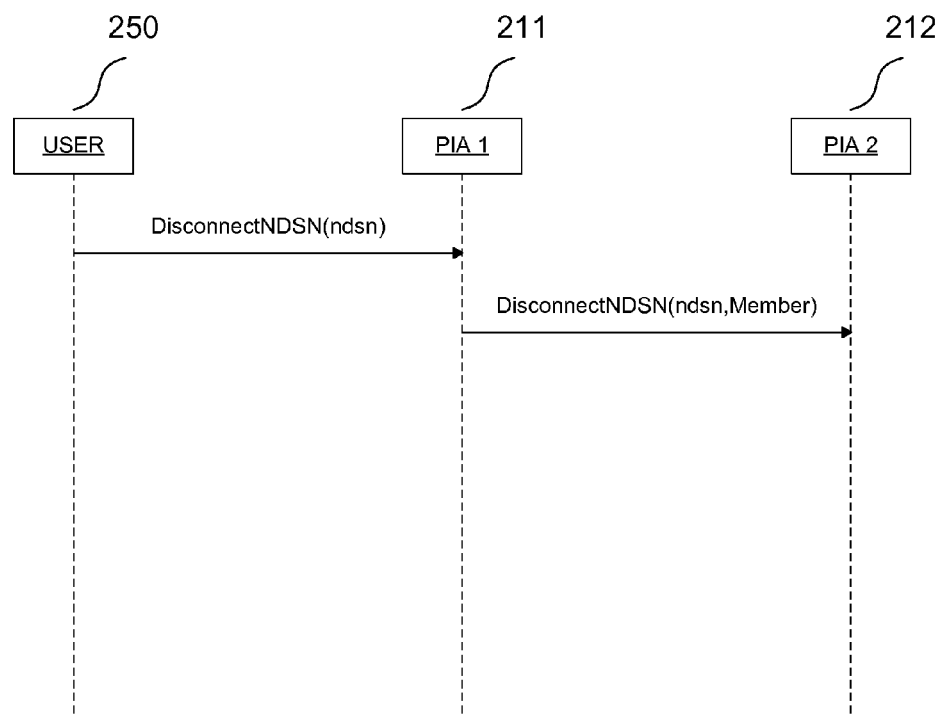
FIG. 41 is a sequence diagram for the interactions associated with a user disconnecting from other members of an NDSN in accordance with one embodiment of the present invention.

To disconnect from other members of the NDSN, the user may employ the Disconnect use case 976 (see FIG. 35). In some embodiments, a user's PIA stores the addresses of PIAs that belong to the members to whom the user is connected. In the example of FIG. 41, the User 250 asks PIA1 211 to disconnect from the members of the NDSN by sending a DisconnectNDSN message to PIA1 211 with arguments ndsn and Member identifying the NDSN and the member. PIA1 211 sends a Disconnect message to PIA2 212 and other PIAs (not shown) that it is connected to, with an argument ndsn that identifies the NDSN.

Figure 42:
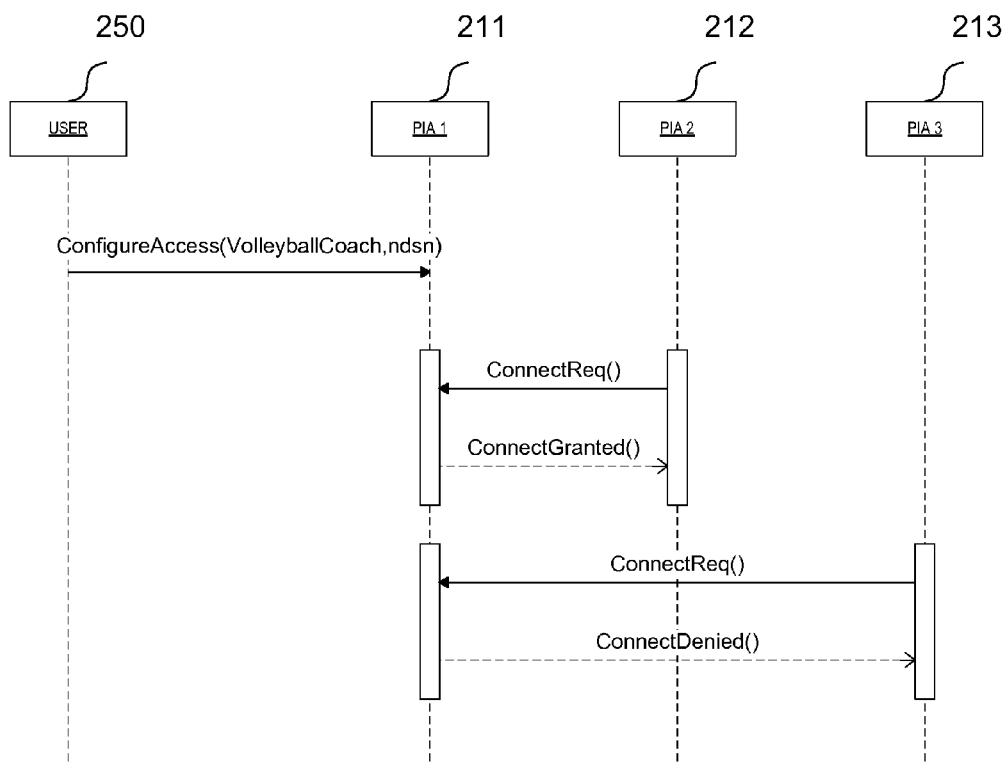
FIG. 42 is a sequence diagram for the interactions associated with a user granting access to other members of an NDSN in accordance with one embodiment of the present invention.

The user 250 may configure the PIA to permit a connection for one or more specific user attributes between himself and other users. In this manner, users can easily connect with each other based on common interests, demographics or other factors. A user employs the Configure use case 973 (see FIG. 35) to configure his NDSN node. For example, a user may configure his PIA to allow connections to any PIA that belongs to a user who coaches volleyball. In the example of FIG. 42, the User 250 asks his PIA1 211 to allow connections to a particular user attribute by sending a ConfigureAccess message to PIA1 211 with arguments VolleyballCoach and ndsn identifying the user attribute and the particular NDSN.

In the example of FIG. 42, PIA2 212 belongs to a user (not shown) that coaches volleyball, and thus when PIA2 212 sends a ConnectReq message to PIA1 211, PIA1 211 automatically responds by sending a ConnectGranted message to PIA2 212. PIA3 213, however, belongs to a user (not shown) who does not coach volleyball, and thus when PIA3 213 sends a ConnectReq message to PIA1 211, PIA1 211 automatically responds by sending a ConnectDenied message to PIA3 213.

Those skilled in the art will recognize that the interactions employed to perform the various functions associated with the NDSN (Discover, Connect, Invite, Configure, etc.) may be executed in a variety of ways not limited to the examples of FIGS. 38-39.

For example, in FIG. 38, PIA3 213 may understand a QueryNDSN message even though it is not a member of an NDSN, and therefore, may respond to the query with a message indicating that it is not a member of an NDSN. Similarly, in FIG. 41, PIA2 212 may respond with a message that acknowledges the disconnection action requested by PIA1 211.

Personal Recommendation System

Figure 55:
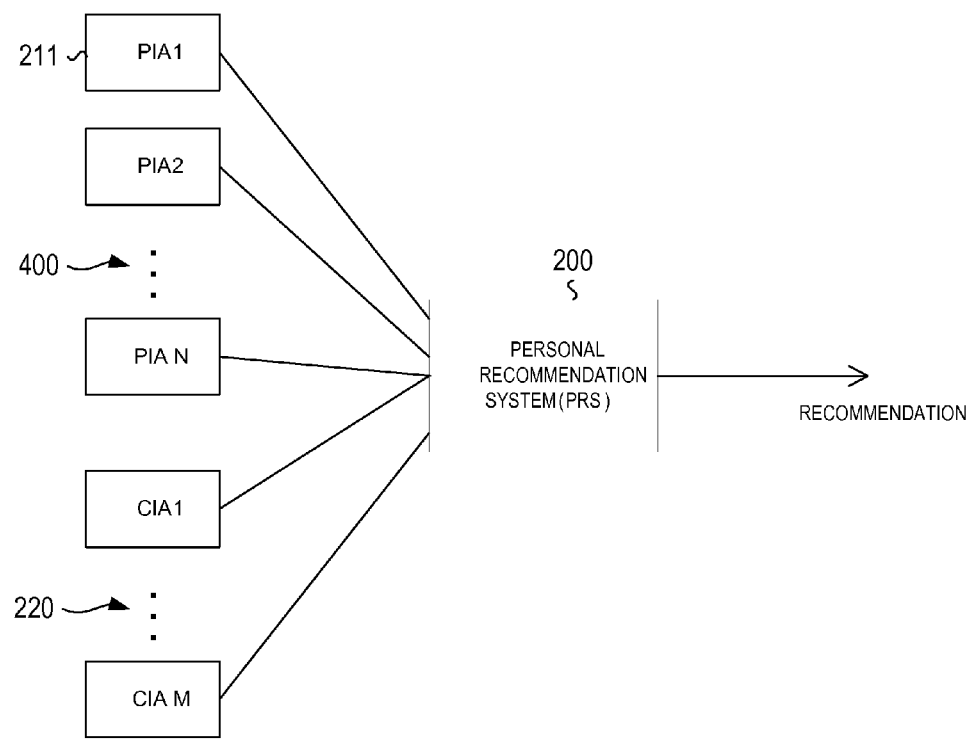
FIG. 55 is a block diagram of the PRS according to one embodiment of the present invention receiving information from PIAs and CIAs.

A personal recommendation system (PRS) provides a user with personalized recommendations based on information obtained from various sources, which may include a user's PIA, CIAs, and other PIAs. In FIG. 55, a user's PRS 200 receives information from the user's PIA 211, other persons' PIAs 400 and multiple CIAs 220, and generates personalized recommendations for the user based on that information.

In one embodiment, the PIAs 400 and CIAs 220 can be configured to generate output data feeds that contain only information associated with content items that users have viewed or listened to repeatedly (using, e.g., a particular threshold for the number of times) and to provide such output data feeds to the PRS 200.

The personalized recommendations may be in various areas which include entertainment (e.g., movies and music), news content, merchandise (e.g., consumer electronic devices), services, and service providers (e.g., restaurants, hotels, and insurance companies). The information on which the recommendations are based may be in various forms, e.g., content adoption statistics, weighted recommendations from others, etc. The user of the PRS 200 can be any person or group or other entity that wishes to obtain personalized recommendations. For example, a user of a PRS 200 might be a consumer who would like recommendations on audio players or a chess club seeking recommendations on setting up a web site for the club.

Figure 103:
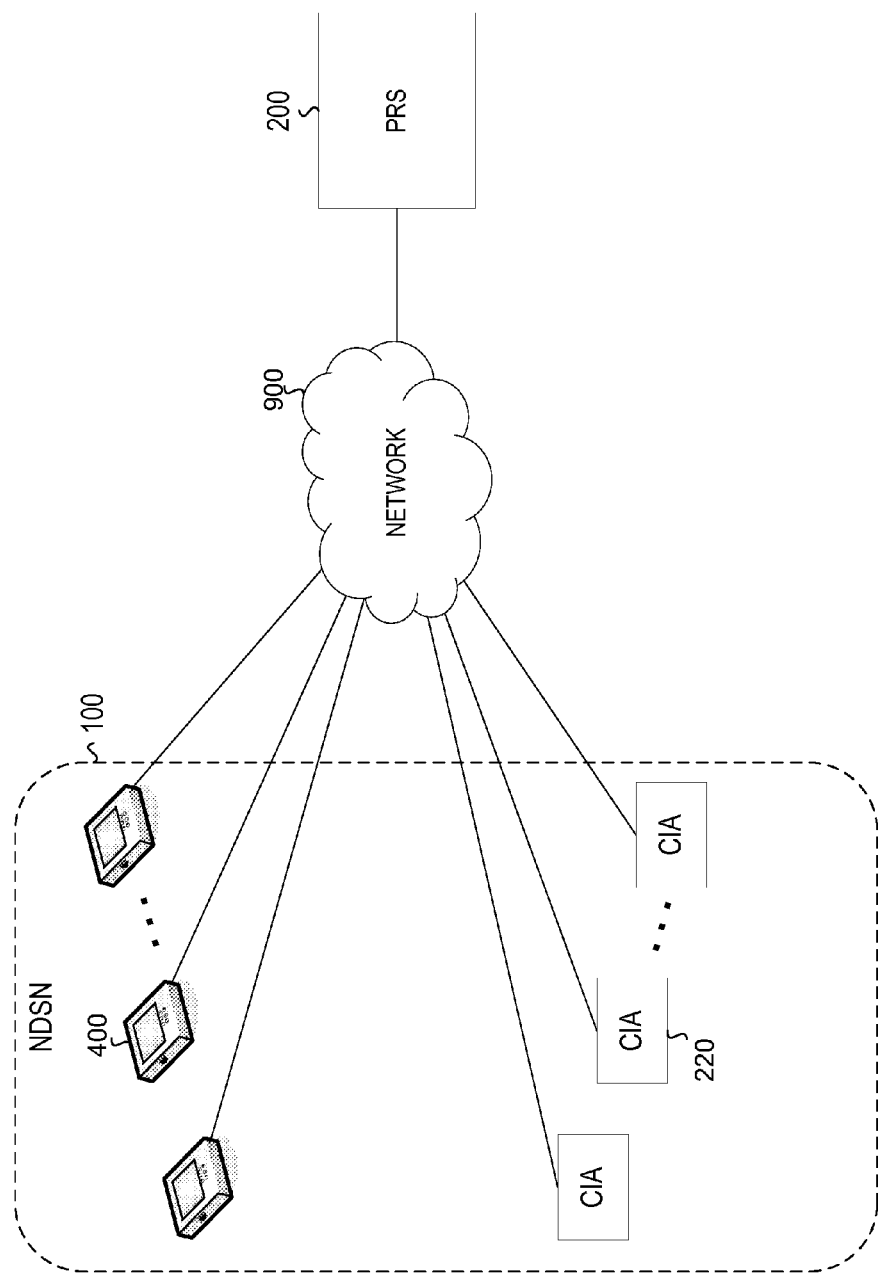
FIG. 103 is system diagram of the interconnection of the PRS and the NDSN according to one embodiment of the present invention.

The PRS 200 may also obtain information from the nodes of a social network. FIG. 103 illustrates an example of the PRS 200 connected by a network 900 to an NDSN 100 that includes PIAs 400 and CIAs 220. As described above, the NDSN 100 is based on peer-to-peer relationships between users and systems; in other embodiments, the PRS 200 obtains information from a social network that is of a centralized nature (e.g., MySpace.com). In the peer-to-peer social network, the nodes of the network are distributed, and the information regarding each node and its relationships with other nodes is distributed as well (since it resides in the nodes); in the centralized network, that information is contained within a centralized system, e.g., a bank of servers operated by the provider of the social network.

The PRS may use a recommendation engine for generating its personalized recommendations. Alternatively, the personalized recommendations may be generated though the use or application of a neural networks, weighted recommendations from other users or entities, weighted commitments of other users, PIAs, CIAs or the adoption statistics of an item for generating its personalized recommendation, as described in greater detail below.

The recommendations generated by the PRS are personalized in that the PRS bases its recommendations, at least in part, on the user's personal information. Personal information encompasses a broad array of types of information about a person's life, social interactions, health, consumer behavior, entertainment consumption, and other aspects of a person's world that can be reduced in any way to data. For example, the personal information of the user of a PRS might be obtained from the user's own PIA. Additionally or alternatively, the user's personal information may be obtained from a social network of which the user is a member.

As noted previously, the personalized recommendations generated by the PRS may be relevant to a variety of areas, including media content (e.g., videos, audio recordings, news broadcasts and articles) and products. Some of the information used to generate the personalized recommendations may be associated with content (e.g., content metadata or the adoption statistics associated with content items). There are numerous mechanisms that would make information about content accessible to the PRS, including: user tagging, labeling/marketing, search engine results, web site metadata, machine-generated tags, inferred information based upon location of the resource. The PRS may become aware of content through direct recommendation, adoption statistics, recommendation engine, and information aggregators (personal and community).

The PRS can gather information in various ways, including, but not limited to, analysis of data obtained from a PIA, "crawling", i.e., traversing, across a social network, and crawling the public Internet or private intranet. Web sites and other points on the network may contain information that can be useful for generating recommendations for the user. For example, a web site on the Internet might contain recommendations for content items (music, video, etc.) by persons that have similar demographics or consumption habits to those of the user.

A user's PIA may be utilized by the user's PRS as a source of information for generating personalized recommendations. For example, a user's past consumption habits and feedback that the user has provided regarding certain content, products, etc., may be available to the PRS from one or more of the PIA's data feeds. In addition, the PIA may be able to provide information to the PRS regarding the user's future consumption plans or preferences. For example, the user may be planning a vacation, and information obtained from the PIA regarding the vacation may be used by the PRS. In short, any personal data that is stored in a PIA may be utilized by the PRS to generate personalized recommendations.

Figure 59:
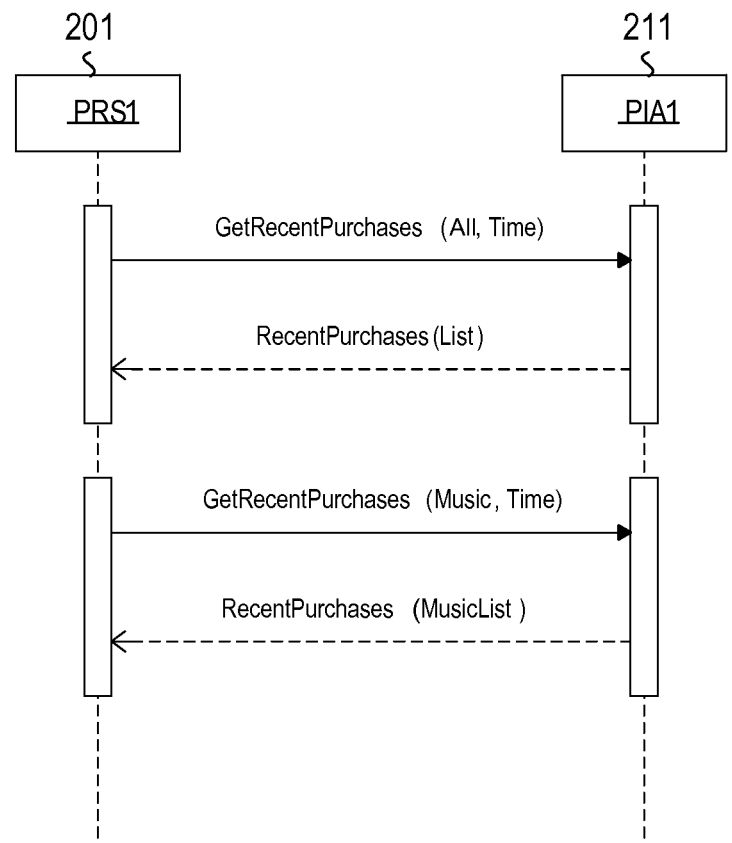
FIG. 59 is a sequence diagram associated with obtaining information from a PIA in accordance with one embodiment of the present invention.

Referring to FIG. 59, PRS1 201 queries PIA1 211 to obtain information that may be relevant to generating a personalized recommendation for the PRS's user (not shown) by sending a GetRecentPurchases message to PIA1 211 with an argument Time specifying the period of time for which recent purchases are sought. PIA1 211 responds by sending a RecentPurchases message to PRS1 201 with an argument List that contains a list of the user's recent purchases over the period of time specified by Time. The list contains a recent subscription to a series of symphony concerts, which suggests that the user may like classical music. Accordingly, PRS1 201 sends another GetRecentPurchases message to PIA1 211, this time with arguments Music and Time identifying the category of purchases and the period of time for which recent music purchases are sought. PIA1 211 responds by sending a RecentPurchases message to PRS1 201 with an argument MusicList that contains a list of the user's recent music purchases, which PRS1 201 can utilize to generate personalized recommendations to the user regarding music.

Those skilled in the art will recognize that the interactions employed to obtain information from PIA1 211 may be executed in a variety of ways not limited to the examples of FIG. 59. For example, in FIG. 59, the GetRecentPurchases message might not have the Time argument, but instead might have an associated default value for the time period.

A PRS may crawl, i.e., traverse the interconnected nodes of a NDSN, in order to obtain information to be used in generating a personalized recommendation for its user. As previously discussed, the nodes of an NDSN may contain information regarding the user's relationships with other members of the NDSN, the preferences, behaviors, commitments (described in more detail below) and user profiles of other members of the NDSN, and implicit and explicit recommendations from other members that may be used for generating recommendations that are targeted to the user of the PRS. In addition, the affinity between the user and other members of the NDSN or the degrees of separation between the user and other members of the NDSN may be taken into account by the PRS while generating recommendations.

Figure 46:
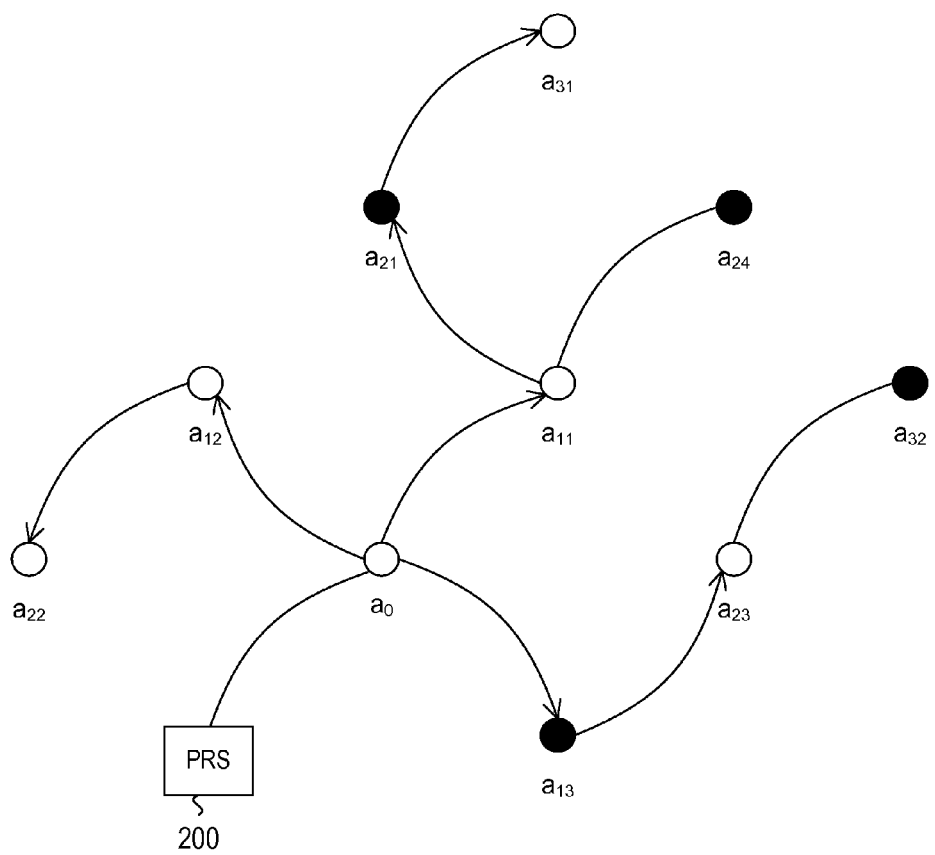
FIG. 46 is an example of the traversal of a projection of the NDSN of FIG. 43.

In order to generate a personalized recommendation for a user, the PRS might require a projection of the NDSN, for example, that includes only those nodes that have components in the dimensions of interest. The PRS traverses the projection of the NDSN to obtain information relevant to generating the recommendation. In the example of FIG. 46, a projection of the NDSN of FIG. 43 based on the Cooking dimension (not shown) includes nodes $a_0$, $a_{11}$, $a_{12}$, $a_{22}$, $a_{23}$ and $a_{31}$ (denoted by the open circles). The node associated with the user, $a_0$, has first-degree connections with nodes $a_{11}$ and $a_{12}$, second-degree connections with nodes $a_{22}$ and $a_{23}$, and a third-degree connection with node $a_{31}$. In order to generate a personalized recommendation based on the projection, the PRS 200, which has access to node $a_0$, traverses the projection (shown by arrows), starting at node $a_0$, and obtains information from each of the nodes in the projection.

Figure 86:
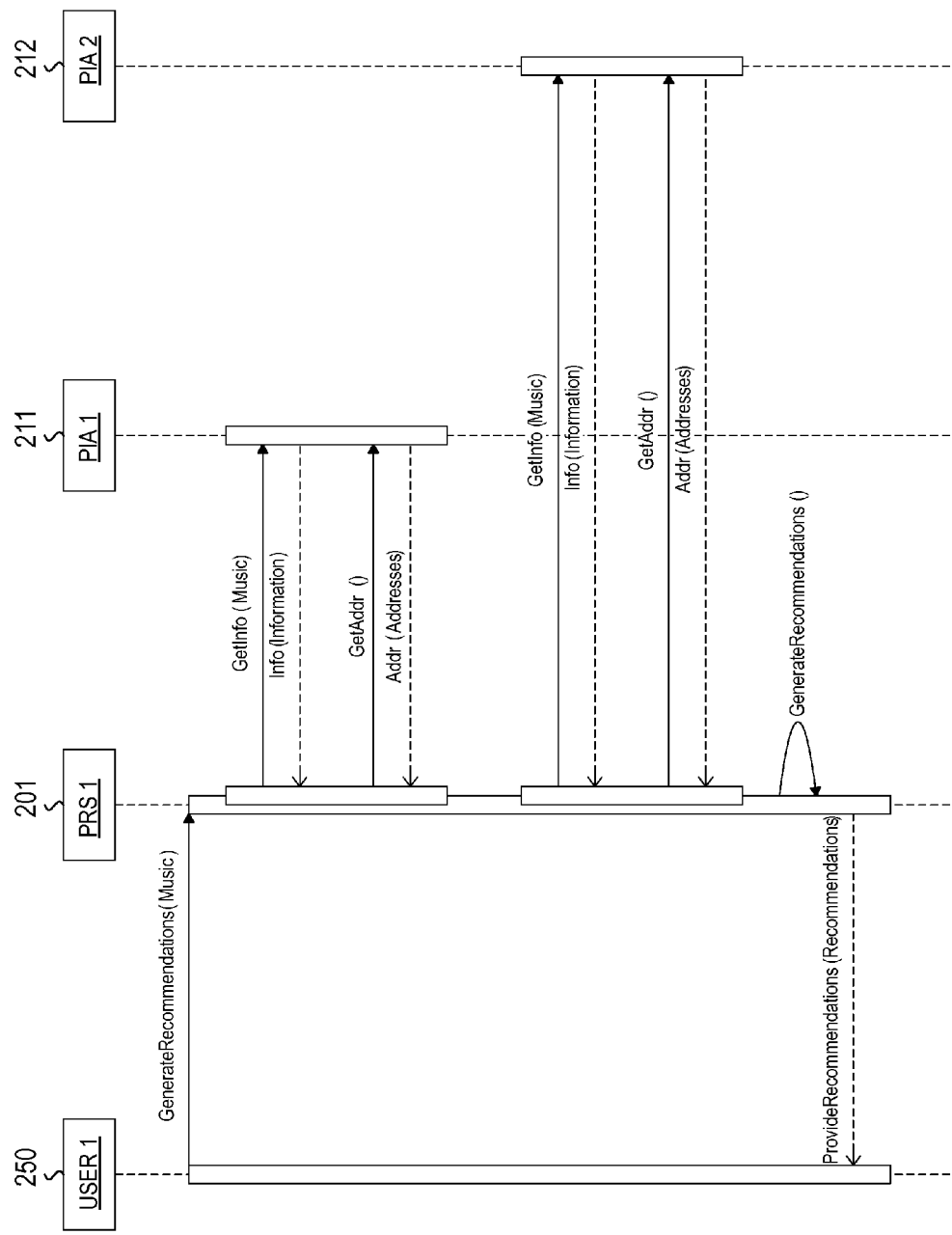
FIG. 86 is a sequence diagram associated with obtaining recommendations from a PRS in accordance with one embodiment of the present invention.

In FIG. 86, which illustrates another example of the PRS traversing a network of PIAs, User1 250 requests his PRS, PRS1 201 to generate recommendations for him regarding music by sending a GetRecommendations message to PRS1

201 with an argument Music specifying the category of recommendations. PRS1 201 utilizes a list (not shown) of PIAs that it knows to be members of the associated NDSN. This list may be generated by various techniques (not shown), e.g., by crawling the Internet or by storing the identities of PIAs that PRS1 201 has connected to in the past.

In the example of FIG. 86, the list of PIAs used by PRS1 201 includes PIA1 211. PRS1 201 obtains information regarding music from PIA1 211 by sending a GetInfo message to PIA1 211, with an argument Music specifying the category of information being requested. PIA1 211 responds by sending an Info message with an argument Information that contains a list of information regarding music.

To obtain the addresses of other PIAs to be queried, PRS1 201 sends a GetAddr message to PIA1 211. PIA1 211 responds by sending an Addr message to PIA1 211 with an argument Addresses that contains a list of addresses of other PIAs in the NDSN. In the example of FIG. 86, this list includes PIA2 212. As described above with respect to PIA1 211, PRS1 201 sends GetInfo and GetAddr messages to PIA2 212 and the other PIAs (not shown) on the list, and receives additional information and addresses from PIA2 212 and the other PIAs in response to those messages.

The iterative process of sending GetInfo and GetAddr messages may be repeated a number of times as determined by PRS1 201, after which PRS1 201 generates recommendations for User1 250 by sending itself a GenerateRecommendations message. Finally, PRS1 201 responds to User1 250 by sending a ProvideRecommendations message with an argument Recommendations containing personalized recommendations regarding music.

Those skilled in the art will recognize that the interactions employed to obtain information may be executed in a variety of ways not limited to the examples of FIG. 86. For example, in FIG. 86, the GetInfo and GetAddr messages might be combined into a single message, where the response to the combined message would contain both information and addresses.

Other mechanisms for providing information about content introduction to the PRS are to publish either self-published content or labeled, i.e., marketed, content. Although the information content introduction provided in such a case would likely be at least partially biased (since information about the same content might also be introduced provided due to user, i.e., non-labeled feedback), such bias could be mitigated by a full disclosure to a user of the content's labeling. For example, the user of the content would be informed that the information about the content was, at least in part, introduced provided due to its label.

Figure 58:
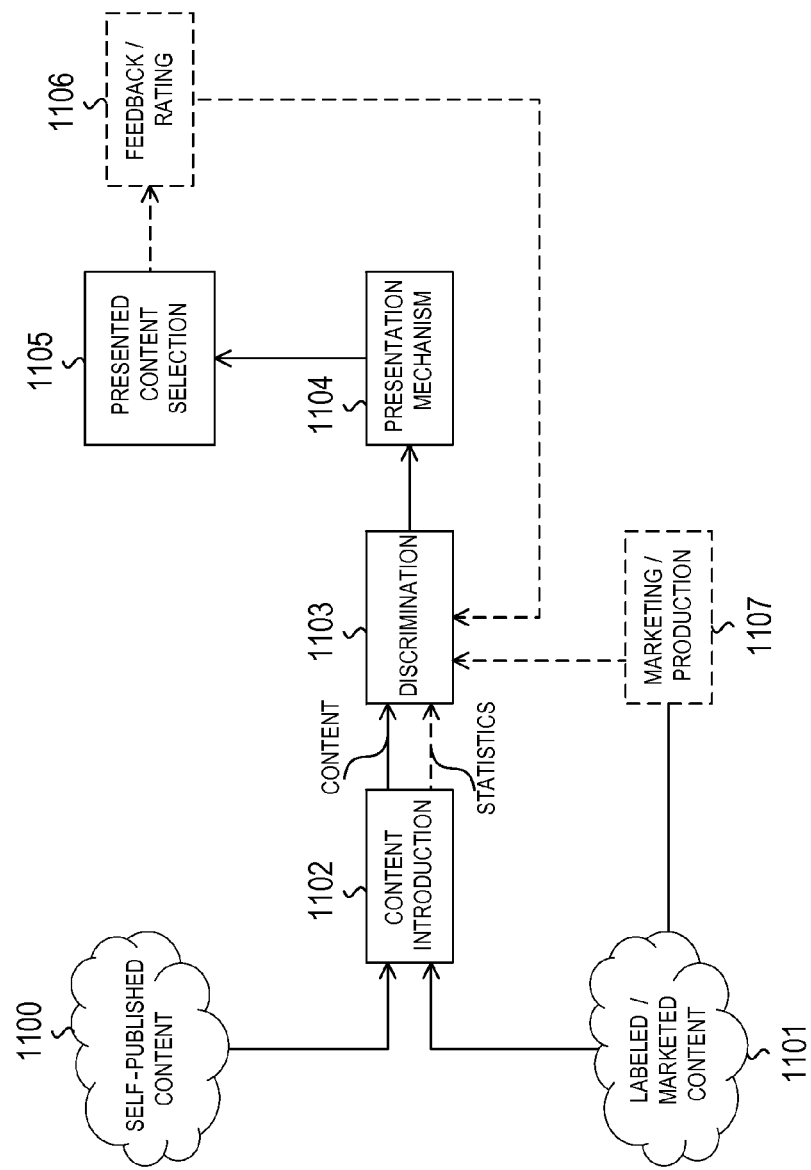
FIG. 58 is a block diagram of the PRS in accordance with one embodiment of the present invention.

Referring to FIG. 58, the PRS may utilize information about both self-published content 1100 and labeled/marketed published content 1101. Self-published content 1100 includes content developed by users, small groups (e.g., organizations, music bands), or other users or groups that develop creative content without the backing of sponsors or other corporate entities. Labeled/marketed published content 1101 includes content which is published/disseminated with the assistance of a label, publisher, content aggregator (e.g., record label, magazine, newspaper) or other entity that has access to a market of content consumers (users) based on their publications, marketing, labeling, and/or advertising.

Information about content is provided to a content introduction stage 1102, whereby users are made aware of the content through a variety of mechanisms, including, but not limited to, publication on a commercial portal for the interchange of video and audio information including portals with social networking functions, publication of content on individually operated websites, or simply through the dissemination of links such as Uniform Resource Locators (URLs) indicating the availability of the published content. The reporting of the availability of self-published content 1100 can also be accomplished by publication of the content links on blogs, newsletters, social networking sites, instant messaging, dissemination of e-mails containing link information, or other electronic, written, or verbal communications indicating the availability of the content to the public or select groups. Information regarding labeled/marketed published content 1101 can be provided to the PRS through a variety of mechanisms, including but not limited to, publication of the availability of content in the label's catalog, promotional tours, advertising, or other promotions of the content and/or creators of the content. For published materials such as editorials, news articles (including audio podcasts and video news reports) and other editorialized content such as content which has been produced with editorialization/supervision, (e.g., because it is associated with a brand or publication), information regarding content can be provided to the PRS by publication of the content in a sponsored broadcast or publication such as a news program, newspaper, or magazine (electronic or printed) carrying a particular brand name.

Table 2 provides examples of some of the possible mechanisms (single source, multiple source, distribution, and marketing, advertising or promotion) for providing information about content to the Internet or to nodes of a social network for both self-published (i.e., user-produced) and labeled (i.e., sponsored, produced or editorialized) content.

TABLE 2

| | CONTENT TYPE | |
|---|---|---|
| MECHANISM | SPONSORED/PRODUCED/ EDITORIALIZED | USER PRODUCED |
| Single Source | From a single server or source (e.g., corporate music site, YouTube, printed or electronic publication); allow access to interested users/nodes. | From a single server or source (e.g., uploading to social network, communication portal such as YouTube, publication on a blog); allow access to interested users/nodes. |
| Multiple Source | From a plurality of servers or sources; allow access to interested users/nodes. | From a plurality of servers or sources; allow access to interested users/nodes. |
| Distribution | Distribution of content (electronic links or physically recorded content) to distributors such as vendors or a plurality of publishers | Distribution of content (electronic links or physically recorded) to distributors such as bloggers or self-publishers |

TABLE 2-continued

| | CONTENT TYPE | |
|---|---|---|
| MECHANISM | SPONSORED/PRODUCED/ EDITORIALIZED | USER PRODUCED |
| | that are accessed by users/nodes and which maintain the content in their catalog. | that are accessed by users/nodes and which maintain the content in their catalog. |
| Marketing/ Advertising/ Promotion | Sponsored tours, advertising, appearances, and e-mail campaigns that raise awareness of the content and which increase the number of users/nodes into which the content is introduced. | Viral marketing, recommendations, blogging, and other user/creator initiated interactions that disseminate the content or that increase the number of users/nodes into which the content is introduced. |

An electronic program guide (EPG) is another source of information that can be utilized by the PRS for generating personalized recommendations. An EPG may be accessible by the PRS over the Internet, e.g., at TitanTV.com. The user of the PRS may have created a customized EPG on such a website, and thus, the user's PRS may obtain information from the EPG website regarding the content that is available to the user based on his location, and the user's viewing habits and preferences.

Individual users may provide information about content by tagging particular content items that they have enjoyed or found interesting. A user who tags content might remain anonymous to other users, or might be identified to all or a subset of other users. Alternatively, a user who tags content might only be identified by anonymous, i.e., not personally-identifiable, information, so that a person or system considering the tagged content would know the demographic profile of the "tagger", but would not be able to specifically identify the tagger.

Another possible mechanism for providing information about content to the PRS is by the direct recommendation, from one contact to another, of a content item. In this mechanism, a user makes the decision to recommend a particular item to another user based on personal knowledge of the likes and tastes of the other user.

Monitoring adoption statistics within a social network is another possible mechanism for providing information about content to the PRS. As awareness of a particular content item moves through a social network, by direct or indirect recommendation between users, its adoption rate can be tracked and used to determine if a content item should be introduced to the user of a particular PRS. The adoption statistics might be tracked separately for each of a number of demographic groups. For example, females between the ages of 10 and 13 might be spreading the word, through the social network, about a song performed by a new band. When a threshold for the number of users in that demographic group with positive opinions about that song has been exceeded, then the information about the content, i.e., the song, would be provided to the PRS. Alternatively, or in combination, the rate of adoption within that demographic group might also be used as a criterion for providing information about content to the PRS. Similarly, adoption amongst those directly or indirectly connected via a particular subset of dimensions of a multidimensional social network may also be used as an indicator for potential recommendation to the user.

A user's PIA may also contain the information that defines a subset of the social network in the context of the user. For example, a PIA may contain information that identifies a user's first-degree contacts and the nature of the relationship (e.g., friend, professional, etc.) between the user and each contact. A CIA could be used in a similar manner, as a CIA contains the social network context information regarding the community. In this way, a set of PIAs and CIAs form a "virtual" social network which is distributed and operates on a peer-to-peer basis.

Figure 54:
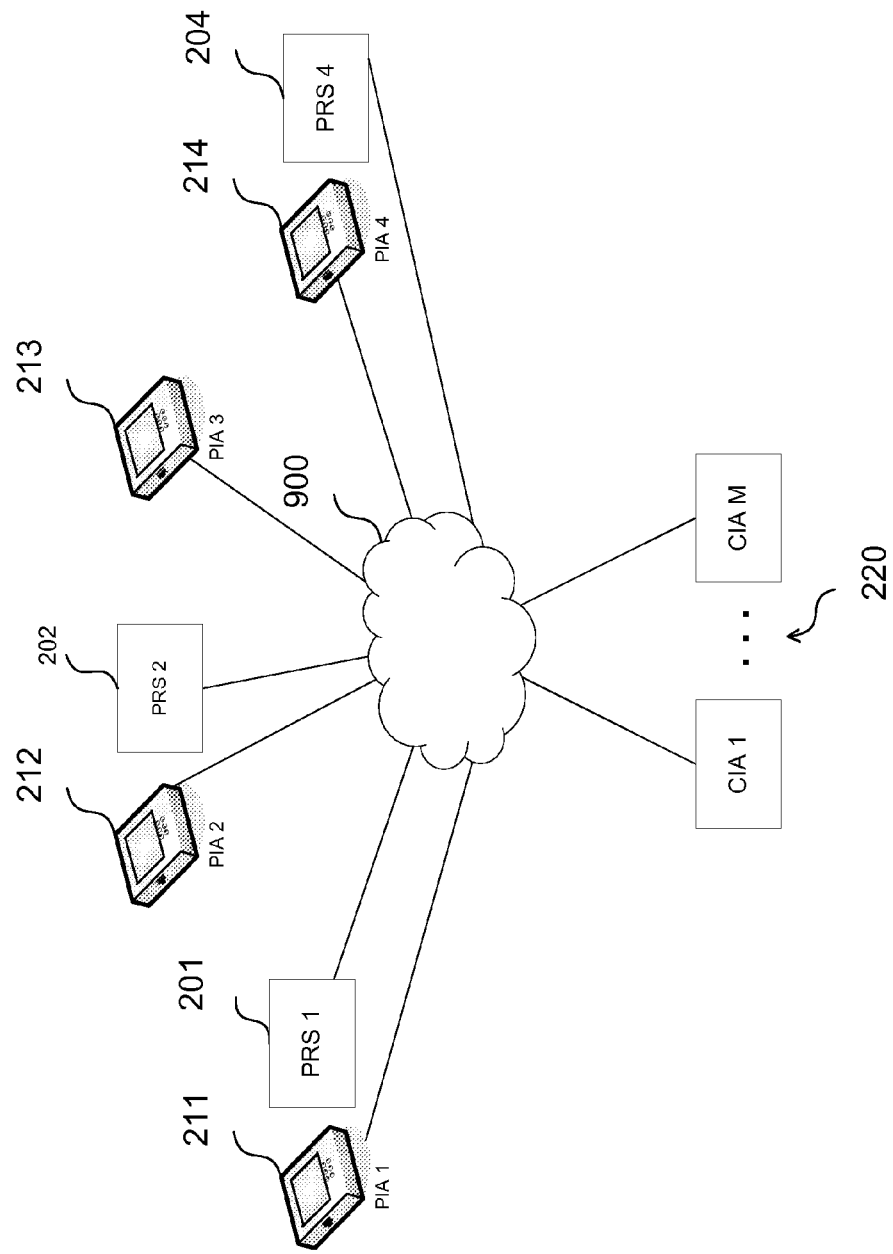
FIG. 54 is a system diagram of the interconnection of personal recommendation systems (PRSs), PIAs and community information aggregators (CIAs) according to one embodiment of the present invention.

FIGS. 54-57 illustrate examples in which multiple PRSs, PIAs and CIAs are interconnected. In FIG. 54, each of four users (not shown), User 1, User 2, User 3 and User 4, has a personal information aggregator, PIA1 211, PIA2 212, PIA3 213 and PIA4 214, respectively. In addition, three of the users, User 1, User2 and User 4 have personal recommendation systems, PRS1 201, PRS2 202 and PRS4 204, respectively; User 3 does not have a PRS. The PIAs and PRSs, as well as a number of CIAs 220, are interconnected through a computer network 900, forming a distributed, peer-to-peer social network.

Figure 56:
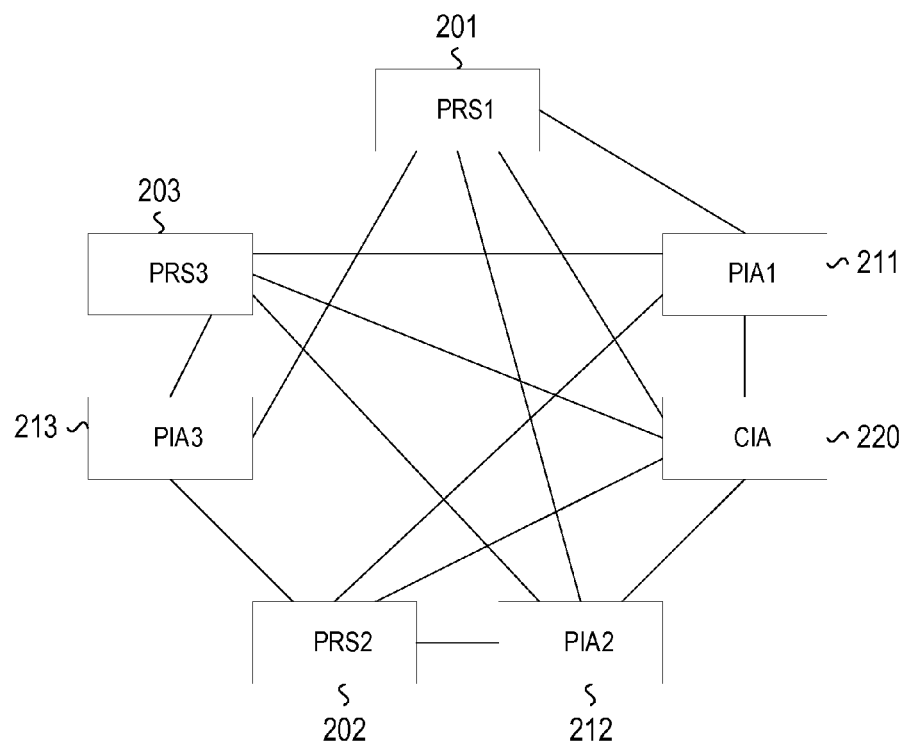
FIG. 56 is a system diagram of the interconnection of PRSs, PIAs and CIAs according to one embodiment of the present invention.

FIG. 56 illustrates an example in which the PRSs and PIAs of three users are interconnected. The PRS belonging to each user obtains its data from its user's PIA, the PIAs of the other two users, and a CIA which obtains its data from the PIAs belonging to its two members. For example, PRS1 201, which belongs to User 1 (not shown) obtains information from PIA1 211 (which belongs to User 1), and PIA2 212 and PIA3 213, which belong, respectively, to User 2 and User 3 (not shown). In addition, PRS1 201 obtains aggregated community information from the CIA 220, which obtains its information from PIA1 211 and PIA2 212.

Figure 57:
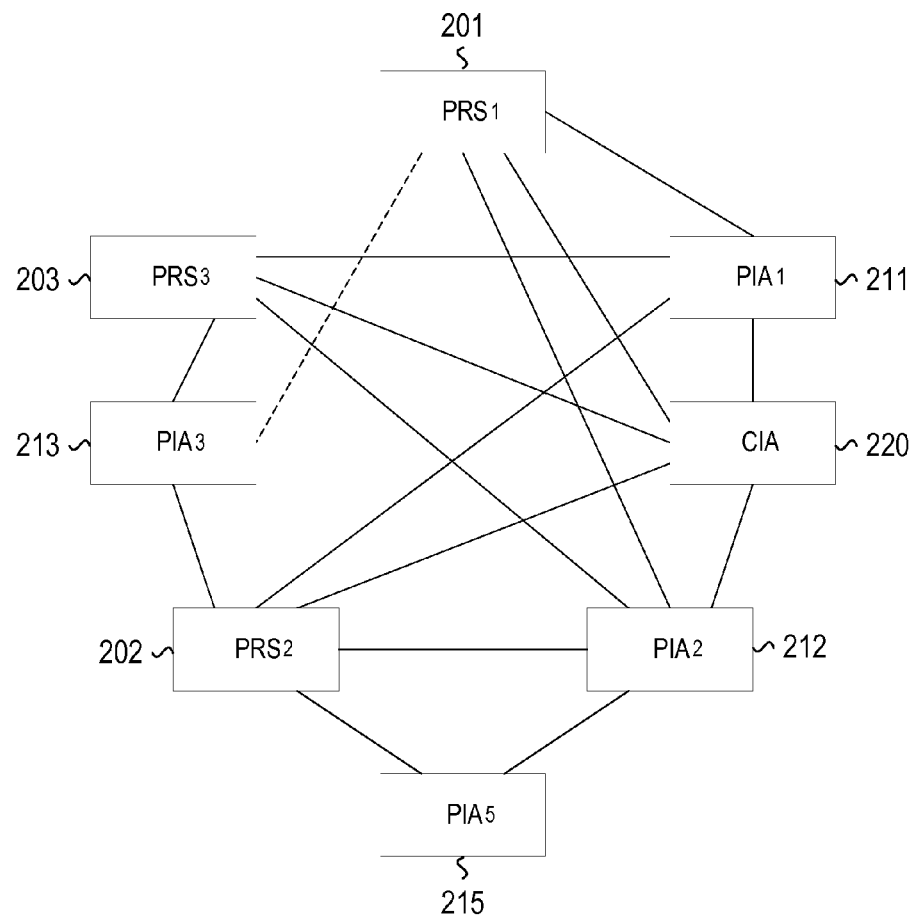
FIG. 57 is a system diagram of the interconnection of PRSs, PIAs and CIAs in an NDSN according to one embodiment of the present invention.

Referring to FIG. 57, in some cases only a subset of the connections between the PRS and PIAs will be traversed based on the applicability of those connections to the nature of the personalized recommendations generated by the PRS. For example, a PRS generating a personalized recommendation for a user regarding music selections might only need to obtain information from the PIAs of persons in the social network that had music preferences that were similar to those of the user.

In FIG. 57, User 1 (not shown) has similar music preferences to those of User 2 (not shown) and to those of the community of users (not shown) associated with the CIA 220, but not to those of User 3 (not shown). Thus, to generate personalized recommendations regarding music for User 1, PRS1 201 incorporates information from PIA1 211, PIA2 212 and the CIA 220, but not from PIA3 213.

In addition, the PRS may traverse connections from one PIA to another PIA to which a direct connection is not already established. This allows the PRS to incorporate data from PIAs with two or more degrees of separation into the recommendation process. Data from such indirectly-connected PIAs may be given lower weight in some embodiments during creation of the recommendation. For example, in FIG. 57, PIA5 215 belongs to User 5 (not shown), who has a first-degree connection to User 2. PRS2 202, which belongs to User 2, incorporates information from PIA5 into the personalized recommendations that it generates for User 2. In addition, PRS1 201 and PRS3 203 each are able to incorporate information from PIA5 215 into their recommendations, due to their indirect connections to PIA5 215 through PIA2 212.

While a CIA may, as noted above, be used to provide information to the PRS, there are also numerous examples of less complex systems that may be used to provide community information to a PRS. For example, one or more weblog ("blog") Internet sites which encompass specific communities of users with common interests (e.g., hobbies, professions, politics, entertainment, etc.) could provide such information. In addition, information provided to the PRS could be obtained from Internet sites devoted to the presentation of popular content, such as YouTube.com™ (video), Upto11.net (music) and digg.com (which has separate communities for technology, science, world & business, sports, videos, entertainment and gaming).

The PRS discriminates the obtained content, by which the appropriateness of the content for a particular user is determined. The discrimination stage 1103 within the PRS uses a variety of mechanisms for choosing the particular content that will be presented to a user, including use of weighted recommendations, a recommendation engine, and a neural network, and adoption statistics.

Weighted recommendations may be used in the process of choosing content, since the recommendations of certain users, demographic groups or labelers might not all be considered to be equal. Weighting might be applied in the discrimination stage in order to reflect the relative importance of each recommender. For example, the recommendations of people that earn more than $70,000 and live in Anchorage might be given a higher weight than recommendations from Sony. As another example, the degree of affinity or similarity in interests between users might be used to weight a user's recommendation.

Similarity refers to the extent to which a user believes that another user has similar interests. For example, a user who has several siblings in their social network may attribute a high degree of affinity to those users, although it may be the case that only a small subset of those siblings have interests or tastes that are highly aligned with the user and as such only a few of the siblings may have a high degree of similarity with the user.

Figure 47:
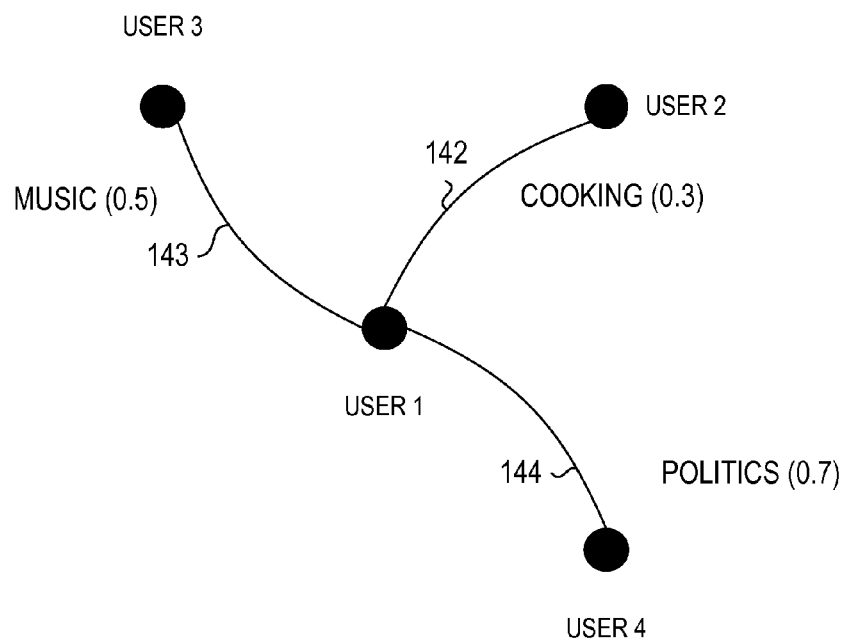
FIG. 47 is an example of weighting information obtained from the NDSN in accordance with one embodiment of the present invention.

In one embodiment, the PRS weights information obtained from a node in an NDSN according to the dimension of the relationship between the node and the node of the PRS user. The personalized recommendations generated by the PRS would thus be influenced by the nature of the dimensions associated with the relationships between two users. In the example of FIG. 47, User 1 has a Cooking relationship 142 with User 2, a Music relationship 143 with User 3, and a Politics relationship 144 with User 4. In order to generate recommendations for User 1, the PRS (not shown) weights information obtained from the Cooking relationship 142 by a factor of 0.3, information obtained from the Music relationship 143 by a factor of 0.5, and information obtained from the Politics relationship 144 by a factor of 0.7. Thus, the recommendations generated by the PRS for User 1 are most strongly influenced by users with whom he has a Politics relationship (User 4), less strongly influenced by users with whom he has a Music relationship (User 3), and least strongly influenced by users with whom he has a Cooking relationship (User 2).

Figure 48:
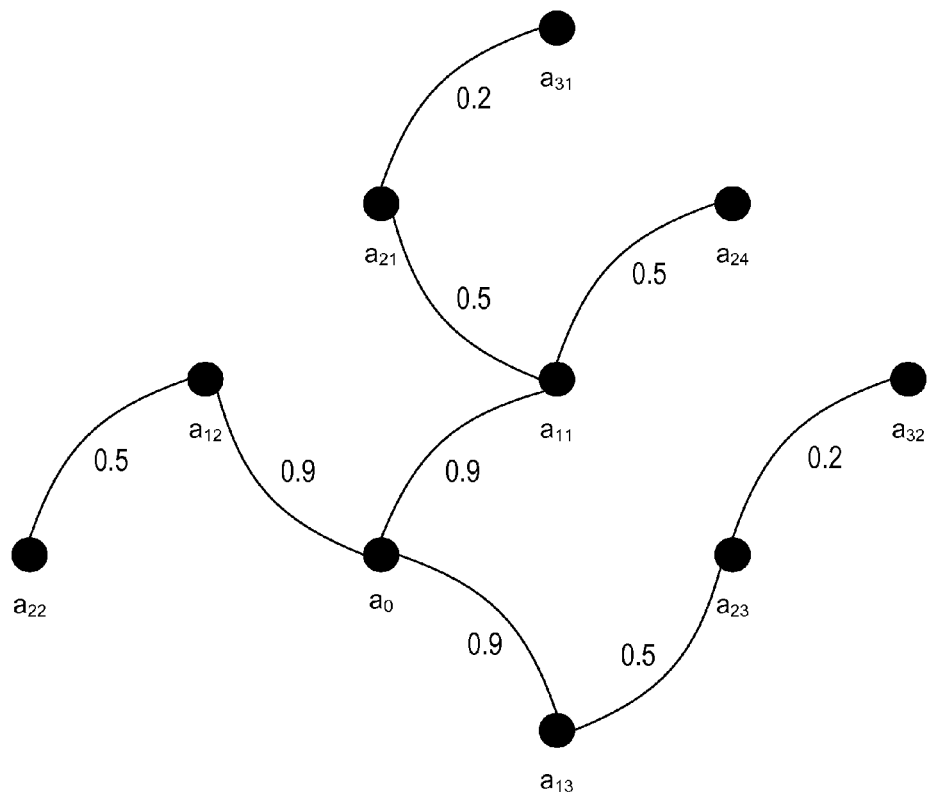
FIG. 48 is an example of weighting information obtained from the NDSN of FIG. 43.

In one embodiment, the PRS weights information obtained from a node in an NDSN according to the degree of separation between the node and the node of the PRS user. This would allow, for example, the PRS to more strongly weight information obtained from "nearby" (in terms of separation) nodes. In the example of FIG. 48, information obtained from first-degree nodes (with respect to the user's node $a_0$) is weighted by a factor of 0.9, information obtained from second-degree nodes by a factor of 0.5, and information obtained from third-degree nodes by a factor of 0.2. Thus, the recommendations generated by the PRS for the user associated with node $a_0$ are most strongly influenced by users associated with first-degree nodes, less strongly influenced by users associated with second-degree nodes, and least strongly influenced by users associated with third-degree nodes.

Figure 49:
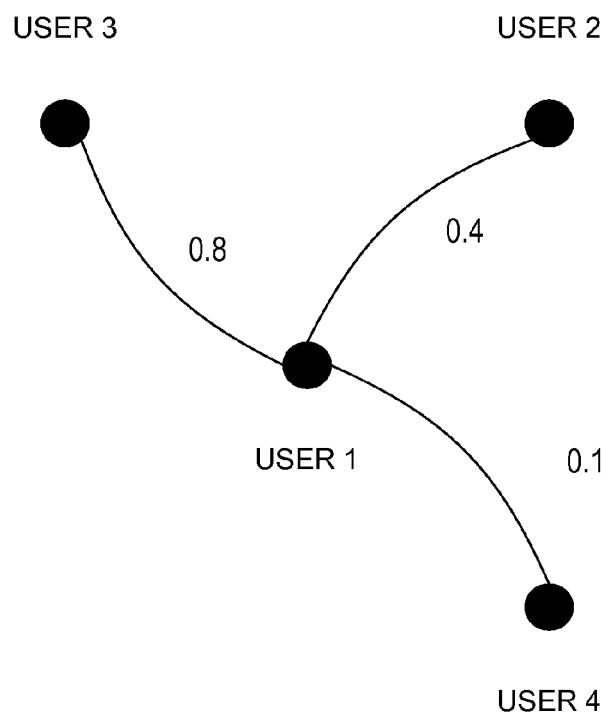
FIG. 49 is an example of weighting information obtained from the NDSN in accordance with one embodiment of the present invention.

In one embodiment, the PRS weights information obtained from a node in an NDSN according to the level of affinity between the node and the node of the PRS user. This would allow, for example, the PRS to more strongly weight information obtained from nodes of users that are more trusted by, or aligned with, the user of the PRS. In the example of FIG. 49, the level of trust between User 1 and User 2 is 0.4, the level of trust between User 1 and User 3 is 0.8, and the level of trust between User 1 and User 4 is 0.1. Thus, the recommendations generated by the PRS for User 1 are most strongly influenced by User 3, less strongly influenced by User 2, and least strongly influenced by User 4.

Those skilled in the art will recognize that the action of weighting the information from the nodes can be accomplished by using a variety of algorithms, and is not limited by the algorithm in the example of FIGS. 46-49.

In one embodiment, a user's PRS receives recommendations for a content item from one or more of the user's contacts or indirect contacts within a social network. The PRS weights each recommendation based on the affinity, similarity of interests and number of degrees of separation between the user and each contact, calculates a sum of the weighted recommendations, and generates a recommendation of the content item to the user, based on the value of the summed recommendations (e.g., if the sum exceeds a given threshold).

Figure 61:
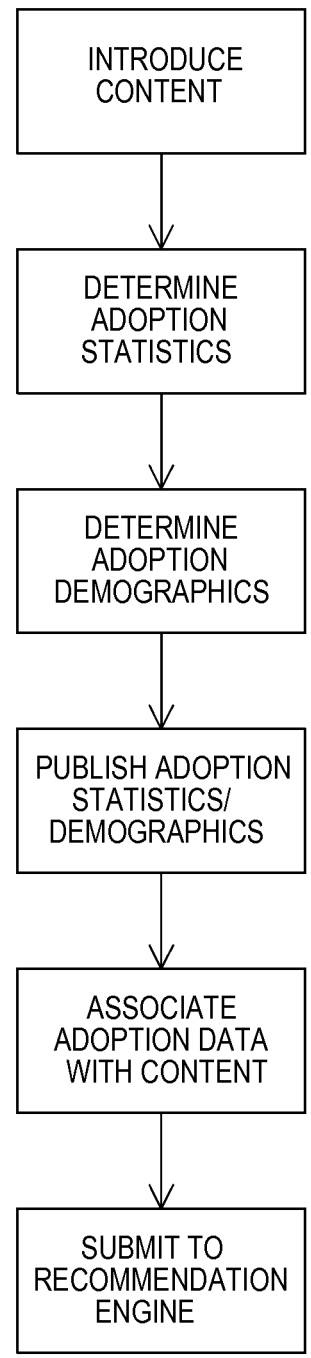
FIG. 61 is a flowchart for a portion of the PRS, in accordance with one embodiment of the present invention.

The output of a recommendation engine might also be used in the discrimination process to select certain content for presentation (i.e., to generate personalized recommendations) to a user. Referring to FIG. 61, in one embodiment, information about content is introduced, the adoption statistics and demographics of the content are determined, combined with the demographics of the adopters (not shown), and published in a manner such that they can be readily associated with the content. Using this method the adoption data (adoption statistics and adoption demographics) can be submitted to and utilized by a recommendation engine. For example, the recommendation engine might use the submitted adoption parameters for generating a recommendation when one or more of the adoption parameters exceed a corresponding threshold.

There are a number of different types of recommendation engines, and each type might be useful for introducing information about content to the PRS. For example, a non-personalized recommendation engine might recommend a content item due to its averaged popularity with multiple users, without regard to the demographic profiles of the users. As another example, a collaborative recommendation engine might recommend a content item to a particular demographic group due to the content item's popularity with users with the same, or similar, demographic profiles. The outputs of the recommendation engines in these examples, as well as the output of other types of recommendation engines, e.g., item-to-item, attribute-based or content-based, may be used to select content for introduction to a content filtering system. Recommendation engines that employ attribute-based and collaborative filtering methods are generally known in the art, and a description thereof is omitted here for convenience only and should not be considered limiting.

Typical examples of recommendation engine types that might be used by the PRS include: attribute-based and collaborative filtering. When used by the PRS, an attribute-based recommendation engine uses content attributes to identify content items that might be suitable for a particular user based on his or her demographic profile, and uses adoption statistics to select the most popular content for recommendation to the user.

A collaborative filtering based recommendation engine used by the PRS identifies content items that might be suitable for the user based on the demographic profiles of the user and other users, and uses adoption statistics to select the most popular content for recommendation to the user.

As an extension to weighted recommendations, a neural network may be used in the discrimination process. Neural networks are generally known in the art, and a detailed description thereof is omitted here for convenience only and should not be considered limiting. In some cases, the weights applied to inputs used by a neural network are computed through a process of "learning", which occurs in a training session before the neural network is placed into operation. Other, more advanced, neural networks use a feedback mechanism to continuously learn, i.e., adjust the weights, during operation.

A neural network may be used to choose content items by feeding recommendations for a particular content item from various sources into the inputs of the neural network. If for example, the weighted sum of recommendations computed by the neural network exceeds a certain number, then the output of the neural network would be non-zero and would indicate that the content item has been chosen for presentation to the users.

Figure 64:
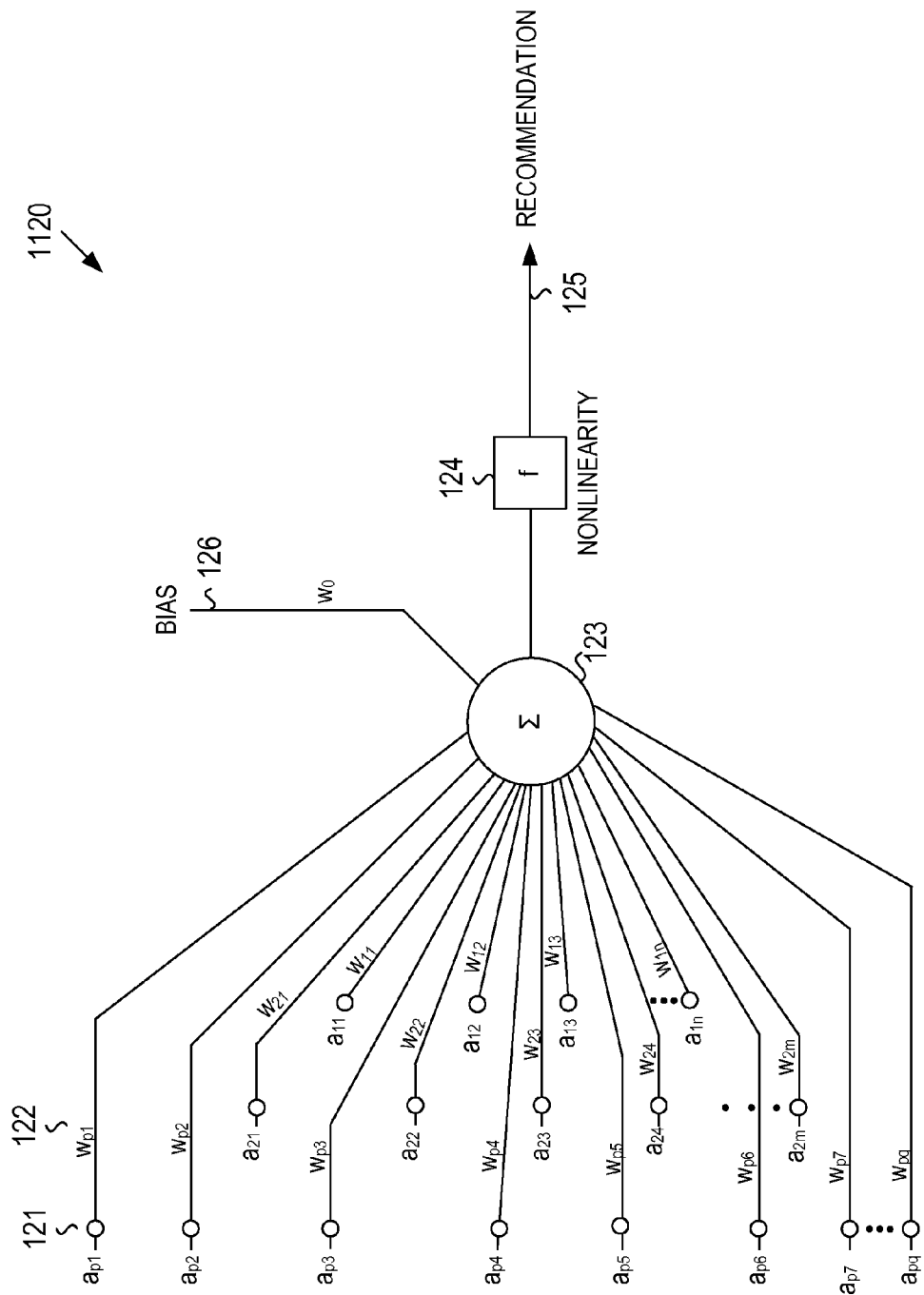
FIG. 64 illustrates an example of a neural network in accordance with one embodiment of the present invention.

Referring to FIG. 64, a single neuron 120 in a neural network is depicted; the neural network includes many such neurons that are interconnected. In this embodiment, recommendations 121 from other users within the social network of the user are used as inputs to the neuron and are multiplied by associated weights ($w_{xz}$) 122. The resulting products and a bias value ($w_0$) 126 are summed in a summing unit 123, and nonlinearly transformed by a function unit (f) 124 to provide a recommendation 125. As will be understood by those skilled in the art, a variety of values for the bias 126 and weights 122, and a variety of nonlinear functions, can be used in the creation of the social-neural network. The values of the bias 126 and the weights 122 can be selected (i.e. the network can be trained) in a variety of ways.

The nonlinear function unit (f) 124 depicted in FIG. 64 may perform one of many nonlinear functions; one of the most commonly-used nonlinear functions is the unit step function, which has a value of zero for inputs less than zero, and a value of one for inputs greater than or equal to zero. A neuron which uses a unit step for its nonlinear f function is well-known as a "perceptron." Other well-known nonlinear functions that are used for a neuron's f function include the sigmoid and the hyperbolic tangent (tanh).

There are a number of well-known architectures (not shown) for interconnecting the individual neurons of a neural network, and any of these may be used in conjunction with a social network and the PRS described herein. Regardless of the specific architecture, most neural networks can be considered to be composed of one or "layers" of neurons. The neurons in the first layer, known as the input layer, are connected to the external inputs of the neural network. The neurons in the last layer, known as the output layer, are similarly connected to the external outputs of the network. In between the input and output layers, there might be one or more "hidden" layers of neurons, in which the neurons are only connected to other neurons within the network.

One of the most commonly-used architectures is the feed-forward (FF) network. In a feed-forward neural network, which is also known as a "multi-layer perceptron" network, the data flows "forward" from input to output, passing through the hidden layers (if there are any). The nonlinear function f in a feed-forward network is commonly chosen to be the sigmoid, which is given by the equation $1/(1+e^{-x})$. The sigmoid is similar to the unit step in that its minimum and maximum values are zero and one, respectively. The sigmoid, however, unlike the unit step, has a simple and continuous derivative, which is more amenable to certain types of learning algorithms.

There are several well-known methods for training a neural network (i.e., selecting the values of the bias 126 and weights 122); one of the most common of these is "supervised learning." In one embodiment using supervised learning, the user provides explicit feedback (not shown) indicating the correctness of the recommendations; this feedback is considered to be the target (i.e. desired) output (i.e. recommendation 125) of the neural network. The error (i.e. difference) between the actual output of the neural network and the target output is calculated, and the weights 122 and the bias ($w_0$) 126 are adjusted according to the error value. In an alternate embodiment, implicit feedback is utilized to train the network to the user's preferences.

As will be understood by those skilled in the art, the recommendations correspond to particular items of content, or in some instances, to very closely related content (e.g., content from a particular creator or group, or content that is in a very closely related genre). Recommendations (explicit or implicit) from users are only applied to the neural network in conjunction with like recommendations. As such, the social-neural network is queried with respect to individual pieces of content or closely related content to determine how many recommendations exist for that particular piece of content or closely related group.

Recommendations from users of different degrees of separation in the social network (represented by $a_{yz}$ in FIG. 64) can be explicit and based on a user in a social network providing an explicit recommendation to other users or a group of users within their social network, or can be implicit and based on their own content consumption habits. For example, the fact that a particular user consistently reads technology articles in The Economist may form the basis for an implicit recommendation from that user to another user within their social network. In one embodiment, shared personal information is used as the basis for recommendations. In this embodiment, a user specifically authorizes the use of their personal information and allows details of their content consumption characteristics to be shared within the social network in order to participate in the recommendation process. Although the details of their content consumption may be shared within the social network, other users are, generally speaking, unable to see the actual content consumption data of the user contributing their content consumption data.

Figure 65:
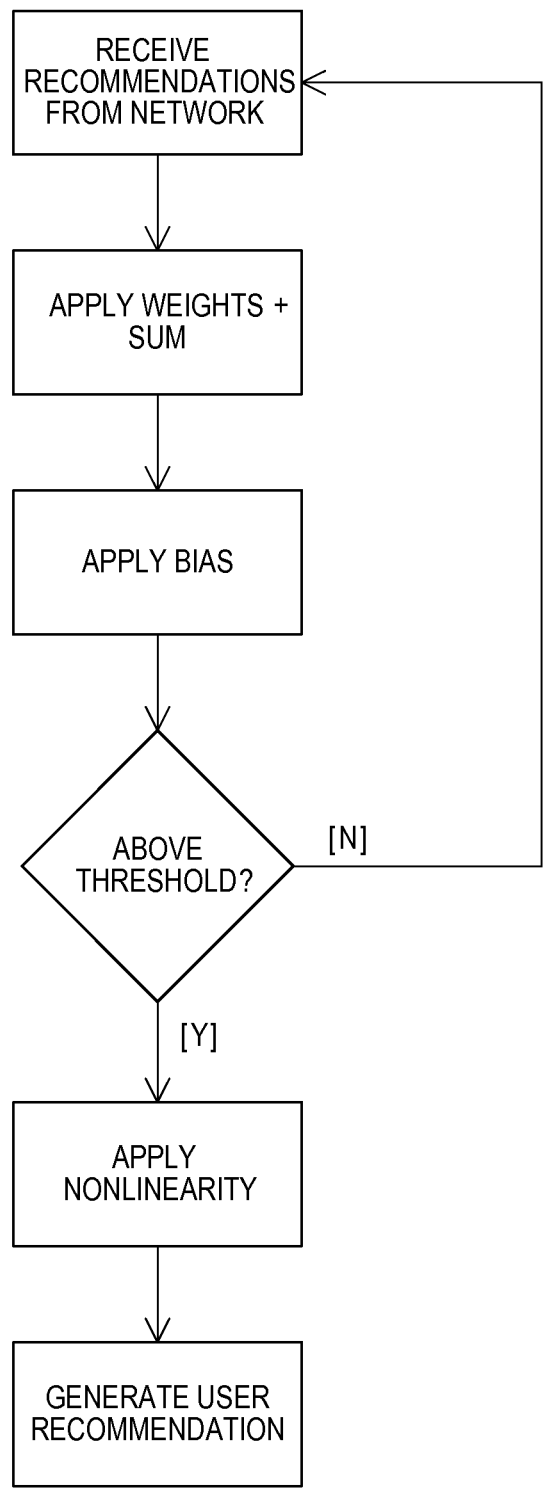
FIG. 65 is a flowchart for a social-neural network aspect of a PRS in accordance with one embodiment of the present invention.

Referring to FIG. 65, in one embodiment, recommendations are received from the network, weights are applied, a bias is applied as required, a threshold is applied to determine if the recommendation for a particular item is strong enough to proceed, a nonlinearity is performed to determine the final strength of the recommendation, and the recommendation is generated.

Adoption statistics may also be used in the discrimination process. For example, if an adoption statistic for a certain content item exceeded a specific threshold then the discrimination stage would select that content item for presentation to the users.

In one embodiment, as the PRS traverses an N-dimensional social network, it determines the number of social network members with sufficient affinity or similarity to the user that have adopted a particular content item. If the number of such adopters exceeds a threshold, the PRS recommends the content item to the user. Alternatively, content that is being adopted very rapidly, but which is not receiving high ratings or which is not selling well, may be filtered out by the PRS.

In FIG. 58, the content, or a reference to the content, is passed onto the discrimination unit 1103 along with relevant statistics. These statistics can include, but are not limited to, adoption and recommendation statistics, intended audience demographics, actual audience demographics, and other parameters which provide an indication as to the reaction of the general public (or select subgroups) to the content. In one embodiment the content includes metadata describing aspects of the data such as intended audience demographic, genre, creator data, or other content relevant information; in another embodiment the metadata is passed to the discrimination unit 1103 separately from the content. In one embodiment the statistics are carried along with the content. In an alternate embodiment content information and statistics are reported separately.

Figure 63:
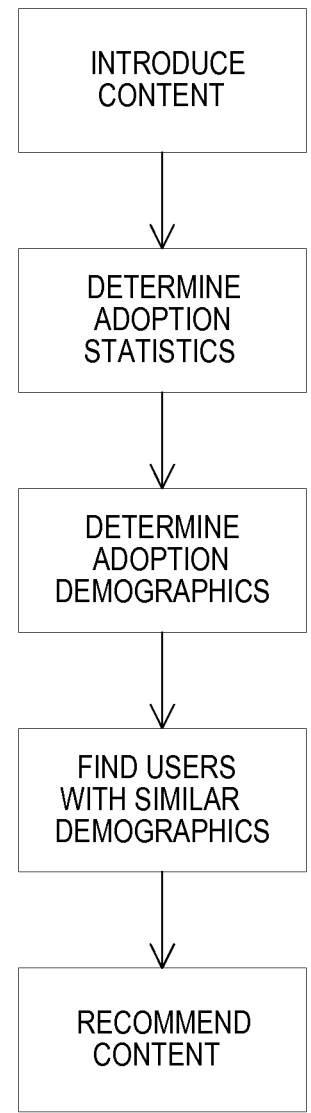
FIG. 63 is a flowchart for selecting content for a PRS in accordance with one embodiment of the present invention.

Referring to FIG. 63, content for a user may be selected without relying on a recommendation engine, but instead using adoption statistics, adoption demographics, adoption preferences (not shown), and adoption behaviors (not shown) with matching of the demographics, preferences and behaviors of the user to match content to the user. Thus, content is introduced and its adoption statistics are determined and monitored, along with the demographics, preferences and behaviors of the adopters to find rapidly adopted content. Adopters with similar demographics, preferences and behaviors to the user are used as the basis for identifying the rapidly adopted content that should be recommended to the user. Preferences and behaviors can include, but are not limited to, listening and reading preferences. In one embodiment, content such as rapidly adopted music is identified, and if it is determined that the demographics and preferences of the population adopting the music is sufficiently similar to the user (e.g., male, 12+ years of education, preferences for jazz and rock), the rapidly adopted content will be presented to the user.

It should be noted that content does not necessarily need to be new to be introduced and to have adoption statistics. In some instances "old" content such as music from decades past may experience a resurgence in popularity, or may simply be being consumed by a particular demographic. For example, a music genre such as jazz-rock fusion may be purchased in nominal amounts relative to new music, but the purchase of a few hundred copies of an album by a specific demographic (not necessarily age specific) may provide the basis for recommendation of that music to other users in the same demographic. In one embodiment the time since the initial introduction of the content is used as a normalizing factor in the calculation of the adoption statistics. For example, the adoption rate of the music that was introduced 30 years ago can be weighted or normalized for that 30 year time period. In one embodiment an appropriate statistical model is applied to model the adoption (e.g., exponential growth followed by decay or other statistical model which models the adoption rate and peak in adoption). Based on the statistical model, an adoption rate that is "high" given that the music (or other content) was originally introduced 30 years ago can be spotted. Based on the identification of this content as "new old" content or "popular classic," the content can be introduced (or reintroduced) to particular niche markets or to the general audience, as appropriate and as suggested by the adoption statistics and demographics of the adopters. For example, if a certain type of content is found to be rapidly adopted by a market consisting of users who were not yet born at the time of the first introduction, it may suggest that the content should in fact be recommended and introduced to the entire population in that age demographic.

There are a variety of different mechanisms by which the PRS may present its personalized recommendations to a user. These include an Electronic Program Guide (EPG), automatic downloading, a recommendation list and a portal.

In some embodiments, the PRS is configured to "push" its personalized recommendations to the user. The PRS monitors the information from its various sources, formulates recommendations to the user, and decides, using criteria provided during configuration, the relative importance of a recommendation. The mechanisms and frequency by which the PRS reports a recommendation to the user are based on the recommendation's relative importance.

In other embodiments, the PRS is configured to permit the user to "pull" (i.e., request) its recommendations as, and when, desired by the user. In yet other embodiments, the PRS is configured in the "push" mode for some categories of recommendations and in the "pull" mode for other categories.

An Electronic Program Guide (EPG) can be configured according to the content choices identified during the discrimination stage. For example, in addition to the EPG's standard list of content, those content items that appear to be the best candidates for offering to a specific user might be placed in a prominent position within the EPG that is presented to the specific user.

Automatic downloading is another mechanism for presenting content to a specific user. Selected content might be, for example, downloaded to a user's Personal Video Recorder (PVR), in which case the list of downloaded content would be presented to the user the next time that he or she used the PVR.

A recommendation list of only those content items that are candidates for the user might be presented, as opposed to the mix of standard and personalized selections that appear in an EPG. This would allow the user to focus only on personalized recommendations, without being distracted by the standard programming selections.

FIG. 85 shows an example of a user interface screen 615 used to present a recommendation list to a user. In this example, a list 176 of recommended videos is presented. The list 176 contains the name of each video, the name of the person that recommended it, the date that the recommendation was made, and the duration of the video. The user interface screen 615 also provides buttons 1217 for the user to view previous recommendations, view saved programs, view audio recommendations or share recommendations.

Another possible mechanism for presentation of content is through a web portal on the Internet. Any of the mechanisms described above (EPG, automatic download, and recommendation list) might be presented when the user uses a web browser to go to his or her portal page on the Internet.

As illustrated in FIG. 58, a presentation mechanism 1104 is utilized to present the content to the user. The presentation mechanism 1104 may include, but is not limited to, an Electronic Program Guide (EPG), a web page indicating recommended content, an e-mail presenting content and content recommendations, automatic downloading of information to a recording device such as a Personal Video Recorders (PVR), a portable music device, and presentation of headlines and appropriate Rich Site Summary or Real Simple Syndication (RSS) links on a news, e-mail, social networking, or other portal.

The content introduction stage 1102, discrimination unit 1103 and presentation mechanism 1104 permit the PRS to present content to the user that it believes will be appropriate for the user based not only on the user parameters such as demographics, preferences, and consumption habits, but also on the adoption of the content by other users. The other users may be within the user's social network, or may be outside the social network but of a similar demographic. Based on content introduction, discrimination, and presentation, the user receives an indication of some type that the content may be applicable to him/her.

Still referring to FIG. 58, presented content may be selected by the user through a presented content selection mechanism or unit 1105. Selection is an indication that the user believes that the content will be of interest to him and can indicate actual purchase or downloading of the content, or may be sampling of the content as can occur when a user samples a song before purchasing the item, or when a user scans an article of interest. With reference to content that may have been automatically downloaded to a PVR or portable music device, selection occurs at the point at which the user accesses the content and begins to play it.

There a number of mechanisms that may be used for providing the feedback rating of content to the PRS. These mechanisms include, explicit rating and implicit rating (e.g., viewing/listening statistics and purchase information).

Feedback or rating of content can be performed by a feedback/rating mechanism 1106, either explicitly or implicitly, and provides an indication as to the appropriateness of the content as determined by the user. In terms of implicit ratings, the user provides an implicit rating by listening, viewing, or reading the content, recommending the content to other users (or providing a negative recommendation), purchasing the content, or other actions which do not require the user to rate the content but which themselves provide an indication as to how much the user likes/dislikes the content.

Explicit feedback and rating can also be utilized in which a user provides direct feedback regarding the recommended content in terms of having liked/disliked the content, applicability of the content, timeliness of the content, or other parameters indicative of their like/dislike for the content.

Figure 81:
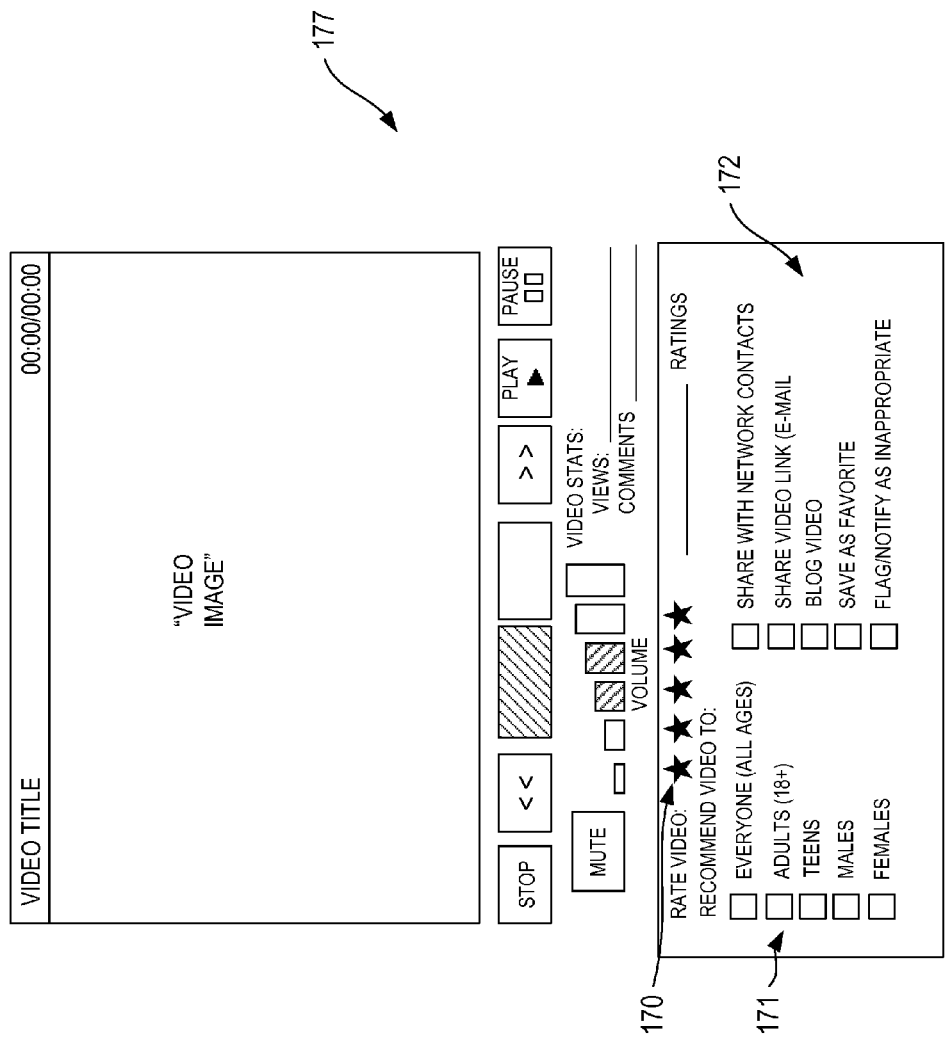
FIG. 81 is an example a user interface screen for recommending video content in accordance with one embodiment of the present invention.

FIG. 81 shows an example of a user interface screen 177 that enables a user to recommend video content during or after viewing a video. In this example, the user can rate the video using the displayed stars 170, and can specify the set of users that will receive the recommendation by making selections with the user group buttons 171. In addition, the user is provided with buttons 172 that enable him to share the video with his social network contacts, send an e-mail message with a link to the video to other persons, write a blog entry regarding the video, save the video in his favorites list, and flag the video as containing inappropriate content.

Figure 82:
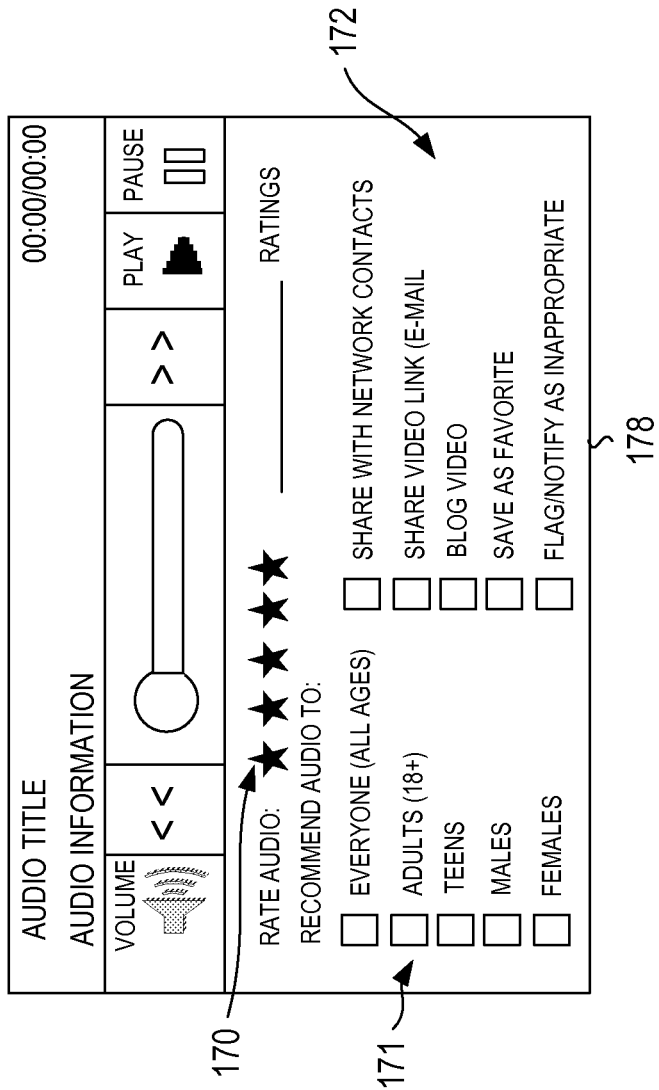
FIG. 82 is an example of a user interface screen for recommending audio content in accordance with one embodiment of the present invention.

FIG. 82 shows an example of a user interface screen 178 that enables a user to recommend audio content during or after listening to the content. As in the video rating screen shown in FIG. 81, the audio rating screen in this example provides buttons for rating the content 170, specifying the user group 171, sharing the content 172, etc.

Figure 84:
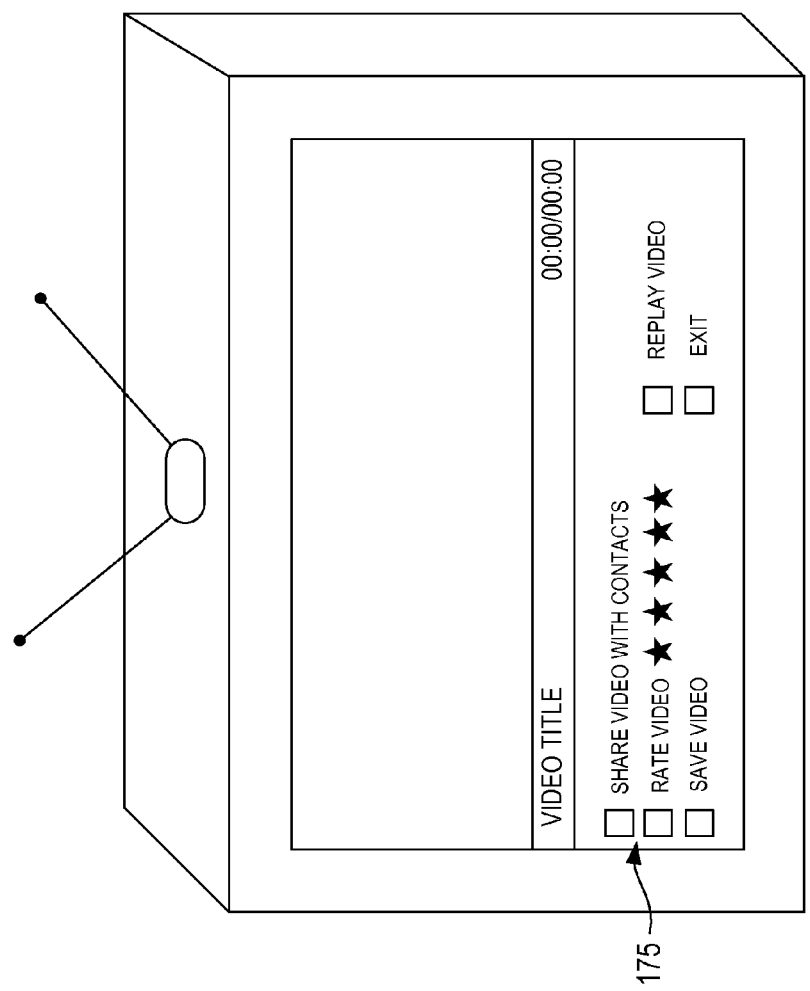
FIG. 84 depicts a video display device that enables a user to make recommendations on video content in accordance with one embodiment of the present invention.

Explicit rating by a user may be used for feedback rating. For example, a user would be provided with a mechanism for explicitly entering his or her rating of a content item. There are numerous ways to provide such a rating mechanism. For example, a user might be prompted at the conclusion of the content to make a selection on a screen. FIG. 84 shows an example of a video display device (e.g., a television) with buttons 175 that allow the user to use a remote control device (not shown) to share, rate and save a video program.

Figure 83:
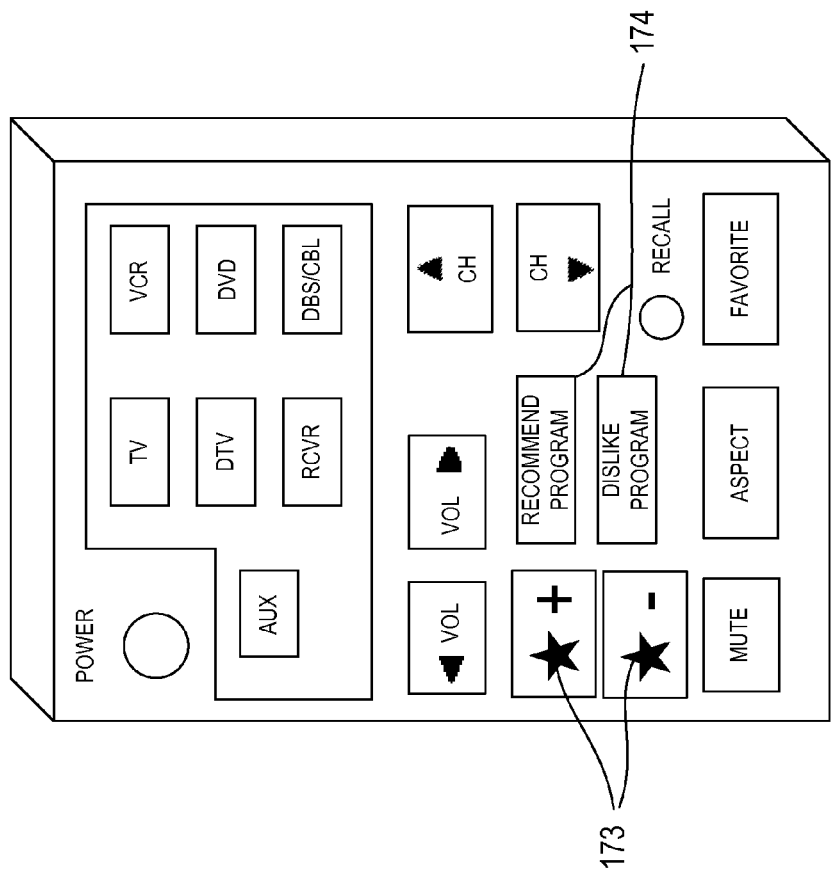
FIG. 83 depicts a handheld remote control device that enables a user to make recommendations on content in accordance with one embodiment of the present invention.

As another example, special-purpose buttons for entering feedback at any time during the content consumption could be provided on a handheld remote control unit. FIG. 83 shows an example of a handheld remote control device that includes a pair of buttons 173 for assigning a "star" rating to a video program and a second pair of buttons 174 for indicating a general recommendation or a dislike of a video program.

A user's implicit rating, e.g., purchase data, might be used for feedback rating as well. For example, the number or rate of a user's purchases of a particular product might be considered to be an implicit favorable rating of the product. Similarly, if a user's purchases of a particular product have become less frequent or there are no such purchases within a given time period, then an unfavorable rating by the user might be implied. It should be noted that a rating (implicit or explicit) is not necessarily limited to an association with a particular product; for example, a rating of a particular product might be considered to be a rating of the entire brand to which the product belongs.

The various statistics associated with a user's content consumption, i.e., viewing and/or listening, habits for particular content may also be used for feedback rating. For example, these statistics may include the number of times that content has been consumed, the frequency of consumption over a given time period, the change in rate of consumption, and the percentage of times that the content was consumed to completion, as opposed to being switched off before the end of the content. These statistics may also be weighted according to the demographics of a user. For example, a child may watch a favorite movie several times within a week, while an older user may not, even if he or she enjoyed the movie. In this example, the absence of repeat viewing by an older person would not be considered to be an indication that the user did not like the movie.

In terms of consumption of the content, the user may listen to a complete recording or play the recording several times, thus indicating a positive implicit rating/feedback. Alternatively, the user may listen to only a portion of the recording and immediately delete it, providing a negative implicit rating/feedback. The consumption habits of a user with respect to a particular piece of content or related pieces of content (e.g., songs from the same band or on a particular album, articles in the same magazine/newspaper, articles by the same editorial writer) can be used as part of the implicit rating/feedback as well as the consumption habits of the recommended content.

Table 3 describes examples of some of the possible mechanisms (user-user, aggregate user and recommendation engine) for recommending content for both explicit and implicit recommendations.

TABLE 3

| RECOMMENDATION MECHANISM | EXPLICIT RECOMMENDATION | IMPLICIT RECOMMENDATION |
| --- | --- | --- |
| User-User | First user generates a recommendation to second user in the form of an e-mail, recommendation list, program guide notification or marking, automatic downloading or recording and presentation in program guide or other recommendation that can be attributed to the first user. | First user's transactions (viewing and listening habits, purchases, surfing) are used as the basis for recommendations to a second user (of sufficient similarity) in the form of recommendation lists, program guide notification or marking, automatic downloading or recording and presentation in program guide or other recommendation that is based on the first user's transactions. |
| Aggregate User | Some form of aggregate user statistics (tabulated number of viewings, listenings, purchases or other transactions) used as the basis for list positioning or other indication of popularity. | Number of viewings or purchases used as the basis for positioning in a program guide, automatic downloading or recording and presentation in program guide, or other mechanism based on aggregate user interaction statistics which are not presented to the user. |
| Recommendation Engine | Recommendation engine provides recommendation to user explicitly acknowledging that content has been recommended. | Recommendation engine causes content to be presented to user without an indication that it has been recommended. |

Figure 60:
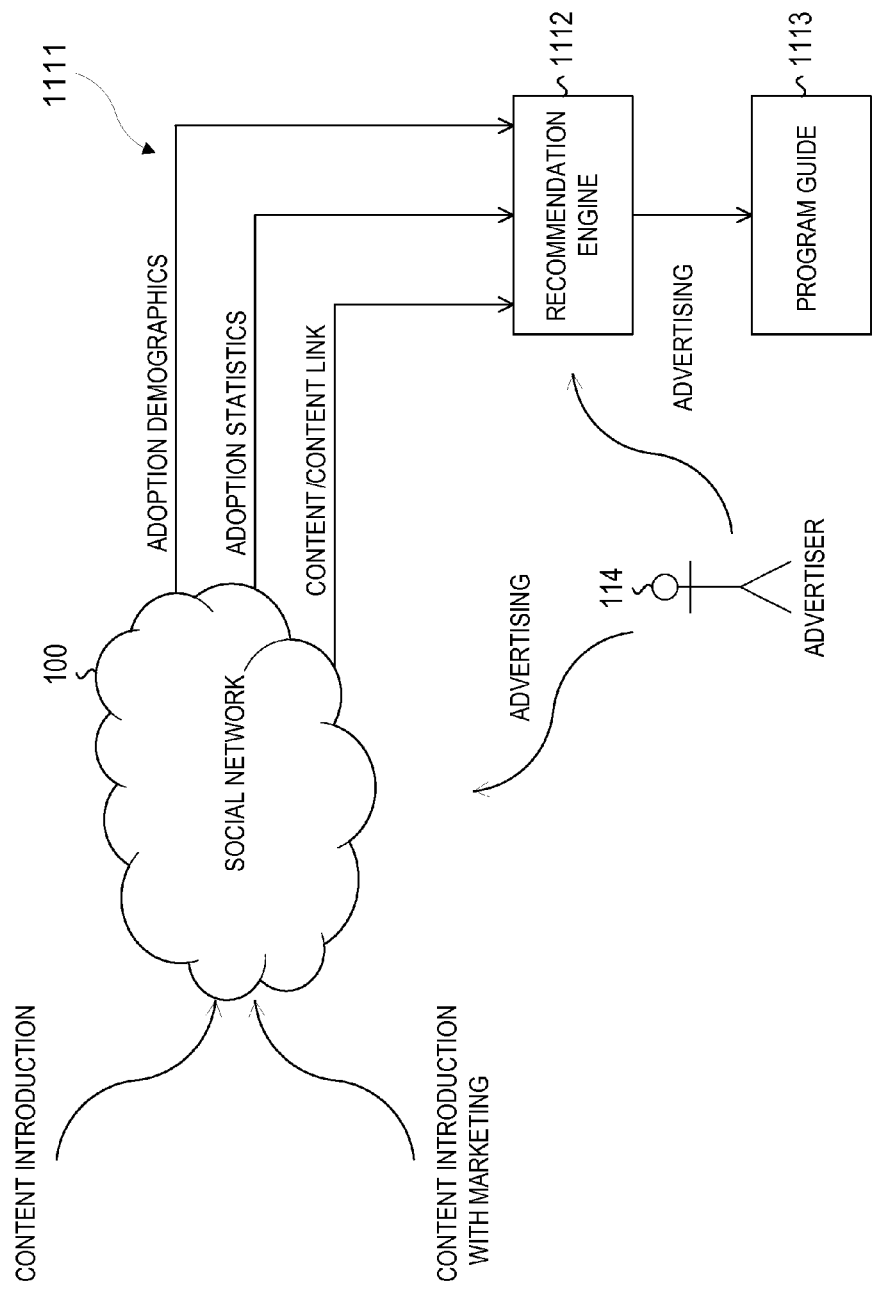
FIG. 60 is a block diagram of a PRS based in part on adoption parameters in accordance with one embodiment of the present invention.

FIG. 60 illustrates one embodiment of the PRS in which information about content is introduced into a social network 100, where that social network includes two or more users who share, in some way, preferences, recommendations, and/or information regarding content. The resulting output 1111 of the social network 100 includes the content or a reference to the location of the content (e.g., link) and the adoption statistics for that content. The demographics of the users that have adopted the content can also be included in the output. This information is fed into a recommendation engine 1112 which provides a recommendation in the form of a listing on a program guide 1113 or other recommendation for the content. As illustrated in FIG. 60 an advertiser 114 (which can also represent a content producer/promoter) may provide advertising to the social network 100 or directly to the recommendation engine 1112 in order to influence the outcome of the discrimination. In one embodiment, the advertised or promoted content is listed as such in the program guide, in order to provide an indication to the user that the recommendation is not entirely objective.

Figure 62:
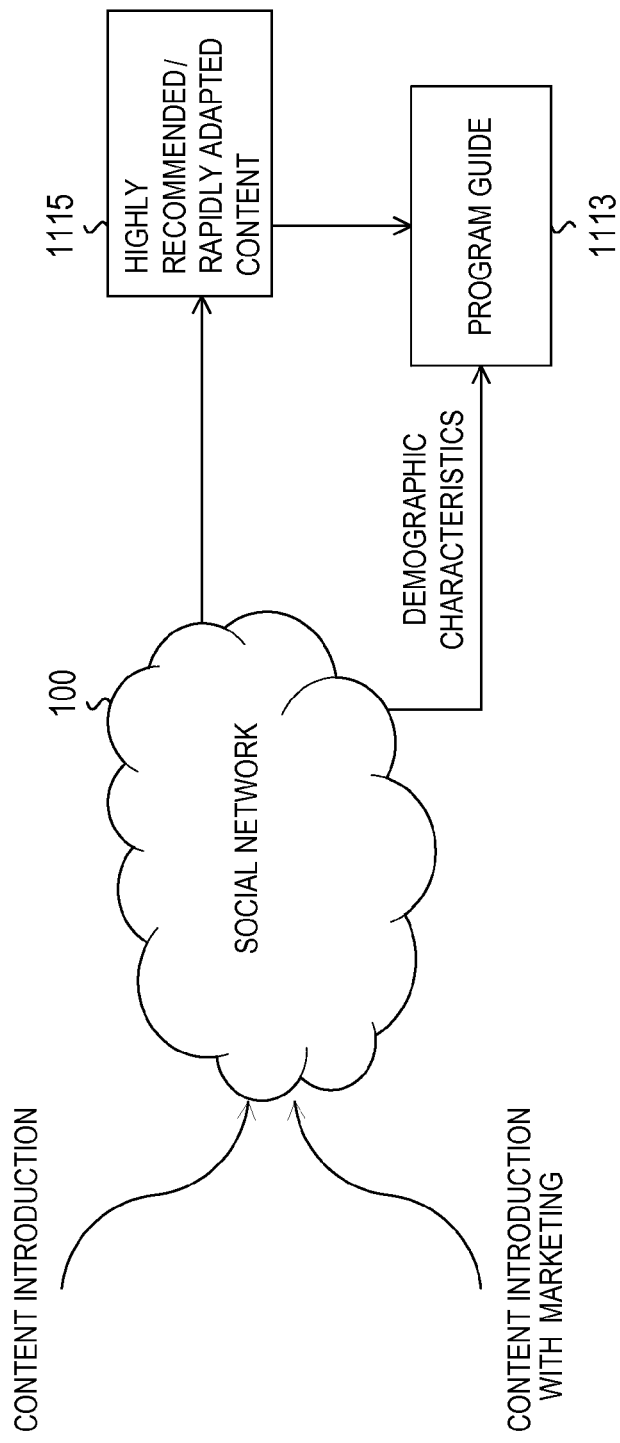
FIG. 62 is a block diagram of a PRS based in part on adoption parameters in accordance with one embodiment of the present invention.

FIG. 62 illustrates an embodiment of the PRS based on adoption parameters in which a recommendation engine is not utilized, but in which the adoption statistics are used within a social network 100, in conjunction with the demographic characteristics of the adopters, as the basis for the presentation of the content to the user. In this embodiment, highly recommended/rapidly adopted content 1115 is presented directly to the presentation mechanism (e.g., program guide 1113) which may filter or organize the content based on both the attributes of the content (e.g., genre) as well as the demographics of the adopters. As such, a set of cartoons which is being rapidly adopted by viewers in the 5-12 year old age demographic (or households known to have or believed to have such viewers) may not be relevant to a household lacking viewers in that age demographic, and may not be predominantly listed in the program guide, or removed entirely. In one embodiment the content which is being rapidly adopted by a demographic group dissimilar to the demographics of the user may be maintained within the program guide in order to provide the user with an indication as to what other demographic groups are finding of interest. The adoption parameters for a particular content item may, in some embodiments, be normalized according to the number of points of introduction of the content item into the social network. For example, if the content was introduced at 1000 different points in the social network, then the adoption parameters might be divided by 1000 to account for the multiple introductions.

Figure 75:
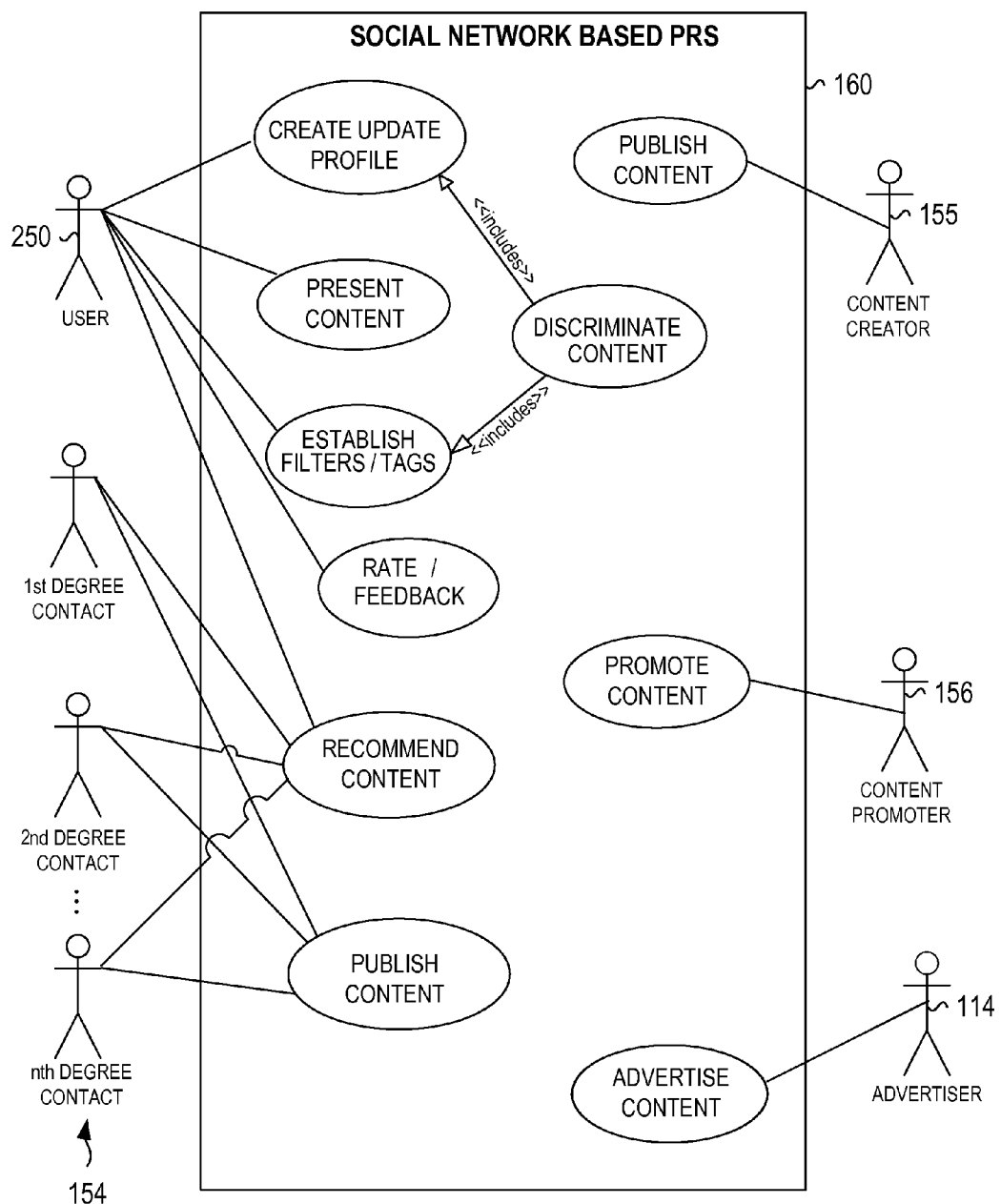
FIG. 75 is a use case diagram for a PRS utilizing a social network in accordance with one embodiment of the present invention.

FIG. 75 is a use case diagram for one embodiment of a social network based PRS 160. The user 250 is presented with content for which he can rate and provide feedback, and make recommendations. In addition, the user 250 can create and update his profile, and can establish filters and tags that are used by the PRS 160 in discriminating content that will be presented to the user. The user's contacts 154, of various degrees of separation, also contribute their content recommendations and can publish content that they recommend. The content is published by a content creator 155, promoted by a content promoter 156 and advertised by an advertiser 114.

Figure 77:
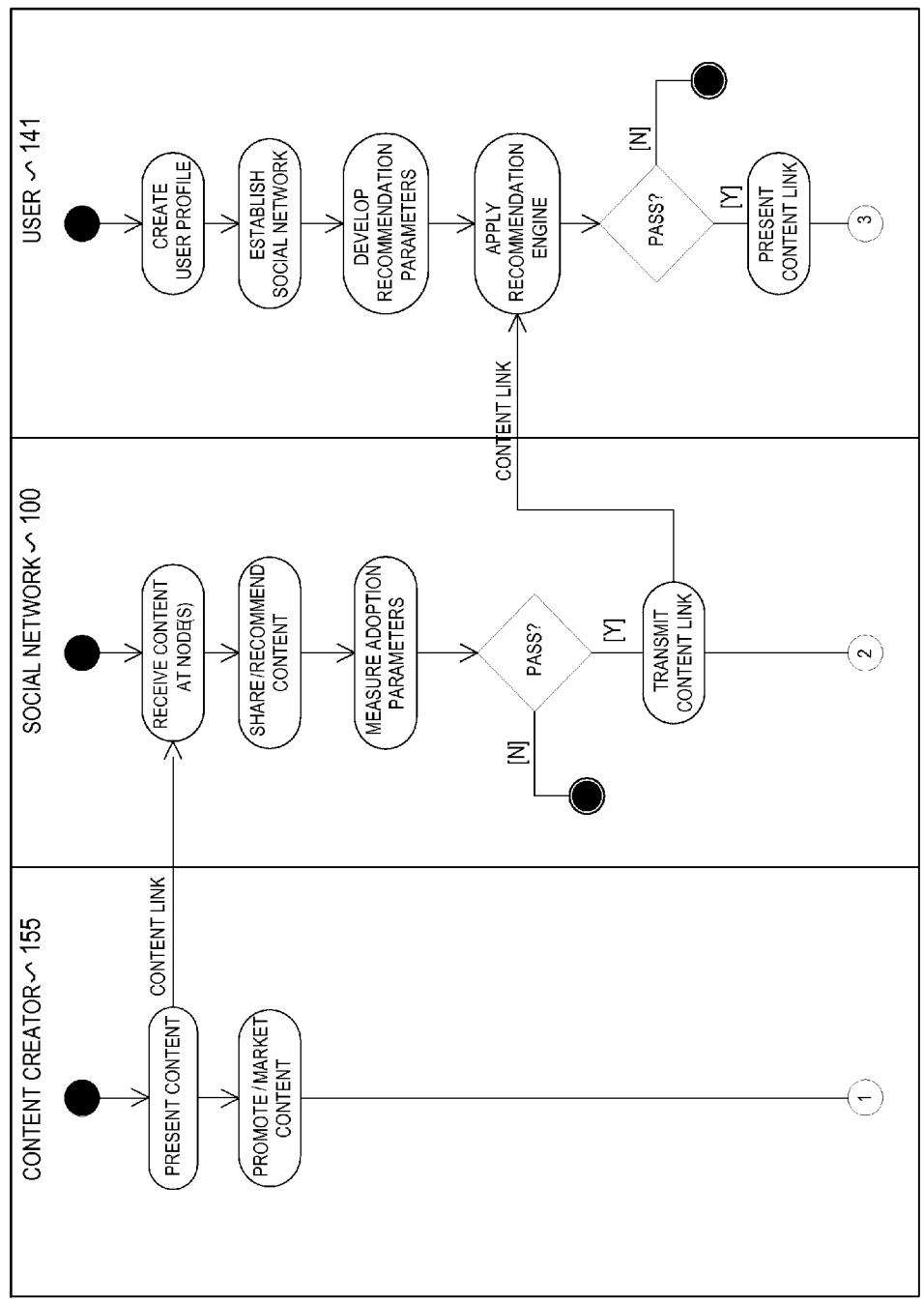
FIGS. 77 and 78 are activity diagrams for a social network based PRS in accordance with one embodiment of the present invention.
Figure 78:
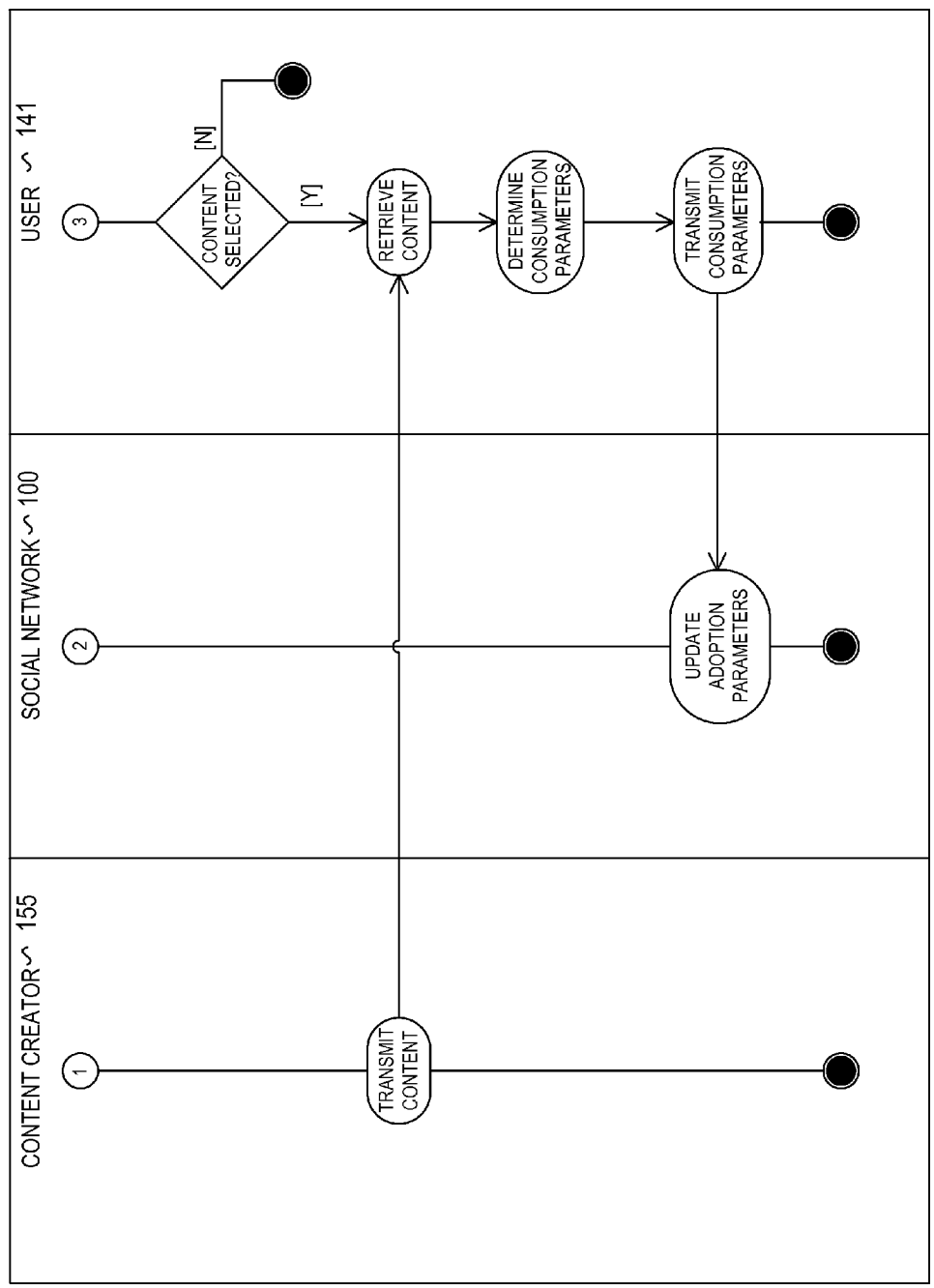

FIGS. 77 and 78 are activity diagrams for one embodiment of a social network based PRS. A user 141 creates his profile, establishes his social network (by linking to contacts), and recommendation parameters for the user 141 are developed. A content creator 155 presents content which is received at various nodes in the social network; the content creator 155 promotes the presented content, and transmits the content for selection by interested users (not shown). After receiving the content, the various nodes in the social network 100 share the content with, and recommend the content to, other contacts in the social network. The adoption parameters associated with the content are measured (and in some embodiments, are normalized), and if they meet a particular set of criteria, the content is applied to a recommendation engine. If the recommendation engine calculates that a recommendation for the content is warranted, then the content is offered to the user 141 by presenting the user 141 with a link to the content. If the user 141 selects the content, then he receives the content which is transmitted by the content creator 155. After the user 141 receives the content, the consumption parameters for the content are updated and are used to update the content's adoption parameters.

Those skilled in the art will recognize that a social network based PRS may perform variations in the depicted order of activities described above with respect to FIGS. 77 and 78. For example, a content creator 155 might begin the activity of promoting the content prior to, or at the same time as, presenting the content, or the activity of measuring adoption parameters might be concurrent with the sharing and recommending of content.

Figure 66:
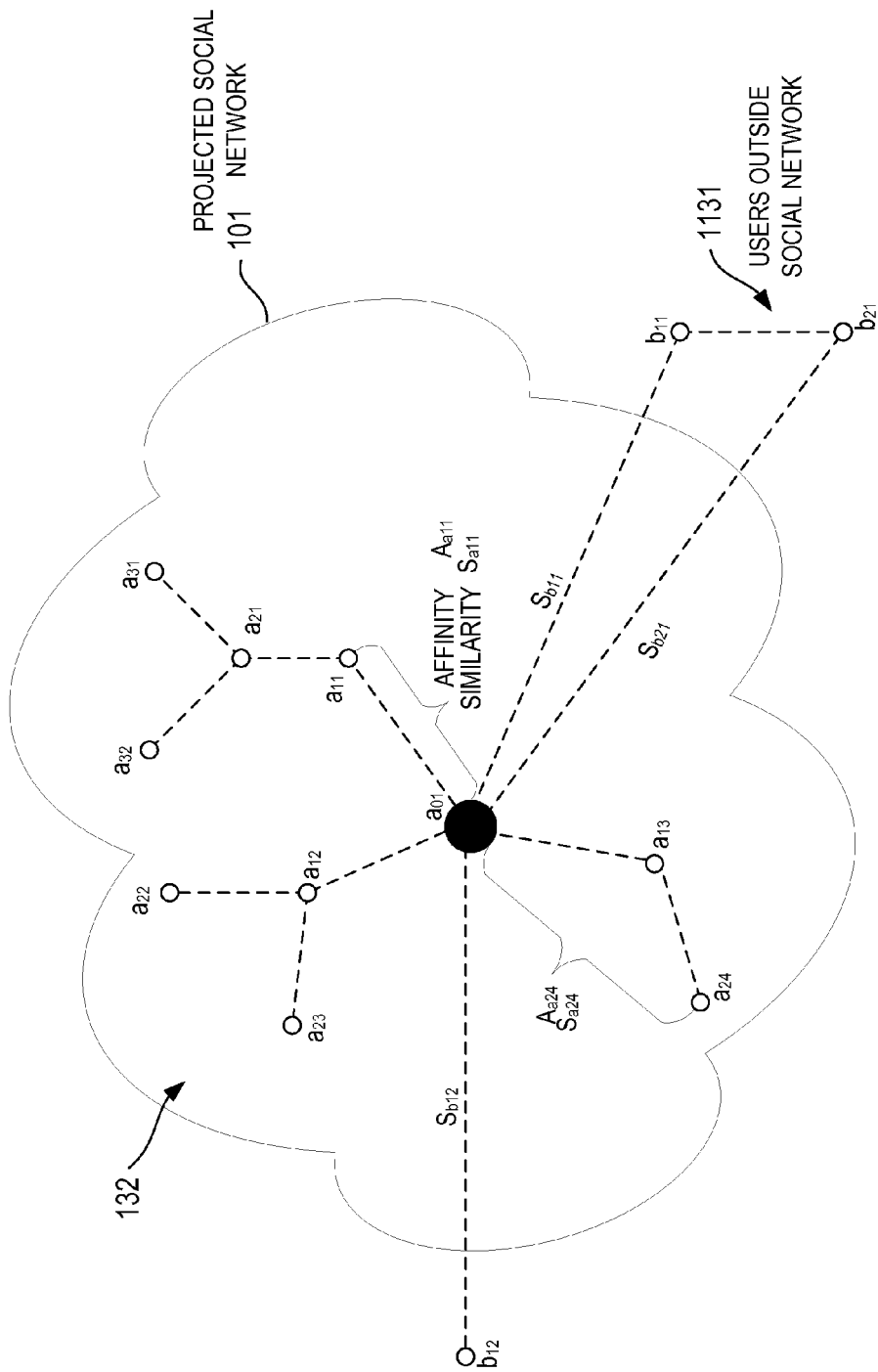
FIG. 66 illustrates a projected social network and users outside of the social network of a particular user in accordance with one embodiment of the present invention.

FIG. 66 illustrates an embodiment of a projected social network 101 in which the contacts within a user's network 132 that are likely to be of use in making a recommendation are identified (projected out from the entire social network) and used as the basis for forming recommendations. In one embodiment the degrees of affinity and similarity between users are utilized to project a particular set of users out from the social network.

As illustrated in FIG. 66, users 1131 outside the social network—essentially users unknown to the user and their first n-degrees of contact—can also be used in establishing recommendations and may be brought into the recommendation process based on similar demographics and interests, regardless of the fact that they are unknown to the user.

Figure 79:
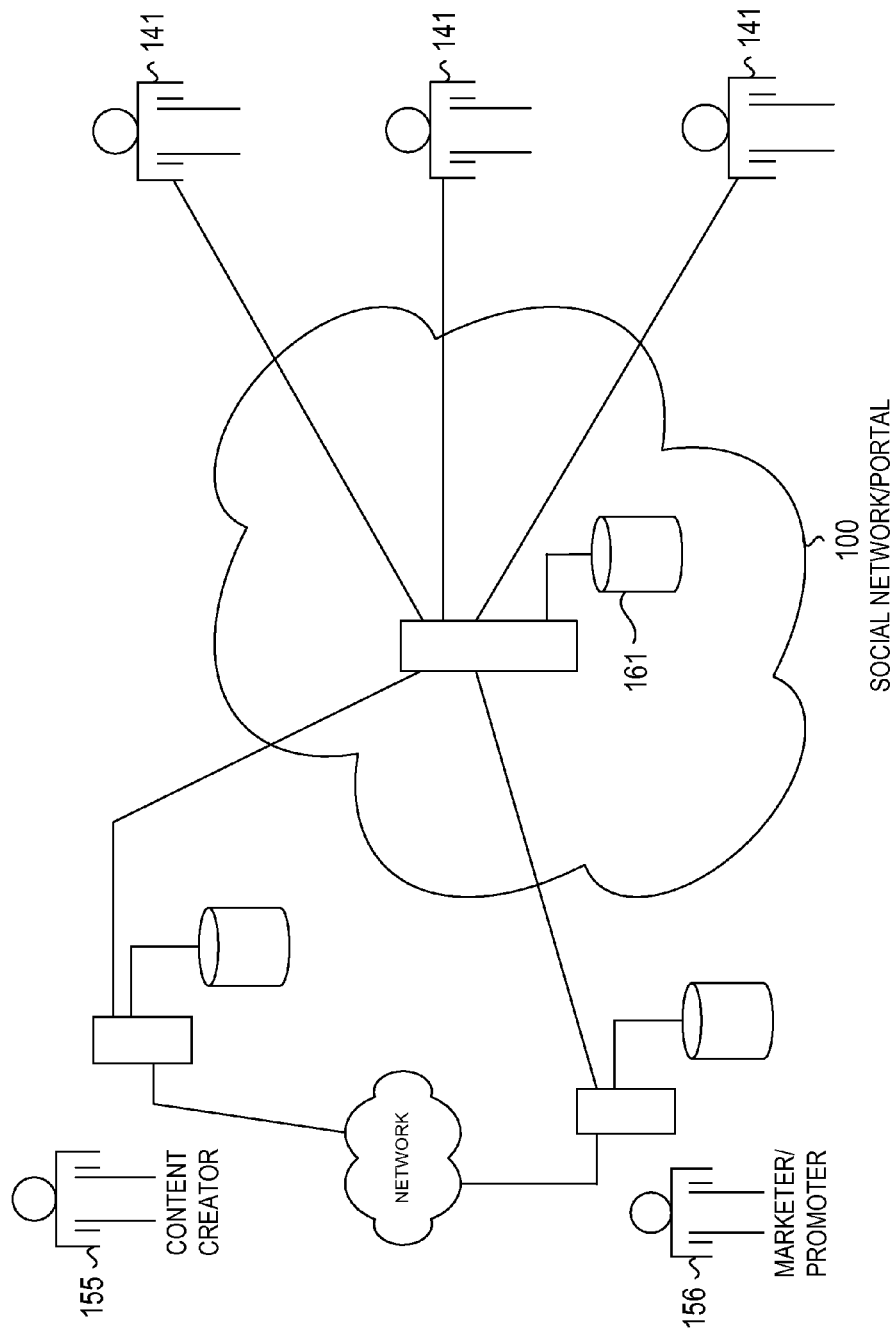
FIG. 79 is an example of a PRS based on a social network embodied within a portal in accordance with one embodiment of the present invention.

FIG. 79 illustrates an embodiment of a PRS based on the use of a social network/portal 100 in which users 141 log onto a server 161 which forms the basis for the social network/portal 100. The server 161 maintains a record of the user's contacts and acts to create the social network 100, monitors recommendations (explicit and implicit) and usage of contacts within the user's social network, and develops recommendations for presentation to the user. These recommendations can be presented to the user through the social network/portal 100 or can be transmitted to the user's media devices (e.g., television, PVR, media device). Content creators 155 and marketers/promoters 156 can also access the social network/portal for the introduction of content or for promotion of that content. The content creator 155 and marketer/promoter 156 can also communicate directly with each other to establish an appropriate arrangement for the transfer of content, control of distribution of content, and for marketing and promotion.

Figure 67:
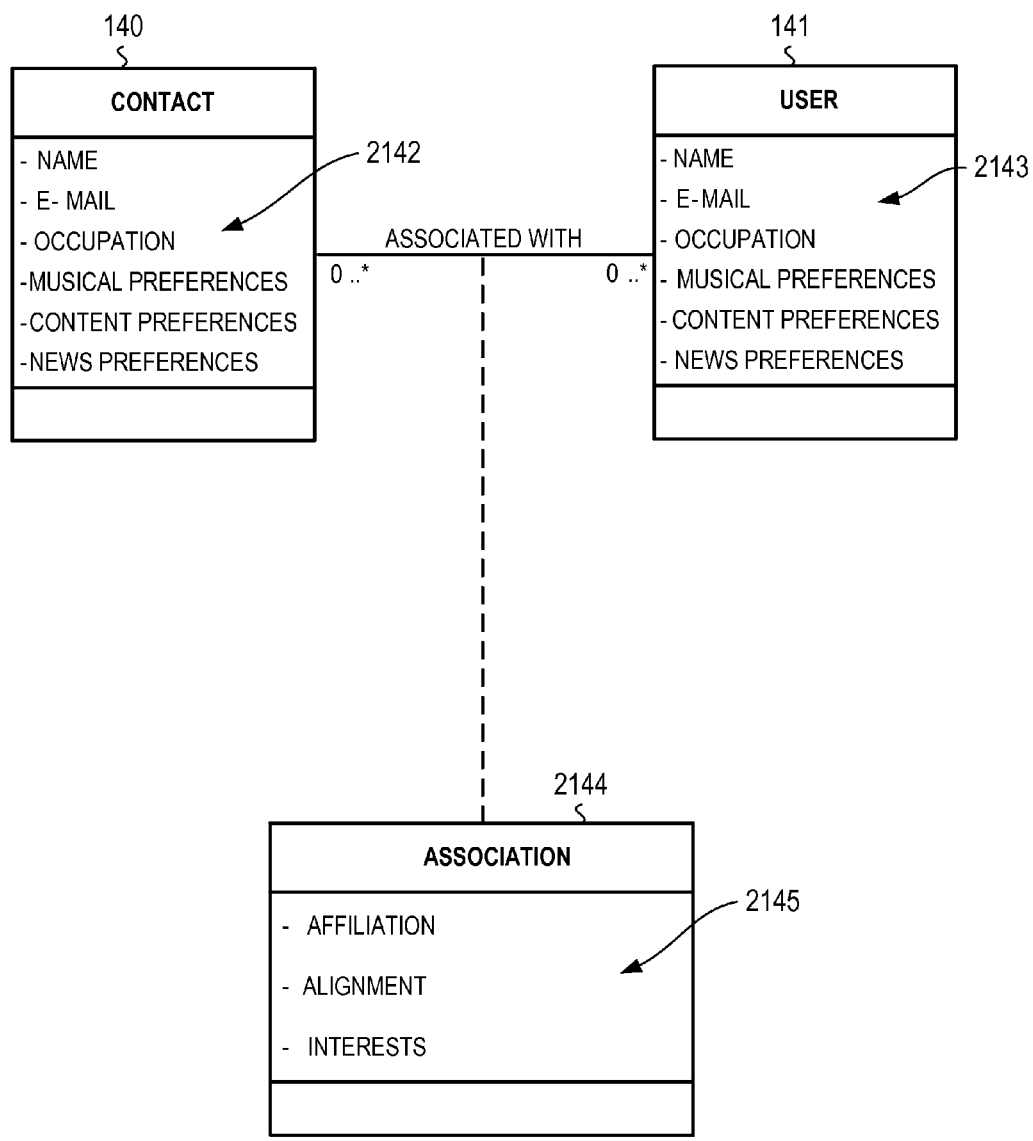
FIG. 67 is a class diagram illustrating the association between a contact and a user in accordance with one embodiment of the present invention.

FIG. 67 is a class diagram which illustrates the association 2144 between a contact 140 and a user 141 in a social network. Any given contact 140 has a zero-to-many association with any given user 141, and vice-versa. In other words, a user 141 may have any number of contacts 140 (including zero). The diagram also depicts the attributes of a contact 2142 and the attributes of a user 2143. For example, a contact 140 or user 141 might have the following attributes: name, e-mail address, occupation, musical preferences (e.g., genre or artist), content preferences (e.g., Woody Allen movies) and news preferences (e.g., CNN). Although the set of attributes in this embodiment are identical for user and contact, other embodiments might have sets of attributes that differ between user and contact.

FIG. 67 also includes the attributes of the association 2145 between contact 140 and user 141. For example, a given association 2144 between a user 141 and a contact 140 may be based on the following attributes 2145: affiliation, alignment and interests. "Affiliation" refers to a relationship based on common membership in a group. For example, a user has an affiliation relationship with other members of a professional organization to which the user belongs. "Alignment" refers to a level of trust that is associated with an entity. "Interests" refers to the extent to which an entity has similar interests.

Figure 76:
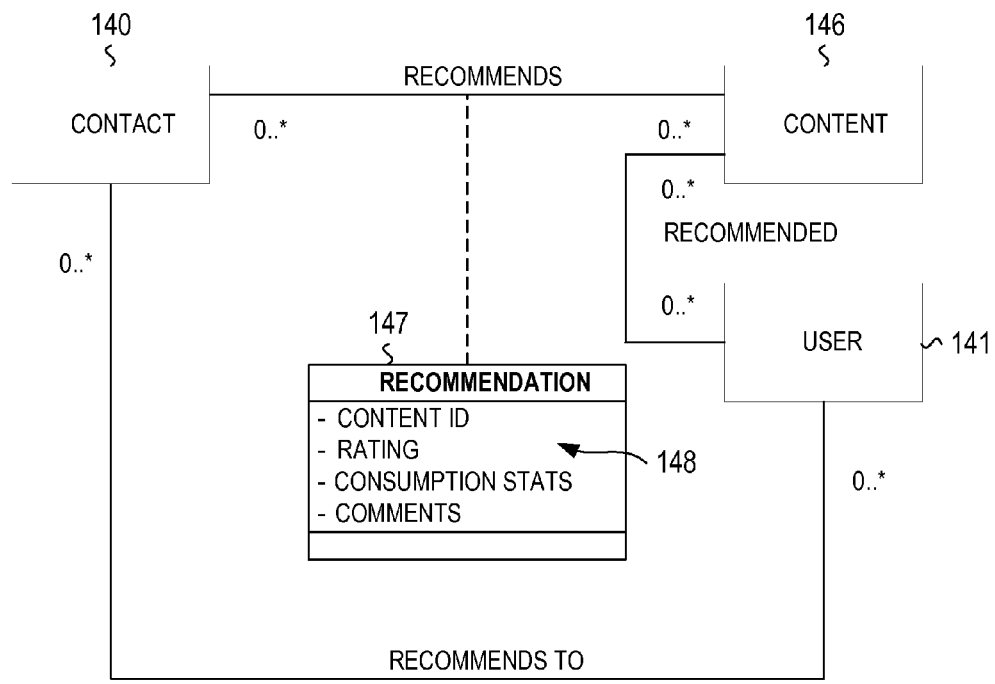
FIG. 76 is a class diagram illustrating the association of a recommendation from a contact to a user for particular content in accordance with one embodiment of the present invention.

FIG. 76 is a class diagram which illustrates the association 147 between contacts 140 and content 146 in a PRS. As depicted in the diagram, a contact 140 has zero-to-many recommendation relationships with items of content 146 and with users 141, and vice-versa. The diagram also depicts the attributes 148 of the recommendation association 147 between a contact 140 and of a content item 146 in this embodiment. For example, the recommendation association 147 might have the following attributes: the ID of the content item, the contact's rating of the content item, the consumption statistics of the content item, and any comments regarding the content item that are provided by the contact.

Figure 68:
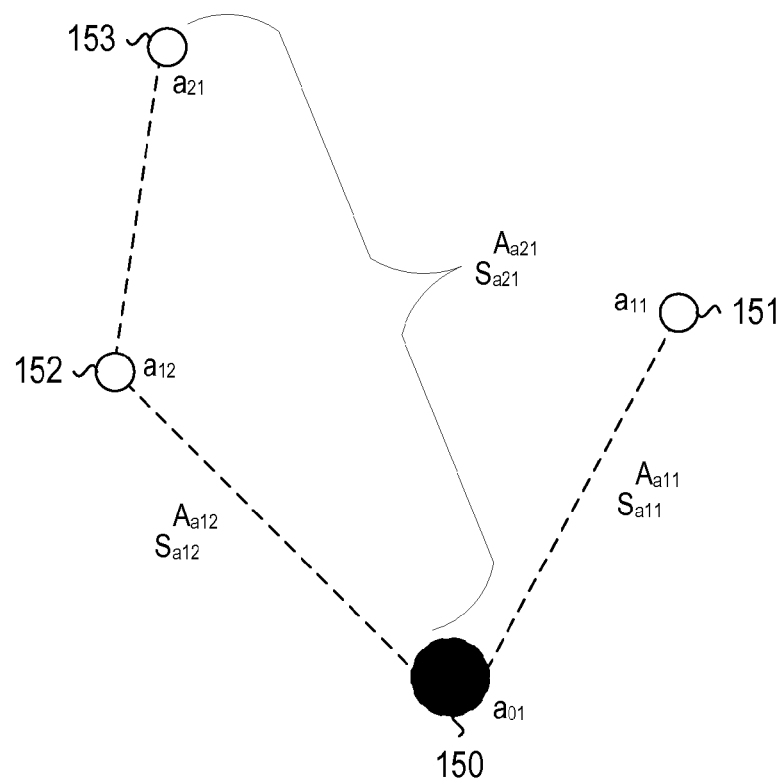
FIG. 68 illustrates relationships between a user and contacts within a social network in accordance with one embodiment of the present invention.

FIG. 68 illustrates how content consumed by first degree contacts (e.g., $a_{11}$ 151 and $a_{12}$ 152) in a user's network (with the user 250 being represented by $a_{01}$) can be used as the basis for recommendations, with those recommendations being weighted by affinity • and similarity S between the user and the first degree contact. An implied affinity and similarity can be developed for users further than one degree of separation based on the affinity and similarity between the second degree contact and the first degree contact. For example, an implied affinity and similarity is developed between user $a_{01}$ and a second degree contact $a_{21}$ based on the degree of affinity and similarity between the user $a_{01}$ and their first degree contact $a_{12}$ (that similarity and affinity indicated as $A_{12}$ and $S_{12}$) and the affinity and similarity between $a_{12}$ and $a_{21}$ (that affinity and similarity not being illustrated). Based on those sets of affinities, an implied affinity and similarity between $a_{01}$ and $a_{21}$ is developed as $\bullet_{21}$ and $S_{21}$. In one embodiment, affinities and similarities are in the range of 0-1 and are multiplied to create an implied affinity and implied similarity. In alternate embodiments, other operations are performed on the affinities and similarities to produce the implied affinities and similarities.

Figure 69:
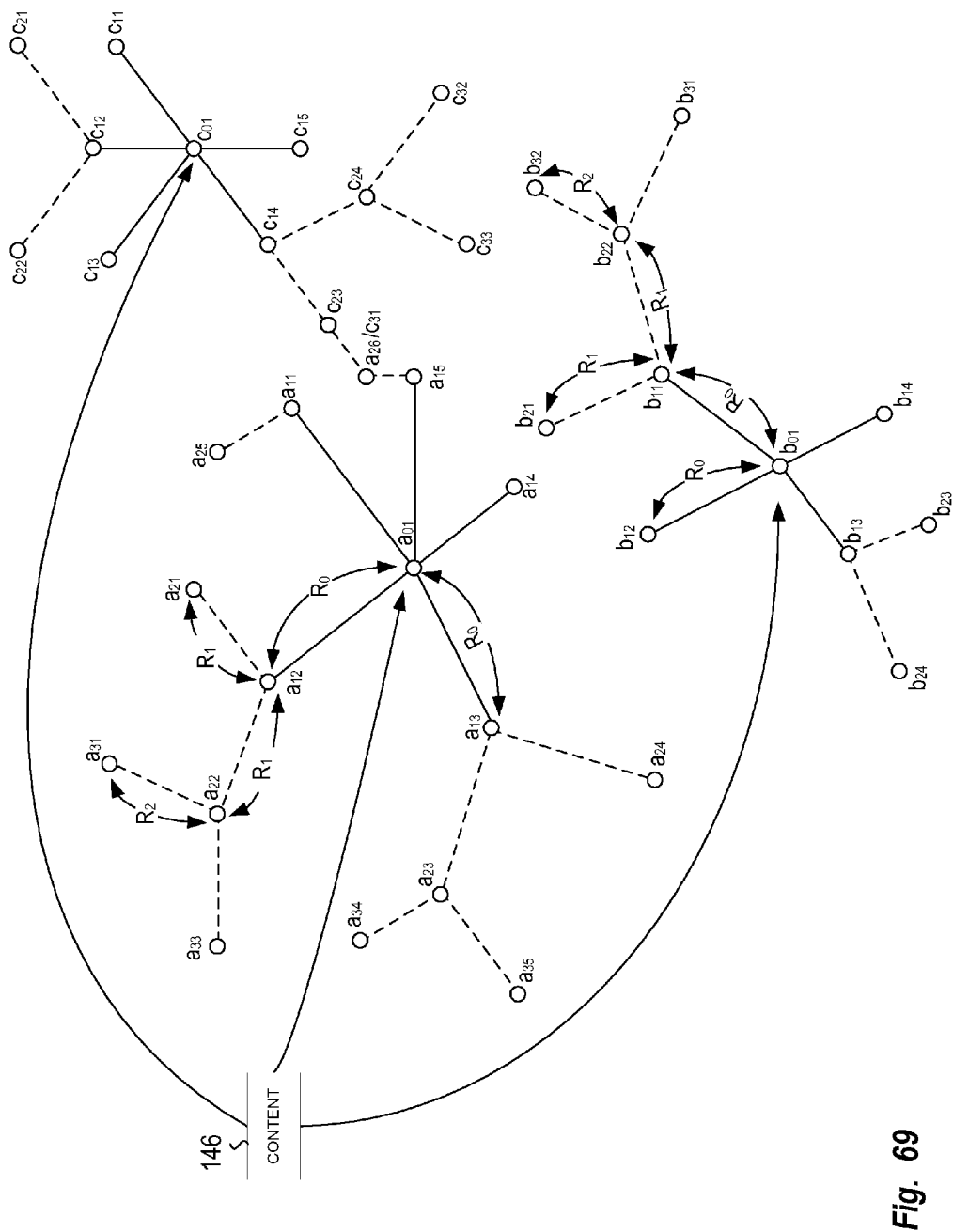
FIG. 69 illustrates content introduction into a social network in accordance with one embodiment of the present invention.

FIG. 69 illustrates content introduction in one embodiment of a social network. In FIG. 69, a particular item of content is introduced to three users within the social network, $a_{01}$, $b_{01}$ and $c_{01}$. "Order-zero" recommendations, $R_0$, of the content are made by $a_{01}$ to two first-degree contacts, $a_{12}$ and $a_{13}$. One of the first-degree contacts, $a_{12}$, then makes "order-one" recommendations $R_1$ of the content to second-degree contacts, $a_{21}$ and $a_{22}$. In this example, the other first-degree contact, $a_{13}$, does not recommend the content to any other contacts. One of the second-degree contacts, $a_{22}$, makes a second-order recommendation $R_2$ to a third-degree contact $a_{31}$. Similarly, an order-zero recommendation, $R_0$, of the content is made by $b_{01}$ to two first-degree contacts, $b_{11}$ and $b_{12}$. First-degree contact $b_{11}$ makes order-one recommendations, $R_1$, to second-degree contacts, $b_{21}$ and $b_{22}$. One of the second-degree contacts, $b_{22}$, makes a second-order recommendation $R_2$ to a third-degree contact $b_{32}$.

Figure 70:
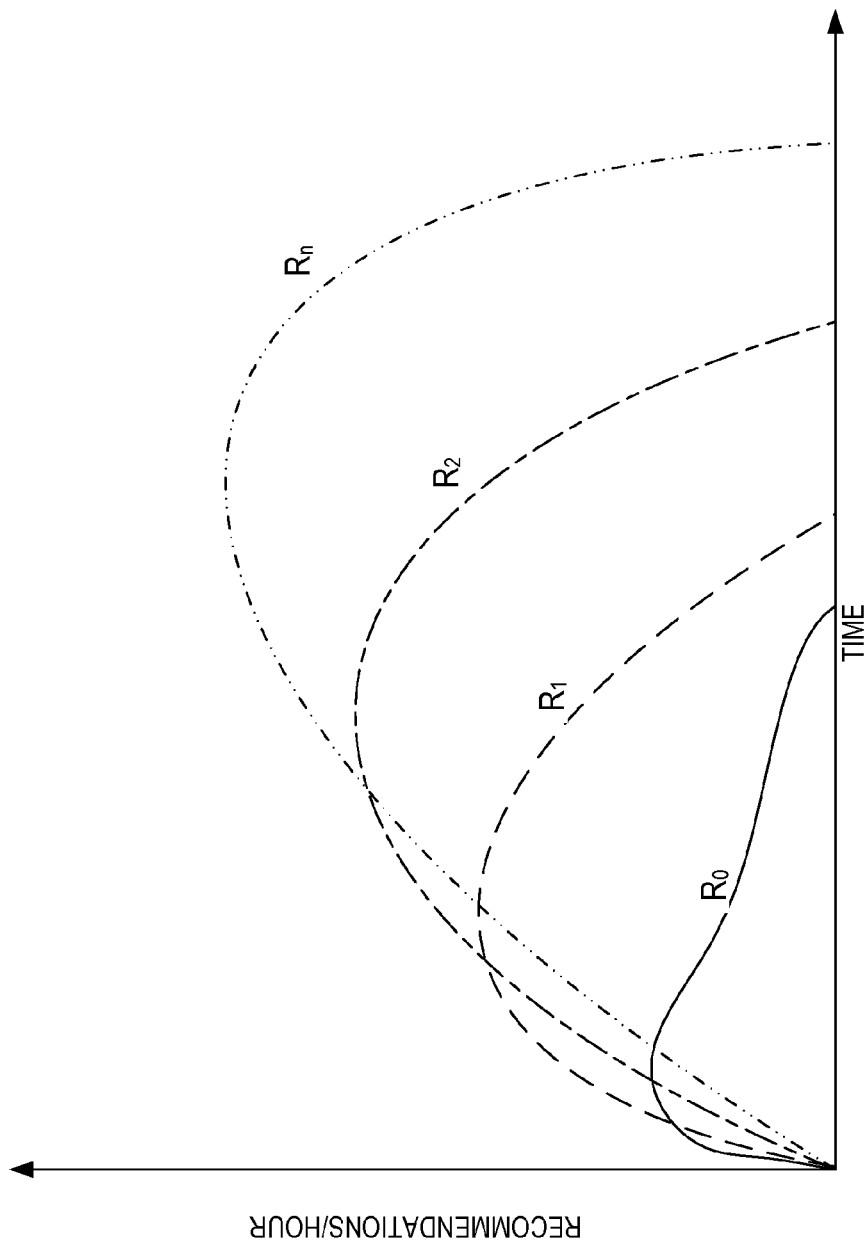
FIG. 70 illustrates an adoption parameter (recommendations/hour) of content as a function of time for various orders of recommendations within a social network in accordance with one embodiment of the present invention.

FIG. 70 illustrates a particular adoption parameter (recommendations/hour) of content as a function of time for various orders of recommendations within one embodiment of a social network. A set of contacts initially receives the content and makes order-zero recommendations, $R_0$, to some or all of their first-degree contacts, who then make order-one recommendations, $R_1$, to some or all of their second-degree contacts, and so on. FIG. 70 shows the typical rise and decay curves for the rates of the different order recommendations. For example, the rate of order-zero recommendations, $R_0$, increases very steeply, and then reaches a peak and decays to zero relatively quickly. As the order of the recommendation increases, the initial rise becomes less steep, and the peaks and decays occur at relatively later times.

Figure 71:
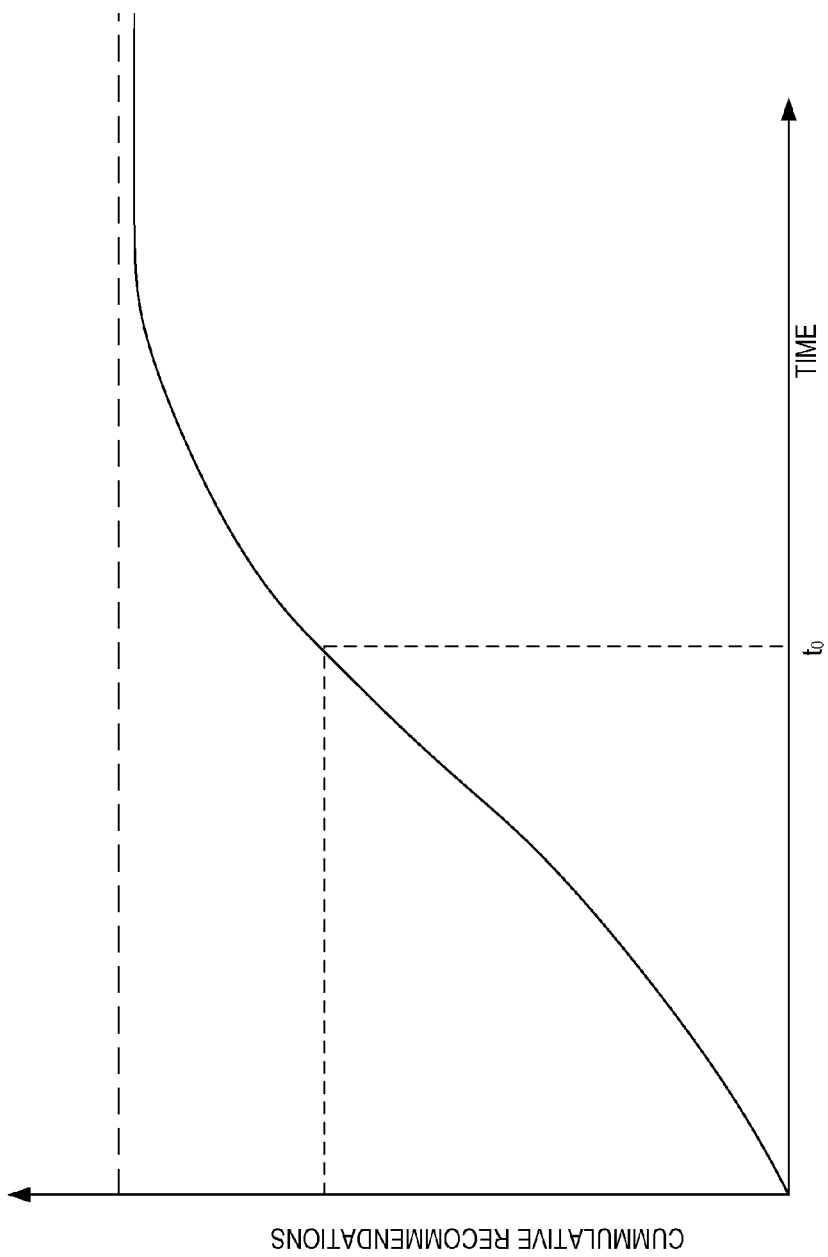
FIG. 71 illustrates cumulative recommendations as a function of time in accordance with one embodiment of the present invention.

FIG. 71 illustrates cumulative recommendations as a function of time in one embodiment of the invention. The various orders of recommendations, R0, R1, etc., are summed and plotted over time. A particular point in time, t0, might represent a threshold, i.e., the "adoption time", used by the PRS to determine that the cumulative recommendations have achieved a certain level of adoption.

FIG. 72 illustrates an example of the characteristics of a node within a social network in one embodiment of the invention. The example shows the number of $1^{st}$ degree contacts, number of $2^{nd}$ degree contacts, etc. associated with a particular node, $a_{01}$. The mean age for each degree of contact is listed, as well as the mean age, mean income and mean years of education over all nodes, and the percentage of nodes in each gender group. Lastly, the mean age, mean income and mean years of education for the subset of nodes that received a recommendation from node $a_{01}$ is listed.

FIG. 73 illustrates recommendation statistics associated with a set of "introduction" nodes in a social network in one embodiment of the invention. In this example content was introduced to 12 "introduction" nodes, and lists the peak recommendation rates and times for the various orders of recommendation ($R_0$, $R_1$, etc.). Also listed are the cumulative (total) recommendations, the adoption time (t0), the total number of recommendations between connected nodes, the numbers of viewings and listenings (both started and completed), the number of recommendations made before the adoption time was reached, and the number of recommendations made before the adoption time was reached normalized by the number of introductions (12 in this example). Some or all of the recommendation statistics can be utilized as "adoption parameters" in, for example, FIGS. 61 and 62.

FIG. 74 illustrates an example of node and recommendation descriptors in one embodiment of the invention. In this example, the node descriptor for node $a_{01}$ lists the $1^{st}$, $2^{nd}$ and $3^{rd}$ degree contacts associated with $a_{01}$. In addition, the linking contact between $a_{01}$ and each of the $2^{nd}$ and $3^{rd}$ degree contacts is listed; for example, $a_{12}$ is the linking contact between $a_{01}$ and $a_{22}$. The recommendation descriptor, in this example, lists the degree-zero, degree-one and degree-two recommendations associated with $a_{01}$, along with the pair of nodes for that particular recommendation. For example, a possible degree-one ($R_1$) recommendation is between the pair of nodes $a_{12}$ and $a_{21}$.

Figure 80:
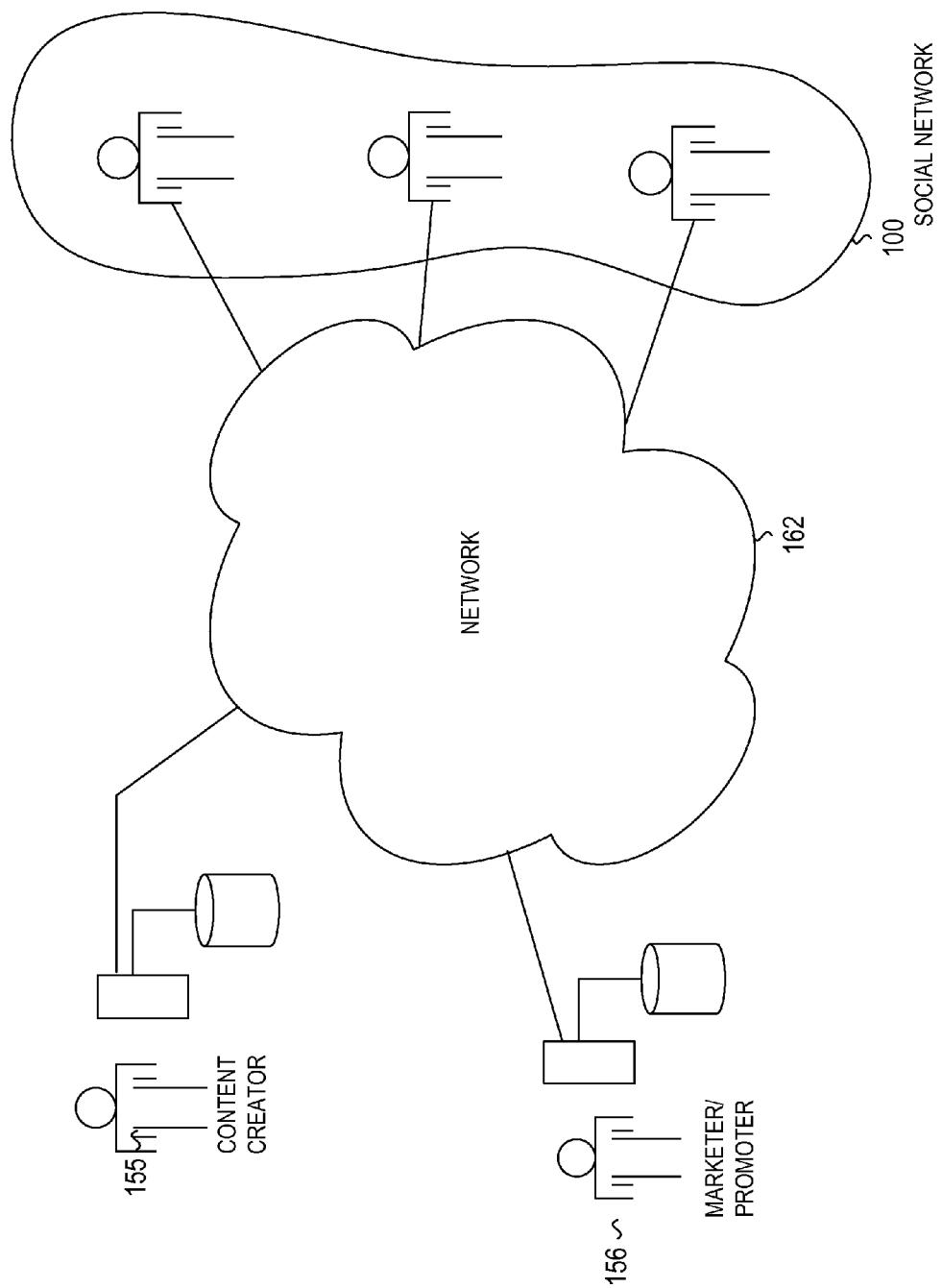
FIG. 80 is an example of a PRS based on a distributed social network in accordance with one embodiment of the present invention.

FIG. 80 illustrates an embodiment of a PRS based on the use of a distributed social network/portal 100 in which users do not need to log onto a centralized server in order to have access to the social network. In this embodiment, the social network is created between users who maintain their lists of contacts. In one embodiment, users' computers maintain lists of n degrees of contacts, thus allowing each user to maintain their own nth degree social network. In this embodiment a user's computer is connected to the other user's computers through a computer network 162 (e.g., the Internet or an intranet), receives recommendations from other users, or can query particular users in the social network to obtain explicit or implicit recommendations. Based on the activities of the general or projected social network, the user's computer can create recommendations for the user. These recommendations can be presented to the user directly on a program guide, or can cause other devices associated with the user to obtain that content directly. In an alternate embodiment, user's computers only contain their direct contacts (address book) and send agents to those contacts to explore the recommendations and activities associated with those users and their first degree contacts. In this embodiment, users only maintain records regarding the activities of their first degree contacts, but can obtain information regarding the activities and recommendations of users beyond the first degree of contact from those contacts. The recommendations are also presented to the user directly on a program guide, or are transferred to a device associated with the user, that device having a program guide or in some instances having the ability to access the content and directly record it for the user. Additionally, content creators 155 and marketers/promoters 156 can also access the distributed social network/portal 100 through the computer network 162 for the introduction of content or for promotion of that content.

Still referring to FIG. 58, an optional marketing/promotion unit 1107 can be used to influence the discrimination unit 103. In one embodiment the discrimination unit 103 is influenced by the purchase of recommendations by the labeled content producer/provider. Although the objectivity of the discrimination unit 103 is reduced due to the monetary rewards provided by paid recommendations, the objectivity of the discrimination unit 103 should not be reduced too drastically, or users will find the content generally disliked and will refuse content associated with that discrimination unit 103. In an alternate embodiment the content that is recommended in part due to financial arrangements between the content producer/provider will be marked as such to discriminate between that content and content that is "pure" with respect to advertising, marketing, and promotion dollars. Alternatively, the discrimination unit 103 takes into account paid advertising, marketing, and promotion, and provides a higher threshold for presentation of materials based on the level of paid advertising, marketing and/or promotion.

Because a PRS provides its user with control over the nature of the recommendations that the user receives, recommendations presented to the user are naturally in the user's best interest, in part because the PRS has access to comprehensive personal information regarding the user. For example, a user's PIA may contain, among other pieces of information, his medical profile and history of grocery purchases. The user's medical profile in the PIA might indicate a diagnosis of diabetes and a history of medications and events (e.g., insulin shock) related to the diagnosis. The purchase information in the PIA might indicate the user's excessive purchases of sugared grocery items. The user's PRS, through its connection to the user's PIA, would have access to the user's medical and purchase information, and thus the PRS would recommend the purchase of grocery items that were favorable towards controlling the user's diabetic condition, such as sugar-free cookies or similar items.

Figure 87:
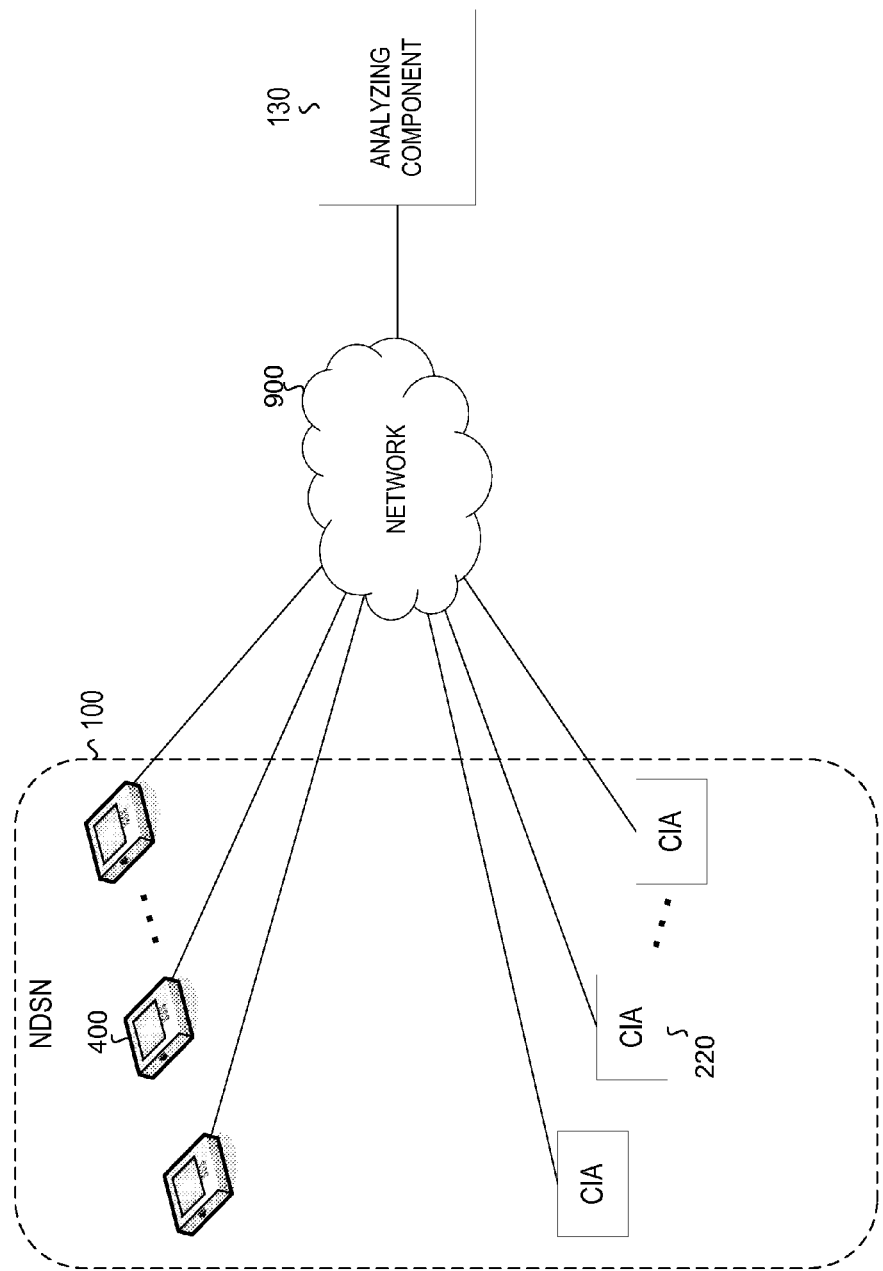
FIG. 87 is a block diagram of a system for analyzing advertisements in accordance with one embodiment of the present invention.

A system for determining the effectiveness of an advertisement campaign provides the ability to monitor presented (i.e., viewed) advertisements, evaluate users' commitments and analyze the effectiveness of an advertisement or an advertising campaign on users based on information obtained from the users' PIAs and other sources of information. FIG. 87 illustrates an embodiment of a the system for analyzing advertisements that includes an analyzing component 130, a plurality of PIAs 400 and CIAs 220 within an NDSN 100 and a computer network 900 for connecting the PIAs 400 and CIAs 220 to the analyzing component 130. Information regarding viewed advertisements and user commitments is obtained by the analyzing component 130 from the PIAs 400 and CIAs 220. The analyzing component 130 performs an analysis of the information obtained from the PIAs 400 and CIAs 220 to determine the effectiveness of an advertisement or an advertising campaign. Optionally, one or more advertisements may be selected by the analyzing component 130 for presentation to users based on the effectiveness analysis.

A user's commitments include actions and behaviors taken by the user, and may be, but are not necessarily, in response to an advertisement or an advertising campaign. An advertisement campaign may include a group or family of advertisements or a single advertisement. The advertisements in a campaign may be related or unrelated to each other and/or may be directed to a single product or product type or multiple different products. Advertisements include, but are not limited to, a solicitation to purchase, or a promotion of, a product or service, brand or manufacturer and can include but are not limited to Internet advertisements (e.g., banners, pop-up ads and video segments), video advertisements (e.g., television, movie theater and cell phone ads), audio advertisements, audio-visual advertisements, advertisements in non-electronic media (e.g., newspapers, magazines, brochures and billboards), infomercials, electronic brochures, electronic billboards, and electronic or printed coupons.

Those skilled in the art will recognize that a presented advertisement need not actually have been seen or heard by the user. That is, a presented advertisement is one to which the user has at least been potentially exposed. Examples of such an advertisement include advertisements in an issue of a magazine to which the user subscribes but has not read, television advertisements that played while the user was not in the room, and billboards that the user did not see while driving down the highway.

Figure 88:
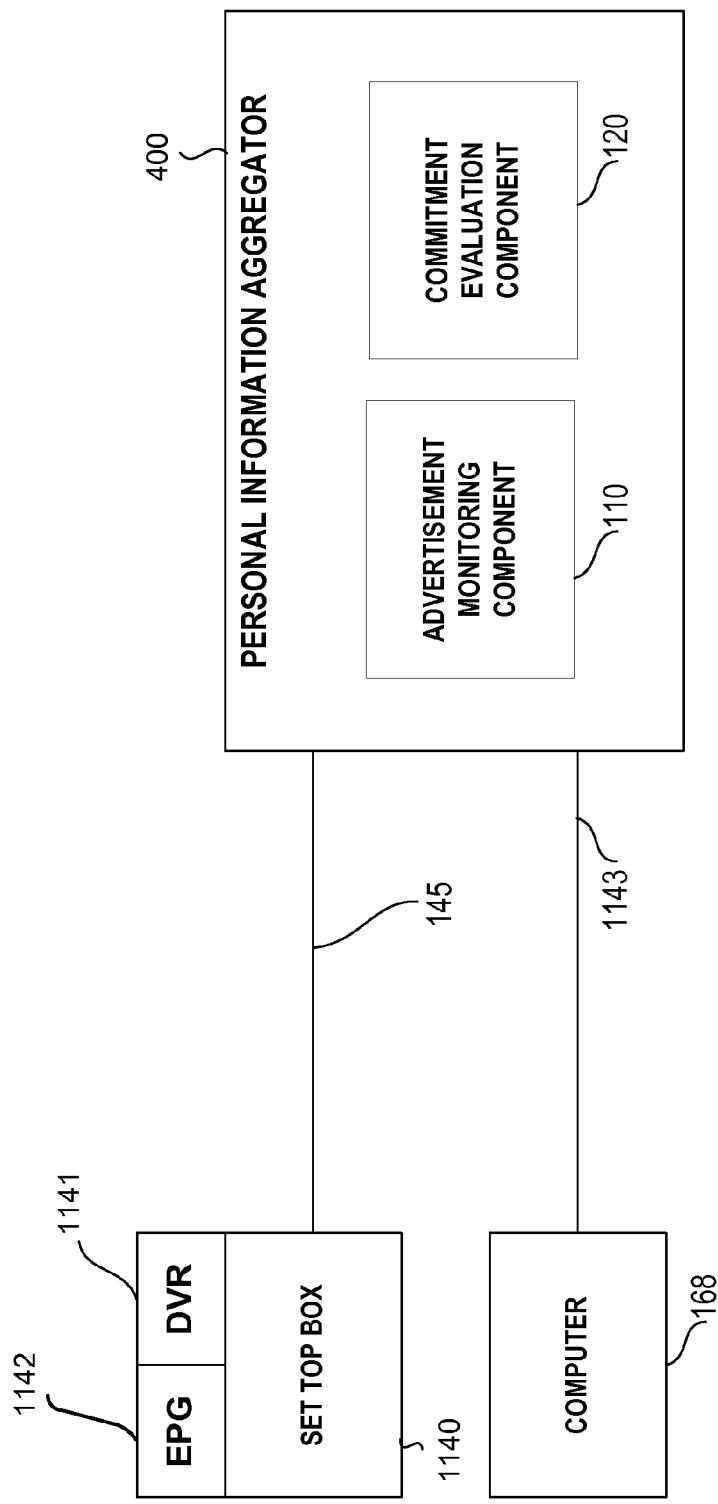
FIG. 88 is a block diagram of a PIA and external components.

FIG. 88 illustrates an example of the PIA 400 that includes an advertisement monitoring component 110 and a commitment evaluation component 120. The PIA 400 is connected to an external set-top box (STB) 1140 through a link 145 and a personal computer 168 through a link 1143. The STB 1140 stores data that includes an electronic program guide 1142 and tracks the user's television program viewing. Data stored in the STB 1140 may include programs watched, advertisements watched, viewing times, fast-forwarded segments, rewound segments and channel changes. The STB 1140 may also include a digital video recorder (DVR) 1141. Programs and advertisements presented during DVR 1141 playback may also be tracked. The DVR 1141 may track which advertisements were viewed, the dates and times that the advertisements were viewed, how often the advertisements were viewed, and whether an advertisement was skipped, e.g., by fast-forwarding, or rewound. The DVR may also track whether an advertisement was watched in full or was partially skipped. Data including the viewing information is transmitted to the PIA 400 for processing and storage by the advertisement monitoring component 110 through link 145. Data may be stored by the STB 1140 for later bulk transmission to the PIA 400, or data may be sent to the PIA 400 as it is generated. The advertisement monitoring component 110 processes the data to create an advertising data feed 600 (see FIG. 91).

The advertisement monitoring component 110 may also observe a user's Internet browsing on a personal computer 160, monitoring for presentation of advertisements. Browsing may take place on the PIA user's computer 160. These advertisements can be text, banners, electronic mail or video ads and are often placed on web sites to generate revenue for the site operator.

Exposure of the user to other advertisements may also be tracked or inferred through tracking of the user's location. For instance, GPS tracking data stored in a PIA may indicate that a user traveled a road upon which a billboard was placed. Similarly, data indicating presence at locations within a shopping mall could be used to infer exposure to advertisements at those locations.

The advertisement monitoring component 110 analyzes the user's viewing data for advertisement data by retrieving advertising data from the raw viewer data. In the TV viewing example, advertisement data includes information about commercials presented, commercials viewed (not fast forwarded), commercials found interesting (repeated, rewound) and products presented within the viewed TV program. Within the Internet monitoring example, the monitoring system can record the type of ad, the brand, the product and the server of the shown ad and whether the user clicked on the ad.

For some analyses, the presentation information derived from PIA data may encompass a combination of any of television viewing, radio listening, billboard exposure, targeted mail exposure, magazine or newspaper exposure, or any other presentation of a stimulus associated with a campaign.

Figure 91:
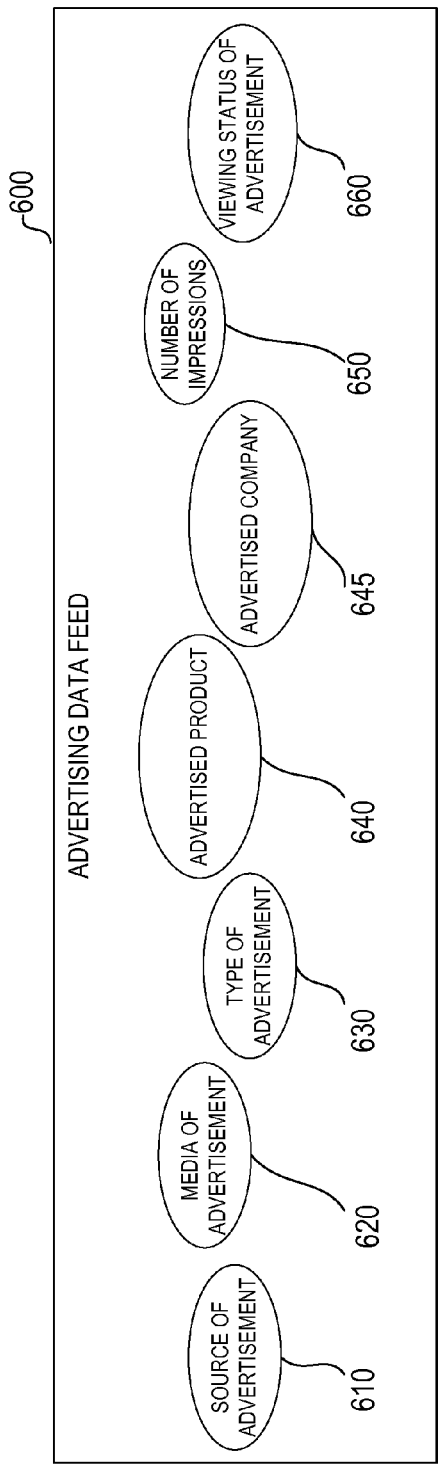
FIG. 91 is an example of an advertisement monitoring component output data feed in accordance with one embodiment of the present invention.

A data feed with the advertising information may be provided as an advertising data feed 600 by the advertisement monitoring component 110. Referring to FIG. 91, the advertising data feed 600 may include fields for source of advertisement (television or Internet) 610; media of advertisement (video, image, text) 620; type of advertisement (service, product, event) 630; advertised product 640; advertised company 645; associated advertising campaign (not shown), number of impressions of advertisement 650 and viewing status of ad (watched, fast-forwarded, rewound, clicked) 660. Those skilled in the art will recognize that the advertising data feed 600 may include additional fields not noted here and/or otherwise be comprised of any combination of fields consistent with data output from the advertisement monitoring component 110.

Figure 93:
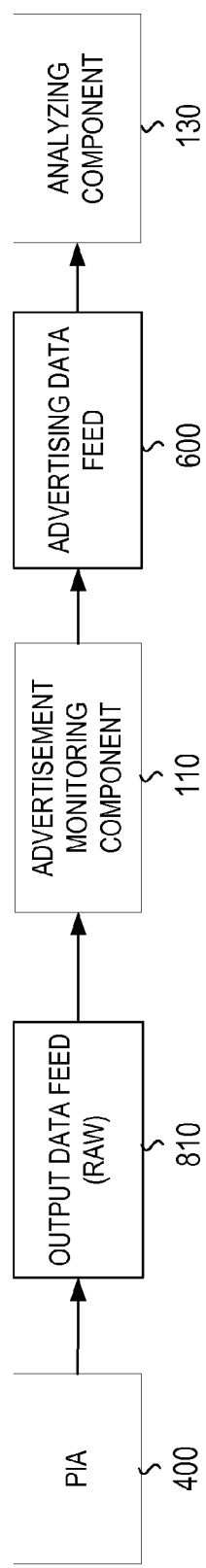
FIG. 93 is a block diagram of the advertisement monitoring component in accordance with one embodiment of the present invention.

In an alternate embodiment, the advertisement monitoring component 110 is external to the PIA. For example, referring to FIG. 93, the PIA 400 provides an output data feed 810 containing the viewing data which the advertisement monitoring component 110 processes for the useful advertisement information. The advertising data feed 600 is then prepared from the processed advertisement data. Those skilled in the art will recognize that the advertisement monitoring component 110 may be implemented by various combinations of features and functionality not limited to the combinations of features and functionality of FIGS. 87, 88, 91 and 93.

The commitment evaluation component 120 (see FIG. 88) evaluates user commitments, which can include, but are not limited to, purchase records, visits to a particular store or web site, or participation in an event. Examples of purchase records include electronic or paper receipts or transaction records from stores, merchants or organizations for purchased products or services. The purchase records data may further include dates and times of purchases, makes, models, sizes, SKU numbers and brands. Further subdivisions could be created among the users of the PIA 100, such as each member of a household. The PIA 100 stores the various types of user data that may be commitment data for use by the commitment evaluation component 120.

Commitment data is categorized and organized. For example, groceries are categorized separately from electronics. Thus, the dairy products purchases are separate from the produce purchases. Purchases can further be divided into purchases by brand, by size, by manufacturer and by store.

Since purchases do not always provide the all the necessary data to analyze the success of an advertisement, other data sources may be examined to obtain a more complete picture of a user's commitments. For example, advertisements may be for non-profit groups that request donations such as time, money or articles of clothing. Other advertisements may be simply for websites or events. The commitment evaluation component 120 may collect various data that indicates a user's commitments, e.g., a history of website accesses, purchase history, adoption of a product or service, calendar entries, viewing history, consumption records, subscription information, donation records, investment records, medical treatment records, Internet download records, service records, phone call records, chat logs and historical positional information. The combined set of data is used in analyzing the effectiveness of advertising on a user.

Figure 92:
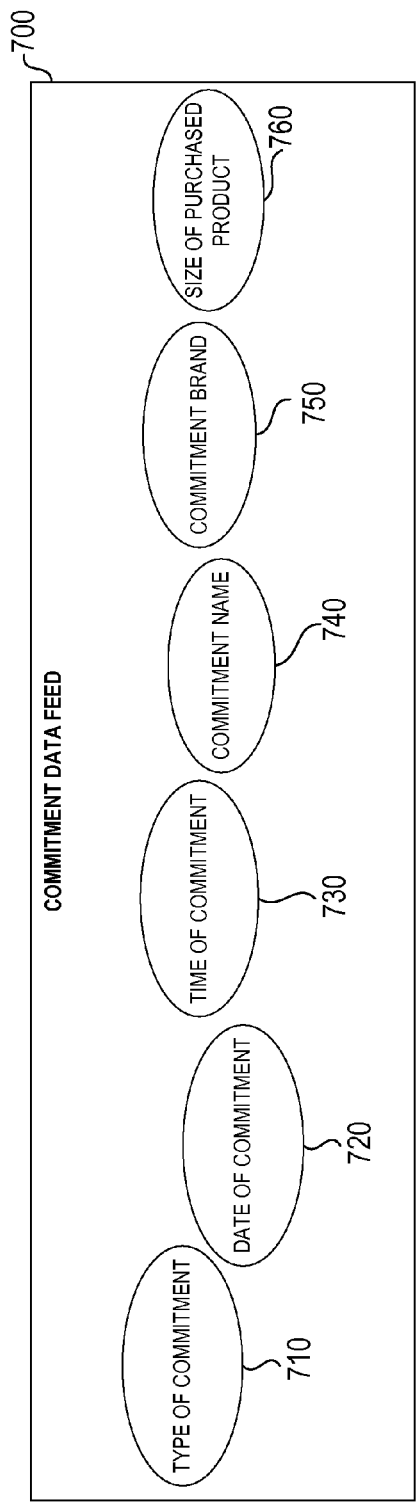
FIG. 92 is an example of a user commitment evaluating component output data feed in accordance with one embodiment of the present invention.

The user commitment evaluation component 120 provides a commitment data feed 700 with the processed user commitment data. Referring to FIG. 92, the user commitment data feed 700 may include fields for type of commitment (event, purchase, website access) 710; date of commitment 720; time of commitment 730; commitment name (event name, product purchased) 740; commitment brand 750 and size of purchased product 760. Those skilled in the art will recognize that the user commitment data feed 700 may include additional fields not noted here and/or otherwise be comprised of any combination of fields consistent with data output from the commitment evaluation component 120.

Figure 94:
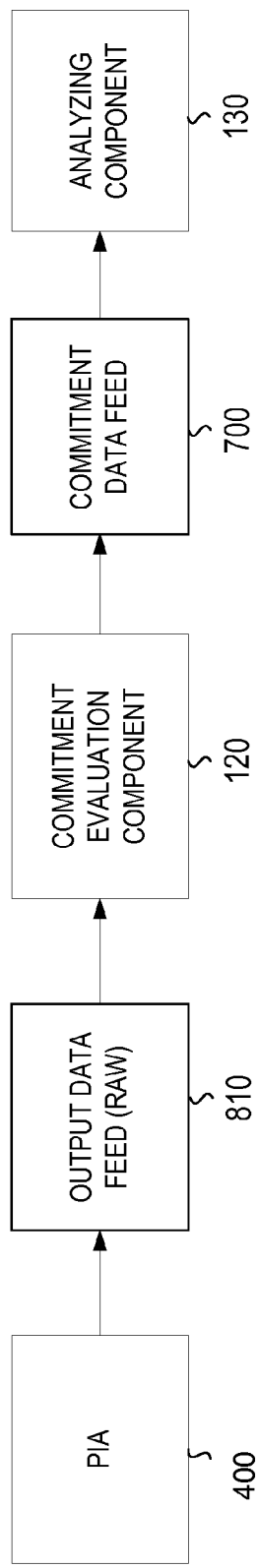
FIG. 94 is a block diagram of the user commitment evaluation component in accordance with one embodiment of the present invention.

In an alternate embodiment, referring to FIG. 94, the commitment evaluation component 120 may be an entity separate from the PIA 400 that accesses the PIA 400 to receive record feeds for processing and formatting. Relevant record feeds are processed, formatted and prepared for analysis. An output data feed 910 is provided from the PIA 400 to the commitment evaluation component 120. Processed data is prepared for output from the commitment evaluation component 120 via commitment data feed 700. In order to access the PIA 400, the commitment evaluation component 120 may be required to be authorized for the access to the PIA 400.

Those skilled in the art will recognize that the user commitment evaluation component 120 may be implemented by various combinations of features and functionality not limited to the combinations of features and functionality of FIGS. 88, 92 and 94.

The analyzing component 130 determines the effectiveness of an advertisement or an advertisement campaign by comparing and/or analyzing the user's viewed advertising data feed 600 to the commitment data feed 700 containing the advertisement and the evaluated user commitments. The data found in the two sources is processed to determine meaningful conclusions about the effect of presented advertising on the user. Effectiveness data may be the result of a simple comparison looking for a user commitment corresponding to a viewed advertisement. The analysis performed by the analyzing component 130 may also involve processing the viewed advertising data feed 600 and the commitment data feed 700 to find a correlation or match between data in the data feeds.

Various forms of data analysis exist in conjunction with the analyzing component 130. More advanced analysis may seek to find a correlation between number of impressions of advertisements for a product and a user commitment to the product. Analysis may be performed on ads to look for ads that are skipped or watched more than once. Analysis to determine effectiveness of advertisement campaigns may also include determining whether the user purchased an advertised product, and if so the quantity and frequency of purchases of the product. Those skilled in the art will understand that many other analysis methods exist that may be performed using the described systems for analyzing the effectiveness of advertisements.

For example, if a user who normally purchases Aquafresh brand toothpaste sees an advertisement for Colgate brand toothpaste on August 25 according to the viewing history data feed, and purchases a tube of Colgate brand toothpaste on August 26, a strong correlation may be made between the events and the advertisement may be given a high effectiveness grade or rating. However, if the user only purchased Colgate brand toothpaste for a duration of two months following the viewing of the Colgate brand toothpaste advertisement, then the advertisement may be given a lower effectiveness rating. In another example, if a user sees a banner ad for a blood donation drive on a website and clicks the advertisement to get more information according to the viewing history feed, and the commitments data feed provides data that the user has a calendar entry for giving blood, the advertising may be deemed effective. However, an advertisement that has been fast forwarded several times or seen often without receiving any corresponding commitments is likely to be deemed to be ineffective.

Other ways that the analyzing component 130 might analyze the user's viewed advertising data feed 600 and commitment data feed 700 is to compute the total number of purchases of an advertised product by the user or the rate of purchase of an advertised product by the user.

Figure 90:
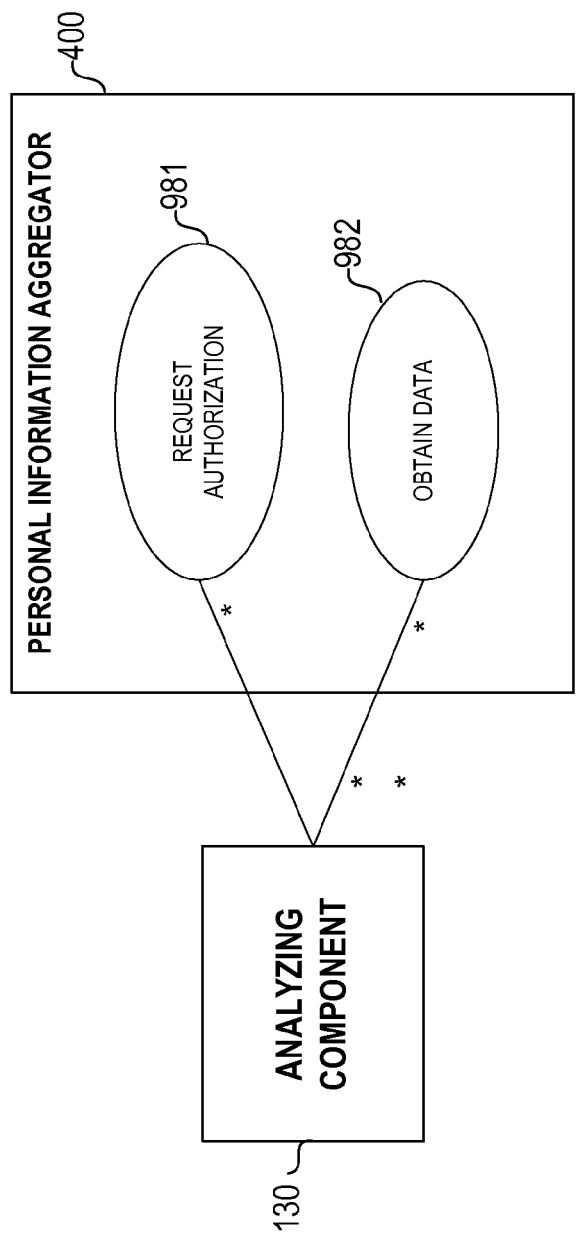
FIG. 90 is a use case diagram of the advertisement analyzing system of FIG. 87.

In order to access the data feeds from a PIA 100, the analyzing component 130 may need to request access from the PIA 100. Referring to FIG. 90, the effectiveness analyzing component 130 includes a Request Authorization use case 981 to request the needed authorizations from the PIA 400. Authorization may be requested for single-use, limited-use or ongoing-use of the data. Once access is granted, the analyzing component 130 requests and receives advertising data feed 600 and commitment data feed 700 from the advertisement monitoring and the commitment evaluation components 110 and 120.

It should be recognized that the analyzing component 130 may access data from numerous PIAs 400 in order to assess the effectiveness of an advertisement campaign across a population. The analyzing component 130 may traverse links of the NDSN 100 to locate additional users for inclusion in an analysis.

In the case of analyzing multiple PIAs 400, multiple processed advertising data feeds 600 and processed commitment data feeds 700 are presented to the analyzing component 130. The analyzing component 130 may determine advertising effectiveness of an advertisement on a group of users organized based on criteria such as a targeted demographic.

The advertising effectiveness analyzing component 130 may obtain the data that the advertisement monitoring component 110 and the user commitment evaluation component 120 have collected by employing the Obtain Data use case 982. The analyzing component 130 may perform analysis on the data received from the advertisement monitoring component 110 and the user commitment evaluation component 120.

The advertisement effectiveness analyzing component 130 may provide a set of results characterizing the effectiveness of an advertisement or a group of advertisements. The results set may be used for targeting future advertisements to a PIA user or a group of PIA users. Targeting may be performed based on the effectiveness of an advertisement or campaign found from analyzing the composite advertising data feed 600 and the composite commitment data feed 700.

In one embodiment, if an advertisement is found effective for a group of similar users within an NDSN 100, the effective advertisement or advertisements similar to the effective advertisement will be presented to individuals exhibiting similar characteristics to the analyzed group. Similarly, if an advertisement was found ineffective, it may be taken out of service completely or no longer shown to users similar to the analyzed group.

In another embodiment, advertisement effectiveness data may be used to select an advertisement for a PIA 400 user having an advertisement opportunity. The PIA user may display qualities similar to users having advertisement effectiveness data feeds. The data from these users may be used to choose an advertisement likely to be effective for the user viewing the advertisement opportunity Those skilled in the art will recognize that the advertising system may be implemented by various combinations of features and functionality not limited to the combinations of features and functionality of FIG. 90.

The PIA may be configured to permit the various advertising analyzer components to access output data feeds that contain personal information stored in the PIA 400. Such configuration may include defining output data feeds, assigning contact (external entity) types, mapping output data feeds to external entities and types, and authorizing access to output data feeds.

Referring again to FIG. 1, where the role of the Entity 207 is played by the advertisement analyzing component 130, the user 250 (i.e., the individual) may define output feeds by employing one of the feed definition use cases 958 (Define Composite Feed, Define Derived Feed, Define Filtered Feed) of the Define Feed use case 953. Contact types may be assigned by the user 250 by employing the Assign Contact Types use case 951. As an example, the user 250 may assign an Advertiser contact type to facilitate access by the advertisement analyzing component 130 (i.e., the Entity 207). The user 250 may also map output data feeds by employing the Map Feeds use case 952. For example, the user 250 may map a Music Purchases output data feed (not shown) to the Advertiser contact type.

As described above, the advertisement analyzing component 130 may request authorization to access output data feeds that contain personal information stored in the PIA 400. To make such an authorization request, the advertisement analyzing component 130 may employ the Request Authorization use case 954. To grant the requested authorization, the user 250 may employ one of the access type use cases 957 (e.g., Allow Single-use Access, Allow Ongoing Access, Allow Limited Access) of the Authorize use case 950.

The user 250 may pre-authorize access for an external entity or type, or alternatively, the user 250 may grant (or deny) authorization independently for each separate authorization request that is received by the PIA 400. If the authorization requested by the various subsystems of the analyzer is granted, then the analyzing systems associated with the analyzer may access the personal information contained in output data feeds of the PIA 400 by employing the Access Information 956 use case.

As discussed previously, various methods exist for interconnecting the advertisement monitoring component 110, commitment evaluation component 120 and the analyzing component 130 with the PIA 100. In the case where the monitoring component 110 and the commitment evaluation component 120 are internal to the PIA 100, data feeds are input into the PIA and processed by the components within the PIA. The analyzing component 130 connects to the PIA 100 through the computer network 900, requesting the user commitment data feed 700 and the presented advertising data feed 600. Once the analyzing component 130 is authenticated and access is approved by the PIA user, the data feeds are transferred through the computer network 900. The analyzing component 130 performs a decision making process for evaluating effectiveness of advertisements viewed by the user.

In one embodiment, the analyzing component 130 is only interested in advertisements seen by a PIA user from one advertising entity, such as an ad network or corporate advertiser. In another embodiment, the analyzer performs analysis on a particular set or category of product advertisements or of advertisements during a certain time frame. For example, analysis may be performed on all car advertisements. In another embodiment, the analyzing component 130 performs analysis on each advertisement presented to the PIA user from advertising data feed 600.

Data may be collected from a plurality of PIAs 100. The analyzing component 130 requests authorization to PIAs for access to the advertising data feed 600 and commitment data feed 700. Access may be requested to each PIA separately as required or alternatively analyzing component 130 may request access to a plurality of PIAs 100 simultaneously.

When multiple PIAs 100 are being analyzed, a plurality of advertising data feeds 600 and commitment data feeds 700 must be combined together at the analyzing component 130. The combination may be performed by combining and sorting like advertisements and commitments from the plurality of users into a composite advertising data feed 600 and a composite commitment data feed 700. It is possible to select only a subset of data feeds for processing into the composite data feeds depending on goals of the analyzing campaign. In another embodiment, the data feeds from each PIA 100 may be analyzed separately and the effectiveness data may be combined for each PIA 100 after completion of analysis at the analyzing component 130.

An output feed from the analyzing component 130 may provide various results of effectiveness. Results of effectiveness may be a simple output providing a list of advertisements that led to a commitment for the presented product from the PIA user. Another result of effectiveness may be a list of all advertisements a user skipped or watched more than once. Another result of effectiveness may provide a correlation between number of times an ad was watched and a user commitment for the presented product. Yet another result of effectiveness may present the average time between the presentation of an ad and the corresponding user commitment, for those ads where a corresponding user commitment exists. In the case of analysis of a plurality of PIAs, the results may provide a percent success for an advertisement campaign. Results may show the effectiveness of advertisements on particular groups based on demographics.

Figure 96:
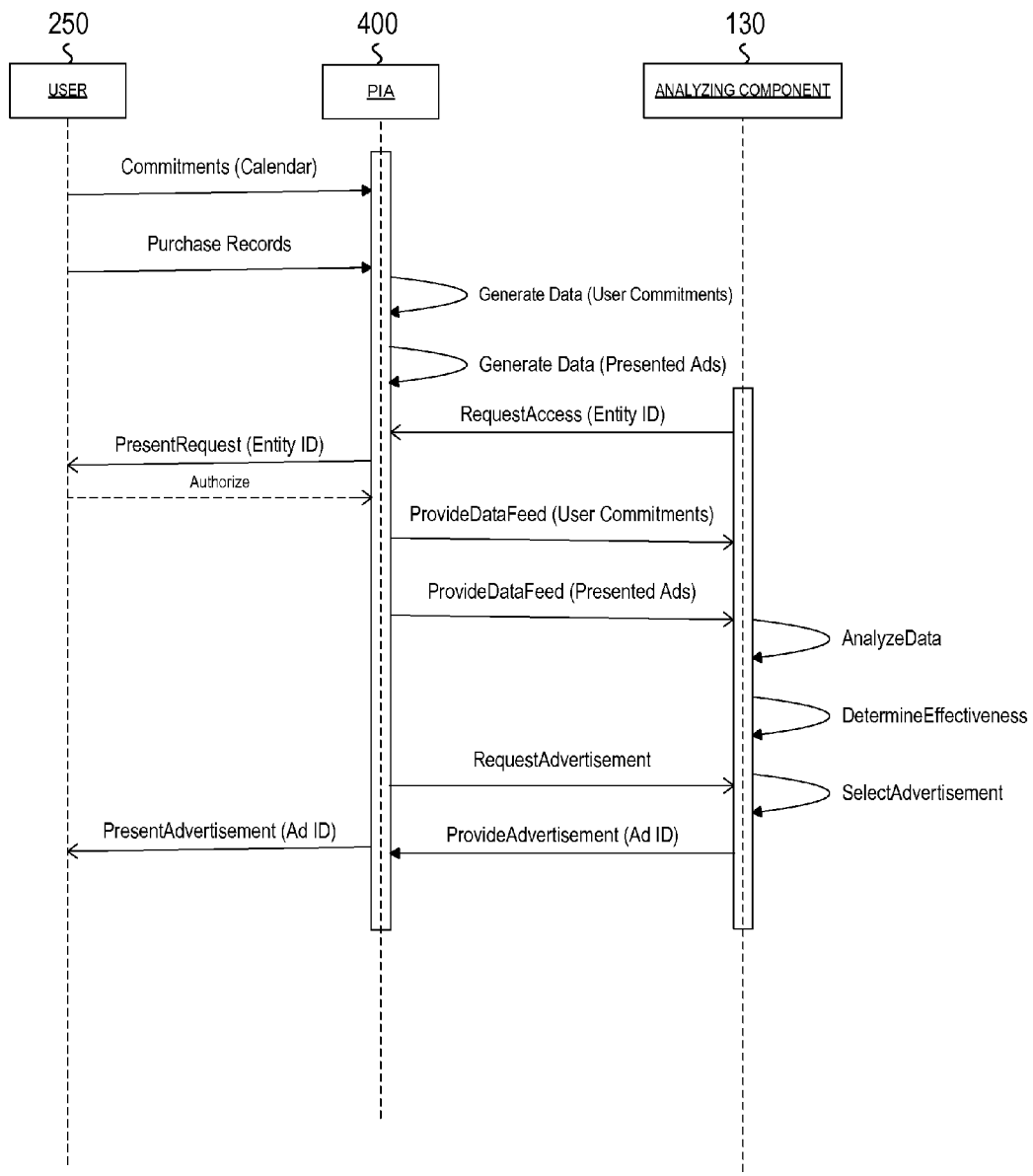
FIG. 96 is a sequence diagram associated with analyzing advertisement effectiveness using data received from a PIA.

Operation of an exemplary embodiment of the advertisement effectiveness analyzing system is shown in FIG. 96. User commitments in the form of calendar entries are entered for storage in the PIA 400. Purchase records are also provided for storage. The information may be provided manually by the user 250 or received by the PIA 400 from an external entity as described above. The PIA 400 generates a user commitments data feed 700 and a viewed advertising data feed 600 from the personal information. When the analyzing component 130 requests access to the PIA 400, the PIA 400 presents the request to the user 250 and receives an authorization from the user 250. The data feeds 600 and 700 are then provided to the analyzing component 130. Once the data feeds are received, the analyzing component 130 analyzes the data to determine the effectiveness of advertisement campaigns. This effectiveness data may then be used to select a new advertisement to be provided to the PIA 400. Once a new opportunity to present advertising becomes available, the PIA 400 may control presenting the advertisement to the user 250.

Figure 97:
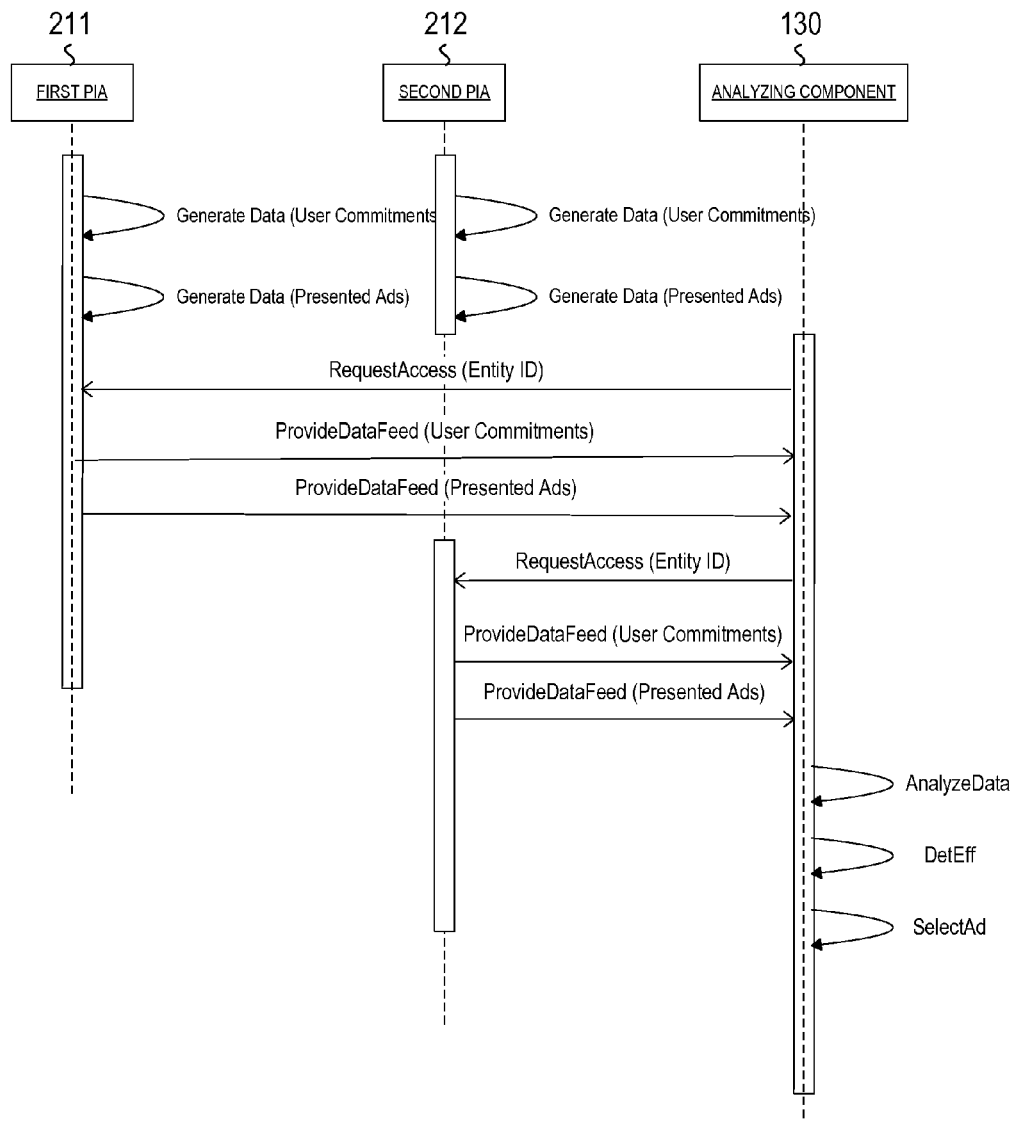
FIG. 97 is a sequence diagram associated with analyzing advertisement effectiveness using data received from two PIAs.

Multiple PIAs, e.g., PIAs contained in a projection of the NDSN, may be analyzed in a similar way as shown in FIG. 97. The analyzing component 130 requests access to a plurality of PIAs, PIA1 211 and PIA2 212. Once access is granted, the user commitments data feed 700 and viewed advertising data feed 600 are provided to the analyzing component 130. The data feeds 600 and 700 are analyzed to determine effectiveness data about advertisement campaigns with respect to the multiple PIA users. The composite effectiveness data may be used to select advertisements for presentation to users displaying similarities to the analyzed PIA users.

Selecting an advertisement for display may be performed in a variety of known methods. For example, an advertiser may provide characteristics and/or target demographics of an advertisement. The analyzing component 130 may determine the effectiveness of advertisements with similar characteristics and/or target demographics to select the proper audience for the advertisement. Alternatively, the analyzing component 130 may analyze advertisement effectiveness data to calculate proper demographics for an advertisement.

In another embodiment, the PIA 400 may request an advertisement for presentation to the user. The request may include a type of advertisement required, such as image, text or video. Analyzing component 130 uses the determined advertisement effectiveness data to select an appropriate advertisement for presentation to the user. The selection may take into account data provided by the PIAs 400 and CIAs 220 of the user and his or her peers.

The analyzing component 130 may send the advertisement data in the form of the advertisement or an advertisement identifier to the PIA 100. Presentation of the advertisement to the user may occur through one of several mediums, including TV through the DVR, over the Internet on a website or web application, in an E-mail, magazine, newspaper or on a billboard.

Information obtained from an NDSN may be used to target advertisements to individuals or groups. An advertising system may be used by one or more advertisers to connect to, and extract information from, the NDSN. The advertising system performs an analysis of the information, and selects advertisements that are targeted to individuals or groups of individuals.

Figure 98:
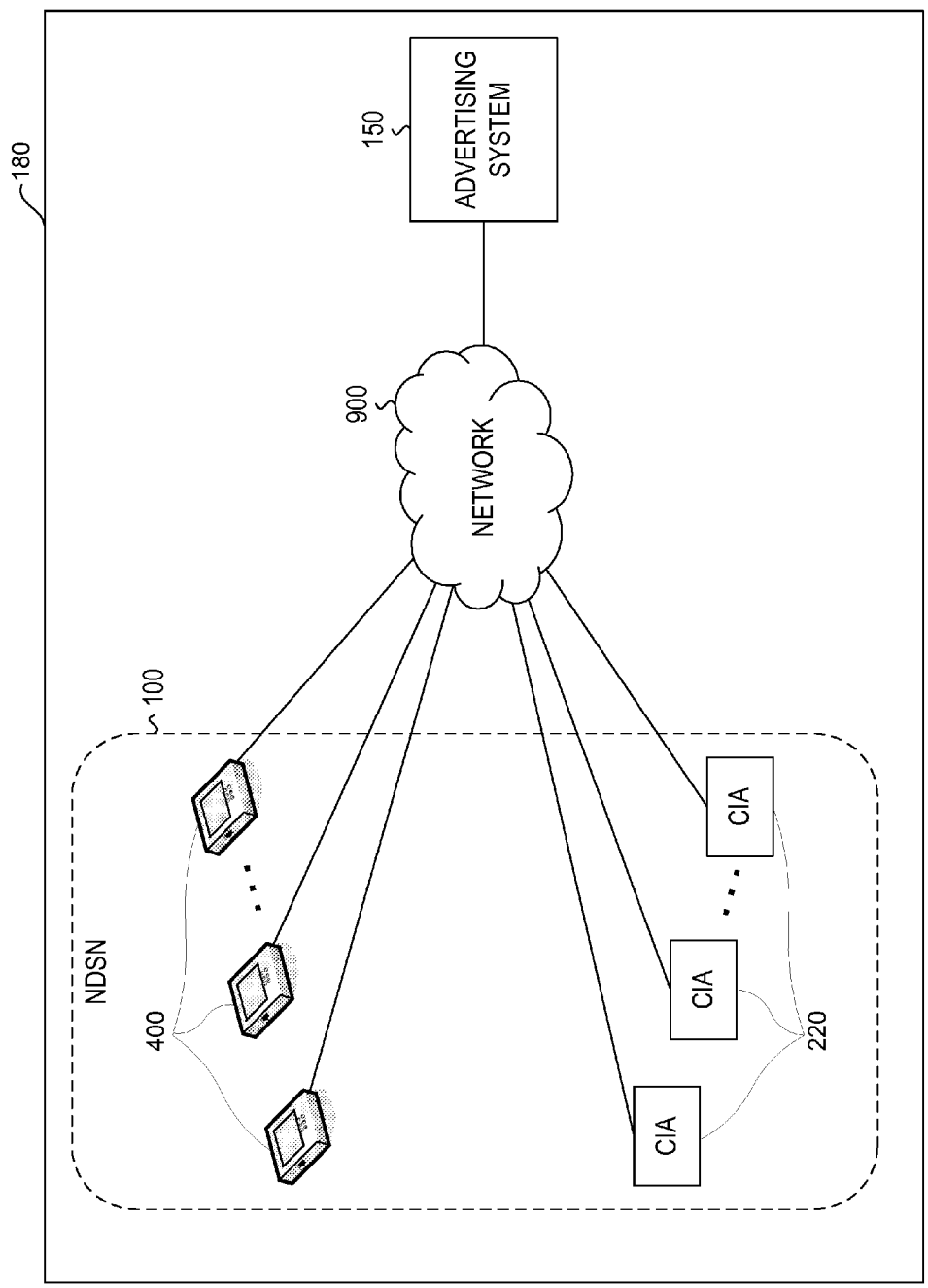
FIG. 98 is a block diagram of a system for targeting advertisements in accordance with one embodiment of the present invention.

Referring to FIG. 98, the system for targeting advertisements 180 includes an NDSN 100 comprising PIAs 400 and CIAs 220 of the persons, communities and other entities (not shown) that participate in the NDSN 100. The PIAs 400 and CIAs 220 are connected by a computer network 900.

Still referring to FIG. 98, the system for targeting advertisements 180 also includes an advertising system 150 which is connected to each of the PIAs 400 and CIAs 220 in the NDSN 100 by the computer network 900. The advertising system 150 may be used by advertisers (not shown) to obtain information from the PIAs 400 and CIAs 220 in the NDSN 100. The advertising system 150 uses the retrieved or collected information, at least in part, to select advertisements that are targeted to participants in the NDSN 100. In addition, the advertising system 150 may present the selected advertisements to the targeted participants of the NDSN 100.

The advertising system 150 provides one or more advertisers with the ability to target advertisements by analyzing personal information regarding or corresponding to individuals, their relationships and behaviors. Personal information obtained and analyzed by the advertising system 150 may be personally identifiable (e.g., the information has a known association with an individual) or anonymous in the sense that an individual's personally identifiable information is suppressed, although an individual can be anonymously associated with the information using, e.g., a user identification number or temporary transaction identifier.

Figure 100:
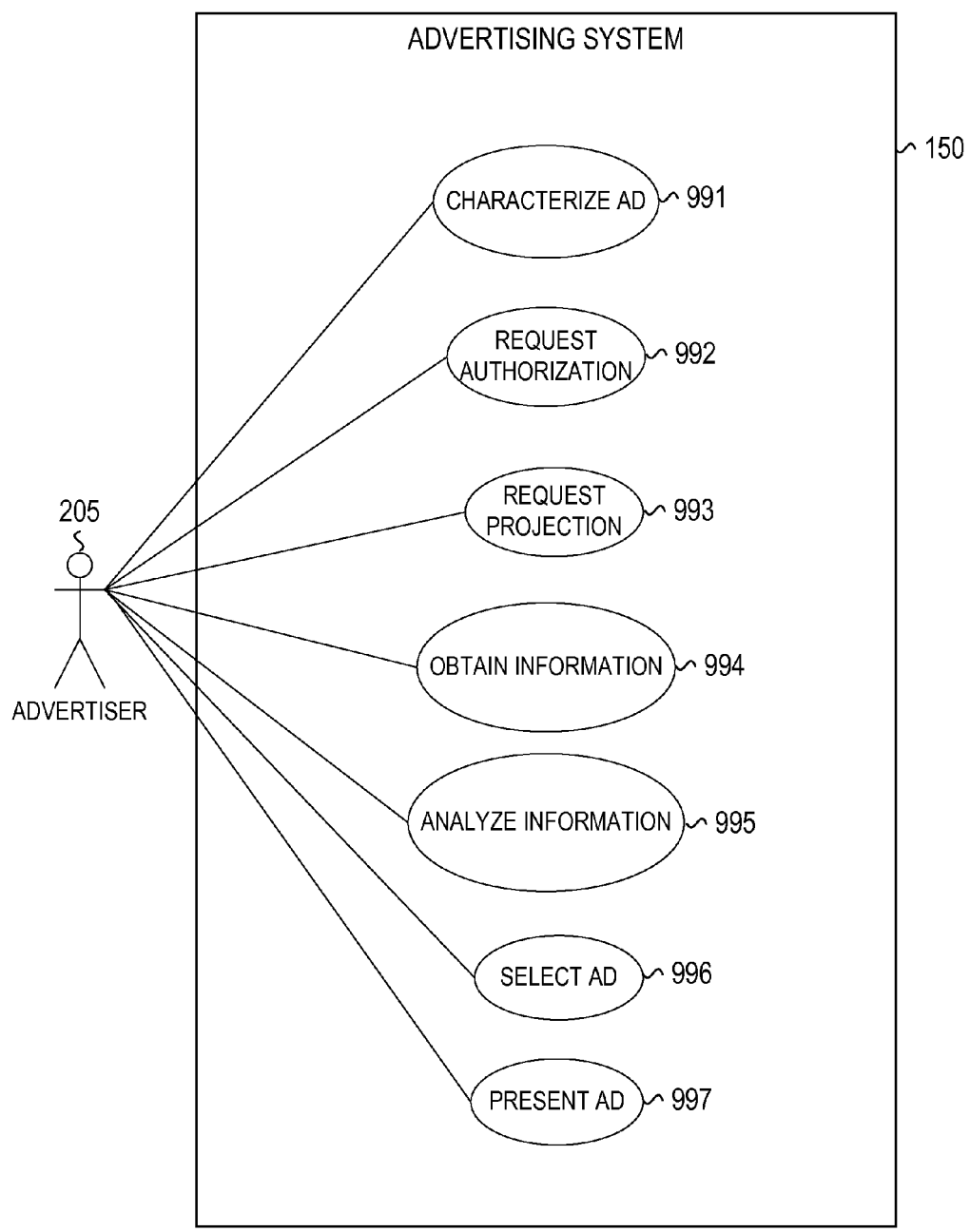
FIG. 100 is a use case diagram for the advertising system of FIG. 99.

In one embodiment, the advertiser 205 may have to receive authorization from one or more of the participants in the NDSN 100 in order to access information from the PIAs 400 and CIAs 220. Referring to FIG. 100, the advertiser 205 may employ the Request Authorization use case 992 to instruct the advertising system 150 to request the needed authorizations from the participants in the NDSN 100. In one embodiment, authorizations may be requested as needed while the advertising system 150 traverses the nodes of the NDSN 100. In an alternate embodiment, authorizations may be requested from a subset of the participants in advance of traversing the nodes of the NDSN 100. Furthermore, authorization may be requested for single-use, limited-use or ongoing-use of the information.

The advertiser 205 may request the advertising system 150 to create a projection of the NDSN 100, based on one or more dimensions of the relationships between participants in the NDSN 100, by employing the Request Projection use case 993. For example, the advertising system 150 may request a projection of the NDSN 100 along an Immediate Family dimension, thereby allowing the advertising system 150 to focus its analysis on the personal information and relationships of the immediate family members of a particular participant in the NDSN 100.

In one embodiment, the projection of the NDSN 100 may be created while the advertising system 150 traverses the nodes of the NDSN 100. In an alternate embodiment, the projection of the NDSN 100 may be created in an initial traversal of the nodes of the NDSN 100, in advance of a subsequent traversal during which information is obtained from the nodes of the projection of the NDSN 100.

Still referring to FIG. 100, the advertiser 205 may obtain the information that the advertising system 150 has collected during its traversal of the nodes of the NDSN 100 by employing the Obtain Information use case 994. In one embodiment, the information may be obtained incrementally while the advertising system 150 is traversing the nodes of the NDSN 100. In an alternate embodiment, the information may be obtained after the advertising system 150 has completed the traversal of the nodes of the NDSN 100.

The information obtained by the advertising system 150 may include group characteristics, advertisement presentation records, records of interactions with advertisements, purchase records and consumption records. Group characteristics allow the advertising system 150 to consider certain participants in the NDSN 100 as belonging to a group. For example, participants may have a group characteristic identifying them as located in a particular geographic area, or as having visited a particular website.

Advertisement presentation records obtained by the advertising system 150 may include records of advertisements that were previously presented to the targeted individual or group, or to other participants in the NDSN 100.

The advertiser 205 may instruct the advertising system 150 to perform an analysis of the information obtained from the nodes of the NDSN 100 by employing the Analyze Information use case 995. In one embodiment, the analysis may be performed incrementally while the advertising system 150 is traversing the nodes of the NDSN 100. In an alternate embodiment, the analysis may be performed after the advertising system 150 has completed the traversal of the nodes of the NDSN 100.

In one embodiment, some or all of the information obtained from the nodes of the NDSN 100 may be weighted by the advertising system 150 before performing an analysis of the information. For example, information obtained from a node of the NDSN 100 may be weighted according to the degrees of separation between the node and the targeted individual.

The analysis performed by the advertising system 150 may include the calculation related to the adoption of items (i.e., products, goods, services, media content, etc.) by participants in the NDSN 100. For example, referring to FIG. 101, if the advertising system 150 is targeting advertisements for music content to User 1, then the analysis may include the calculation of adoption statistics for music content items that have been purchased and consumed by the participants included in the projection of the NDSN 100 along the Music dimension. Adoption statistics calculated by the advertising system 150 may include adoption rate and time-to-peak adoption rate. In addition, adoption statistics may be normalized (i.e., scaled by) the number of initial introductions of the content to participants in the NDSN 100.

The advertising system 150 may analyze records of advertisement presentation that may be included in the information accumulated during the traversal of the nodes of the NDSN 100. For example, referring to FIG. 101, if the advertising system 150 is targeting advertisements for music content to User 1, then the analysis may include the identification of the most prevalent music-related advertisements that have been viewed or heard by the participants included in the projection of the NDSN 100 along the Music dimension.

The analysis by the advertising system 150 of the information accumulated during the traversal of the nodes of the NDSN 100 may include metrics related to the number of nodes that are traversed or the degrees of separation between those nodes. For example, if the advertising system 150 is targeting advertisements for vacation packages to User 1, the analysis may include determining the size of the immediate family of User 1 by calculating the number of nodes contained in a projection of the NDSN 100 based on an Immediate Family dimension. As another example, referring to FIG. 101, if the advertising system 150 is targeting advertisements for music content to User 1, the analysis may include calculating the number of first-degree, second-degree, etc. relationships between the nodes contained in the projection of the NDSN 100 along the Music dimension. The analysis may also include calculating the distribution of participants among the degrees of separation with User 1. For example, the distribution among first, second and third-degree relationships with User 1 might be 70, 20 and 10 percent respectively.

Referring again to FIG. 100, the advertiser 205 may characterize advertisements by employing the Characterize Ad use case 991. Characterization of advertisements results in the creation of advertisement characterization metadata which may be used by the advertising system 150 for selecting advertisements that are targeted to participants in the NDSN 100. Such metadata may include, but is not limited to, product categories (e.g., type of automobile, music genre, male grooming, etc.) and target demographics.

Advertisements can be characterized in a number of ways, including but not limited to characterization of the advertisement by noting the demographics of the market of the intended audience for the advertisement. For example, an advertisement for motorcycles may be characterized as intended for the single male audience in the 18-25 range, whereas an advertisement for a retirement village may be characterized as intended for married couples with high net worth in the 50-65 age bracket.

Advertisements can also be characterized based on the intended behaviors or states of the target audience. For example the advertisement may be characterized as intended for a target market that buys more than $100 of dairy products per month, or for individuals suffering from a specific illness.

Advertisements can also be characterized based on the genre or type of the advertisement (e.g., humorous, informational, or price-based) or the specific product or service being advertised (e.g., breakfast cereal, or low-interest mortgages).

The advertiser 205 may instruct the advertising system 150 to select one or more advertisements that are targeted to participants in the NDSN 100 by employing the Select Ad use case 996.

Selecting of advertisements can occur through a number of processes and algorithms which provide for the ability to compare properties of the advertisement or characterization parameters associated with the advertisement (e.g., intended market, general viewing rate of the advertisement, or viewing rate for a particular market) with properties of the individual or group being proposed as the recipient of the advertisement. In one embodiment, one or more advertisement characterization parameters are examined and compared against one or more parameters associated with the proposed recipient. The parameters can include, but are not limited to, personal information. If the number of matching parameters reaches or exceeds a threshold, the advertisement is selected. In an alternate embodiment, Boolean logic is applied to the parameters (advertisement characterization parameters in some combination with parameters of the proposed recipient) and advertisements are selected based on the fulfillment of the Boolean expression. In another embodiment, advertisement characterization parameters are correlated with the parameters associated with the individual or group, and advertisements showing a sufficiently high correlation with the parameters of the individual or group are selected.

In some embodiments, the advertising system 150 may select advertisements that are targeted to an individual, at least in part, by matching the demographics of the individual to the characterizations of advertisements, and by using the results of analyzing the information accumulated during the traversal of the nodes of the NDSN 100. The characterizations of the advertisements managed by the advertising system 150 may be correlated with the demographics of the targeted individual to identify those advertisements that are potential candidates for selection. The advertising system 150 may analyze information accumulated during the traversal of the nodes of the NDSN 100, and select one or more advertisements targeted to the individual based on that information.

For example, if the correlation of an advertisement's characterizations with an individual's demographics exceeds a threshold, then the advertisement may be identified as a potential candidate for selection. Of those identified candidates, the advertisement for the product with the highest adoption rate among participants in a projection of the NDSN 100, or among participants with demographics or preferences that are similar to those of the target individual, may be selected for targeting the individual.

As a second example, the advertising system 150 may determine an advertisement that was most frequently presented to participants in the NDSN 100, or in a projection of the NDSN 100, and select that advertisement, or one or more other advertisements that have similar characteristics to that advertisement, for targeting the individual.

As a third example, the advertising system 150 may select one or more advertisements whose characterizations match the size of a projection (i.e., the number of nodes in the projection) of the NDSN 100.

As a fourth example, the advertising system 150 may select one or more advertisements whose characterizations match the distribution of participants among the degrees of separation with the target individual.

The advertiser 205 may instruct the advertising system 150 to present one or more selected advertisements to participants in the NDSN 100 by employing the Present Ad use case 997. Presentation of an advertisement may encompass a wide variety of mechanisms and types of media, and may depend upon factors such as the type of product or service, format of the advertisement, and available distribution channels. For example, the advertising system 150 may present advertisements to participants in the NDSN 100 by transmitting the advertisements over the computer network 900 to the PIAs 400.

Those skilled in the art will recognize that analyzing the information accumulated during the traversal of the nodes of the NDSN 100 and selecting targeted advertisements may be accomplished by using a variety of algorithms and may result in a variety of metrics and statistical parameters, and is not limited by the algorithms, metrics and statistical parameters described above.

Those skilled in the art will also recognize that the system for targeting advertisements may include a large number of participants in the NDSN 100, and that the selection of various implementation elements and methods may therefore be based on the size of the NDSN 100. For example, a projection of the NDSN 100 may be stored and used to reduce the execution time of subsequent targeting operations. As another example, obtaining on-going use authorization from the nodes of the stored projection may also add efficiency to subsequent targeting operations.

Those skilled in the art will recognize that the advertising system may be implemented by various combinations of features and functionality not limited to the combinations of features and functionality of FIG. 100.

Figure 102:
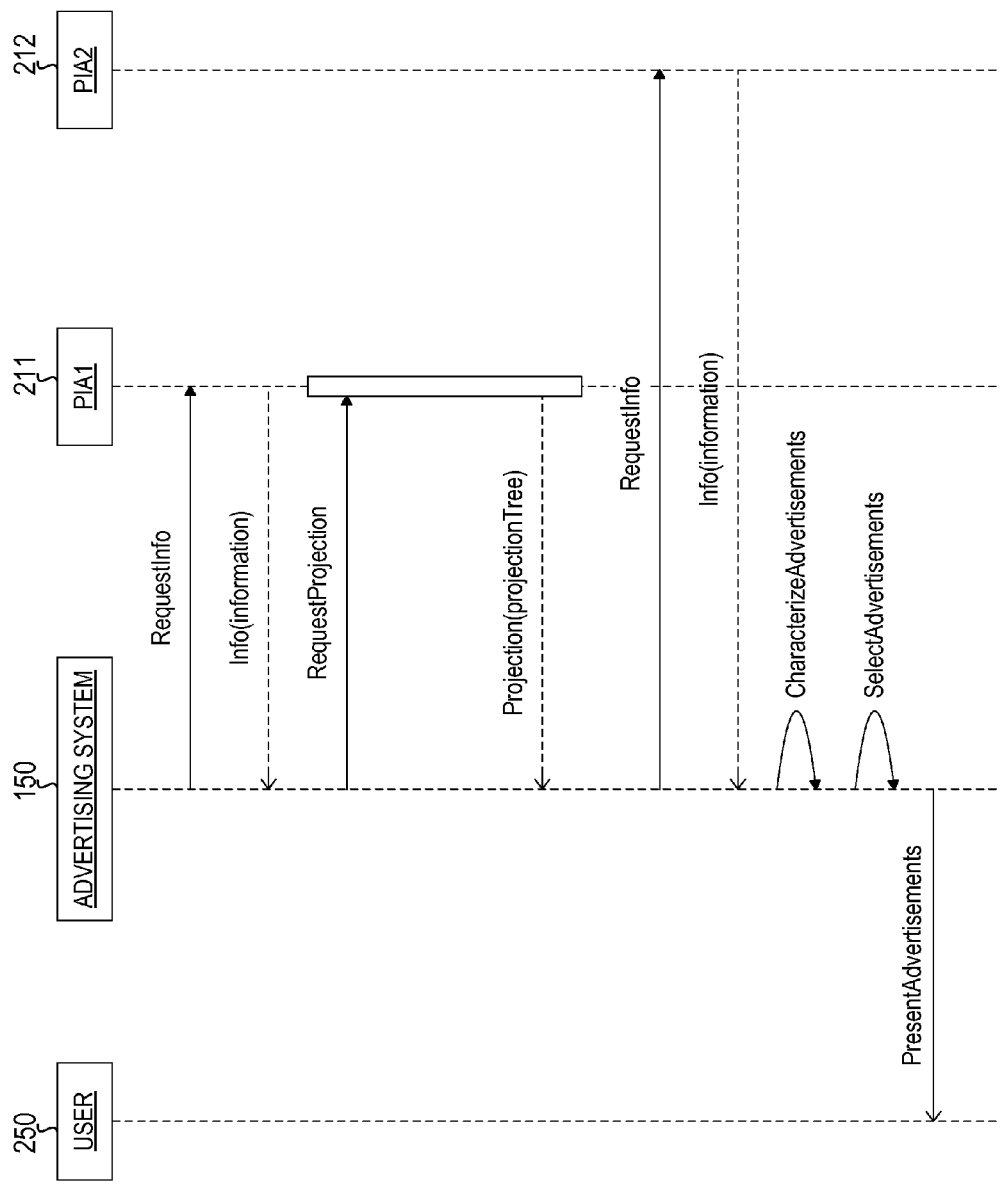
FIG. 102 is a sequence diagram associated with targeting advertisements in accordance with one embodiment of the present invention.

FIG. 102 illustrates a sequence of steps corresponding to the selection and presentation by one embodiment of the advertising system 150 of one or more targeted advertisements. The advertising system 150 obtains personal information corresponding to the User 250 by sending a RequestInfo message to PIA1 211 and receiving an Info message from PIA1 211. The advertising system 150 requests a projection of the NDSN 100 by sending a RequestProjection message to PIA1 211 and receiving a Projection message from PIA1 211. In this example, the projection of the NDSN 100 contained in the projectionTree argument includes PIA2 212. The advertising system 150 obtains personal information corresponding to the user of PIA2 212 by sending a RequestInfo message to PIA2 212 and receiving an Info message from PIA2 212.

The advertising system 150 characterizes advertisements by sending itself a CharacterizeAdvertisements message. The advertising system 150 selects one more advertisements based at least in part on the obtained personal information and the characterizations of the advertisements by sending itself a SelectAdvertisements message. Finally, the advertising system 150 presents the advertisements to the User 250 by sending a PresentAdvertisements message to the User 250.

Those skilled in the art will recognize that selecting and presenting targeted advertisements may be accomplished by various sets and sequences of steps, and that the advertising system 150 is not limited to the steps, or the order of the steps, illustrated in FIG. 102.

The PIAs 400 and CIAs 220 may be configured to permit access by the advertising system 150, which may require authorization to obtain information from the PIAs 400 and CIAs 220. In one embodiment, authorization for the advertising system 150 is obtained from an initial subset of the participants of the NDSN 100, e.g., from a marketing promotional effort. Access to an initial subset of the NDSN 100 provides the advertising system 150 with "points of entry" to the NDSN 100; additional authorizations can be requested as the advertising system traverses the nodes of the NDSN 100 that have relationships with the initial subset of nodes.

Figure 101:
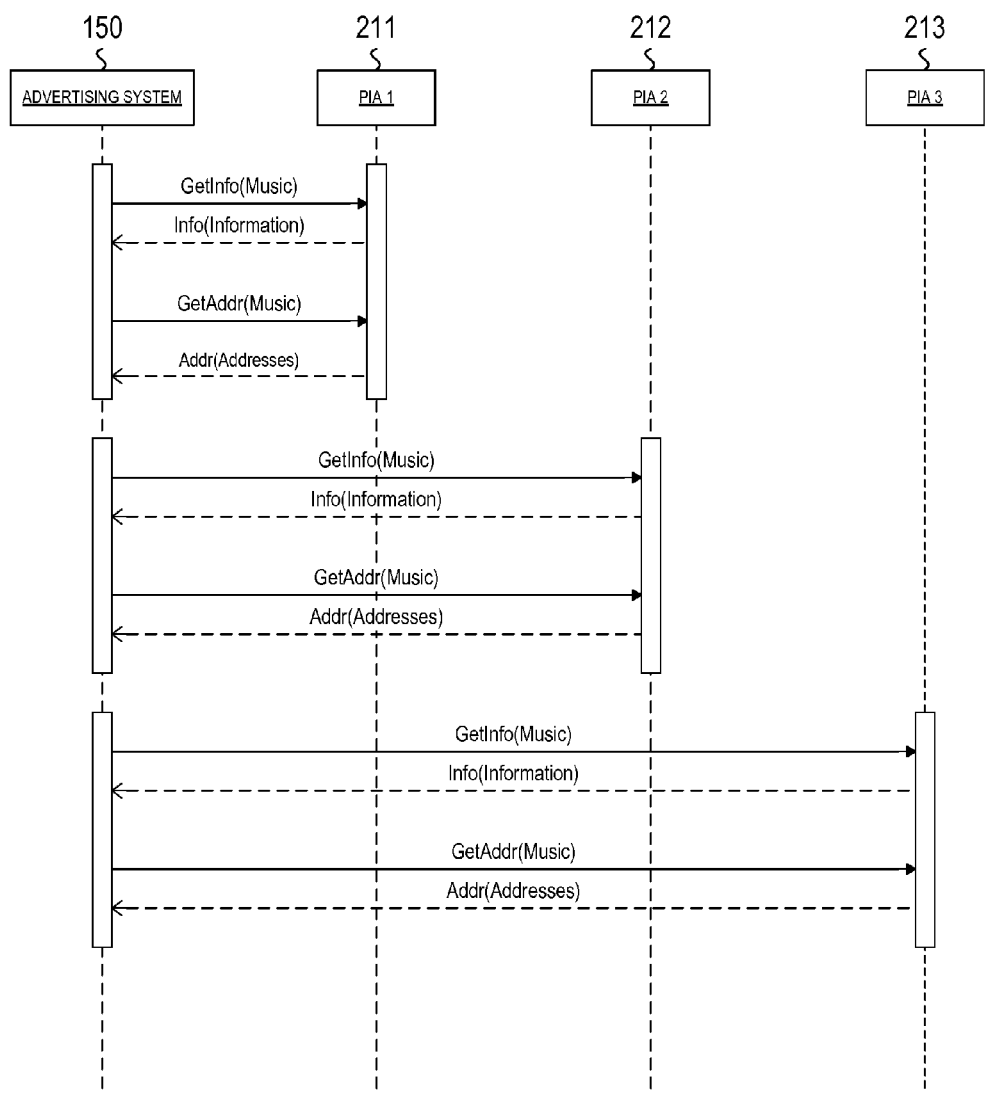
FIG. 101 is a sequence diagram associated with traversing an NDSN in accordance with one embodiment of the present invention.

In the example of FIG. 101, the advertising system 150 has authorization to access the information stored in PIA1 211, which is included in the initial subset of nodes available to the advertising system 150. The advertising system 150, which in this example is seeking to target advertisements for music content to the user (User 1, not shown) of PIA1 211, begins to traverse the NDSN 100 by sending a GetInfo message to PIA1 211, with an argument Music specifying the category of information being requested. PIA1 211 responds by sending an Info message with an argument Information that contains a list of information regarding music. This information may include purchase records (e.g., records of recent music purchases made by the user), consumption records (e.g., records of the user's recent music listening history) and advertisement presentation records (e.g., records of advertisements recently viewed by the user).

To obtain an incremental projection of the NDSN 100 along the dimension of Music, the addresses of other PIAs to be queried, the advertising system 150 sends a GetAddr message to PIA1 211 with an argument Music indicating the dimension of the projection. PIA1 211 responds by sending an Addr message with an argument Addresses that contains a list of addresses of other nodes in the NDSN 100 whose users have tastes in music similar to those of User 1. This list comprises a portion of the projection of NDSN 100 sought by the advertising system 150, and is used by the advertising system 150 to continue traversing the nodes of the NDSN 100.

In the example of FIG. 101, the Addresses list sent by PIA1 211 includes PIA2 212. As described above with respect to PIA1 211, the advertising system 150 sends GetInfo and GetAddr messages to PIA2 212 and the other nodes (not shown) on the list, and receives additional information and addresses from PIA2 212 and the other nodes in response to those messages.

The iterative process of sending GetInfo and GetAddr messages may be repeated a number of times as determined by the advertising system 150. For example, the iterations may be terminated when the degrees of separation between User 1 and the users of the nodes in the Addresses list exceeds a threshold. In the example of FIG. 101, the Addresses list sent by PIA2 212 includes PIA3 213. The advertising system 150 sends GetInfo and GetAddr messages to PIA3 213 and the other nodes (not shown) on the Addresses list received from PIA2 212, and so on. Thus, a projection of the NDSN 100 comprising participants in the NDSN 100 with musical tastes similar to those of User 1 is incrementally created, and the advertising system 150 accumulates information relevant to music content from the participants included in that projection.

Those skilled in the art will recognize that the interactions employed to obtain information and traverse the nodes may be executed in a variety of ways not limited to the examples of FIG. 101. For example, in FIG. 101, the GetInfo and GetAddr messages might be combined into a single message, where the response to the combined message would contain both information and addresses.

The computer network 900 enables the advertising system 150, PIAs 400 and CIAs 220 to communicate with each other through the exchange of messages and data. Multiple communication paths through the computer network 900 are possible at any given time. For example, the advertising system 150 can simultaneously communicate with one or more PIAs 400 and one or more CIAs 220.

The PIA may be used to generate notifications to the user based on the user's itinerary, which can include the user's current location, travel plans, and meeting and event plans. Examples of events that might be contained in the user's itinerary are concerts, theater performances, dance performances, movie screenings, exhibitions, conferences, social gatherings and business gatherings.

The information contained in the itinerary can be compiled from input data feeds from a variety of sources, for example, Microsoft Outlook™ or an automated location system, such as a GPS receiver. In addition, the user's itinerary can contain information that is inferred from other information, such as that contained in e-mails and text messages.

In one embodiment, personal information for the first individual is accessed, and the system obtains a projection of the NDSN 100 for the first individual. The personal information of the individuals in the projection of the NDSN 100 is examined to determine the extent to which those individuals have overlapping events, locations, or other time or location dependent parameters which warrant notification. In the event that there are parameters which suggest or trigger notification, that notification can be sent to the first individual, second individual, or both.

In one embodiment, the location of either the first or second individual can be monitored through the use of a Global Positioning Satellite (GPS) or other location system, with the current location of the individual being utilized in part to generate a notification.

As an example of one embodiment of the invention, the first individual may be flying from New York, their hometown, to Los Angeles, Calif. for business. Upon arrival in Los Angeles, the first individual's location becomes known to the system through their GPS enabled cell phone. The system can create a projection of the NDSN 100 based on the dimensionalities of professional contacts and friends with similar musical interests. Individuals in the projection of the NDSN 100 can be notified of the presence of the second individual in Los Angeles. Alternatively, personal information of the individuals in the projection of the NDSN 100 can be examined to determine possible events of interest that appear on the calendars of the individuals in the projection of the NDSN 100, and notifications can be sent to the first individual. As such, the first individual may be notified of a concert of interest, and may also be notified that an individual in the social network is planning on attending that concert.

As another example, the other individual's itinerary might reveal that he plans to travel to a particular city. The user might be interested in asking the other individual to visit a relative of the user that resides in that city, in which case the user's PIA would notify the user of the other individual's plans.

In one embodiment, the system operates from a centralized portal or server that either contains or accesses the personal information of the first individual and second individual, performs the projection of the NDSN 100, and generates notifications as appropriate. In another embodiment, the system operates from a local computing device associated with the first individual, and collects information either from a centralized portal or server or directly from devices associated with other individuals. Based on the collected information and determination of the projection of the NDSN 100, the system generates the appropriate notifications. In yet another embodiment, the system operates in a completely distributed manner, with projections and notifications being developed by the computing device associated with each individual.

A portable identification device (PID) may be carried by a user and used to facilitate the uploading of data to the user's PIA from a location that the user visits, such as a retail location or a physician's office. The PID provides an identifier of the user's PIA to a local system (e.g., a cash register) at the location. The identifier may be the address of the user's PIA, or the system may convert the identifier into the address. For example, the local system may use the identifier to look up a uniform resource locator (URL) for the user's PIA in a database, and then use a domain name system (DNS) lookup to obtain the Internet protocol (IP) address of the PIA. The local system uses the address of the user's PIA to access the PIA and requests authorization to upload personal information (e.g., a record of the user's purchase) to the user's PIA. If authorization is received from the user's PIA, the local system uploads the authorized personal information.

In some embodiments, the PID communicates with the local system through a wireless interface (e.g., WiFi, RFID) or a bar code reader. Depending upon the implementation, the PID may either send the identifier to the local system or the local system may read the identifier from the PID. In other embodiments, the PID is physically interfaced with the local system, e.g., by direct electrical contacts.

In one embodiment, the user's PIA, upon receiving the authorization request from the local system, notifies the user of the authorization request by sending a notification message to a user interface device associated with the user's PIA, e.g., the user's cell phone. The user must approve the authorization request via the user interface device in order for the PIA to authorize the local system to upload the personal information.

The embodiments of the present invention may be implemented with any combination of hardware and software. If implemented as a computer-implemented apparatus, the present invention is implemented using means for performing all of the steps and functions described above.

Figure 89:
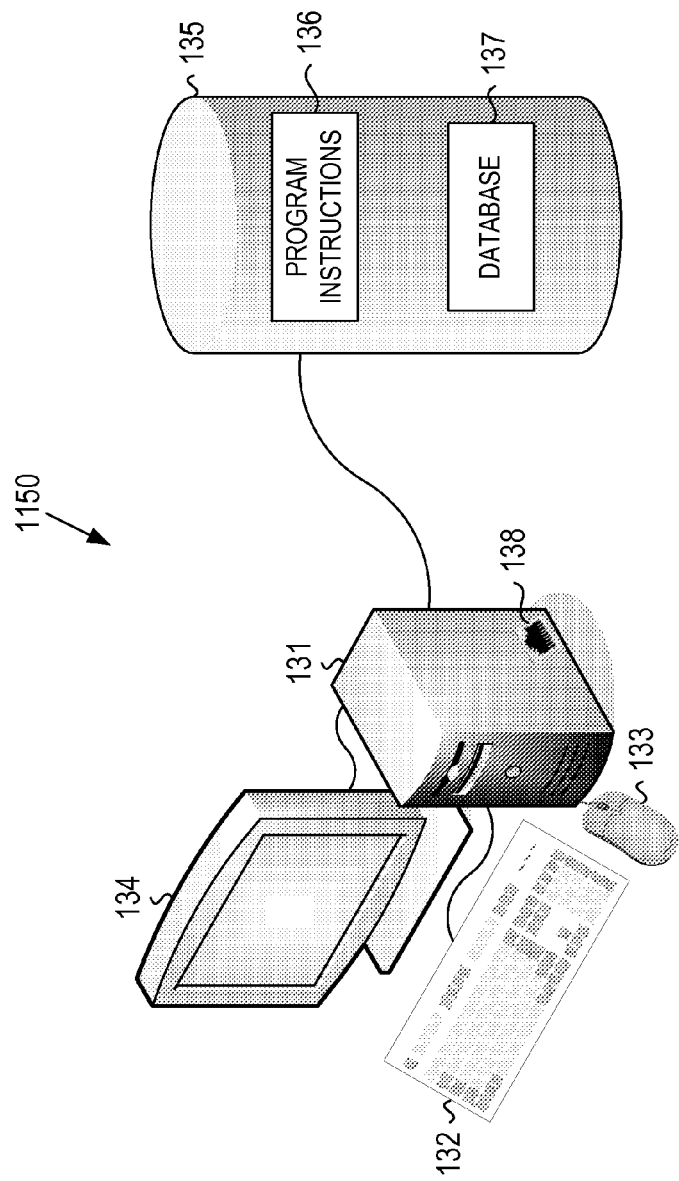
FIG. 89 is a block diagram of a computer system for realization of an embodiment of the present invention.

FIG. 89 illustrates a block diagram of a computer system 1150 for realization of a computer-implemented apparatus that may form all or a part of one or more implementation(s) or embodiment(s) of the present invention. The computer system 1150 includes a computer 131, a keyboard 132, a mouse 133, and a monitor 134. The computer 131 has a network port 138 for connecting to the computer network 900 (not shown). The computer 131 is connected to a storage device 135 which contains the program instructions 136 for the software application that provides the logical functions of the computer-implemented apparatus. The storage device 135 also contains a database 137 for storing data.

Those skilled in the art will recognize that the program instructions 136 for software applications implementing all or a portion of one or more embodiment(s) of the present invention may be written in a programming language such as Java or C++, and that the database 137 may be implemented with a database package such as Microsoft Access™ or a database management system (DBMS) such as Microsoft SQL Server™, Microsoft SQL Server CE™, IBM DB2™, mySQL or postgreSQL.

Figure 95:
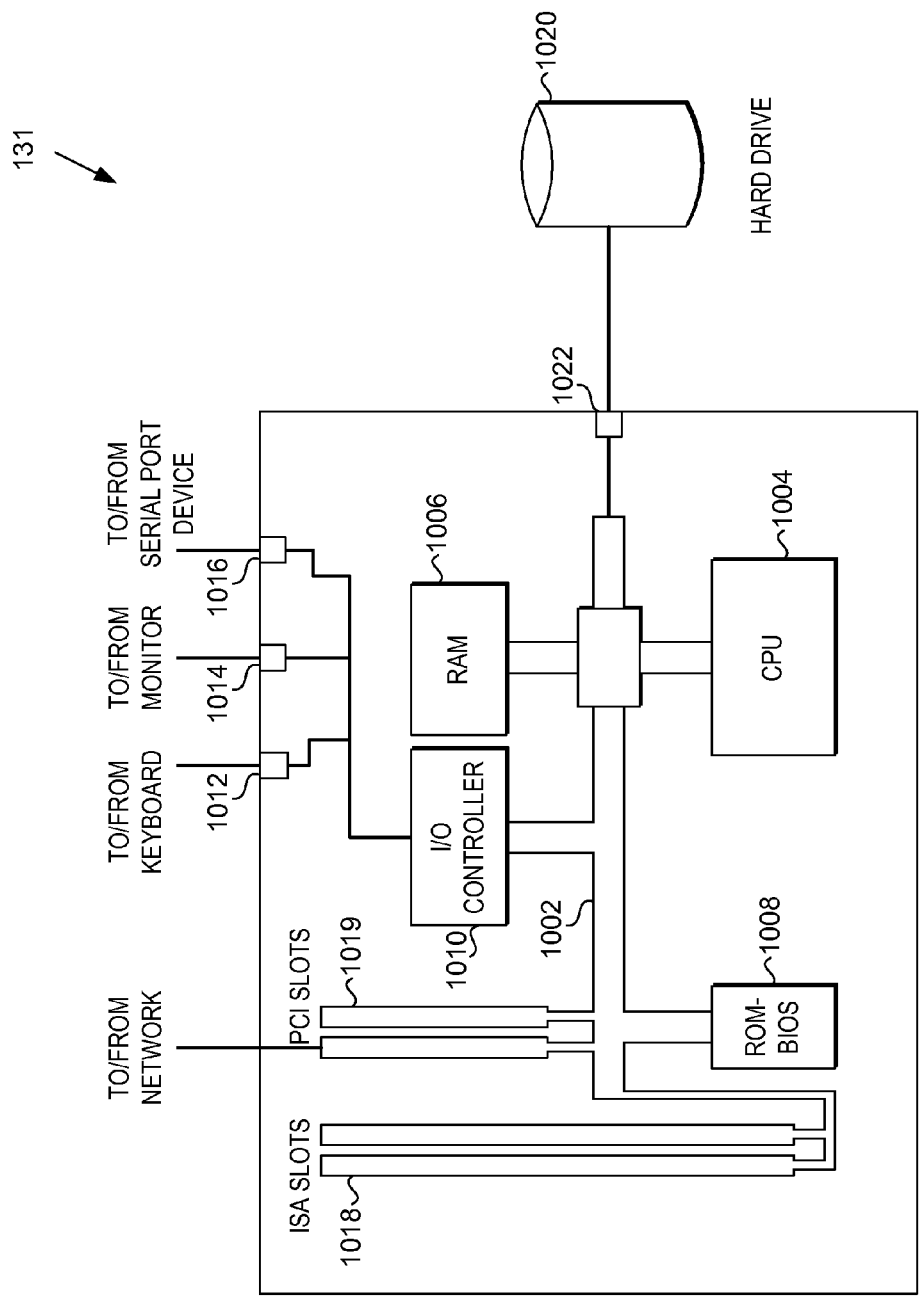
FIG. 95 is a block diagram of a computer system through which the implementation of an embodiment of the present invention may be realized.

FIG. 95 illustrates a block diagram of the computer 131. A system bus 1002 transports data amongst the CPU 1004, the RAM 1006, Read Only Memory—Basic Input Output System (ROM-BIOS) 1008 and other components. The CPU 1004 accesses a hard drive 1020 through a disk controller 1022. The standard input/output devices are connected to the system bus 1002 through the I/O controller 1010. The keyboard 132 (not shown) is attached to the I/O controller 1010 through a keyboard port 1012 and the monitor 134 (not shown) is connected through a monitor port 1014. The serial port device (not shown) uses a serial port 1016 to communicate with the I/O controller 1010. Industry Standard Architecture (ISA) expansion slots 1018 and Peripheral Component Interconnect (PCI) expansion slots 1019 allow additional cards to be placed into the computer. In one embodiment, the computer 131 has a network port 138 as described above.

Those skilled in the art will recognize that a part of, or the entirety of, an implementation of an embodiment of the present invention may be implemented as a web-based application that includes a web server and a browser application residing on a client computer.

The embodiments of the present invention can be included in an article of manufacture (e.g., one or more computer program products) having, for instance, computer useable media. The media has embodied therein, for instance, computer readable program code means for providing and facilitating the mechanisms of the present invention. The article of manufacture can be included as part of a computer system or sold separately.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of the present invention is not limited to the particular examples and implementations disclosed herein, but is intended to cover modifications within the spirit and scope thereof as defined by the appended claims and any and all equivalents thereof.

We claim:

1. A method of determining lifestyle recommendations for a first individual, the method comprising:
    receiving, by a personal information aggregator comprising a computing processor, personal information corresponding to the first individual comprising lifestyle information, healthcare information, and financial information;
    storing at least a portion of the personal information corresponding to the first individual, wherein access to the stored personal information is controlled by the first individual;
    receiving lifestyle information corresponding to one or more second individuals connected to the first individual via a social network;
    determining, by the personal information aggregator, a weight for each of the second individuals, wherein each weight is based on a degree of separation between the second individual and the first individual in the social network;
    determining, by the personal information aggregator, a set of lifestyle recommendations for the first individual based on at least the stored lifestyle information corresponding to the first individual, the stored healthcare information corresponding to the first individual, the lifestyle information corresponding to the second individuals, and the respective weights corresponding to the second individuals;
    substituting at least one lifestyle recommendation from the set of lifestyle recommendations based on the stored financial information corresponding to the first individual; and
    providing the set of lifestyle recommendations to the first individual.

2. The method of claim 1, wherein storing the at least a portion of the personal information corresponding to the first individual includes storing the lifestyle information corresponding to the first individual and the healthcare information corresponding to the first individual in a computing device that is in the possession of the first individual.

3. The method of claim 1, wherein determining the set of lifestyle recommendations for the first individual includes determining a diet recommendation for the first individual.

4. The method of claim 1, wherein determining the set of lifestyle recommendations for the first individual includes determining a diet schedule for the first individual.

5. The method of claim 1, wherein determining the set of lifestyle recommendations for the first individual includes determining an exercise schedule for the first individual.

6. The method of claim 1, wherein receiving the personal information corresponding to the first individual includes receiving at least one of demographic information, food purchase information, food consumption information, nutrition information, exercise information and fitness information corresponding to the first individual.

7. The method of claim 1, wherein receiving the personal information corresponding to the first individual includes receiving at least one of medical records and diet information corresponding to the first individual.

8. The method of claim 7, wherein the medical records include at least one of the first individual's health history, medical examination findings, lab test results, surgical history, obstetric history, medical allergies, family history, social history, habits, immunization history, growth chart, referrals information, education materials provided to the first individual, future plans for care, instructions for self-care and return visits information.

9. The method of claim 1, wherein receiving the personal information corresponding to the first individual includes receiving at least a portion of the personal information over a computer network from an entity other than the first individual.

10. The method of claim 9, wherein the entity is selected from the group consisting of a healthcare provider, a healthcare organization, and an insurance provider.

11. A computer-implemented method for determining lifestyle recommendations for a first individual, the method comprising:
    receiving, by a computing processor from a personal information aggregator corresponding to the first individual, personal information corresponding to the first individual comprising lifestyle information, healthcare information, and financial information;
    receiving lifestyle information corresponding to one or more second individuals connected to the first individual via a social network;
    determining, by the computing processor, a weight for each of the second individuals, wherein each weight is based on a degree of separation between the second individual and the first individual in the social network;
    determining, by the computing processor, a set of lifestyle recommendations based on at least a portion of the lifestyle information corresponding to the first individual, a portion of the healthcare information corresponding to the first individual, a portion of the lifestyle information corresponding to the second individuals, and the respective weights of the second individuals;
    substituting at least one lifestyle recommendation from the set of lifestyle recommendations based on the financial information corresponding to the first individual; and
    providing the set of lifestyle recommendations to the first individual.

12. The method of claim 11, wherein determining the set of lifestyle recommendations includes determining a diet recommendation for the first individual.

13. The method of claim 11, wherein determining the set of lifestyle recommendations includes determining a diet schedule for the first individual.

14. The method of claim 11, wherein determining the set of lifestyle recommendations includes determining an exercise schedule for the first individual.

15. The method of claim 11, wherein receiving, from the personal information aggregator corresponding to the first individual, the personal information corresponding to the first individual includes receiving at least one of demographic information, food purchase information, food consumption information, nutrition information, exercise information and fitness information corresponding to the first individual.

16. The method of claim 11, wherein receiving, from the personal information aggregator corresponding to the first individual, the personal information corresponding to the first individual includes receiving at least one of medical records and diet information corresponding to the first individual.

17. The method of claim 16, wherein the medical records include at least one of the first individual's health history, medical examination findings, lab test results, surgical history, obstetric history, medical allergies, family history, social history, habits, immunization history, growth chart, referrals information, education materials provided to the first individual, future plans for care, instructions for self-care and return visits information.

18. The method of claim 11, wherein receiving the personal information corresponding to the first individual includes receiving at least a portion of the personal information from the personal information aggregator over a computer network, and wherein the personal information aggregator is operated by an entity other than the first individual.

19. The method of claim 18, wherein the entity is selected from the group consisting of a healthcare provider, a healthcare organization, and an insurance provider.

20. An apparatus for determining lifestyle recommendations, the apparatus comprising:
a first input interface for receiving, from a personal information aggregator corresponding to a first individual, personal information corresponding to the first individual comprising lifestyle information, healthcare information, and financial information;
a second input interface for receiving lifestyle information corresponding to one or more second individuals connected to the first individual via as social network;
a first processor for determining a weight for each of the second individuals, wherein each weight is based on a degree of separation between the second individual and the first individual in the social network;
a second processor for determining a set of lifestyle recommendations based on at least as portion of the lifestyle information corresponding to the first individual, at least a portion of the healthcare information corresponding to the first individual, at least a portion of the lifestyle information corresponding to the second individuals, and the respective weights of the second individuals;
a third processor for substituting one or more lifestyle recommendations from the set of lifestyle recommendations based on the financial information corresponding to the first individual; and
an output interface for providing the set of lifestyle recommendations to the first individual.

21. The apparatus of claim 20, wherein at least one of the lifestyle recommendations in the set of lifestyle recommendations is a diet recommendation.

22. The apparatus of claim 20, wherein at least one of the lifestyle recommendations in the set of lifestyle recommendations is a diet schedule.

23. The apparatus of claim 20, wherein at least one of the lifestyle recommendations in the set of lifestyle recommendations is an exercise schedule.

24. The apparatus of claim 20, wherein at least a portion of the personal information corresponding to the first individual is received over a computer network from an entity other than the first individual.

25. An article of manufacture for determining lifestyle recommendations for a first individual, the article of manufacture comprising a machine-readable medium holding machine-executable instructions for performing a method comprising:
receiving, by a computing processor from a personal information aggregator corresponding to the first individual, personal information corresponding to the first individual comprising lifestyle information, healthcare information, and financial information;
receiving lifestyle information corresponding to one or more second individuals connected to the first individual via a social network;
determining, by the computing processor, a weight for each of the second individuals, wherein each weight is based on a degree of separation between the second individual and the first individual in the social network;
determining, by the computing processor, a set of lifestyle recommendations based on at least a portion of the lifestyle information corresponding to the first individual, a portion of the healthcare information corresponding to the first individual, the lifestyle information corresponding to the one or more second individuals, and the respective weights of the second individuals;
substituting at least one lifestyle recommendation from the set of lifestyle recommendations based on the financial information corresponding to the first individual; and
providing at least one of the one or more lifestyle recommendations to the first individual.

26. The article of manufacture of claim 25, wherein determining the set of lifestyle recommendations includes determining a diet recommendation for the first individual.

27. The article of manufacture of claim 25, wherein determining the set of lifestyle recommendations includes determining a diet schedule for the first individual.

28. The article of manufacture of claim 25, wherein determining the set of lifestyle recommendations includes determining an exercise schedule for the first individual.

29. The article of manufacture of claim 25, wherein receiving, the personal information corresponding to the first individual includes receiving at least a portion of the personal information from the personal information aggregator over a computer network, and wherein the personal information aggregator is operated by an entity other than the first individual.

* * * * *